(12) United States Patent
Maue et al.

(10) Patent No.: US 10,047,076 B2
(45) Date of Patent: Aug. 14, 2018

(54) HALOGEN-SUBSTITUTED COMPOUNDS

(71) Applicants: BAYER CROPSCIENCE AKTIENGESELLSCHAFT, Duesseldorf (DE); Niklas Tim Bretschneider, Lohmar (DE); Uta Bretschneider, Lohmar (DE)

(72) Inventors: Michael Maue, Langenfeld (DE); Anne Decor, Langenfeld (DE); Thomas Bretschneider, Lohmar (DE); Julia Johanna Hahn, Duesseldorf (DE); Werner Hallenbach, Monheim (DE); Reiner Fischer, Monheim (DE); Hans-Georg Schwarz, Dorsten (DE); Ulrich Goergens, Ratingen (DE); Kerstin Ilg, Cologne (DE); Klaus Raming, Leverkusen (DE); Johannes Koebberling, Neuss (DE); Walter Huebsch, Wuppertal (DE); Andreas Turberg, Haan (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 115 days.

(21) Appl. No.: 15/300,057

(22) PCT Filed: Apr. 1, 2015

(86) PCT No.: PCT/EP2015/057155
§ 371 (c)(1),
(2) Date: Sep. 28, 2016

(87) PCT Pub. No.: WO2015/150442
PCT Pub. Date: Oct. 8, 2015

(65) Prior Publication Data
US 2017/0137413 A1    May 18, 2017

(30) Foreign Application Priority Data

Apr. 2, 2014  (EP) .................................... 14163157

(51) Int. Cl.
| | | |
|---|---|---|
| *C07D 417/04* | (2006.01) | |
| *C07D 413/04* | (2006.01) | |
| *C07D 409/04* | (2006.01) | |
| *C07D 403/04* | (2006.01) | |
| *A01N 43/80* | (2006.01) | |
| *A01N 43/653* | (2006.01) | |
| *A01N 43/56* | (2006.01) | |
| *A01N 43/78* | (2006.01) | |
| *A01N 43/82* | (2006.01) | |
| *C07D 405/04* | (2006.01) | |

(52) U.S. Cl.
CPC .......... *C07D 417/04* (2013.01); *A01N 43/56* (2013.01); *A01N 43/653* (2013.01); *A01N 43/78* (2013.01); *A01N 43/80* (2013.01); *A01N 43/82* (2013.01); *C07D 403/04* (2013.01); *C07D 405/04* (2013.01); *C07D 409/04* (2013.01); *C07D 413/04* (2013.01)

(58) Field of Classification Search
None
See application file for complete search history.

(56) References Cited

U.S. PATENT DOCUMENTS

| | | | |
|---|---|---|---|
| 2014/0005245 A1* | 1/2014 | Jung .................... | A01N 43/647 514/407 |
| 2015/0099766 A1 | 4/2015 | Maue et al. | |
| 2017/0114021 A1* | 4/2017 | Maue .................. | C07D 231/12 |

FOREIGN PATENT DOCUMENTS

| | | |
|---|---|---|
| WO | 2004/080972 A1 | 9/2004 |
| WO | 2007/002559 A1 | 1/2007 |
| WO | 2009/152025 A1 | 12/2009 |
| WO | 2010/051926 A2 | 5/2010 |
| WO | 2012/107434 A1 | 8/2012 |

* cited by examiner

*Primary Examiner* — Kamal A Saeed
(74) *Attorney, Agent, or Firm* — McBee Moore Woodward & Vanik IP, LLC

(57) ABSTRACT

The invention relates inter alia to halogen-substituted compounds of the general formula (I)

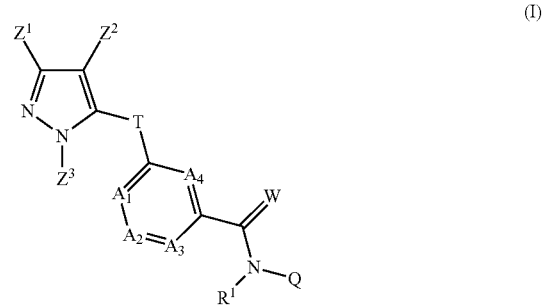

(I)

in which the $A_1$-$A_4$, T, W, Q, $R^1$ and $Z^1$-$Z^3$ radicals are as defined in the description. Also described are processes for preparing the compounds of the formula (I). The compounds according to the invention are especially suitable for controlling insects, arachnids and nematodes in agriculture, and ectoparasites in veterinary medicine.

14 Claims, No Drawings

HALOGEN-SUBSTITUTED COMPOUNDS

CROSS REFERENCE TO RELATED APPLICATIONS

This application is a § 371 National State Application of PCT/EP2015/057155, filed Apr. 1, 2015, which claims priority to European Application No. 14163157.2 filed Apr. 2, 2014.

BACKGROUND OF THE INVENTION

Field of the Invention

The present application relates to novel halogen-substituted compounds, to processes for their preparation and to their use for controlling animal pests, in particular arthropods and especially insects, arachnids and nematodes.

Description of Related Art

It is known that similar compounds are used as FAAH inhibitors [WO2009-152025], LXR modulators [WO2007-002559] and ATP binding cassette transporter modulators [WO2004-080972].

Modern crop protection compositions have to meet many demands, for example in relation to extent, persistence and spectrum of their action and possible use. Questions of toxicity and of combinability with other active compounds or formulation auxiliaries play a role, as does the question of the expense that the synthesis of an active compound requires. In addition, resistances can occur. For all these reasons, the search for novel crop protection compositions can never be considered to be complete, and there is a constant need for novel compounds having improved properties compared to the known compounds at least in relation to individual aspects.

SUMMARY

It was an object of the present invention to provide compounds which broaden the spectrum of the pesticides in various aspects and/or improve their activity.

Surprisingly, it has now been found that certain halogen-substituted compounds and their N-oxides and salts have biological properties and are particularly suitable for controlling animal pests, and can therefore be employed particularly well in the agrochemical field and in the animal health sector.

The halogen-substituted compounds according to the invention are defined by the general formula (I)

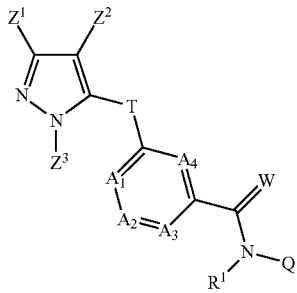

(I)

in which
$R^1$ represents hydrogen, optionally substituted alkyl, alkenyl, alkynyl, cycloalkyl, cycloalkylalkyl, alkylcarbonyl, alkoxycarbonyl, arylalkyl, heteroarylalkyl,
the chemical moieties
$A_1$ represents $CR^2$ or nitrogen,
$A_2$ represents $CR^3$ or nitrogen,
$A_3$ represents $CR^4$ or nitrogen, and
$A_4$ represents $CR^5$ or nitrogen,
but where not more than three of the chemical moieties $A_1$ to $A_4$ simultaneously represent nitrogen;
$R^2$, $R^3$, $R^4$ and $R^5$ independently of one another represent hydrogen, halogen, cyano, nitro, optionally substituted alkyl, cycloalkyl, alkoxy, N-alkoxyiminoalkyl, alkylsulphanyl, alkylsulphinyl, alkylsulphonyl, N-alkylamino or N,N-dialkylamino;
  if neither of the $A_2$ and $A_3$ moieties represents nitrogen, $R^3$ and $R^4$ together with the carbon atom to which they are bonded may form a 5- or 6-membered ring containing 0, 1 or 2 nitrogen atoms and/or 0 or 1 oxygen atom and/or 0 or 1 sulphur atom, or
  if neither of the $A_1$ and $A_2$ moieties represents nitrogen, $R^2$ and $R^3$ together with the carbon atom to which they are bonded may form a 6-membered ring containing 0, 1 or 2 nitrogen atoms;
W represents oxygen or sulphur;
Q represents hydrogen, formyl, hydroxy, amino or one of the optionally substituted moieties alkyl, alkyloxy, alkenyl, alkynyl, cycloalkyl, heterocycloalkyl, cycloalkylalkyl, heterocycloalkylalkyl, arylalkyl, heteroarylalkyl or represents a moiety N-alkylamino, N-alkylcarbonylamino, N,N-dialkylamino; or
Q represents a mono- or polyunsaturated 5- to 6-membered carbocycle which may optionally be interrupted by heteroatoms and is optionally mono- or poly substituted by V, where
V represents halogen, cyano, nitro, optionally substituted alkyl, alkenyl, alkynyl, cycloalkyl, alkoxy, N-alkoxyiminoalkyl, alkylsulphanyl, alkylsulphinyl, alkylsulphonyl, N,N-dialkylamino;
T represents one of the 5-membered heteroaromatic systems T1-T35 shown below, where the bond to the pyrazolyl head group is indicated by an asterisk,

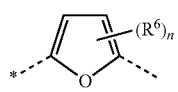

T1

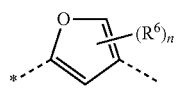

T2

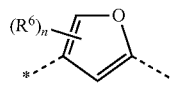

T3

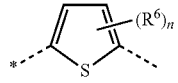

T4

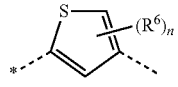

T5

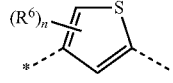

T6

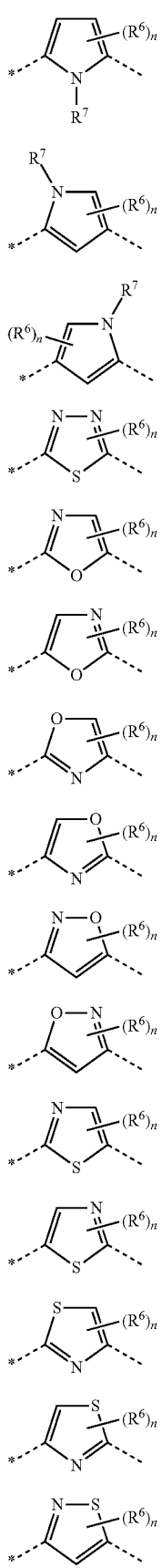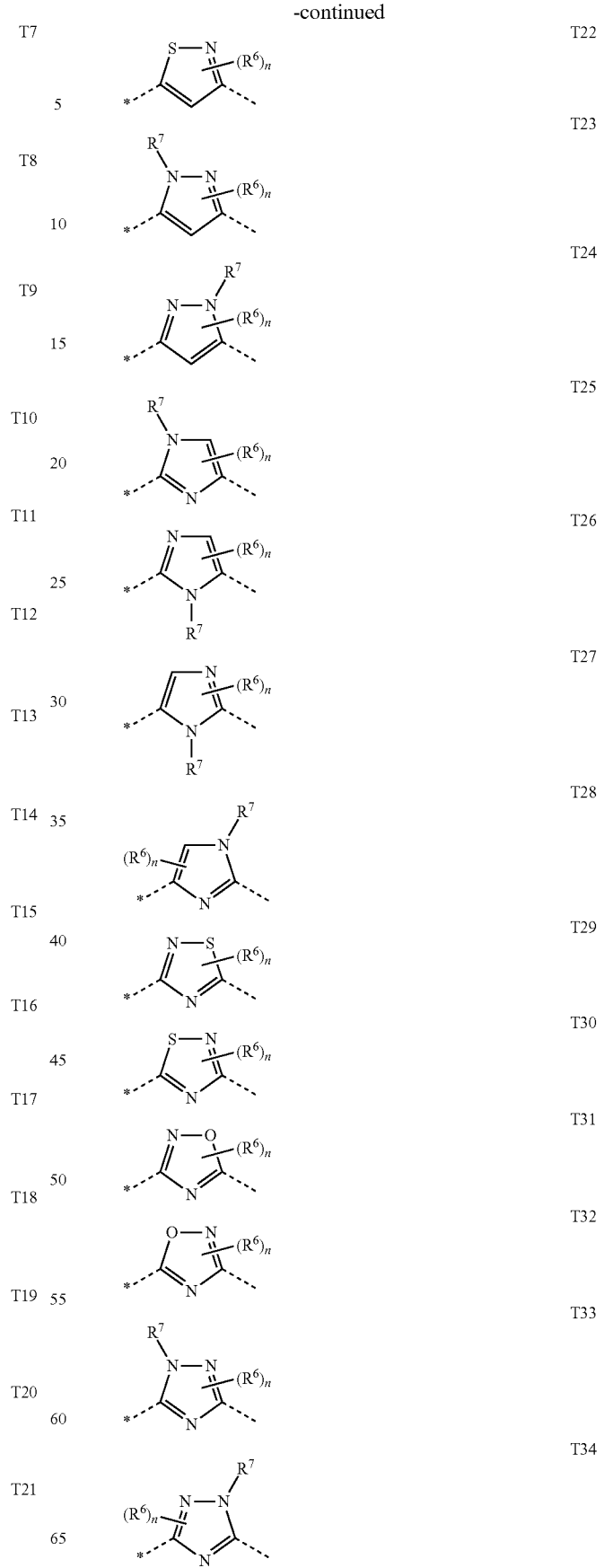

-continued

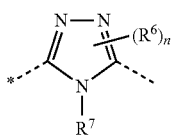
T35 where
R⁶ independently of one another represent halogen, cyano, nitro, amino or optionally substituted alkyl, alkyloxy, alkylcarbonyl, alkylsulphanyl, alkylsulphinyl, alkylsulphonyl, and
n represents the values 0-2;
R⁷ represents hydrogen, or optionally substituted alkyl or cycloalkyl in which optionally one methylene group is substituted by a heteroatom;
Z¹ represents optionally substituted haloalkyl or halocycloalkyl, and
Z² represents hydrogen, halogen, cyano, nitro, amino or optionally substituted alkyl, alkylcarbonyl, alkylsulphanyl, alkylsulphinyl, alkylsulphonyl, and
Z³ represents hydrogen or optionally substituted alkyl, cycloalkyl, heterocycloalkyl, alkenyl, alkynyl, where
if T is T23 or T24, one of the radicals Z¹, Z² or Z³ is substituted by at least 3 halogen atoms.

DETAILED DESCRIPTION OF A PREFERRED EMBODIMENT

Preference is given to defining compounds of the formula (I)

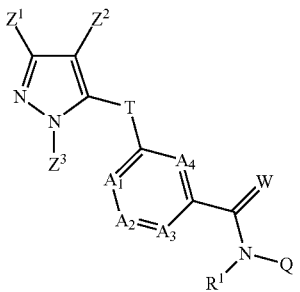
(I)

in which
R¹ represents hydrogen, optionally substituted $C_1$-$C_6$-alkyl, $C_3$-$C_6$-alkenyl, $C_3$-$C_6$-alkynyl, $C_3$-$C_7$-cycloalkyl, $C_3$-$C_7$-cycloalkyl-$C_1$-$C_3$-alkyl, $C_1$-$C_6$-alkylcarbonyl, $C_1$-$C_6$-alkoxycarbonyl, aryl-($C_1$-$C_3$)-alkyl, heteroaryl-($C_1$-$C_3$)-alkyl,
the chemical moieties
$A_1$ represents $CR^2$ or nitrogen,
$A_2$ represents $CR^3$ or nitrogen,
$A_3$ represents $CR^4$ or nitrogen, and
$A_4$ represents $CR^5$ or nitrogen,
but where not more than three of the chemical moieties $A_1$ to $A_4$ simultaneously represent nitrogen;
$R^2$, $R^3$, $R^4$ and $R^5$ independently of one another represent hydrogen, halogen, cyano, nitro, optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino, N,N-di-$C_1$-$C_6$-alkylamino, or
if neither of the $A_2$ and $A_3$ moieties is nitrogen, $R^3$ and $R^4$ together with the carbon atom to which they are bonded may form a 5- or 6-membered ring containing 0, 1 or 2 nitrogen atoms and/or 0 or 1 oxygen atom and/or 0 or 1 sulphur atom, or
if neither of the $A_1$ and $A_2$ moieties is nitrogen, $R^2$ and $R^3$ together with the carbon atom to which they are bonded may form a 6-membered ring containing 0, 1 or 2 nitrogen atoms;
W represents oxygen or sulphur;
Q represents hydrogen, formyl, hydroxy, amino or one of the optionally substituted moieties $C_1$-$C_6$-alkyl, $C_3$-$C_6$-alkenyl, $C_3$-$C_6$-alkynyl, $C_3$-$C_6$-cycloalkyl, $C_1$-$C_5$-heterocycloalkyl, $C_1$-$C_4$-alkoxy, $C_3$-$C_6$-cycloalkyl-$C_1$-$C_6$-alkyl, aryl-($C_1$-$C_3$)-alkyl, heteroaryl-($C_1$-$C_3$)-alkyl or represents a moiety N—$C_1$-$C_4$-alkylamino, N—$C_1$-$C_4$-alkylcarbonylamino, N,N-di-$C_1$-$C_4$-alkylamino; or
Q represents a mono- to triunsaturated 5- to 6-membered carbocycle which is optionally mono- or polysubstituted by V or a mono- to triunsaturated 5- or 6-membered heterocyclic ring which is optionally polysubstituted by V, where
V independently of one another represent halogen, cyano, nitro, optionally substituted $C_1$-$C_6$-alkyl, $C_1$-$C_4$-alkenyl, $C_1$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N,N-di-($C_1$-$C_6$-alkyl)amino;
T represents one of the 5-membered heteroaromatic systems T1-T35 shown below, where the bond to the pyrazolyl head group is indicated by an asterisk,

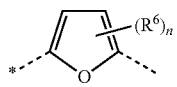
T1

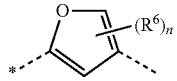
T2

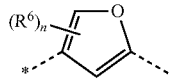
T3

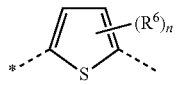
T4

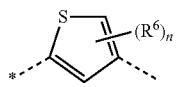
T5

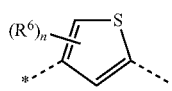
T6

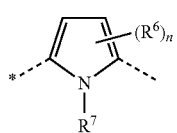
T7

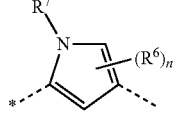
T8

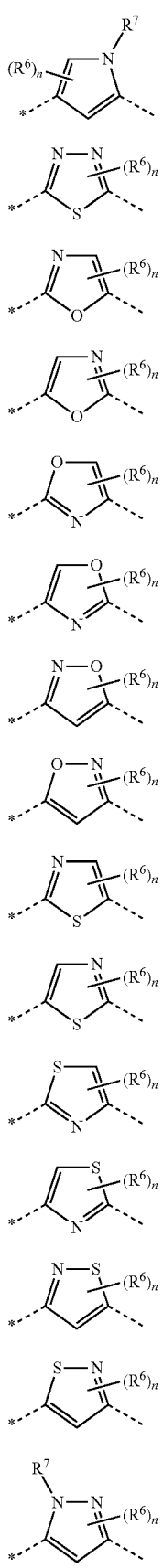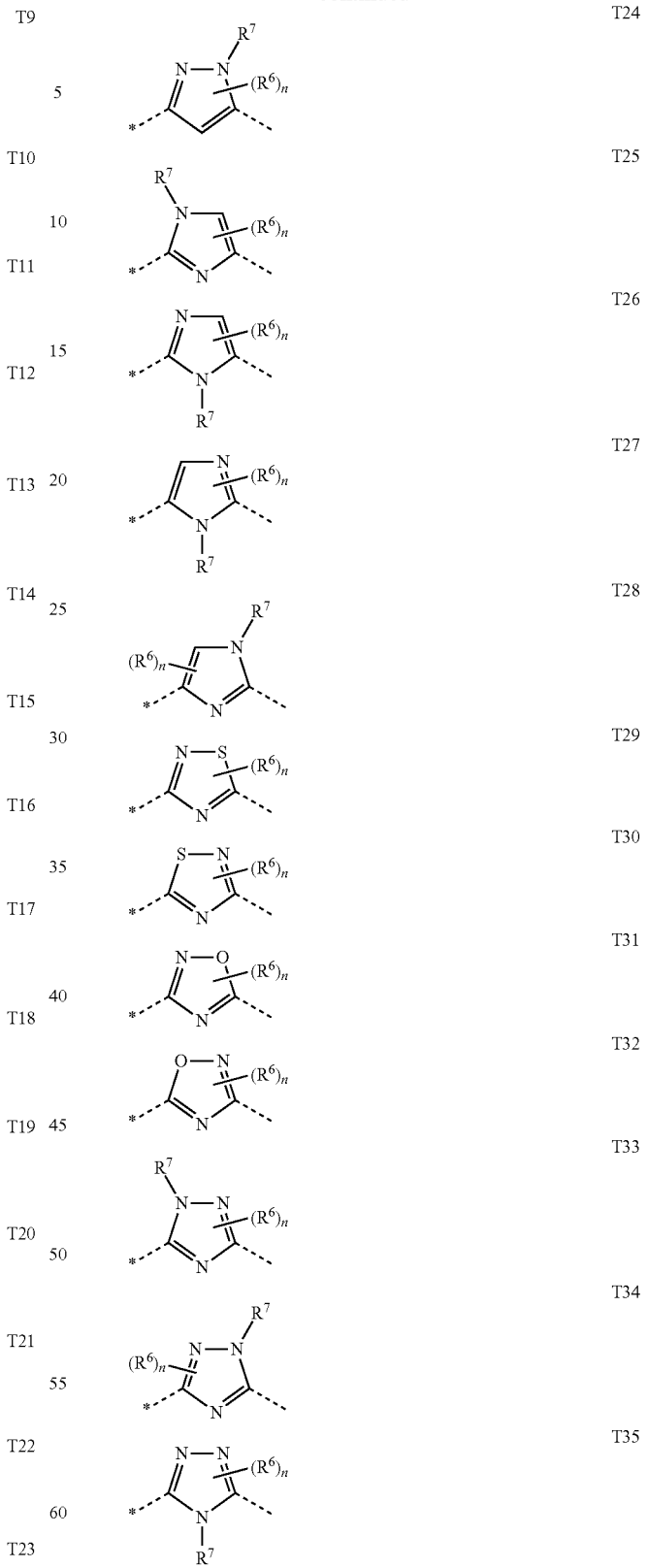
where
R[6] independently of one another represent halogen, cyano, nitro, amino or optionally halogen-substituted $C_1$-$C_6$- alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and n represents the values 0-1;

$R^7$ represents hydrogen, or optionally substituted $C_1$-$C_6$-alkyl or $C_3$-$C_6$-cycloalkyl in which optionally one methylene group may be substituted by heteroatoms;

$Z^1$ represents optionally substituted $C_1$-$C_6$-haloalkyl, $C_3$-$C_6$-halocycloalkyl, and $Z^2$ represents hydrogen, halogen, cyano, nitro, amino or optionally substituted $C_1$-$C_6$-alkyl, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and $Z^3$ represents hydrogen or optionally substituted $C_1$-$C_6$-alkyl, $C_3$-$C_6$-cycloalkyl, $C_3$-$C_5$-heterocycloalkyl, $C_3$-$C_6$-alkenyl, $C_3$-$C_6$-alkynyl, where if T is T23 or T24, one of the radicals $Z^1$, $Z^2$ or $Z^3$ is substituted by at least 3 halogen atoms.

Particular preference is given to defining compounds of the formula (I)

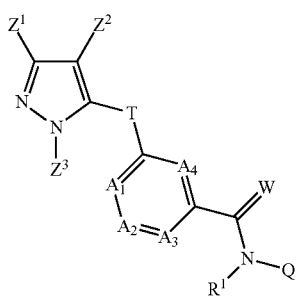
(I)

in which $R^1$ represents hydrogen or represents $C_1$-$C_6$-alkyl, $C_3$-$C_6$-alkenyl, $C_3$-$C_6$-alkynyl, $C_3$-$C_7$-cycloalkyl, $C_3$-$C_7$-cycloalkyl-$C_1$-$C_3$-alkyl, $C_1$-$C_6$-alkylcarbonyl, $C_1$-$C_6$-alkoxycarbonyl, aryl-($C_1$-$C_3$)-alkyl, heteroaryl-($C_1$-$C_3$)-alkyl which are optionally mono- to pentasubstituted independently of one another by fluorine, chlorine, cyano, alkoxy and alkoxycarbonyl, the chemical moieties $A_1$ represents $CR^2$ or nitrogen, $A_2$ represents $CR^3$ or nitrogen, $A_3$ represents $CR^4$ or nitrogen, and $A_4$ represents $CR^5$ or nitrogen, but where not more than three of the chemical moieties $A_1$ to $A_4$ simultaneously represent nitrogen;

$R^2$, $R^3$, $R^4$ and $R^5$ independently of one another represent hydrogen, fluorine, chlorine, bromine, iodine, cyano, nitro or represent $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino or N,N-di-$C_1$-$C_6$-alkylamino which are optionally mono- to pentasubstituted by fluorine, chlorine, cyano or $C_1$-$C_4$-alkoxy;

W represents oxygen or sulphur;

Q represents hydrogen, hydroxy, formyl, amino or one of the moieties $C_1$-$C_6$-alkyl, $C_3$-$C_6$-alkenyl, $C_3$-$C_6$-alkynyl, $C_3$-$C_6$-cycloalkyl, $C_2$-$C_6$-heterocycloalkyl, $C_1$-$C_4$-alkoxy, $C_1$-$C_6$-alkyl-$C_3$-$C_6$-cycloalkyl, $C_3$-$C_6$-cycloalkyl-$C_1$-$C_6$-alkyl, $C_1$-$C_6$-hydroxyalkyl, aryl-($C_1$-$C_3$)-alkyl, heteroaryl-($C_1$-$C_3$)-alkyl, N—$C_1$-$C_4$-alkylamino, N—$C_1$-$C_4$-alkylcarbonylamino or N,N-di-$C_1$-$C_4$-alkylamino which are optionally mono- or polysubstituted independently of one another by hydroxy, nitro, amino, fluorine, chlorine, bromine, iodine, $C_1$-$C_4$-alkoxy, cyano, hydroxycarbonyl, $C_1$-$C_4$-alkoxycarbonyl, carbamoyl, thiocarbamoyl, $C_1$-$C_4$-alkylcarbamoyl, $C_3$-$C_6$-cycloalkylcarbamoyl, phenyl; or Q represents aryl substituted by 0, 1, 2 or 3 substituents V or a 5- or 6-membered heteroaromatic system substituted by 0, 1, 2 or 3 substituents V, where V independently of one another represent fluorine, chlorine, bromine, iodine, cyano, nitro, optionally substituted $C_1$-$C_6$-alkyl, $C_2$-$C_4$-alkenyl, $C_2$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N,N-di-($C_1$-$C_6$-alkyl)amino;

T represents one of the 5-membered heteroaromatic systems T1-T35 shown below, where the bond to the pyrazolyl head group is indicated by an asterisk,

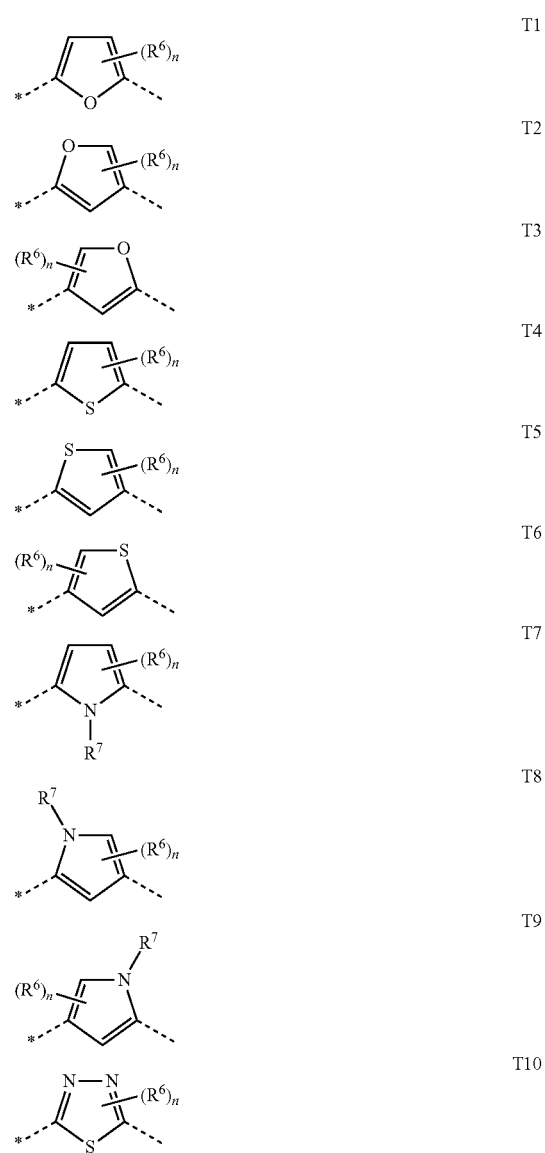

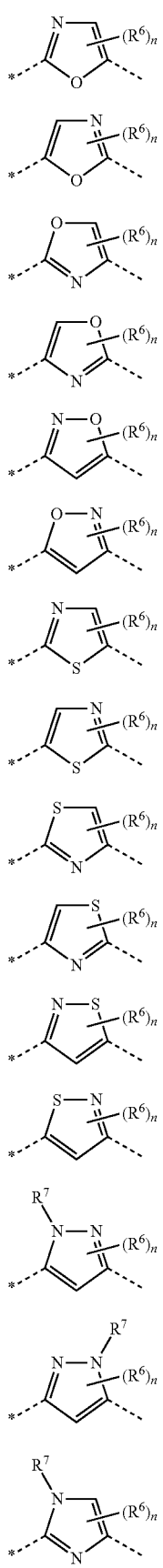
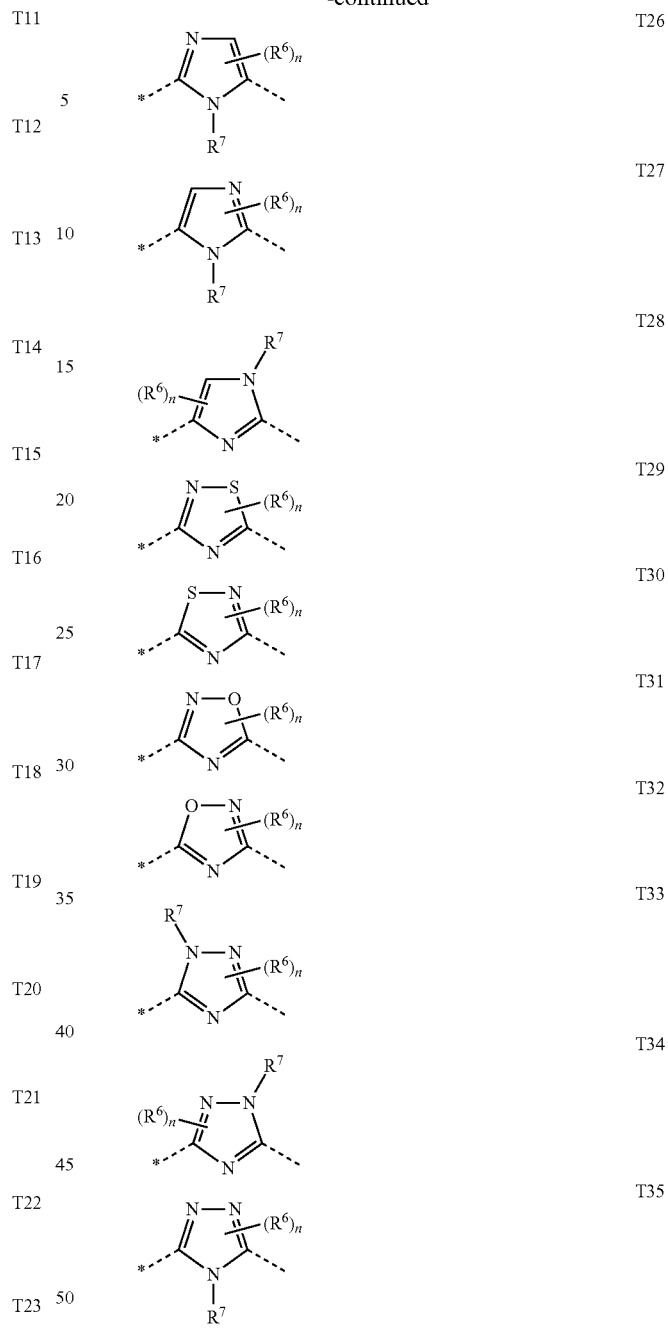

where
R⁶ independently of one another represent fluorine, chlorine, bromine, iodine, cyano, nitro, amino or represent $C_1$-$C_6$-alkyl, $C_1$-$C_6$-alkoxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl which are optionally mono- to pentasubstituted by fluorine or chlorine, and n represents the values 0-1;

R⁷ represents hydrogen, or $C_1$-$C_6$-alkyl or $C_3$-$C_6$-cycloalkyl in which optionally one methylene group may be substituted by heteroatoms and which are optionally mono- to pentasubstituted by fluorine, chlorine, cyano or $C_1$-$C_4$-alkoxy; $Z^1$ represents optionally substituted $C_1$-$C_6$-haloalkyl, $C_3$-$C_6$-halocycloalkyl, and $Z^2$ represents hydrogen, halogen, cyano, nitro, amino or optionally mono- to pentasubstituted $C_1$-$C_6$-alkyl, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and $Z^3$ represents hydrogen or represents $C_1$-$C_6$-alkyl, $C_3$-$C_6$-cycloalkyl, $C_1$-$C_4$-alkenyl, $C_1$-$C_4$-alkynyl which are optionally mono- to pentasubstituted by fluorine, chlorine, cyano or $C_1$-$C_4$-alkoxy;

where if T is T23 or T24, one of the radicals $Z^1$, $Z^2$ or $Z^3$ is substituted by at least 3 halogen atoms.

Very particular preference is given to defining compounds of the formula (I)

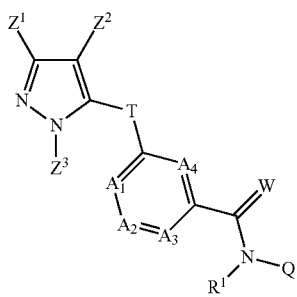

(I)

in which $R^1$ represents hydrogen, methyl, ethyl, n-propyl, isopropyl, n-butyl, isobutyl, s-butyl, t-butyl, 2,2-difluoroethyl, 2,2,2-trifluoroethyl, methoxymethyl, ethoxymethyl, propoxymethyl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 6-chloropyrid-3-ylmethyl;

the chemical moieties $A_1$ represents $CR^2$ or nitrogen, $A_2$ represents $CR^3$ or nitrogen, $A_3$ represents $CR^4$ or nitrogen, and $A_4$ represents $CR^5$ or nitrogen, but where not more than three of the chemical moieties $A_1$ to $A_4$ simultaneously represent nitrogen;

$R^2$ and $R^5$ independently of one another represent hydrogen, methyl, fluorine or chlorine and $R^3$ and $R^4$ independently of one another represent hydrogen, fluorine, chlorine, bromine, iodine, cyano, nitro, methyl, ethyl, cyclopropyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, trifluoromethylsulphinyl;

W represents oxygen or sulphur;

Q represents hydrogen, methyl, ethyl, n-propyl, 1-methylethyl, 1,1-dimethylethyl, 1-methylpropyl, n-butyl, 2-methylpropyl, 2-methylbutyl, hydroxyethyl, 2-hydroxypropyl, cyanomethyl, 2-cyanoethyl, 2-fluoroethyl, 2,2-difluoroethyl, 2,2,2-trifluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-methylcyclopropyl, 1-trifluoromethylcyclopropyl, 1-carbamoylcyclopropyl, 1-thiocarbamoylcyclopropyl, 1-methoxycarbonylcyclopropyl, 1-(N-methylcarbamoyl)cyclopropyl, 1-(N-cyclopropylcarbamoyl)cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, oxetan-3-yl, thietan-3-yl, 1-oxidothietan-3-yl, 1,1-dioxidothietan-3-yl, isoxazol-3-ylmethyl, 1,2,4-triazol-3-ylmethyl, 3-methyloxetan-3-ylmethyl, benzyl, 2,6-difluorophenylmethyl, 3-fluorophenylmethyl, 2-fluorophenylmethyl, 4-fluorophenylmethyl, 2,5-difluorophenylmethyl, 1-phenylethyl, 4-chlorophenylethyl, 2-trifluoromethylphenylethyl, 1-pyridin-2-ylethyl, pyridin-2-ylmethyl, 5-fluoropyridin-2-ylmethyl, (6-chloropyridin-3-yl)methyl, pyrimidin-2-ylmethyl, methoxy, 2-ethoxy ethyl, 2-(methylsulphanyl) ethyl, 1-methyl-2-(ethylsulphanyl)ethyl, 2-methyl-1-(methylsulphanyl)propan-2-yl, methoxy carbonyl, methoxycarbonylmethyl, $NH_2$, N-ethylamino, N-allylamino, N,N-dimethylamino, N,N-diethylamino; or Q represents phenyl, naphthyl, pyridazine, pyrazine, pyrimidine, triazine, pyridine, pyrazole, thiazole, isothiazole, oxazole, isoxazole, triazole, imidazole, furan, thiophene, pyrrole, oxadiazole, thiadiazole each substituted by 0, 1, 2 or 3 substituents V, where V independently of one another represent fluorine, chlorine, bromine, iodine, cyano, nitro, methyl, ethyl, difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino;

T represents one of the 5-membered heteroaromatic systems T1-T35 shown below, where the bond to the pyrazolyl head group is indicated by an asterisk,

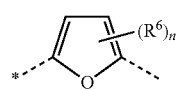

T1

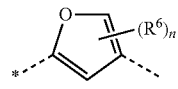

T2

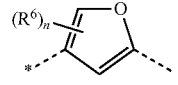

T3

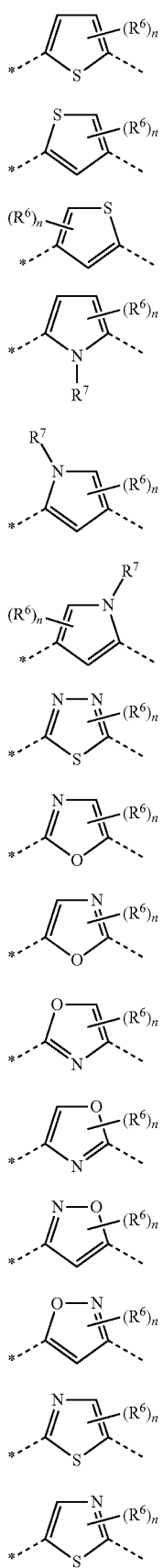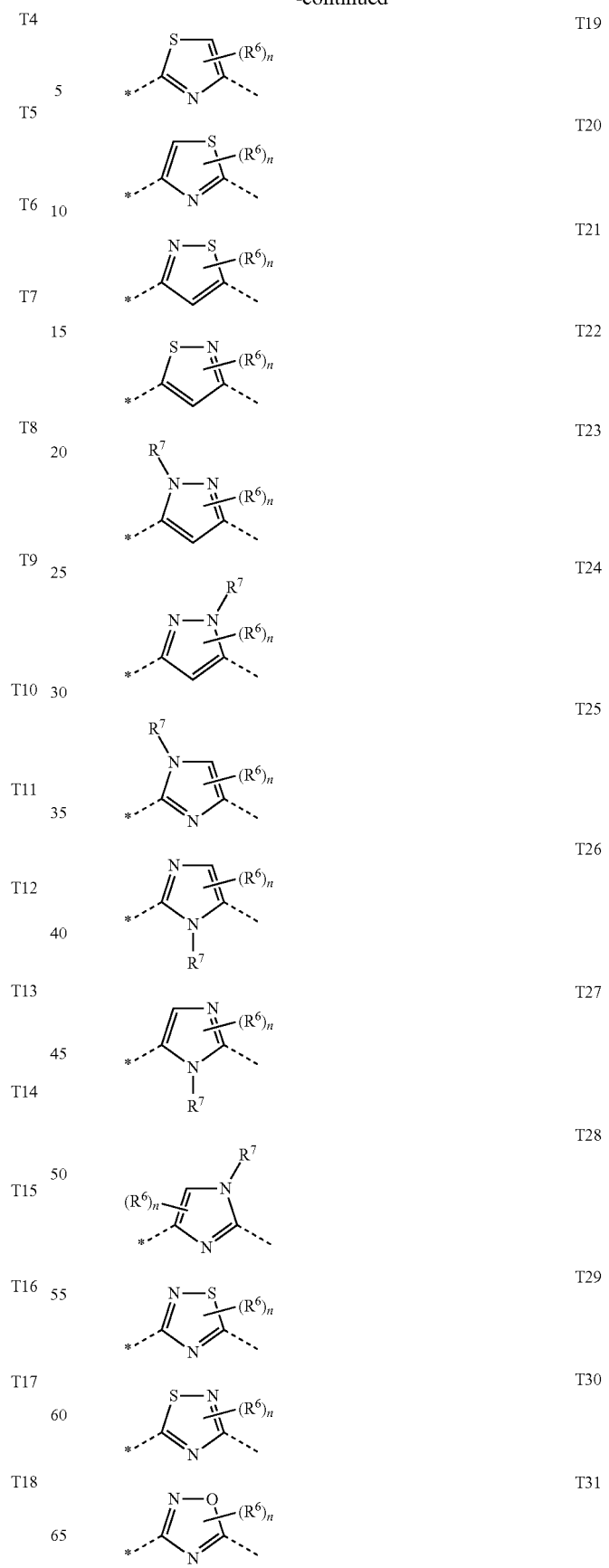

-continued

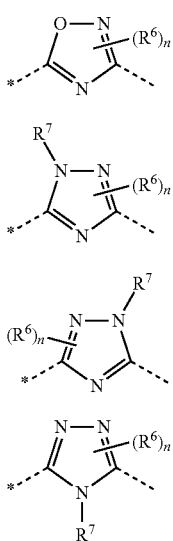

where
R⁶ independently of one another represent fluorine, chlorine, bromine, iodine, cyano, nitro, amino, methyl, ethyl, n-propyl, 1-methylethyl, tert-butyl, trifluoromethyl, difluoromethyl, methoxy, ethoxy, trifluoromethoxy, 2,2-difluoroethoxy, 2,2,2-trifluoroethoxy, methylcarbonyl, ethylcarbonyl, trifluoromethylcarbonyl, methylsulphanyl, methylsulphinyl, methylsulphonyl, trifluoromethylsulphonyl, trifluoromethylsulphanyl, trifluoromethylsulphinyl, and
n represents the values 0-1;
R⁷ represents hydrogen, methyl, ethyl, n-propyl, isopropyl, n-butyl, isobutyl, s-butyl, t-butyl, ethenyl, 1-propenyl, 2-propenyl, 1-propynyl, 1-butynyl, difluoromethyl, trifluoromethyl, 1-fluoroethyl, 1-fluoro-1-methylethyl, 2-fluoroethyl, 2,2-difluoroethyl, 2,2,2-trifluoroethyl, cyclopropyl, cyclobutyl, cyclopentyl, cyclohexyl;
Z¹ represents difluoromethyl, trichloromethyl, chlorodifluoromethyl, dichlorofluoromethyl, trifluoromethyl, bromodichloromethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, heptafluoro-n-propyl, heptafluoroisopropyl, nonafluoro-n-butyl, 1-chlorocyclopropyl, 1-fluorocyclopropyl, 1-bromocyclopropyl, 1-trifluoromethylcyclopropyl or 2,2-difluoro-1-methylcyclopropyl, and
Z² represents hydrogen, fluorine, chlorine, bromine, iodine, cyano, nitro, amino, methyl, ethyl, n-propyl, 1-methylethyl, 1,1-dimethylethyl, difluoromethyl, trichloromethyl, chlorodifluoromethyl, dichlorofluoromethyl, trifluoromethyl, bromodichloromethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-t-butyl, heptafluoro-n-propyl, heptafluoroisopropyl, nonafluoro-n-butyl, methylsulphanyl, methylsulphinyl, methylsulphonyl, ethylsulphanyl, ethylsulphinyl, ethylsulphonyl, trifluoromethylsulphanyl, trifluoromethylsulphinyl, trifluoromethylsulphonyl, chlorodifluoromethylsulphanyl, chlorodifluoromethylsulphinyl, chlorodifluoromethylsulphonyl, dichlorofluoromethylsulphanyl, dichlorofluoromethylsulphinyl, dichlorofluoromethylsulphonyl and
Z³ represents hydrogen, methyl, ethyl, n-propyl, isopropyl, n-butyl, isobutyl, s-butyl, t-butyl, prop-2-enyl, prop-2-ynyl, but-3-ynyl, difluoromethyl, trifluoromethyl, 1-fluoroethyl, 1-fluoro-1-methylethyl, 2-fluoroethyl, 2,2-difluoroethyl, 2,2,2-trifluoroethyl;
where if T is T23 or T24, one of the radicals Z¹, Z² or Z³ is substituted by at least 3 halogen atoms.

Especially preferred are compounds of the general formula (I) in which
Z¹ represents trifluoromethyl, 1-chlorocyclopropyl, 1-fluorocyclopropyl or pentafluoroethyl,
Z² represents trifluoromethyl, nitro, methylsulphanyl, methylsulphinyl, methylsulphonyl, fluorine, chlorine, bromine, cyano or iodine;
Z³ represents methyl, ethyl, n-propyl or hydrogen,
R¹ represents hydrogen, methyl, ethyl, n-propyl, isopropyl, n-butyl, isobutyl, s-butyl, t-butyl, methoxymethyl, ethoxymethyl, propoxymethyl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 6-chloropyrid-3-ylmethyl,
A¹ and A⁴ represent CH and A2 represents CH or N,
A₃ represents CR⁴ and
R⁴ represents fluorine, chlorine, bromine, iodine or methyl,
T represents one of the 5-membered heteroaromatic systems T1-T35 shown below, where the bond to the pyrazolyl head group is indicated by an asterisk,

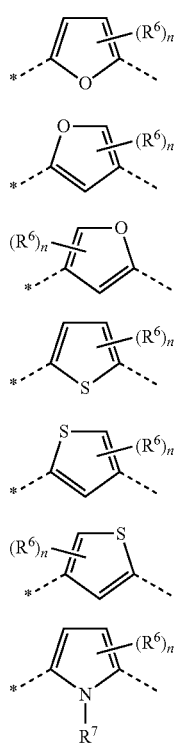

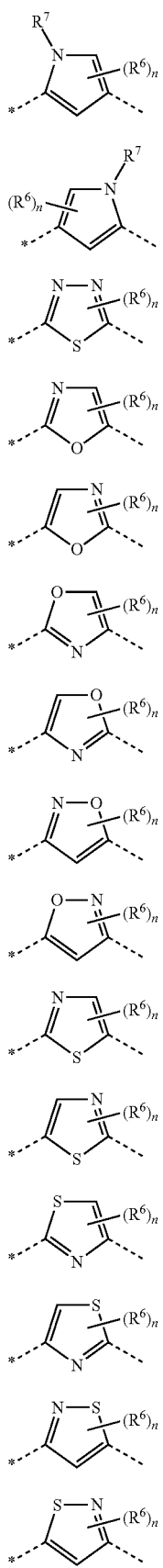
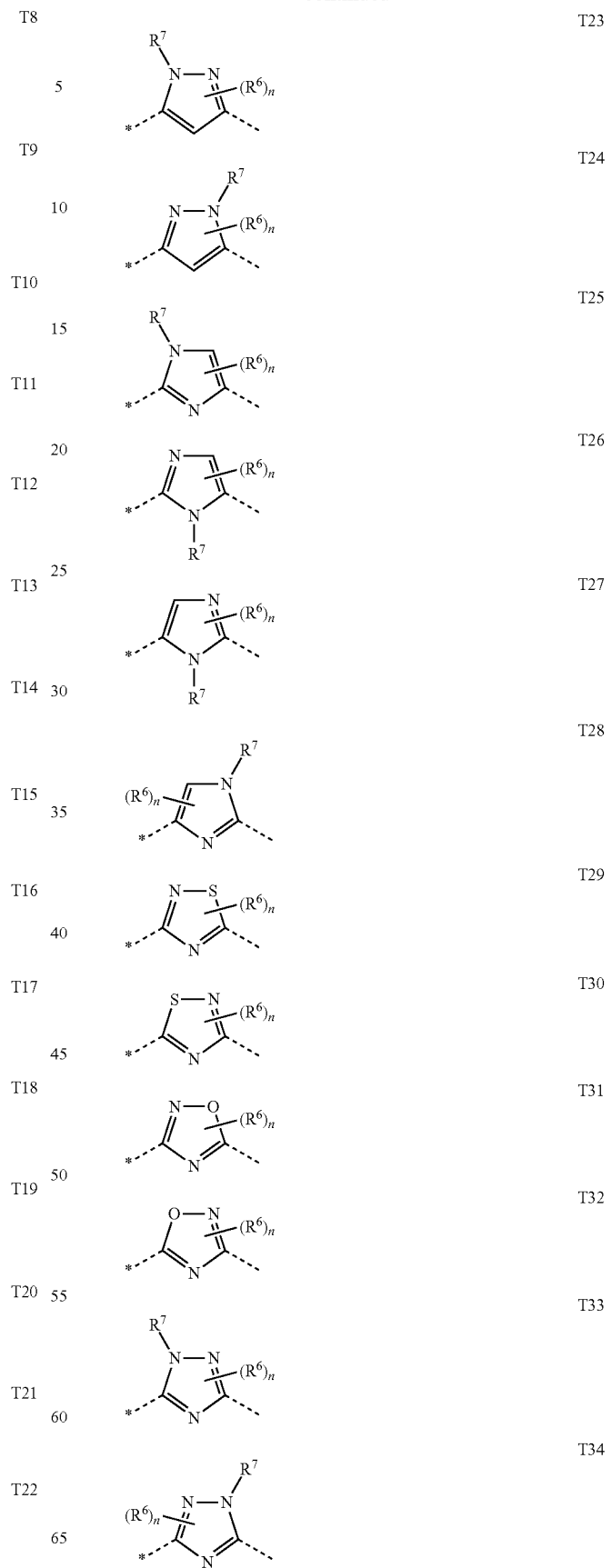

-continued

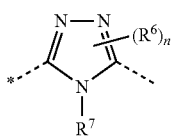
T35 where
R[6] represents hydrogen, methyl, ethyl, 2-methylethyl, 2,2-dimethylethyl, fluorine, chlorine, bromine, iodine, nitro, trifluoromethyl, amino, and
n represents the values 0-1;
W represents oxygen and
Q represents hydrogen, methyl, ethyl, n-propyl, 1-methylethyl, 1,1-dimethylethyl, n-butyl, 1-methylpropyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-methylcyclopropyl, 1-trifluoromethylcyclopropyl, 1-carbamoylcyclopropyl, 1-thiocarbamoylcyclopropyl, 1-methoxycarbonylcyclopropyl, 1-(N-methylcarbamoyl)cyclopropyl, 1-(N-cyclopropylcarbamoyl)cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, oxetan-3-yl, thietan-3-yl, 1-oxidothietan-3-yl, 1,1-dioxidothietan-3-yl, isoxazol-3-ylmethyl, 1,2,4-triazol-3-ylmethyl, 3-methyloxetan-3-ylmethyl, benzyl, 2,6-difluorophenylmethyl, 3-fluorophenylmethyl, 2-fluorophenylmethyl, 4-fluorophenylmethyl, 2,5-difluorophenylmethyl, 1-phenylethyl, 4-chlorophenylethyl, 2-trifluoromethylphenylethyl, 1-pyridin-2-ylethyl, pyridin-2-ylmethyl, (6-chloropyridin-3-yl)methyl, 5-fluoropyridin-2-ylmethyl, pyrimidin-2-ylmethyl, methoxy, 2-ethoxy ethyl, 2-(methylsulphanyl)ethyl, 1-methyl-2-(ethylsulphanyl)ethyl, 2-methyl-1-(methylsulphanyl)propan-2-yl, methoxycarbonyl, methoxycarbonylmethyl, NH$_2$, N-ethylamino, N-allylamino, N,N-dimethylamino, N,N-diethylamino; or
Q represents phenyl, naphthyl, pyridazine, pyrazine, pyrimidine, triazine, pyridine, pyrazole, thiazole, isothiazole, oxazole, isoxazole, triazole, imidazole, furan, thiophene, pyrrole, oxadiazole, thiadiazole substituted by 0, 1, 2 or 3 substituents V, where
V independently of one another represent fluorine, chlorine, bromine, iodine, cyano, nitro, methyl, ethyl, difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino;
where if T is T23 or T24, one of the radicals Z$^1$, Z$^2$ or Z$^3$ is substituted by at least 3 halogen atoms.

Special preference is furthermore given to the compounds in each case defined by one of the general formulae (Iaa)-(Ibi) in which the radicals A$_1$-A$_4$, n, W, Q, R$^1$ and Z$^1$-Z$^3$ have the general, preferred or particularly preferred meanings described in each case above.

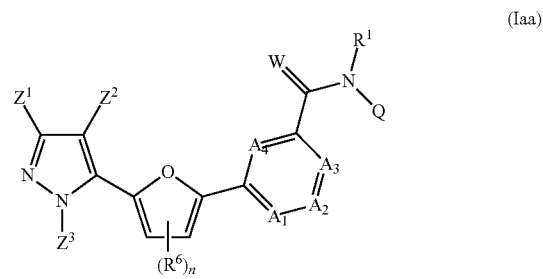
(Iaa)

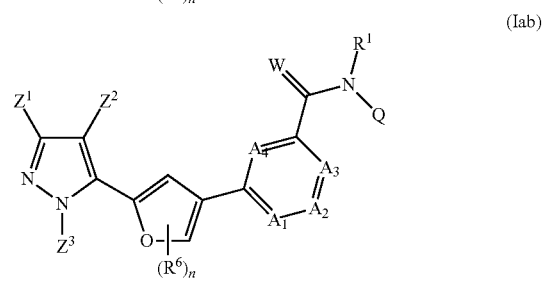
(Iab)

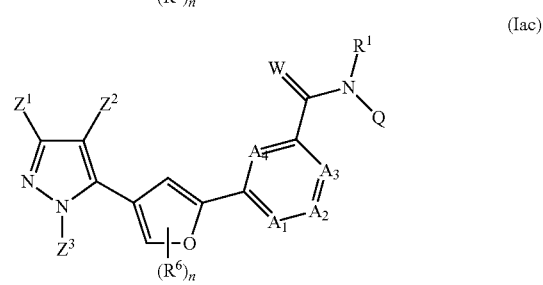
(Iac)

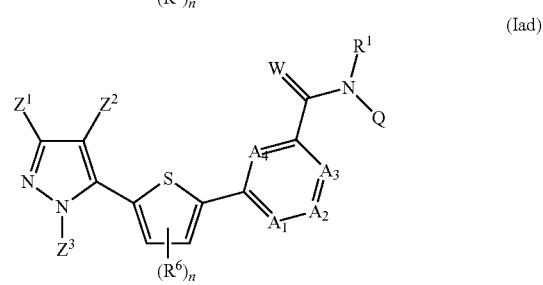
(Iad)

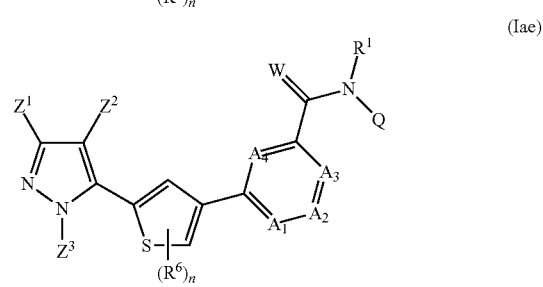
(Iae)

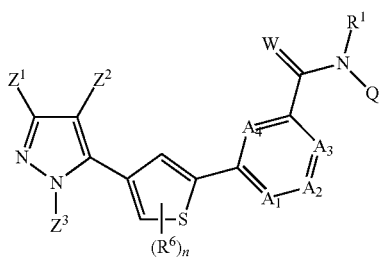
(Iaf)
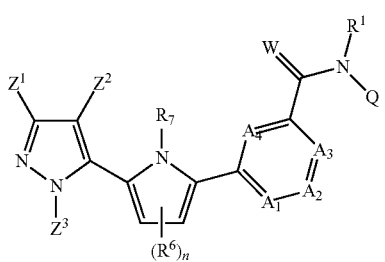
(Iag)
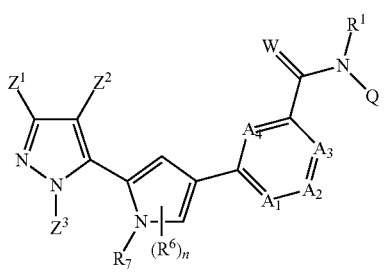
(Iah)
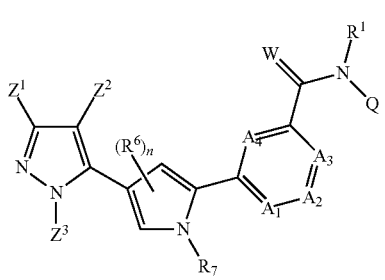
(Iai)
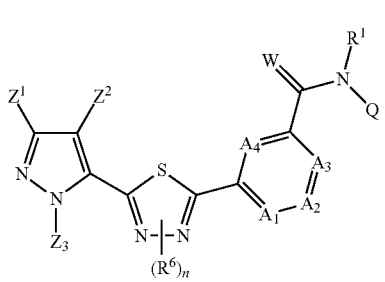
(Iaj)
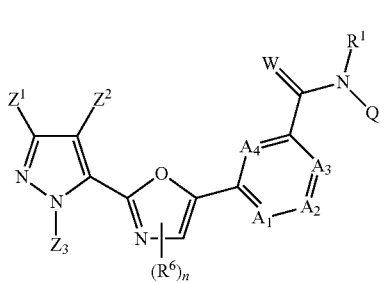
(Iak)
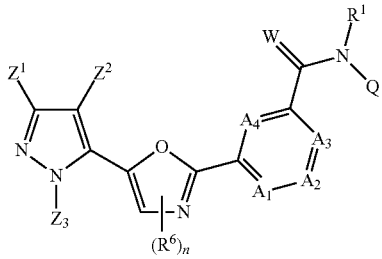
(Ial)
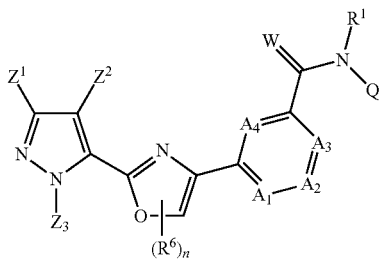
(Iam)
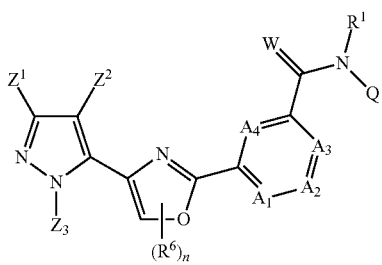
(Ian)
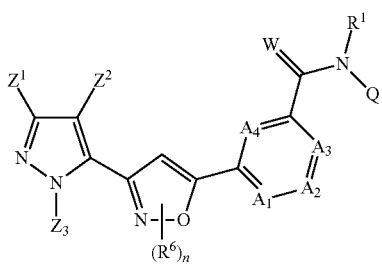
(Iao)
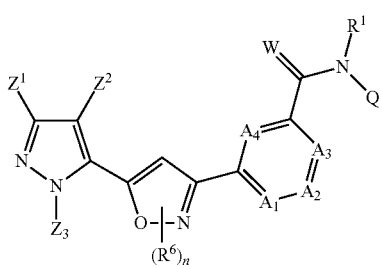
(Iap)
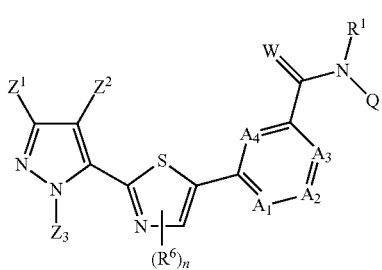
(Iaq)

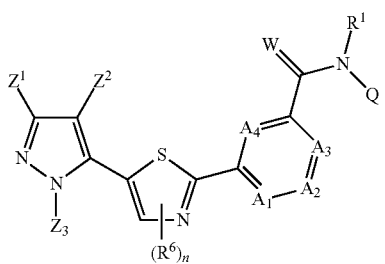
(Iar)
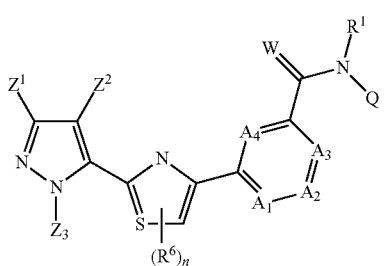
(Ias)
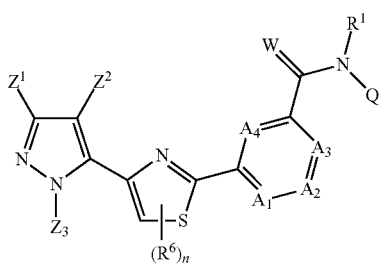
(Iat)
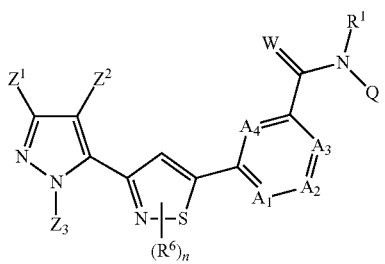
(Iau)
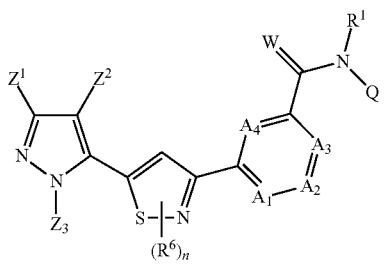
(Iav)
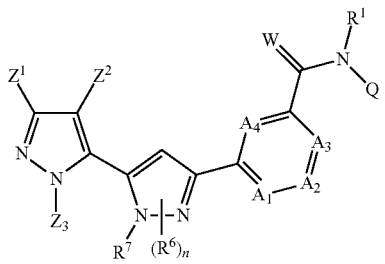
(Iaw)
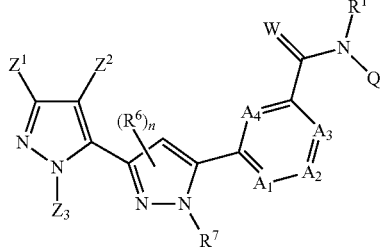
(Iax)
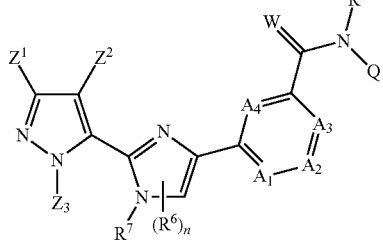
(Iay)
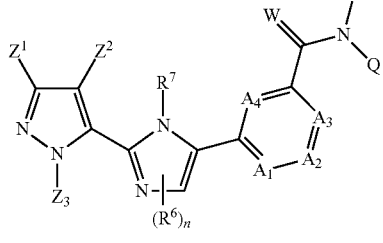
(Iaz)
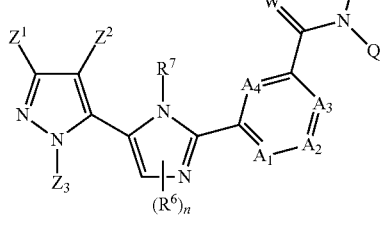
(Iba)
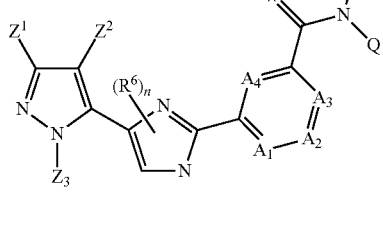
(Ibb)
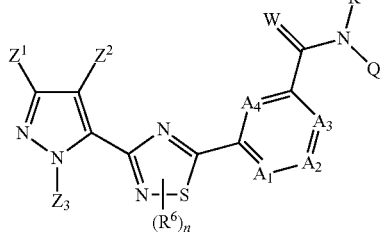
(Ibc)

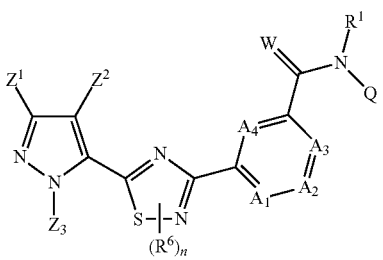
(Ibd)

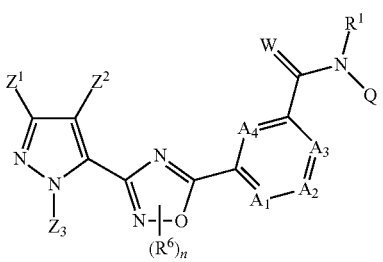
(Ibe)

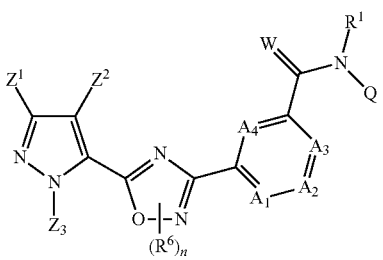
(Ibf)

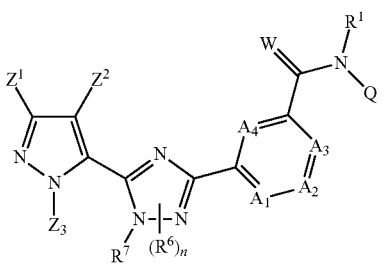
(Ibh)

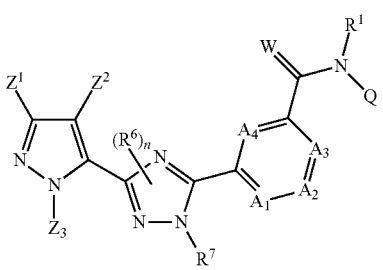
(Ibi)

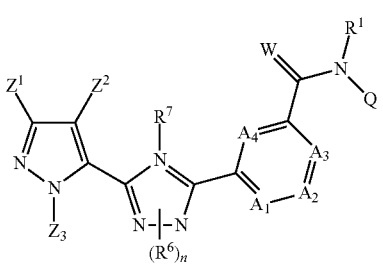

where for the case of the general formulae (Iaw) and (Iax) one of the radicals $Z^1$, $Z^2$ or $Z^3$ is substituted by at least 3 halogen atoms.

Especially preferred are compounds of the formula (Iap).

Special preference is furthermore given to compounds of the formula (Ibg).

Special preference is furthermore given to compounds of the formula (Iac).

Special preference is furthermore given to compounds of the formula (Iaq).

Special preference is furthermore given to compounds of the formula (Ibd).

Special preference is furthermore given to compounds of the formula (Ibe).

Special preference is furthermore given to compounds of the formula (Ibf).

Special preference is furthermore given to compounds of the formula (Ibh).

Special preference is furthermore given to compounds of the formula (Ibi).

Special preference is furthermore given to compounds of the formula (Iaf).

Special preference is furthermore given to compounds of the formula (Iaa).

Preference is furthermore given to compounds of the formulae (Iap), (Ibg), (Iac), (Iaq), (Ibd), (Ibe), (Ibf), (Ibh), (Ibi), (Iaf) and (Iaa) in which W represents oxygen.

Preference is furthermore given to compounds of the formulae (Iap), (Ibg), (Iac), (Iaq), (Ibd), (Ibe), (Ibf), (Ibh), (Ibi), (Iaf) and (Iaa) in which W represents oxygen and $R^1$ represents hydrogen.

Preference is furthermore given to compounds of the formulae (Iap), (Ibg), (Iac), (Iaq), (Ibd), (Ibe), (Ibf), (Ibh), (Ibi), (Iaf) and (Iaa) in which, if present, $R^6$, $R^{6a}$, $R^{6b}$, $R^7$ represent hydrogen or $C_1$-$C_4$-alkyl, preferably hydrogen.

Very particular preference is given to compounds of the general formulae (Iaa)-(Ibi) in which $Z^1$ represents $CF_2CF_3$, $Z^2$ represents $CF_3$, $Z^3$ represents $CH_3$, the radicals $R^1$ and $R^6$ represent hydrogen, $A^1$ and $A^4$ represent CH and $A^2$ represents CH or N, $A^3$ represents C—Cl, W represents oxygen and $R^1$ represents hydrogen and Q represents hydrogen, halogenated $C_1$-$C_4$-alkyl such as trifluoroethyl (e.g. $CH_2CF_3$), cyclopropyl which is optionally substituted by cyano or by halogenated $C_1$-$C_4$-alkyl, such as cyclopropyl, 1-(cyano)cyclopropyl, 1-(trifluoromethyl)cyclopropyl, phenyl which is optionally substituted by 1, 2 or 3 substituents (preferably by one substituent) independently of one another selected from the group consisting of $C_1$-$C_4$-alkyl, $C_1$-$C_4$-alkoxy, Cl, F, I, such as phenyl or benzyl or 4-fluorophenyl.

Very particular preference is given to compounds of the general formulae (Iap), (Ibg), (Iac), (Iaq), (Ibd), (Ibe), (Ibf), (Ibh), (Ibi), (Iaf) and (Iaa) in which $Z^1$ represents $CF_2CF_3$, $Z^2$ represents $CF_3$, $Z^3$ represents $CH_3$, the radicals $R^1$ and $R^6$ represent hydrogen, $A^1$ and $A^4$ represent CH and $A^2$ represents CH or N, $A^3$ represents C—Cl or C—H, W represents oxygen and $R^1$ represents hydrogen and Q represents hydrogen, halogenated $C_1$-$C_4$-alkyl such as trifluoroethyl (e.g. $CH_2CF_3$), cyclopropyl which is optionally substituted by cyano or by halogenated $C_1$-$C_4$-alkyl, such as cyclopropyl, 1-(cyano)cyclopropyl, 1-(trifluoromethyl)cyclopropyl, phenyl which is optionally substituted by 1, 2 or 3 substituents (preferably by one substituent) independently of one another selected from the group consisting of $C_1$-$C_4$-alkyl, $C_1$-$C_4$-alkoxy, Cl, F, I, such as phenyl or benzyl or 4-fluorophenyl.

Special preference is also given to compounds of the general formula (Iap) in which Q is selected from the group consisting of: halogenated $C_1$-$C_4$-alkyl, such as trifluoroethyl (e.g. $CH_2CF_3$), cyclopropyl which is optionally substituted by cyano or by halogenated $C_1$-$C_4$-alkyl, such as 1-(cyano)cyclopropyl or 1-(trifluoromethyl)cyclopropyl, thiethan-3-yl, 2-oxo-2-(2,2,2-trifluoroethylamino)ethyl.

Special preference is also given to compounds of the general formula (Iap) in which $Z^1$ represents $CF_2CF_3$, $Z^2$ represents $CF_3$, $Z^3$ represents $CH_3$, the radicals $R^1$ and $R^6$ represent hydrogen, $A^1$ and $A^4$ represent CH and $A^2$ represents CH, $A^3$ represents C—Cl, W represents oxygen and $R^1$ represents hydrogen and Q is selected from the group consisting of: halogenated $C_1$-$C_4$-alkyl, such as trifluoroethyl (e.g. $CH_2CF_3$), cyclopropyl which is optionally substituted by cyano or by halogenated $C_1$-$C_4$-alkyl, such as 1-(cyano)cyclopropyl or 1-(trifluoromethyl)cyclopropyl, thiethan-3-yl, 2-oxo-2-(2,2,2-trifluoroethylamino)ethyl.

Special preference is also given to compounds of the general formula (Ibg) in which Q is selected from the group consisting of: halogenated $C_1$-$C_4$-alkyl, such as trifluoroethyl (e.g. $CH_2CF_3$), cyclopropyl which is optionally substituted by cyano or by halogenated $C_1$-$C_4$-alkyl, such as cyclopropyl, phenyl which is optionally substituted by 1, 2 or 3 substituents (preferably by one substituent) independently of one another selected from the group consisting of $C_1$-$C_4$-alkyl, $C_1$-$C_4$-alkoxy, Cl, F, I, such as phenyl or benzyl.

Special preference is also given to compounds of the general formula (Ibg) in which $Z^1$ represents $CF_2CF_3$, $Z^2$ represents $CF_3$, $Z^3$ represents $CH_3$, the radicals $R^1$ and $R^7$ represent hydrogen or $C_1$-$C_4$-alkyl, $A^1$ and $A^4$ represent CH and $A^2$ represents CH, $A^3$ represents C—Cl, W represents oxygen and $R^1$ represents hydrogen and Q is selected from the group consisting of: halogenated $C_1$-$C_4$-alkyl, such as trifluoroethyl (e.g. $CH_2CF_3$), cyclopropyl which is optionally substituted by cyano or by halogenated $C_1$-$C_1$-alkyl, such as cyclopropyl, phenyl which is optionally substituted by 1, 2 or 3 substituents (preferably by one substituent) independently of one another selected from the group consisting of $C_1$-$C_4$-alkyl, $C_1$-$C_4$-alkoxy, Cl, F, I, such as phenyl or benzyl.

Special preference is also given to compounds of the general formula (Ibh) in which Q is selected from the group consisting of: halogenated $C_1$-$C_4$-alkyl, such as trifluoroethyl (e.g. $CH_2CF_3$), cyclopropyl which is optionally substituted by cyano or by halogenated $C_1$-$C_4$-alkyl, such as cyclopropyl, phenyl which is optionally substituted by 1, 2 or 3 substituents (preferably by one substituent) independently of one another selected from the group consisting of $C_1$-$C_4$-alkyl, $C_1$-$C_4$-alkoxy, Cl, F, I, such as benzyl.

Special preference is also given to compounds of the general formula (Ibh) in which $Z^1$ represents $CF_2CF_3$, $Z^2$ represents $CF_3$, $Z^3$ represents $CH_3$, the radicals $R^1$ and $R^7$ represent hydrogen, $A^1$ and $A^4$ represent CH and $A^2$ represents CH, $A^3$ represents C—Cl, W represents oxygen and $R^1$ represents hydrogen and Q is selected from the group consisting of: halogenated $C_1$-$C_4$-alkyl, such as trifluoroethyl (e.g. $CH_2CF_3$), cyclopropyl which is optionally substituted by cyano or by halogenated $C_1$-$C_4$-alkyl, such as cyclopropyl, phenyl which is optionally substituted by 1, 2 or 3 substituents (preferably by one substituent) independently of one another selected from the group consisting of $C_1$-$C_4$-alkyl, $C_1$-$C_4$-alkoxy, Cl, F, I, such as benzyl.

In a particularly preferred embodiment, Q in compounds of the formulae (Iap), (Ibg), (Iac), (Iaq), (Ibd), (Ibe), (Ibf), (Ibh), (Ibi), (Iaf) and (Iaa) represents 1-cyanocyclopropyl or cyclopropyl.

According to the invention, "alkyl"—on its own or as part of a chemical group—represents straight-chain or branched hydrocarbons preferably having 1 to 6 carbon atoms such as, for example, methyl, ethyl, n-propyl, isopropyl, n-butyl, isobutyl, s-butyl, t-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Also preferably alkyl groups having 1 to 4 carbon atoms, such as inter alia methyl, ethyl, n-propyl, isopropyl, n-butyl, isobutyl, s-butyl or t-butyl. The alkyl groups according to the invention may be substituted by one or more identical or different radicals.

According to the invention, "alkenyl"—alone or as part of a chemical group—represents straight-chain or branched hydrocarbons, preferably having 2 to 6 carbon atoms and at least one double bond, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl. Also preferably alkenyl groups having 2 to 4 carbon atoms, such as inter alia 2-propenyl, 2-butenyl or 1-methyl-2-propenyl. The alkenyl groups according to the invention may be substituted by one or more identical or different radicals.

According to the invention, "alkynyl"—alone or as part of a chemical group—represents straight-chain or branched hydrocarbons, preferably having 2 to 6 carbon atoms and at least one triple bond, for example 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-3-butynyl, 1,2-dimethyl-3-butynyl, 2,2-dimethyl-3-butynyl, 1-ethyl-3-butynyl, 2-ethyl-3-butynyl, 1-ethyl-1-methyl-2-propynyl and 2,5-hexadiynyl. Also preferably alkynyl groups having 2 to 4 carbon atoms, such as inter alia ethynyl, 2-propynyl or 2-butynyl-2-propenyl. The alkynyl groups according to the invention may be substituted by one or more identical or different radicals.

According to the invention, "cycloalkyl"—alone or as part of a chemical group—represents mono-, bi- or tricyclic hydrocarbons, preferably having 3 to 10 carbons, for example cyclopropyl, cyclobutyl, cyclopentyl, cyclohexyl, cycloheptyl, cyclooctyl, bicyclo[2.2.1]heptyl, bicyclo[2.2.2]octyl or adamantyl. Also preferably cycloalkyl groups having 3, 4, 5, 6 or 7 carbon atoms, such as inter alia cyclopropyl or cyclobutyl. The cycloalkyl groups according to the invention may be substituted by one or more identical or different radicals.

According to the invention, "alkylcycloalkyl" represents mono-, bi- or tricyclic alkylcycloalkyl, preferably having 4 to 10 or 4 to 7 carbon atoms, for example ethylcyclopropyl, isopropylcyclobutyl, 3-methylcyclopentyl and 4-methylcyclohexyl. Also preferably alkylcycloalkyl groups having 4, 5 or 7 carbon atoms, such as inter alia ethylcyclopropyl or 4-methylcyclohexyl. The alkylcycloalkyl groups according to the invention may be substituted by one or more identical or different radicals.

According to the invention, "cycloalkylalkyl" represents mono-, bi- or tricyclic cycloalkylalkyl, preferably having 4 to 10 or 4 to 7 carbon atoms, for example cyclopropylmethyl, cyclobutylmethyl, cyclopentylmethyl, cyclohexylmethyl and cyclopentylethyl. Also preferably cycloalkylalkyl groups having 4, 5 or 7 carbon atoms, such as inter alia cyclopropylmethyl or cyclobutylmethyl. The cycloalkylalkyl groups according to the invention may be substituted by one or more identical or different radicals.

According to the invention, "halogen" represents fluorine, chlorine, bromine or iodine, especially fluorine, chlorine or bromine.

The halogen-substituted chemical groups according to the invention, for example haloalkyl, halocycloalkyl, haloalkyloxy, haloalkylsulphanyl, haloalkylsulphinyl or haloalkylsulphonyl, are mono- or polysubstituted by halogen up to the maximum possible number of substituents. In the case of polysubstitution by halogen, the halogen atoms may be identical or different, and may all be bonded to one carbon atom or may be bonded to a plurality of carbon atoms. Here, halogen represents in particular fluorine, chlorine, bromine or iodine, preferably fluorine, chlorine or bromine and more preferably fluorine.

According to the invention, "halocycloalkyl" represents mono-, bi- or tricyclic halocycloalkyl, preferably having 3 to 10 carbon atoms, such as inter alia 1-fluorocyclopropyl, 2-fluorocyclopropyl or 1-fluorocyclobutyl. Also preferably halocycloalkyl having 3, 5 or 7 carbon atoms. The halocycloalkyl groups according to the invention may be substituted by one or more identical or different radicals.

According to the invention, "haloalkyl", "haloalkenyl" or "haloalkynyl" represents halogen-substituted alkyl, alkenyl or alkynyl groups having preferably 1 to 9 identical or different halogen atoms such as, for example, monohaloalkyl such as $CH_2CH_2Cl$, $CH_2CH_2F$, $CHClCH_3$, $CHFCH_3$, $CH_2Cl$, $CH_2F$; perhaloalkyl such as $CCl_3$ or $CF_3$ or $CF_2CF_3$; polyhaloalkyl such as $CHF_2$, $CH_2F$, $CH_2CHFCl$, $CHCl_2$, $CF_2CF_2H$, $CH_2CF_3$. The same applies to haloalkenyl and other halogen-substituted radicals. Haloalkoxy is, for example, $OCF_3$, $OCHF_2$, $OCH_2F$, $OCF_2CF_3$, $OCH_2CF_3$ and $OCH_2CH_2Cl$.

Further examples for haloalkyl groups are trichloromethyl, chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 2,2,2-trichloroethyl, 2-chloro-2,2-difluoroethyl, pentafluoroethyl and pentafluoro-t-butyl. Preference is given to haloalkyl groups having 1 to 4 carbon atoms and 1 to 9, preferably 1 to 5, identical or different halogen atoms selected from fluorine, chlorine and bromine. Particular preference is given to haloalkyls having 1 or 2 carbon atoms and 1 to 5 identical or different halogen atoms selected from fluorine and chlorine, such as, inter alia, difluoromethyl, trifluoromethyl or 2,2-difluoroethyl.

According to the invention, "hydroxyalkyl" represents straight-chain or branched alcohol, preferably having 1 to 6 carbon atoms, for example methanol, ethanol, n-propanol, isopropanol, n-butanol, isobutanol, s-butanol and t-butanol. Also preferably hydroxyalkyl groups having 1 to 4 carbon atoms. The hydroxyalkyl groups according to the invention may be substituted by one or more identical or different radicals.

According to the invention, "alkoxy" represents straight-chain or branched O-alkyl, preferably having 1 to 6 carbon atoms, for example methoxy, ethoxy, n-propoxy, isopropoxy, n-butoxy, isobutoxy, s-butoxy and t-butoxy. Also preferably alkoxy groups having 1 to 4 carbon atoms. The alkoxy groups according to the invention may be substituted by one or more identical or different radicals.

According to the invention, "haloalkoxy" represents halogen-substituted straight-chain or branched O-alkyl, preferably having 1 to 6 carbon atoms, such as inter alia difluoromethoxy, trifluoromethoxy, 2,2-difluoroethoxy, 1,1,2,2-tetrafluoroethoxy, 2,2,2-trifluoroethoxy and 2-chloro-1,1,2-trifluoroethoxy. Also preferably haloalkoxy groups having 1 to 4 carbon atoms. The haloalkoxy groups according to the invention may be substituted by one or more identical or different radicals.

According to the invention, "alkylsulphanyl" represents straight-chain or branched S-alkyl, preferably having 1 to 6 carbon atoms, for example methylthio, ethylthio, n-propylthio, isopropylthio, n-butylthio, isobutylthio, s-butylthio and t-butylthio. Also preferably alkylsulphanyl groups having 1 to 4 carbon atoms. The alkylsulphanyl groups according to the invention may be substituted by one or more identical or different radicals.

Examples of haloalkylsulphanylalkyl groups, i.e. halogen-substituted alkylsulphanyl groups, are inter alia difluoromethylthio, trifluoromethylthio, trichloromethylthio, chlorodifluoromethylthio, 1-fluoroethylthio, 2-fluoroethylthio, 2,2-difluoroethylthio, 1,1,2,2-tetrafluoroethylthio, 2,2,2-trifluoroethylthio or 2-chloro-1,1,2-trifluoroethylthio.

According to the invention, "alkylsulphinyl" represents straight-chain or branched alkylsulphinyl, preferably having 1 to 6 carbon atoms, for example methylsulphinyl, ethylsulphinyl, n-propylsulphinyl, isopropylsulphinyl, n-butylsulphinyl, isobutylsulphinyl, s-butylsulphinyl and t-butylsulphinyl. Also preferably alkylsulphinyl groups having 1 to 4 carbon atoms. The alkylsulphinyl groups according to the invention may be substituted by one or more identical or different radicals.

Examples of haloalkylsulphinyl groups, i.e. halogen-substituted alkylsulphinyl groups, are inter alia difluoromethylsulphinyl, trifluoromethylsulphinyl, trichloromethylsulphinyl, chlorodifluoromethylsulphinyl, 1-fluoroethylsulphinyl, 2-fluoroethylsulphinyl, 2,2-difluoroethylsulphinyl, 1,1,2,2-tetrafluoroethylsulphinyl, 2,2,2-trifluoroethylsulphinyl and 2-chloro-1,1,2-trifluoroethylsulphinyl.

According to the invention, "alkylsulphonyl" represents straight-chain or branched alkylsulphonyl, preferably having 1 to 6 carbon atoms, for example methylsulphonyl, ethylsulphonyl, n-propylsulphonyl, isopropylsulphonyl, n-butylsulphonyl, isobutylsulphonyl, s-butylsulphonyl and t-butylsulphonyl. Also preferably alkylsulphonyl groups having 1 to 4 carbon atoms. The alkylsulphonyl groups according to the invention may be substituted by one or more identical or different radicals.

Examples of haloalkylsulphonyl groups, i.e. halogen-substituted alkylsulphonyl groups, are inter alia difluoromethylsulphonyl, trifluoromethylsulphonyl, trichloromethylsulphonyl, chlorodifluoromethylsulphonyl, 1-fluoroethylsulphonyl, 2-fluoroethylsulphonyl, 2,2-difluoroethylsulphonyl, 1,1,2,2-tetrafluoroethylsulphonyl, 2,2,2-trifluoroethylsulphonyl and 2-chloro-1,1,2-trifluoroethylsulphonyl.

According to the invention, "alkylcarbonyl" represents straight-chain or branched alkyl-C(=O), preferably having 2 to 7 carbon atoms, such as methylcarbonyl, ethylcarbonyl, n-propylcarbonyl, isopropylcarbonyl, s-butylcarbonyl and t-butylcarbonyl. Also preferably alkylcarbonyls having 1 to 4 carbon atoms. The alkylcarbonyls according to the invention may be substituted by one or more identical or different radicals.

According to the invention, "cycloalkylcarbonyl" represents straight-chain or branched cycloalkylcarbonyl preferably having 3 to 10 carbon atoms in the cycloalkyl moiety such as, for example, cyclopropylcarbonyl, cyclobutylcarbonyl, cyclopentylcarbonyl, cyclohexylcarbonyl, cycloheptylcarbonyl, cyclooctylcarbonyl, bicyclo[2.2.1]heptyl, bicyclo[2.2.2]octylcarbonyl and adamantylcarbonyl. Also preferably cycloalkylcarbonyl having 3, 5 or 7 carbon atoms in the cycloalkyl moiety. The cycloalkylcarbonyl groups according to the invention may be substituted by one or more identical or different radicals.

According to the invention, "alkoxycarbonyl"—alone or as part of a chemical group—represents straight-chain or branched alkoxycarbonyl, preferably having 1 to 6 carbon atoms or 1 to 4 carbon atoms in the alkoxy moiety, for example methoxycarbonyl, ethoxycarbonyl, n-propoxycarbonyl, isopropoxycarbonyl, s-butoxycarbonyl and t-butoxycarbonyl. The alkoxycarbonyl groups according to the invention may be substituted by one or more identical or different radicals.

According to the invention, "alkylaminocarbonyl" represents straight-chain or branched alkylaminocarbonyl having preferably 1 to 6 carbon atoms or 1 to 4 carbon atoms in the alkyl moiety, for example methylaminocarbonyl, ethylaminocarbonyl, n-propylaminocarbonyl, isopropylaminocarbonyl, s-butylaminocarbonyl and t-butylaminocarbonyl. The alkylaminocarbonyl groups according to the invention may be substituted by one or more identical or different radicals.

According to the invention, "N,N-dialkylaminocarbonyl" represents straight-chain or branched N,N-dialkylaminocarbonyl having preferably 1 to 6 carbon atoms or 1 to 4 carbon atoms in the alkyl moiety, such as, for example, N,N-dimethylaminocarbonyl, N,N-diethylaminocarbonyl, N,N-di(n-propylamino)carbonyl, N,N-di(isopropylamino)carbonyl and N,N-di-(s-butylamino)carbonyl. The N,N-dialkylaminocarbonyl groups according to the invention may be substituted by one or more identical or different radicals.

According to the invention, "aryl" represents a mono-, bi- or polycyclic aromatic system having preferably 6 to 14, in particular 6 to 10 ring carbon atoms such as, for example, phenyl, naphthyl, anthryl, phenanthrenyl, preferably phenyl. In addition, aryl also represents polycyclic systems such as tetrahydronaphthyl, indenyl, indanyl, fluorenyl, biphenyl, where the bonding site is on the aromatic system. The aryl groups according to the invention may be substituted by one or more identical or different radicals.

Examples of substituted aryls are the arylalkyls, which may likewise be substituted by one or more identical or different radicals in the alkyl and/or aryl moiety. Examples of such arylalkyls include benzyl and 1-phenylethyl.

According to the invention, "heterocycle", "heterocyclic ring" or "heterocyclic ring system" represents a carbocyclic ring system having at least one ring in which at least one carbon atom is replaced by a heteroatom, preferably by a heteroatom from the group consisting of N, O, S, P, B, Si, Se, and which is saturated, unsaturated or heteroaromatic and may be unsubstituted or substituted by a substituent Z, where the point of attachment is located at a ring atom. Unless defined otherwise, the heterocyclic ring contains preferably 3 to 9 ring atoms, especially 3 to 6 ring atoms, and one or more, preferably 1 to 4, especially 1, 2 or 3, heteroatoms in the heterocyclic ring, preferably from the group of N, O and S, although no two oxygen atoms should be directly adjacent to one another. The heterocyclic rings usually contain not more than 4 nitrogen atoms and/or not more than 2 oxygen atoms and/or not more than 2 sulphur atoms. When the heterocyclyl radical or the heterocyclic ring is optionally substituted, it may be fused to other carbocyclic or heterocyclic rings. In the case of optionally substituted heterocyclyl, the invention also embraces polycyclic systems, for example 8-azabicyclo[3.2.1]octanyl or 1-azabicyclo[2.2.1]heptyl. In the case of optionally substituted heterocyclyl, the invention also embraces spirocyclic systems, for example 1-oxa-5-azaspiro[2.3]hexyl.

Heterocyclyl groups according to the invention are, for example, piperidinyl, piperazinyl, morpholinyl, thiomorpholinyl, dihydropyranyl, tetrahydropyranyl, dioxanyl, pyrrolinyl, pyrrolidinyl, imidazolinyl, imidazolidinyl, thiazolidinyl, oxazolidinyl, dioxolanyl, dioxolyl, pyrazolidinyl, tetrahydrofuranyl, dihydrofuranyl, oxetanyl, oxiranyl, azetidinyl, aziridinyl, oxazetidinyl, oxaziridinyl, oxazepanyl, oxazinanyl, azepanyl, oxopyrrolidinyl, dioxopyrrolidinyl, oxomorpholinyl, oxopiperazinyl and oxepanyl.

Of particular significance are heteroaryls, i.e. heteroaromatic systems. According to the invention, the expression "heteroaryl" represents heteroaromatic compounds, i.e. fully unsaturated aromatic heterocyclic compounds covered by the above definition of heterocycles. Preferably 5- to 7-membered rings having 1 to 3, preferably 1 or 2, identical or different heteroatoms from the abovementioned group.

Heteroaryls according to the invention are, for example, furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl. The heteroaryl groups according to the invention may also be substituted by one or more identical or different radicals.

Substituted groups such as a substituted alkyl, alkenyl, alkynyl, cycloalkyl, aryl, phenyl, benzyl, heterocyclyl and heteroaryl radical are, for example, a substituted radical derived from the unsubstituted base structure, where the substituents are, for example, one or more, preferably 1, 2 or 3, radicals from the group of halogen, alkoxy, alkylsulphanyl, hydroxyl, amino, nitro, carboxyl or a group equivalent to the carboxyl group, cyano, isocyano, azido, alkoxycarbonyl, alkylcarbonyl, formyl, carbamoyl, mono- and N,N-dialkylaminocarbonyl, substituted amino such as acylamino, mono- and N,N-dialkylamino, trialkylsilyl and optionally substituted cycloalkyl, optionally substituted aryl, optionally substituted heterocyclyl, where each of the latter cyclic groups may also be bonded via heteroatoms or divalent functional groups such as in the alkyl radicals mentioned, and alkylsulphinyl, including both enantiomers of the alkylsulphonyl group, alkylsulphonyl, alkylphosphinyl, alkylphosphonyl and, in the case of cyclic radicals (="cyclic base structure"), also alkyl, haloalkyl, alkylsulphanylalkyl, alkoxyalkyl, optionally substituted mono- and N,N-dialkylaminoalkyl and hydroxyalkyl.

The term "substituted groups", such as substituted alkyl etc., includes, as substituents, in addition to the saturated hydrocarbonaceous radicals mentioned, corresponding unsaturated aliphatic and aromatic radicals such as optionally substituted alkenyl, alkynyl, alkenyloxy, alkynyloxy, alkenylthio, alkynylthio, alkenyloxycarbonyl, alkynyloxycarbonyl, alkenylcarbonyl, alkynylcarbonyl, mono- and N,N-dialkenylaminocarbonyl, mono- and dialkynylaminocarbonyl, mono- and N,N-dialkenylamino, mono- and N,N-dialkynylamino, trialkenylsilyl, trialkynylsilyl, optionally substituted cycloalkenyl, optionally substituted cycloalkynyl, phenyl, phenoxy etc. In the case of substituted cyclic radicals with aliphatic components in the ring, cyclic systems with those substituents bonded to the ring by a double bond are also included, for example those having an alkylidene group such as methylidene or ethylidene, or an oxo group, imino group or substituted imino group.

If two or more radicals form one or more rings, these may be carbocyclic, heterocyclic, saturated, partially saturated, unsaturated, for example also aromatic and further-substituted.

The substituents mentioned by way of example ("first substituent level") may, if they contain hydrocarbonaceous moieties, optionally be further substituted therein ("second substituent level"), for example by one of the substituents as defined for the first substituent level. Corresponding further substituent levels are possible. The term "substituted radical" preferably embraces just one or two substituent levels.

Preferred substituents for the substituent levels are, for example, amino, hydroxy, halogen, nitro, cyano, isocyano, mercapto, isothiocyanato, carboxyl, carboxamide, $SF_5$, aminosulphonyl, alkyl, cycloalkyl, alkenyl, cycloalkenyl, alkynyl, N-monoalkylamino, N,N-dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylsulphanyl, cycloalkylsulphanyl, alkenylthio, cycloalkenylthio, alkynylthio, alkylsulphenyl and alkylsulphinyl, where both enantiomers of the alkylsulphinyl group are included, alkylsulphonyl, N-monoalkylaminosulphonyl, N,N-dialkylaminosulphonyl, alkylphosphinyl, alkylphosphonyl, where in the case of alkylphosphinyl and alkylphosphonyl both enantiomers are included, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino, benzylamino, heterocyclyl and trialkylsilyl.

Substituents composed of more than one substituent level are preferably alkoxyalkyl, alkylsulphanylalkyl, alkylsulphanylalkoxy, alkoxyalkoxy, phenethyl, benzyloxy, haloalkyl, halocycloalkyl, haloalkoxy, haloalkylsulphanyl, haloalkylsulphinyl, haloalkylsulphonyl, haloalkanoyl, haloalkylcarbonyl, haloalkoxycarbonyl, haloalkoxyalkoxy, haloalkoxyalkylsulphanyl, haloalkoxyalkanoyl, haloalkoxyalkyl.

In the case of radicals having carbon atoms, preference is given to those having 1 to 6 carbon atoms, preferably 1 to 4 carbon atoms, particularly 1 or 2 carbon atoms. Preference is generally given to substituents from the group of halogen, for example fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Particular preference is given to the substituents methyl, methoxy, fluorine and chlorine.

Substituted amino such as mono- or disubstituted amino means a radical from the group of the substituted amino radicals which are N-substituted, for example, by one or two identical or different radicals from the group consisting of alkyl, hydroxy, amino, alkoxy, acyl and aryl; preferably N-mono- and N,N-dialkylamino, (for example methylamino, ethylamino, N,N-dimethylamino, N,N-diethylamino, N,N-di-n-propylamino, N,N-diisopropylamino or N,N-dibutylamino), N-mono- or N,N-dialkoxyalkylamino groups (for example N-methoxymethylamino, N-methoxyethylamino, N,N-di(methoxymethyl)amino or N,N-di(methoxyethyl)amino), N-mono- and N,N-diarylamino, such as optionally substituted anilines, acylamino, N,N-diacylamino, N-alkyl-N-arylamino, N-alkyl-N-acylamino and also saturated N-heterocycles; preference is given here to alkyl radicals having 1 to 4 carbon atoms; here, aryl is preferably phenyl or substituted phenyl; for acyl, the definition given further below applies, preferably $(C_1-C_4)$-alkanoyl. The same applies to substituted hydroxylamino or hydrazino.

According to the invention, the term "cyclic amino groups" encompasses heteroaromatic or aliphatic ring systems having one or more nitrogen atoms. The heterocycles are saturated or unsaturated, consist of one or more optionally fused ring systems and optionally include further heteroatoms, for example one or two nitrogen, oxygen and/or sulphur atoms. In addition, the term also embraces groups having a spiro ring or a bridged ring system. The number of atoms which form the cyclic amino group is not limited and may be, for example, in the case of a one-ring system 3 to 8 ring atoms, and in the case of a two-ring system 7 to 11 atoms.

Examples of cyclic amino groups having saturated and unsaturated monocyclic groups having a nitrogen atom as heteroatom include 1-azetidinyl, pyrrolidino, 2-pyrrolidin-1-yl, 1-pyrrolyl, piperidino, 1,4-dihydropyrazin-1-yl, 1,2,5,6-tetrahydropyrazin-1-yl, 1,4-dihydropyridin-1-yl, 1,2,5,6-tetrahydropyridin-1-yl, homopiperidinyl; examples of cyclic amino groups having saturated and unsaturated monocyclic groups having two or more nitrogen atoms as heteroatoms include 1-imidazolidinyl, 1-imidazolyl, 1-pyrazolyl, 1-triazolyl, 1-tetrazolyl, 1-piperazinyl, 1-homopiperazinyl, 1,2-dihydropiperazin-1-yl, 1,2-dihydropyrimidin-1-yl, perhydropyrimidin-1-yl, 1,4-diazacycloheptan-1-yl; examples of cyclic amino groups having saturated and unsaturated monocyclic groups having one or two oxygen atoms and one to three nitrogen atoms as heteroatoms, for example oxazolidin-3-yl, 2,3-dihydroisoxazol-2-yl, isoxazol-2-yl, 1,2,3-oxadiazin-2-yl, morpholino, examples of cyclic amino groups having saturated and unsaturated monocyclic groups having one to three nitrogen atoms and one to two sulphur atoms as heteroatoms include thiazolidin-3-yl, isothiazolin-2-yl, thiomorpholino, or dioxothiomorpholino; examples of cyclic amino groups having saturated and unsaturated fused cyclic groups include indol-1-yl, 1,2-dihydrobenzimidazol-1-yl, perhydropyrrolo[1,2-a]pyrazin-2-yl; examples of cyclic amino groups having spirocyclic groups include 2-azaspiro[4.5]decan-2-yl; examples of cyclic amino groups having bridged heterocyclic groups include 2-azabicyclo[2.2.1]heptan-7-yl.

Substituted amino also includes quaternary ammonium compounds (salts) having four organic substituents on the nitrogen atom.

Optionally substituted phenyl is preferably phenyl which is unsubstituted or mono- or polysubstituted, preferably up to trisubstituted, by identical or different radicals from the group of halogen, $(C_1-C_4)$-alkyl, $(C_1-C_4)$-alkoxy, $(C_1-C_4)$-alkoxy-$(C_1-C_4)$-alkoxy, $(C_1-C_4)$-alkoxy-$(C_1-C_4)$-alkyl, $(C_1-C_4)$-haloalkyl, $(C_1-C_4)$-haloalkoxy, $(C_1-C_4)$-alkylsulphanyl, $(C_1-C_4)$-haloalkylsulphanyl, cyano, isocyano and nitro, for example o-, m- and p-tolyl, dimethylphenyls, 2-, 3- and 4-chlorophenyl, 2-, 3- and 4-fluorophenyl, 2-, 3- and 4-trifluoromethyl- and -trichloromethylphenyl, 2,4-, 3,5-, 2,5- and 2,3-dichlorophenyl, o-, m- and p-methoxy phenyl.

Optionally substituted cycloalkyl is preferably cycloalkyl, which is unsubstituted or mono- or polysubstituted, preferably up to trisubstituted, by identical or different radicals from the group of halogen, cyano, $(C_1-C_4)$-alkyl, $(C_1-C_4)$-alkoxy, $(C_1-C_4)$-alkoxy-$(C_1-C_4)$-alkoxy, $(C_1-C_4)$-alkoxy-$(C_1-C_4)$-alkyl, $(C_1-C_4)$-haloalkyl and $(C_1-C_4)$-haloalkoxy, especially substituted by one or two $(C_1-C_4)$-alkyl radicals.

Optionally substituted heterocyclyl is preferably heterocyclyl which is unsubstituted or mono- or polysubstituted, preferably up to trisubstituted, by identical or different radicals from the group of halogen, cyano, $(C_1-C_4)$-alkyl, $(C_1-C_4)$-alkoxy, $(C_1-C_4)$-alkoxy-$(C_1-C_4)$-alkoxy, $(C_1-C_4)$-alkoxy-$(C_1-C_4)$-alkyl, $(C_1-C_4)$-haloalkyl, $(C_1-C_4)$-haloalkoxy, nitro and oxo, especially mono- or polysubstituted by radicals from the group of halogen, $(C_1-C_4)$-alkyl, $(C_1-C_4)$-alkoxy, $(C_1-C_4)$-haloalkyl and oxo, most preferably substituted by one or two $(C_1-C_4)$-alkyl radicals.

Examples of alkyl-substituted heteroaryl groups are furylmethyl, thienylmethyl, pyrazolylmethyl, imidazolylmethyl, 1,2,3- and 1,2,4-triazolylmethyl, isoxazolylmethyl, thiazolylmethyl, isothiazolylmethyl, 1,2,3-, 1,3,4-, 1,2,4- and 1,2,5-oxadiazolylmethyl, azepinylmethyl, pyrrolylmethyl, pyridylmethyl, pyridazinylmethyl, pyrimidinylmethyl, pyrazinylmethyl, 1,3,5-, 1,2,4- and 1,2,3-triazinylmethyl, 1,2,4-, 1,3,2-, 1,3,6- and 1,2,6-oxazinylmethyl, oxepinylmethyl, thiepinylmethyl and 1,2,4-diazepinylmethyl.

Salts which are suitable according to the invention of the compounds according to the invention, for example salts with bases or acid addition salts, are all customary non-toxic salts, preferably agriculturally and/or physiologically acceptable salts. For example salts with bases or acid addition salts. Preference is given to salts with inorganic bases such as, for example, alkali metal salts (e.g. sodium, potassium or caesium salts), alkaline earth metal salts (e.g. calcium or magnesium salts), ammonium salts or salts with organic bases, in particular with organic amines, such as, for example, triethylammonium, dicyclohexylammonium, N,N'-dibenzylethylenediammonium, pyridinium, picolinium or ethanolammonium salts, salts with inorganic acids (e.g. hydrochlorides, hydrobromides, dihydrosulphates, trihydrosulphates or phosphates), salts with organic carboxylic acids or organic sulphoacids (e.g. formates, acetates, trifluoroacetates, maleates, tartrates, methanesulphonates, benzenesulphonates or 4-toluenesulphonates). It is well known that t-amines, for example some of the compounds according to the invention, are capable of forming N-oxides, which are likewise salts according to the invention.

The compounds according to the invention may, depending on the nature of the substituents, be in the form of geometric and/or optically active isomers or corresponding isomer mixtures in different compositions. These stereoisomers are, for example, enantiomers, diastereomers, atropisomers or geometric isomers. The invention thus encompasses pure stereoisomers and any desired mixtures of these isomers.

If appropriate, the compounds according to the invention may be present in various polymorphic forms or as a mixture of different polymorphic forms. Both the pure polymorphs and the polymorph mixtures are provided by the invention and can be used in accordance with the invention.

Use

The invention also relates to methods for controlling animal pests, in which compounds of the general formula (I) according to the invention are allowed to act on animal pests and/or their habitat. The control of the animal pests is preferably conducted in agriculture and forestry, and in material protection.

The compounds of the formula (I) according to the invention, given good plant compatibility and favourable homeotherm toxicity and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in aquacultures, in forests, in gardens and leisure facilities, in the protection of stored products and of materials, and in the hygiene sector. They can preferably be used as crop protection compositions. They are active against normally sensitive and resistant species and against all or some stages of development. The abovementioned pests include:

pests from the phylum of the Arthropoda, especially from the class of the Arachnida, for example *Acarus* spp., *Aceria kuko, Aceria sheldoni, Aculops* spp., *Aculus* spp., *Amblyomma* spp., *Amphitetranychus viennensis, Argas* spp., *Boophilus* spp., *Brevipalpus* spp., *Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., *Epitrimerus pyri, Eutetranychus* spp., *Eriophyes* spp., *Glycyphagus domesticus, Halotydeus destructor, Hemitarsonemus* spp., *Hyalomma* spp., *Ixodes* spp., *Latrodectus* spp., *Loxosceles* spp., *Metatetranychus* spp., *Neutrombicula autumnalis, Nuphersa* spp., *Oligonychus* spp., *Ornithodorus* spp., *Ornithonyssus* spp., *Panonychus* spp., *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., *Tetranychus* spp., *Trombicula alfreddugesi, Vaejovis* spp., *Vasates lycopersici*;

from the class of the Chilopoda, for example, *Geophilus* spp., *Scutigera* spp.;

from the order or the class of the Collembola, for example, *Onychiurus armatus*;

from the class of the Diplopoda, for example, *Blaniulus guttulatus*;

from the class of the Insecta, for example from the order of the Blattodea, for example *Blattella asahinai, Blattella germanica, Blatta orientalis, Leucophaea maderae, Panchlora* spp., *Parcoblatta* spp., *Periplaneta* spp., *Supella longipalpa*;

from the order of the Coleoptera, for example, *Acalymma vittatum, Acanthoscelides obtectus, Adoretus* spp., *Agelastica alni, Agriotes* spp., *Alphitobius diaperinus, Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Baris caerulescens, Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptolestes ferrugineus, Cryptorhynchus lapathi, Cylindrocopturus* spp., *Dermestes* spp., *Diabrotica* spp., *Dichocrocis* spp., *Dicladispa armigera, Diloboderus* spp., *Epilachna* spp., *Epitrix* spp., *Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., *Lachnosterna consanguinea, Lasioderma serricorne,*

*Latheticus oryzae, Lathridius* spp., *Lema* spp., *Leptinotarsa decemlineata, Leucoptera* spp., *Lissorhoptrus oryzophilus, Lixus* spp., *Luperomorpha xanthodera, Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Necrobia* spp., *Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllophaga helleri, Phyllotreta* spp., *Popillia japonica, Premnotrypes* spp., *Prostephanus truncatus, Psylliodes* spp., *Ptinus* spp., *Rhizobius ventralis, Rhizopertha dominica, Sitophilus* spp., *Sitophilus oryzae, Sphenophorus* spp., *Stegobium paniceum, Sternechus* spp., *Symphyletes* spp., *Tanymecus* spp., *Tenebrio molitor, Tenebrioides mauretanicus, Tribolium* spp., *Trogoderma* spp., *Tychius* spp., *Xylotrechus* spp., *Zabrus* spp.;

from the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Calliphora vicina, Ceratitis capitata, Chironomus* spp., *Chrysomyia* spp., *Chrysops* spp., *Chrysozona pluvialis, Cochliomyia* spp., *Contarinia* spp., *Cordylobia anthropophaga, Cricotopus sylvestris, Culex* spp., *Culicoides* spp., *Culiseta* spp., *Cuterebra* spp., *Dacus oleae, Dasyneura* spp., *Delia* spp., *Dermatobia hominis, Drosophila* spp., e.g. *Drosophila suzukii, Echinocnemus* spp., *Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., *Lucilia* spp., *Lutzomyia* spp., *Mansonia* spp., *Musca* spp., *Oestrus* spp.,

*Oscinella frit, Paratanytarsus* spp., *Paralauterborniella subcincta, Pegomyia* spp., *Phlebotomus* spp., *Phorbia* spp., *Phormia* spp., *Piophila casei, Prodiplosis* spp., *Psila rosae, Rhagoletis* spp., *Sarcophaga* spp., *Simulium* spp., *Stomoxys* spp., *Tabanus* spp., *Tetanops* spp., *Tipula* spp.;

from the order of the Heteroptera, for example, *Anasa tristis, Antestiopsis* spp., *Boisea* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Homoptera, for example, *Acizzia acaciaebaileyanae, Acizzia dodonaeae, Acizzia uncatoides, Acrida turrita, Acyrthosipon* spp., *Acrogonia* spp., *Aeneolamia* spp., *Agonoscena* spp., *Aleyrodes proletella, Aleurolobus barodensis, Aleurothrixus floccosus, Allocaridara malayensis, Amrasca* spp., *Anuraphis cardui, Aonidiella* spp., *Aphanostigma piri, Aphis* spp., *Arboridia apicalis, Arytainilla* spp., *Aspidiella* spp., *Aspidiotus* spp., *Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., *Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus ficus, Cicadulina mbila, Coccomytilus halli, Coc-* *cus* spp., *Cryptomyzus ribis, Cryptoneossa* spp., *Ctenarytaina* spp., *Dalbulus* spp., *Dialeurodes citri, Diaphorina citri, Diaspis* spp., *Drosicha* spp., *Dysaphis* spp., *Dysmicoccus* spp., *Empoasca* spp., *Eriosoma* spp., *Erythroneura* spp., *Eucalyptolyma* spp., *Euphyllura* spp., *Euscelis bilobatus, Ferrisia* spp., *Geococcus coffeae, Glycaspis* spp., *Heteropsylla cubana, Heteropsylla spinulosa, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Macrosteles facifrons, Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nettigoniclla spectra, Nilaparvata lugens, Oncometopia* spp., *Orthezia praelonga, Oxya chinensis, Pachypsylla* spp., *Parabemisia myricae, Paratrioza* spp., *Parlatoria* spp., *Pemphigus* spp., *Peregrinus maidis, Phenacoccus* spp., e.g. *Phenacoccus madeirensis, Phloeomyzus passerinii, Phorodon humuli, Phylloxera* spp., *Pinnaspis aspidistrae, Planococcus* spp., *Prosopidopsylla flava, Protopulvinaria pyriformis, Pseudaulacaspis pentagona, Pseudococcus* spp., e.g. *Pseudococcus viburni, Psyllopsis* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoideus titanus, Schizaphis graminum, Selenaspidus articulatus, Sogata* spp., *Sogatella furcifera, Sogatodes* spp., *Stictocephala festina, Siphoninus phillyreae, Tenalaphara malayensis,*

*Tetragonocephela* spp., *Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii, Zygina* spp.;

from the order of the Hymenoptera, for example *Acromyrmex* spp., *Athalia* spp., *Atta* spp., *Diprion* spp., *Hoplocampa* spp., *Lasius* spp., *Monomorium pharaonis, Sirex* spp., *Solenopsis invicta, Tapinoma* spp., *Urocerus* spp., *Vespa* spp., *Xeris* spp.;

from the order of the Isopoda, for example, *Armadillidium vulgare, Oniscus asellus, Porcellio scaber;* from the order of the Isoptera, for example, *Coptotermes* spp., *Cornitermes cumulans, Cryptotermes* spp., *Incisitermes* spp., *Microtermes obesi, Odontotermes* spp., *Reticulitermes* spp.;

from the order of the Lepidoptera, for example, *Achroia grisella, Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., *Choristoneura* spp., *Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp.,

*Malacosoma neustria, Maruca testulalis, Mamstra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella, Plusia* spp., *Plutella xylostella, Prays* spp., *Prodenia* spp., *Protoparce* spp., *Pseudaletia* spp., *Pseudaletia unipuncta, Pseudoplusia includens, Pyrausta nubilalis, Rachiplusia nu, Schoenobius* spp., *Scirpophaga* spp., *Scirpophaga innotata, Scotia segetum, Sesamia* spp., *Sesamia inferens, Sparganothis* spp., *Spodoptera* spp., *Spodoptera praefica, Stathmopoda* spp., *Stomopteryx subsecivella, Synanthedon* spp., *Tecia solanivora, Thermesia gemmatalis, Tinea cloacella, Tinea pellionella, Tineola bisselliella, Tortrix* spp., *Trichophaga tapetzella, Trichoplusia* spp., *Tryporyza incertulas, Tuta absoluta, Virachola* spp.;

from the order of the Orthoptera or Saltatoria, for example, *Acheta domesticus, Dichroplus* spp., *Gryllotalpa* spp., *Hieroglyphus* spp., *Locusta* spp., *Melanoplus* spp., *Schistocerca gregaria;* from the order of the Phthiraptera, for example, *Damalinia* spp., *Haematopinus* spp., *Linognathus* spp., *Pediculus* spp., *Phylloera vastatrix, Phtirus pubis, Trichodectes* spp.;

from the order of the Psocoptera, for example, *Lepinotus* spp., *Liposcelis* spp.;

from the order of the Siphonaptera, for example, *Ceratophyllus* spp., *Ctenocephalides* spp., *Pulex irritans, Tunga penetrans, Xenopsylla cheopsis;* from the order of the Thysanoptera, for example, *Anaphothrips obscurus, Baliothrips biformis, Drepanothrips reuteri, Enneothrips flavens, Frankliniella* spp., *Heliothrips* spp., *Hercinothrips femoralis, Rhipiphorothrips cruentatus, Scirtothrips* spp., *Taeniothrips cardamomi, Thrips* spp.;

from the order of the Zygentoma (=Thysanura), for example, *Ctenolepisma* spp., *Lepisma saccharina, Lepismodes inquilinus, Thermobia domestica;* from the class of the Symphyla, for example, *Scutigerella* spp.;

pests from the phylum of the Mollusca, especially from the class of the Bivalvia, for example *Dreissena* spp., and from the class of the Gastropoda, for example *Anion* spp., *Biomphalaria* spp., *Bulinus* spp., *Deroceras* spp., *Galba* spp., *Lymnaea* spp., *Oncomelania* spp., *Pomacea* spp., *Succinea* spp.;

animal parasites from the phyla of the Plathelminthes and Nematoda, for example *Ancylostoma duodenale, Ancylostoma ceylanicum, Ancylostoma braziliensis, Ancylostoma* spp., *Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Strongyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti;* plant pests from the phylum of the Nematoda, i.e. plant-parasitic nematodes, more particularly *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus* spp., *Trichodorus* spp., *Tylenchulus* spp., *Xiphinema* spp., *Helicotylenchus* spp., *Tylenchorhynchus* spp., *Scutellonema* spp., *Paratrichodorus* spp., *Meloinema* spp., *Paraphelenchus* spp., *Aglenchus* spp., *Belonolaimus* spp., *Nacobbus* spp., *Rotylenchulus* spp., *Rotylenchus* spp., *Neotylenchus* spp., *Paraphelenchus* spp., *Dolichodorus* spp., *Hoplolaimus* spp., *Punctodera* spp., *Criconemella* spp., *Quinisulcius* spp., *Hemicycliophora* spp., *Anguina* spp., *Subanguina* spp., *Hemicriconemoides* spp., *Psilenchus* spp.,

*Pseudohalenchus* spp., *Criconemoides* spp., *Cacopaurus* spp.

In addition, it is possible to control, from the sub-kingdom of the Protozoa, the order of the Coccidia, for example *Eimeria* spp.

Formulations

The present invention further relates to formulations and use forms prepared therefrom as crop protection compositions and/or pesticides, for example drench, drip and spray liquors, comprising at least one of the active compounds according to the invention. The use forms optionally comprise further crop protection agents and/or pesticides and/or action-improving adjuvants, such as penetrants, e.g. vegetable oils, for example rapeseed oil, sunflower oil, mineral oils, for example paraffin oils, alkyl esters of vegetable fatty acids, for example rapeseed oil methyl ester or soybean oil methyl ester, or alkanol alkoxylates, and/or spreaders, for example alkylsiloxanes, and/or salts, for example organic or inorganic ammonium or phosphonium salts, for example ammonium sulphate or diammonium hydrogenphosphate, and/or retention promoters, for example dioctyl sulphosuccinate or hydroxypropyl guar polymers, and/or humectants, for example glycerol, and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. If appropriate, the formulations comprise, as well as one or more active compounds according to the invention, further active agrochemical compounds.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which improves the biological activity of the formulation without having biological activity itself. Examples of adjuvants are agents which promote retention, the spreading characteristics, adhesion to the leaf surface or penetration.

These formulations are produced in a known manner, for example by mixing the active compounds with auxiliaries, for example extenders, solvents and/or solid carriers and/or further auxiliaries, for example surfactants. The formulations are produced either in suitable facilities or else before or during application.

Auxiliaries used may be those substances which are suitable for imparting particular properties, such as particular physical, technical and/or biological properties, to the formulation of the active compound or to the use forms prepared from these formulations (for example ready-to-use crop protection compositions such as spray liquors or seed-dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents essentially include: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water.

In principle, it is possible to use any suitable solvents. Suitable solvents are, for example, aromatic hydrocarbons, for example toluene, xylene or alkylnaphthalenes, chlorinated aromatic or aliphatic hydrocarbons, for example chlorobenzene, chloroethylene or methylene chloride, aliphatic hydrocarbons, for example cyclohexane, paraffins, mineral oil fractions, mineral and vegetable oils, alcohols, for example methanol, ethanol, isopropanol, butanol or glycol and the ethers and esters thereof, ketones, for example acetone, methyl ethyl ketone, methyl isobutyl ketone or cyclohexanone, strongly polar solvents such as dimethyl sulphoxide, and water.

In principle, it is possible to use any suitable carriers. Useful carriers especially include: for example ammonium salts and natural rock flours such as kaolins, aluminas, talc, chalk, quartz, attapulgite, montmorillonite or diatomaceous earth, and synthetic rock flour such as finely divided silica, aluminium oxide and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, corn cobs and tobacco stalks.

It is also possible to use liquefied gaseous extenders or solvents. Especially suitable are those extenders or carriers which are gaseous at standard temperature and under standard pressure, for example aerosol propellants such as halohydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous when one of the active compounds and/or one of the inert carriers is insoluble in water and when application is carried out in water.

Further auxiliaries which may be present in the formulations and the use forms derived therefrom are dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

In addition, stabilizers, such as low-temperature stabilizers, preservatives, antioxidants, light stabilizers or other agents which improve chemical and/or physical stability, may be present. In addition, foam formers or defoamers may be present.

Moreover, the formulations and use forms derived therefrom may comprise, as additional auxiliaries, also stickers such as carboxymethyl cellulose, natural and synthetic pulverulent, particulate or latex-type polymers, such as gum arabic, polyvinyl alcohol, polyvinyl acetate and natural phospholipids such as cephalins and lecithins, and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the active compounds can be combined with any solid or liquid additive which is commonly used for formulation purposes.

Useful retention promoters include all those substances which reduce dynamic surface tension, for example dioctyl sulphosuccinate, or increase viscoelasticity, for example hydroxypropylguar polymers.

Useful penetrants in the present context are all those substances which are typically used to improve the penetration of agrochemically active compounds into plants. Penetrants are defined in this context by their ability to penetrate from the (generally aqueous) application liquor and/or from the spray coating into the cuticle of the plant and hence increase the mobility of active compounds in the cuticle. The method described in the literature (Baur et al., 1997, Pesticide Science 51, 131-152) can be used for determining this property. Examples include alcohol alkoxylates, for example coconut fat ethoxylate (10) or isotridecyl ethoxylate (12), fatty acid esters, for example rapeseed oil methyl ester or soya oil methyl ester, fatty amine alkoxylates, for example tallowamine ethoxylate (15) or ammonium salts and/or phosphonium salts, for example ammonium sulphate or diammonium hydrogenphosphate.

The formulations contain preferably between 0.00000001% and 98% by weight of active compound or more preferably between 0.01% and 95% by weight of active compound, more preferably between 0.5% and 90% by weight of active compound, based on the weight of the formulation.

The active compound content of the use forms (crop protection compositions) prepared from the formulations can vary within wide limits. The active compound concentration of the use forms may typically be between 0.00000001% and 95% by weight of active compound, preferably between 0.00001% and 1% by weight, based on the weight of the use form. Application is accomplished in a customary manner appropriate to the use forms.

Insecticides/Acaricides/Nematicides

The active compounds specified here with their common names are known and are described for example in "The Pesticide Manual", 16th ed., British Crop Protection Council 2012, or can be searched for on the Internet (e.g. http://www.alanwood.net/pesticides).

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulfan or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrins (pyrethrum), resmethrin, silafluofen, tefluthrin, tetramethrin, tetramethrin [(1R) isomers], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulfoxaflor.

(5) Allosteric activators of the nicotinergic acetylcholine receptor (nAChR), for example spinosyns, e.g. spinetoram and spinosad.

(6) Chloride channel activators, for example, avermectins/milbemycins, e.g. abamectin, emamectin benzoate, lepimectin and milbemectin.

(7) Juvenile hormone imitators, for example, juvenile hormone analogues, e.g. hydroprene, kinoprene and methoprene or fenoxycarb or pyriproxyfen.

(8) Active compounds having unknown or nonspecific mechanisms of action, for example alkyl halides, e.g. methyl bromide and other alkyl halides; or chloropicrine or sulphuryl fluoride or borax or tartar emetic.

(9) Selective antifeedants, e.g. pymetrozine or flonicamid.

(10) Mite growth inhibitors, e.g. clofentezine, hexythiazox and diflovidazin or etoxazole.

(11) Microbial disruptors of the insect gut membrane, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron or organotin compounds, e.g. azocyclotin, cyhexatin and fenbutatin oxide or propargite or tetradifon.

(13) Oxidative phosphorylation decouplers that interrupt the H proton gradient, for example chlorfenapyr, DNOC and sulfluramid.

(14) Nicotinergic acetylcholine receptor antagonists, for example bensultap, cartap hydrochloride, thiocyclam, and thiosultap-sodium.

(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting disruptors, dipteran, for example cyromazine.

(18) Ecdysone receptor agonists, for example chromafenozide, halofenozide, methoxyfenozide and tebufenozide.

(19) Octopaminergic agonists, for example amitraz.

(20) Complex-III electron transport inhibitors, for example hydramethylnon or acequinocyl or fluacrypyrim.

(21) Complex-I electron transport inhibitors, for example METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase, for example tetronic and tetramic acid derivatives, e.g. spirodiclofen, spiromesifen and spirotetramat.

(24) Complex-IV electron transport inhibitors, for example phosphines, e.g. aluminium phosphide, calcium phosphide, phosphine and zinc phosphide or cyanide.

(25) Complex-II electron transport inhibitors, for example cyenopyrafen and cyflumetofen.

(28) Ryanodine receptor effectors, for example diamides, e.g. chlorantraniliprole, cyantraniliprole and flubendiamide, further active compounds having an unknown mechanism of action, for example afidopyropen, azadirachtin, benclothiaz, benzoximate, bifenazate, bromopropylate, chinomethionat, cryolite, dicofol, diflovidazin, fluensulfone, flometoquin, flufenerim, flufenoxystrobin, flufiprole, fluopyram, flupyradifurone, fufenozide, heptafluthrin, imidaclothiz, iprodione, meperfluthrin, paichongding, pyflubumide, pyrifluquinazon, pyriminostrobin, tetramethylfluthrin and iodomethane; and also preparations based on *Bacillus firmus* (I-1582, BioNeem, Votivo), and also the following known effective compounds: 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) and 1-{2-fluoro-4-methyl-5-[(2,2,2-trifluoroethyl) sulphinyl]phenyl}-3-(trifluoromethyl)-1H-1,2,4-triazole-5-amine (known from WO2006/043635), {1 [(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl-ethylcarbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{5-[3-chloro-5-(trifluoromethyl)phenyl]-5-(trifluoromethyl)-4,5-dihydro-1,2-oxazol-3-yl}-N-{2-oxo-2-[(2,2,2-trifluoroethyl)amino]ethyl}-1-naphthamide (known from WO2009/002809), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 3-chloro-N-(2-cyanopropan-2-yl)-N-[4-(1,1,1,2,3,3,3-heptafluoropropan-2-yl)-2-methylphenyl]phthalamide (known from WO2012/034472), 8-chloro-N-[(2-chloro-5-methoxyphenyl)sulphonyl]-6-(trifluoromethyl)imidazo[1,2-a]pyridine-2-carboxamide (known from WO2010/129500), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), (5S,8R)-1-[(6-chloropyridin-3-yl)methyl]-9-nitro-2,3,5,6,7,8-hexahydro-1H-5,8-epoxyimidazo[1,2-a]azepine (known from WO2010/069266), (2E)-1-[(6-chloropyridin-3-yl)methyl]-N'-nitro-2-pentylidenehydrazinecarboximidamide (known from WO2010/060231), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969).

Fungicides (1) Inhibitors of ergosterol biosynthesis such as, for example, (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulphate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifin (65472-88-0), (1.33) nuarimol (63284-71-9), (1.34) oxpoconazole (174212-12-5), (1.35) paclobutrazole (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafin (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl)cycloheptanol (129586-32-9), (1.61) methyl 1-(2,2-dimethyl-2,3-dihydro-1H-inden-1-yl)-1H-imidazole-5-carboxylate (110323-95-0), (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl]1H-imidazole-1-carbothioate (111226-71-2).

(2) Respiration inhibitors (respiratory chain inhibitors) such as, for example, (2.1) bixafen (581809-46-3), (2.2) boscalid (188425-85-6), (2.3) carboxin (5234-68-4), (2.4) diflumetorim (130339-07-0), (2.5) fenfuram (24691-80-3), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam mixture of the syn-epimeric racemate 1RS,4SR,9RS and the anti-epimeric racemate 1RS,4SR,9SR (881685-58-1), (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamid (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1, 2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7), (2.28) 5,8-difluoro-N-[2-(2-fluoro-4-{[4-(trifluoromethyl)pyridin-2-yl]oxy}phenyl)ethyl]quinazoline-4-amine (1210070-84-0) (known from WO2010025451), (2.29) N-[9-(dichloromethylene)-1,2,3,4-tetrahydro-1,4-methanonaphthalen-5-yl]-3-(difluoromethyl)-1-methyl-1H-pyrazole-4-carboxamide, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) Respiration inhibitors (respiratory chain inhibitors) acting on complex III of the respiratory chain such as, for example, (3.1) ametoctradin (865318-97-4), (3.2) amisulbrom (348635-87-0), (3.3) azoxystrobin (131860-33-8), (3.4) cyazofamid (120116-88-3), (3.5) coumethoxystrobin (850881-30-0), (3.6) coumoxystrobin (850881-70-8), (3.5) dimoxystrobin (141600-52-4), (3.6) enestroburin (238410-11-2) (known from WO 2004/058723), (3.9) famoxadone (131807-57-3) (known from WO 2004/058723), (3.10) fenamidone (161326-34-7) (known from WO 2004/058723), (3.11) fenoxystrobin (918162-02-4), (3.12) fluoxastrobin (361377-29-9) (known from WO 2004/058723), (3.13) kresoxim-methyl (143390-89-0) (known from WO 2004/058723), (3.14) metominostrobin (133408-50-1) (known from WO 2004/058723), (3.15) orysastrobin (189892-69-1) (known from WO 2004/058723), (3.16) picoxystrobin (117428-22-5) (known from WO 2004/058723), (3.17) pyraclostrobin (175013-18-0) (known from WO 2004/058723), (3.18) pyrametostrobin (915410-70-7) (known from WO 2004/058723), (3.19) pyraoxystrobin (862588-11-2) (known from WO 2004/058723), (3.20) pyribencarb (799247-52-2) (known from WO 2004/058723), (3.21) triclopyricarb (902760-40-1), (3.22) trifloxystrobin (141517-21-7) (known from WO 2004/058723), (3.23) (2E)-2-(2-{[6-(3-chloro-2-methylphenoxy)-5-fluoropyrimidin-4-yl]oxy}phenyl)-2-(methoxyimino)-N-methylethanamide (known from WO 2004/058723), (3.24) (2E)-2-(methoxyimino)-N-methyl-2-(2-{[({(1E)-1-[3-(trifluoromethyl)phenyl]ethylidene}amino)oxy]methyl}phenyl)ethanamide (known from WO 2004/058723), (3.25) (2E)-2-(methoxyimino)-N-methyl-2-{2-[(E)-({1-[3-(trifluoromethyl)phenyl]ethoxy}imino)methyl]phenyl}ethanamide (158169-73-4), (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide (119899-14-8), (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino]methyl}sulphanyl)methyl]phenyl}-3-methoxyprop-2-enoate (149601-03-6), (3.31) N-(3-ethyl-3,5,5-trimethylcyclohexyl)-3-(formylamino)-2-hydroxybenzamide (226551-21-9), (3.32) 2-{2-[(2,5-dimethylphenoxy)methyl]phenyl}-2-methoxy-N-methylacetamide (173662-97-0) and (3.33) (2R)-2-{2-[(2,5-dimethylphenoxy)methyl]phenyl}-2-methoxy-N-methylacetamide (394657-24-0).

(4) Inhibitors of mitosis and cell division, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolid (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1,2,4]triazolo[1,5-a]pyrimidine (214706-53-3) and (4.14) 3-chloro-5-(6-chloropyridin-3-yl)-6-methyl-4-(2,4,6-trifluorophenyl)pyridazine (1002756-87-7).

(5) Compounds having multisite activity, for example (5.1) Bordeaux mixture (8011-63-0), (5.2) captafol (2425-06-1), (5.3) captan (133-06-2) (known from WO 02/12172), (5.4) chlorothalonil (1897-45-6), (5.5) copper preparations such as copper hydroxide (20427-59-2), (5.6) copper naphthenate (1338-02-9), (5.7) copper oxide (1317-39-1), (5.8) copper oxychloride (1332-40-7), (5.9) copper sulphate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) zinc metiram (9006-42-2), (5.27) copper-oxine (10380-28-6), (5.28) propamidine (104-32-5), (5.29) propineb (12071-83-9), (5.30) sulphur and sulphur preparations, for example calcium polysulphide (7704-34-9), (5.31) thiram (137-26-8), (5.32) tolylfluanid (731-27-1), (5.33) zineb (12122-67-7) and (5.34) ziram (137-30-4).

(6) Resistance inductors, for example (6.1) acibenzolar-S-methyl (135158-54-2), (6.2) isotianil (224049-04-1), (6.3) probenazole (27605-76-1) and (6.4) tiadinil (223580-51-6).

(7) Inhibitors of amino acid and protein biosynthesis such as, for example, (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0) and (7.8) 3-(5-fluoro-3,3,4,4-tetramethyl-3,4-dihydroisoquinolin-1-yl)quinoline (861647-32-7) (known from WO2005070917).

(8) ATP production inhibitors, for example (8.1) fentin acetate (900-95-8), (8.2) fentin chloride (639-58-7), (8.3) fentin hydroxide (76-87-9) and (8.4) silthiofam (175217-20-6).

(9) Inhibitors of cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of lipid and membrane synthesis, for example (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Melanin biosynthesis inhibitors such as, for example, (11.1) carpropamid (104030-54-8), (11.2) diclocymet (139920-32-4), (11.3) fenoxanil (115852-48-7), (11.4) fthalide (27355-22-2), (11.5) pyroquilon (57369-32-1), (11.6) tricyclazole (41814-78-2) and (11.7) 2,2,2-trifluoroethyl {3-methyl-1-[(4-methylbenzoyl)amino]butan-2-yl}carbamate (851524-22-6) (known from WO2005042474).

(12) Inhibitors of nucleic acid synthesis, for example (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazole (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Signal transduction inhibitors, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Decouplers, for example (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds such as, for example, (15.1) benthiazole (21564-17-0), (15.2) bethoxazine (163269-30-5), (15.3) capsimycin (70694-08-5), (15.4) carvone (99-49-0), (15.5) chinomethionat (2439-01-2), (15.6) pyriofenone (chlazafenone) (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-36-5), (15.15) difenzoquat (49866-87-7), (15.16) difenzoquat methylsulphate (43222-48-6), (15.17) diphenylamine (122-39-4), (15.18) EcoMate, (15.19) fenpyrazamine (473798-59-3), (15.20) flumetover (154025-04-4), (15.21) fluoromid (41205-21-4), (15.22) flusulfamide (106917-52-6), (15.23) flutianil (304900-25-2), (15.24) fosetyl-aluminium (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methyl isothiocyanate (556-61-6), (15.31) metrafenone (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and its salts (87-86-5), (15.40) phenothrin, (15.41) phosphoric acid and its salts (13598-36-2), (15.42) propamocarb-fosetylate, (15.43) propanosine-sodium (88498-02-6), (15.44) proquinazid (189278-12-4), (15.45) pyrimorph (868390-90-3), (15.45e) (2E)-3-(4-tert-butylphenyl)-3-(2-chloropyridin-4-yl)-1-(morpholin-4-yl) prop-2-en-1-one (1231776-28-5), (15.45z) (2Z)-3-(4-tert-butylphenyl)-3-(2-chloropyridin-4-yl)-1-(morpholin-4-yl) prop-2-en-1-one (1231776-29-6), (15.46) pyrrolnitrin (1018-71-9) (known from EP-A 1 559 320), (15.47) tebufloquin (376645-78-2), (15.48) tecloftalam (76280-91-6), (15.49) tolnifanide (304911-98-6), (15.50) triazoxide (72459-58-6), (15.51) trichlamide (70193-21-4), (15.52) zarilamid (84527-51-5), (15.53) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate (517875-34-2) (known from WO2003035617), (15.54) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-79-6), (15.55) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9), (15.56) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9), (15.57) 1-(4-methoxyphenoxy)-3,3-dimethylbutan-2-yl 1H-imidazole-1-carboxylate (111227-17-9), (15.58) 2,3,5,6-tetrachloro-4-(methylsulphonyl)pyridine (13108-52-6), (15.59) 2,3-dibutyl-6-chlorothieno[2,3-d]pyrimidin-4 (3H)-one (221451-58-7), (15.60) 2,6-dimethyl-1H,5H-[1,4]dithiino[2,3-c:5,6-c']dipyrrole-1,3,5,7(2H, 6H)-tetrone, (15.61) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7), (15.62) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl) ethanone (1003316-54-8), (15.63) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (1003316-51-5), (15.64) 2-butoxy-6-iodo-3-propyl-4H-chromen-4-one, (15.65) 2-chloro-5-[2-chloro-1-(2,6-difluoro-4-methoxyphenyl)-4-methyl-1H-imidazol-5-yl]pyridine, (15.66) 2-phenylphenol and its salts (90-43-7), (15.67) 3-(4,4,5-trifluoro-3,3-dimethyl-3,4-dihydroisoquinolin-1-yl) quinoline (861647-85-0) (known from WO2005070917), (15.68) 3,4,5-trichloropyridine-2,6-dicarbonitrile (17824-85-0), (15.69) 3-[5-(4-chlorophenyl)-2,3-dimethyl-1,2-oxazolidin-3-yl]pyridine, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiole, (15.73) 5-chloro-N'-phenyl-N'-(prop-2-yn-1-yl)thiophene-2-sulphonohydrazide (134-31-6), (15.74) 5-fluoro-2-[(4-fluorobenzyl) oxy]pyrimidine-4-amine (1174376-11-4) (known from WO2009094442), (15.75) 5-fluoro-2-[(4-methylbenzyl)oxy]pyrimidine-4-amine (1174376-25-0) (known from WO2009094442), (15.76) 5-methyl-6-octyl[1,2,4]triazolo[1,5-a]pyrimidine-7-amine, (15.77) ethyl-(2Z)-3-amino-2-cyano-3-phenylprop-2-enoate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl) (cyano)methyl]-3-[3-methoxy-4-(prop-2-yn-1-yloxy)phenyl]propanamide, (15.81) N-[(5-bromo-3-chloropyridin-2-yl)methyl]-2,4-dichloropyridine-3-carboxamide, (15.82) N-[1-(5-bromo-3-chloropyridin-2-yl)ethyl]-2,4-dichloropyridine-3-carboxamide, (15.83) N-[1-(5-bromo-3-chloropyridin-2-yl) ethyl]-2-fluoro-4-iodopyridine-3-carboxamide, (15.84) N-{(E)-[(cyclopropylmethoxy)imino][6-(difluoromethoxy)-2,3-difluorophenyl]methyl}-2-phenylacetamide (221201-92-9), (15.85) N-{(Z)-[(cyclopropylmethoxy)imino][6-(difluoromethoxy)-2,3-difluorophenyl]methyl}-2-phenylacetamide (221201-92-9), (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6), (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide (922514-07-6), (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide (922514-48-5), (15.90) pentyl-{6-[({[(1-methyl-1H-tetrazol-5-yl)(phenyl)methylidene]amino}oxy)methyl]pyridin-2-yl}carbamate, (15.91) phenazine-1-carboxylic acid, (15.92) quinolin-8-ol (134-31-6), (15.93) quinolin-8-ol sulphate (2:1) (134-31-6) and (15.94) tert-butyl {6-[({[(1-methyl-1H-tetrazol-5-yl)(phenyl)methylene]amino}oxy)methyl]pyridin-2-yl}carbamate.

(16) Further compounds such as, for example, (16.1) 1-methyl-3-(trifluoromethyl)-N-[2'-(trifluoromethyl)biphenyl-2-yl]-1H-pyrazole-4-carboxamide, (16.2) N-(4'-chlorobiphenyl-2-yl)-3-(difluoromethyl)-1-methyl-1H-pyrazole-4-carboxamide, (16.3) N-(2',4'-dichlorobiphenyl-2-yl)-3-(difluoromethyl)-1-methyl-1H-pyrazole-4-carboxamide, (16.4) 3-(difluoromethyl)-1-methyl-N-[4'-(trifluoromethyl)biphenyl-2-yl]-1H-pyrazole-4-carboxamide, (16.5) N-(2',5'-difluorobiphenyl-2-yl)-1-methyl-3-(trifluoromethyl)-1H-pyrazole-4-carboxamide, (16.6) 3-(difluoromethyl)-1-methyl-N-[4'-(prop-1-yn-1-yl)biphenyl-2-yl]-1H-pyrazole-4-carboxamide, (16.7) 5-fluoro-1,3-dimethyl-N-[4'-(prop-1-yn-1-yl)biphenyl-2-yl]-1H-pyrazole-4-carboxamide, (16.8) 2-chloro-N-[4'-(prop-1-yn-1-yl)biphenyl-2-yl]pyridine-3-carboxamide, (16.9) 3-(difluoromethyl)-N-[4'-(3,3-dimethylbut-1-yn-1-yl)biphenyl-2-yl]-1-methyl-1H-pyrazole-4-carboxamide, (16.10) N-[4'-(3,3-dimethylbut-1-yn-1-yl)biphenyl-2-yl]-5-fluoro-1,3-dimethyl-1H-pyrazole-4-carboxamide, (16.11) 3-(difluoromethyl)-N-(4'-ethynylbiphenyl-2-yl)-1-methyl-1H-pyrazole-4-carboxamide, (16.12) N-(4'-ethynylbiphenyl-2-yl)-5-fluoro-1,3-dimethyl-1H-pyrazole-4-carboxamide, (16.13) 2-chloro-N-(4'-ethynylbiphenyl-2-yl)pyridine-3-carboxamide, (16.14) 2-chloro-N-[4'-(3,3-dimethylbut-1-yn-1-yl)biphenyl-2-yl]pyridine-3-carboxamide (known from EP-A 1 559 320), (16.15) 4-(difluoromethyl)-2-methyl-N-[4'-(trifluoromethyl)biphenyl-2-yl]-1,3-thiazole-5-carboxamide, (16.16) 5-fluoro-N-[4'-(3-hydroxy-3-methylbut-1-yn-1-yl)biphenyl-2-yl]-1,3-dimethyl-1H-pyrazole-4-carboxamide, (16.17) 2-chloro-N-[4'-(3-hydroxy-3-methylbut-1-yn-1-yl)biphenyl-2-yl]pyridine-3-carboxamide, (16.18) 3-(difluoromethyl)-N-[4'-(3-methoxy-3-methylbut-1-yn-1-yl)biphenyl-2-yl]-1-methyl-1H-pyrazole-4-carboxamide, (16.19) 5-fluoro-N-[4'-(3-methoxy-3-methylbut-1-yn-1-yl)biphenyl-2-yl]-1,3-dimethyl-1H-pyrazole-4-carboxamide, (16.20) 2-chloro-N-[4'-(3-methoxy-3-methylbut-1-yn-1-yl)biphenyl-2-yl]pyridine-3-carboxamide, (16.21) (5-bromo-2-methoxy-4-methylpyridin-3-yl)(2,3,4-trimethoxy-6-methylphenyl)methanone, (16.22) N-[2-(4-{[3-(4-chlorophenyl)prop-2-yn-1-yl]oxy}-3-methoxyphenyl)ethyl]-N2-(methylsulphonyl)valinamide (220706-93-4), (16.23) 4-oxo-4-[(2-phenylethyl)amino]butanoic acid and (16.24) but-3-yn-1-yl {6-[({[(Z)-(1-methyl-1H-tetrazol-5-yl)(phenyl)methylene]amino}oxy)methyl]pyridin-2-yl}carbamate.

All the mixing components mentioned in classes (1) to (16), as the case may be, may form salts with suitable bases or acids if they are capable of doing so on the basis of their functional groups.

Another possibility is a mixture with other known active compounds, such as herbicides, fertilizers, growth regulators, safeners, semiochemicals, or else with agents for improving the plant properties.

Plants and Parts of Plants

All plants and plant parts can be treated in accordance with the invention. Plants are understood here to mean all plants and plant populations such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Parts of plants shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Parts of plants also include harvested material and vegetative and generative propagation material, for example cuttings, tubers, rhizomes, slips and seeds.

The treatment according to the invention of the plants and plant parts with the active compounds is carried out directly or by allowing them to act on the surroundings, habitat or storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been grown by conventional breeding, by mutagenesis or by recombinant DNA techniques. They may be cultivars, varieties, biotypes or genotypes.

Transgenic Plants, Seed Treatment and Integration Events

Depending on the plant species or plant cultivars, and the location and growth conditions (soils, climate, vegetation period, diet) thereof, the treatment according to the invention may also result in superadditive ("synergistic") effects. For example, the following effects extending beyond the effects that are actually to be expected are possible: reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, increased storage life and/or processability of the harvested products.

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better storage life and/or processability of the harvested products. Further and particularly emphasized examples of such properties are an improved defence of the plants against animal and microbial pests, such as against insects, mites, phytopathogenic fungi, bacteria and/ or viruses, and also increased tolerance of the plants to certain herbicidally active compounds. Examples of transgenic plants include the important crop plants, such as cereals (wheat, rice), maize, soya beans, potatoes, sugarbeet, tomatoes, peas and other vegetable types, cotton, tobacco, oilseed rape, and also fruit plants (with the following fruits: apples, pears, citrus fruits and grapes), particular emphasis being given to maize, soya beans, potatoes, cotton, tobacco and oilseed rape. Traits that are particularly emphasized are improved defence of the plants against insects, arachnids, nematodes, slugs and snails by toxins formed in the plants, especially those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF, and also combinations thereof) (referred to hereinafter as "Bt plants"). Traits that are also particularly emphasized are the improved defence of plants against fungi, bacteria and viruses by systemic acquired resistance (SAR), systemin, phytoalexins, elicitors and also resistance genes and correspondingly expressed proteins and toxins. Traits that are additionally particularly emphasized are the increased tolerance of the plants to certain active herbicidal compounds, for example imidazolinones, sulphonylureas, glyphosate or phosphinothricin (for example the "PAT" gene). The genes which impart the desired properties ("traits") in question may also be present in combinations with one another in the transgenic plants. Examples of "Bt plants" include maize varieties, cotton varieties, soya varieties and potato varieties which are sold under the trade names YIELD GARD® (for example maize, cotton, soya), KnockOut® (for example maize), StarLink® (for example maize), Bollgard® (cotton), Nucotn® (cotton) and NewLeaf® (potato). Examples of herbicide-tolerant plants include maize varieties, cotton varieties and soya bean varieties which are sold under the commercial names Roundup Ready® (tolerance to glyphosate e g maize, cotton, soya beans), Liberty Link® (tolerance to phosphinothricin, e.g. oilseed rape), IMI® (tolerance to imidazolinones) and STS® (tolerance to sulphonylureas, e.g. maize). Herbicide-resistant plants (bred conventionally for herbicide tolerance) also include the varieties sold under the Clearfield® name (e.g. maize). Of course, these statements also apply to plant cultivars which have these genetic traits or genetic traits which are yet to be developed and will be developed and/or marketed in the future.

The plants listed can be treated in accordance with the invention in a particularly advantageous manner with the compounds of the general formula (I) and/or the active compound mixtures according to the invention. The areas of preference stated above for the active compounds or mixtures also apply to the treatment of these plants. Particular emphasis is given to the treatment of plants with the compounds or mixtures specifically mentioned in the present text.

Crop Protection—Types of Treatment

The treatment of the plants and plant parts with the compounds of the formula (I) according to the invention is carried out directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, furthermore by dry seed treatment, wet seed treatment, slurry treatment, by incrusting, by coating with one or more coats, etc. It is furthermore possible to apply the active compounds by the ultra-low volume method or to inject the active compound preparation or the active compound itself into the soil.

A preferred direct treatment of the plants is foliar application, i.e. compounds of the formula (I) according to the invention are applied to the foliage, in which case the treatment frequency and the application rate may be adjusted according to the level of infestation with the pest in question.

In the case of systemically active compounds, the compounds of the formula (I) according to the invention also get into the plants via the root system. The plants are then treated by the action of the compounds of the formula (I) according to the invention on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I) according to the invention, or by soil application, meaning that the compounds of the formula (I) according to the invention are introduced in solid form (e.g. in the form of granules) into the locus of the plants. In the case of paddy rice crops, this can also be accomplished by metering the invention in a solid application form (for example as granules) into a flooded paddy field.

Seed Treatment

The control of animal pests by the treatment of the seed of plants has long been known and is the subject of constant improvements. Nevertheless, the treatment of seed gives rise to a series of problems which cannot always be solved in a satisfactory manner. Thus, it is desirable to develop methods for protecting the seed and the germinating plant which dispense with, or at least reduce considerably, the additional application of crop protection compositions during storage, after sowing or after emergence of the plants. It is additionally desirable to optimize the amount of active compound used so as to provide optimum protection for the seed and the germinating plant from attack by animal pests, but without damage to the plant itself by the active compound used. More particularly, methods for the treatment of seed should also take account of the intrinsic insecticidal or nematicidal properties of pest-resistant or -tolerant transgenic plants, in order to achieve optimum protection of the seed and of the germinating plant with minimum expenditure of crop protection products.

The present invention therefore also relates, more particularly, to a method for protection of seed and germinating plants from attack by pests, by treating the seed with a compound of the formula (I) according to the invention. The method according to the invention for protecting seed and germinating plants against attack by pests comprises a method in which the seed is treated simultaneously in one operation or sequentially with an active compound of the formula (I) and mixing components. It also comprises a method in which the seed is treated at different times with an active compound of the formula (I) and a mixing component.

The invention likewise relates to the use of the compounds of the formula (I) according to the invention for treatment of seed for protection of the seed and the resulting plant from animal pests.

The invention further relates to seed which has been treated with a compound of the formula (I) according to the invention for protection from animal pests. The invention also relates to seed which has been treated simultaneously with an active compound of the formula (I) and a mixing component. The invention further relates to seed which has been treated at different times with an active compound of the formula (I) and a mixing component. In the case of seed which has been treated at different times with an active compound of the formula I and a mixing component, the individual active compounds in the composition according to the invention may be present on the seed in different layers. In this case, the layers comprising an active compound of the formula (I) and a mixing component may optionally be separated by an intermediate layer. The invention also relates to seed where an active compound of the formula (I) and a mixing component have been applied as a component of a coating or as a further layer or further layers in addition to a coating.

The invention further relates to seed which, after the treatment with the compound of the formula (I) according to the invention, is subjected to a film-coating process to prevent dust abrasion on the seed.

One of the advantages of the present invention is that the particular systemic properties of the compositions according to the invention mean that treatment of the seed with these compositions protects not only the seed itself but also the resulting plants after emergence from animal pests. In this way, the immediate treatment of the crop at the time of sowing or shortly thereafter can be dispensed with.

A further advantage is that the treatment of the seed with the compound of the formula (I) according to the invention can enhance germination and emergence of the treated seed.

It is likewise considered to be advantageous that compounds of the formula (I) according to the invention can especially also be used for transgenic seed.

It should also be mentioned that compounds of the formula (I) according to the invention can be used in combination with signalling technology compositions, leading, for example, to better colonization by symbionts, for example *rhizobia*, mycorrhizae and/or endophytic bacteria or fungi, and/or to optimized nitrogen fixation.

The compositions according to the invention are suitable for protection of seed of any plant variety which is used in agriculture, in the greenhouse, in forests or in horticulture. More particularly, this includes seed of cereals (for example wheat, barley, rye, millet and oats), maize, cotton, soya beans, rice, potatoes, sunflowers, coffee, tobacco, canola, oilseed rape, beets (for example sugarbeets and fodder beets), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape and rice.

As already mentioned above, the treatment of transgenic seed with a compound of the formula (I) according to the invention is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for the treatment of transgenic seed containing at least one heterologous gene originating from *Bacillus* sp. The heterologous gene is more preferably derived from *Bacillus thuringiensis*.

In the context of the present invention, the compound of the formula (I) according to the invention is applied to the seed alone or in a suitable formulation. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. Thus, for example, it is possible to use seed which has been harvested, cleaned and dried down to a moisture content which allows storage. Alternatively, it is also possible to use seed which, after drying, has been treated with, for example, water and then dried again, for example priming.

In general, in the treatment of the seed, it has to be ensured that the amount of the composition according to the invention and/or further additives applied to the seed is chosen such that the germination of the seed is not impaired and the plant which arises therefrom is not damaged. This has to be ensured particularly in the case of active compounds which can exhibit phytotoxic effects at certain application rates.

The compositions according to the invention can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The compounds of the formula (I) usable in accordance with the invention can be converted to the customary seed-dressing formulations, such as solutions, emulsions, suspensions, powders, foams, slurries or other coating compositions for seed, and also ULV formulations.

These formulations are produced in a known manner, by mixing compounds of the formula (I) with customary additives, for example customary extenders and solvents or diluents, dyes, wetters, dispersants, emulsifiers, antifoams, preservatives, secondary thickeners, stickers, gibberellins and also water.

Useful dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of active agrochemical compounds. Preference is given to using alkyl naphthalenesulphonates, such as diisopropyl or diisobutyl naphthalenesulphonates.

Suitable dispersants and/or emulsifiers which may be present in the seed-dressing formulations usable in accordance with the invention are all nonionic, anionic and cationic dispersants customary for the formulation of active agrochemical compounds. Preference is given to using nonionic or anionic dispersants or mixtures of nonionic or anionic dispersants. Suitable nonionic dispersants include in particular ethylene oxide/propylene oxide block polymers, alkylphenol poly glycol ethers and tristyrylphenol polyglycol ethers, and the phosphated or sulphated derivatives thereof. Suitable anionic dispersants are especially lignosulphonates, polyacrylic acid salts and arylsulphonate/formaldehyde condensates.

Antifoams which may be present in the seed-dressing formulations usable in accordance with the invention are all foam-inhibiting substances customary for formulation of active agrochemical compounds. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute preparations thereof, can also be used to dress seed of transgenic plants. In this case, additional synergistic effects may also occur in interaction with the substances formed by expression.

For treatment of seed with the seed-dressing formulations usable in accordance with the invention, or the preparations prepared therefrom by adding water, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed-dressing formulations usable in accordance with the invention can be varied within a relatively wide range. It is guided by the particular content of the compounds of the formula (I) according to the invention in the formulations and by the seed. The application rates of the compound of the formula (I) are generally between 0.001 and 50 g per kilogram of seed, preferably between 0.01 and 15 g per kilogram of seed.

Animal Health

In addition, the active compounds/active compound combinations according to the invention can be used to control a multitude of different pests, including, for example, harmful sucking insects, biting insects and other pests which are plant parasites, stored material pests, pests which destroy industrial materials, and hygiene pests including parasites in the animal health sector, and for the control thereof, for example the elimination and eradication thereof. The present invention thus also includes a method for controlling pests.

In the animal health field, i.e. in the field of veterinary medicine, the active compounds according to the invention are active against animal parasites, especially ectoparasites or endoparasites. The term endoparasites includes especially helminths and protozoa, such as coccidia. Ectoparasites are typically and preferably arthropods, especially insects and acarids.

In the field of veterinary medicine, the compounds according to the invention having favourable homeotherm toxicity are suitable for the control of parasites encountered in animal breeding and animal husbandry in livestock, breeding, zoo, laboratory, experimental and domestic animals. They are active against all or specific stages of development of the parasites.

Agricultural livestock include, for example, mammals, such as sheep, goats, horses, donkeys, camels, buffalo, rabbits, reindeer, fallow deer and especially cattle and pigs; or poultry such as turkeys, ducks, geese and especially chickens; or fish or crustaceans, for example in aquaculture; or, as the case may be, even insects such as bees.

Domestic animals include, for example, mammals, such as hamsters, guinea pigs, rats, mice, chinchillas, ferrets or especially dogs, cats; cage birds; reptiles; amphibians or aquarium fish.

In a preferred embodiment, the compounds according to the invention are administered to mammals.

In another preferred embodiment, the compounds according to the invention are administered to birds, namely cage birds or especially poultry.

The use of the active compounds according to the invention for the control of animal parasites is intended to reduce or prevent illness, cases of deaths and performance losses (in the case of meat, milk, wool, hides, eggs, honey and the like), so that more economical and simpler animal keeping is enabled and better animal well-being is achievable.

In relation to the field of animal health, the term "control" or "controlling" means that the active compounds can effectively reduce the incidence of the respective parasite in an animal infected with such parasites to a harmless degree. More specifically, "controlling" as used herein means that the active compound can kill the respective parasite, inhibit its growth, or inhibit its proliferation.

Examples of arthropods include, but without any limitation:

from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wil-* helmia spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order of the Siphonapterida, for example *Pulex* spp., *Ctenocephalides* spp., *Tunga* spp., *Xenopsylla* spp., *Ceratophyllus* spp.; from the order of the Heteropterida,
for example *Cimex* spp., *Triatoma* spp., *Rhodnius* spp., *Panstrongylus* spp.; and also nuisance and hygiene pests from the order of the Blattarida.

In addition, among the arthropods, examples of Acari include the following, but without any limitation:
from the subclass of the Acari (Acarina) and the order of the Metastigmata, for example from the family of Argasidae like *Argas* spp., *Ornithodorus* spp., *Otobius* spp., from the family of Ixodidae like *Ixodes* spp., *Amblyomma* spp., *Rhipicephalus* (*Boophilus*) spp., *Dermacentor* spp., *Haemophysalis* spp., *Hyalomma* spp., *Rhipicephalus* spp. (the original genus of multi-host ticks); from the order of Mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombicula* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Examples of parasitic protozoa include, but without any limitation:
Mastigophora (Flagellata), for example Trypanosomatidae, for example *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica*, for example Trichomonadidae, for example *Giardia lamblia, G. canis.*

Sarcomastigophora (Rhizopoda) such as Entamoebidae, for example *Entamoeba histolytica, Hartmanellidae*, for example *Acanthamoeba* sp., *Harmanella* sp.

Apicomplexa (Sporozoa), such as Eimeridae, for example *Eimeria acervulina, E. adenoides, E. alabamensis, E. anatis, E. anserina, E. arloingi, E. ashata, E. auburnensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E. spec., E. stiedai, E. suis, E. tenella, E. truncata, E. truttae, E. zuernii,*

*Globidium* spec., *Isospora belli, I. canis, I. felis, I. ohioensis, I. rivolta, I. spec., I. suis, Cystisospora* spec., *Cryptosporidium* spec., in particular *C. parvum*; such as Toxoplasmadidae, for example *Toxoplasma gondii, Hammondia heydornii, Neospora caninum, Besnoitia besnoitii*; such as Sarcocystidae, for example *Sarcocystis bovicanis, S. bovihominis, S. ovicanis, S. ovifelis, S. neurona, S.* spec., *S. suihominis*, such as Leucozoidae, for example *Leucozytozoon simondi*, such as Plasmodiidae, for example *Plasmodium berghei, P. falciparum, P. malariae, P. ovale, P. vivax, P.* spec., such as Piroplasmea, for example *Babesia argentina, B. bovis, B. canis, B.* spec., *Theileria parva, Theileria* spec., such as Adeleina, for example *Hepatozoon canis, H.* spec.

Examples of pathogenic endoparasites, which are helminths, include platyhelmintha (e.g. monogenea, cestodes and trematodes), roundworms, acanthocephala, and pentastoma. Further helminths include, but without any limitation:
Monogenea: for example: *Gyrodactylus* spp., *Dactylogyrus* spp., *Polystoma* spp.

Cestodes: from the order of the Pseudophyllidea, for example: *Diphyllobothrium* spp., *Spirometra* spp., *Schistocephalus* spp., *Ligula* spp., *Bothridium* spp., *Diplogonoporus* spp.

From the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

Trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.

Roundworms: Trichinellida, for example *Trichuris* spp., *Capillaria* spp., *Trichomosoides* spp., *Trichinella* spp.

From the order of the Tylenchida, for example: *Micronema* spp., *Strongyloides* spp.

From the order of the Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp.

From the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp.

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp.

From the order of the Echinorhynchida, for example, *Acanthocephalus* spp., *Echinorhynchus* spp., *Leptorhynchoides* spp.

Pentastoma: from the order of the Porocephalida, for example, *Linguatula* spp.

In the veterinary field and in animal keeping, the active compounds according to the invention are administered by methods commonly known in the art, such as enterally, parenterally, dermally or nasally, in the form of suitable preparations. Administration may be prophylactic or therapeutic.

Thus, one embodiment of the present invention refers to compounds according to the invention for use as a medicament.

A further aspect relates to compounds according to the invention for use as an antiendoparasitic agent, in particular a helminthicidal agent or antiprotozoic agent. For example, compounds according to the invention are suitable for use as an antiendoparasitic agent, in particular a helminthicidal agent or antiprotozoic agent, for example in animal husbandry, in animal keeping, in animal housing and in the hygiene sector.

Yet a further aspect relates to compounds according to the invention for use as an antiectoparasitic agent, in particular an arthropodicidal agent, such as an insecticide or acaricide. For example, compounds according to the invention are suitable for use as an antiectoparasitic agent, especially an arthropodicidal agent such as an insecticide or acaricide, for example in animal keeping, in animal husbandry, in animal housing and in the hygiene sector.

Vector Control

The compounds of the formula (I) according to the invention can also be used in vector control. In the context of the present invention, a vector is an arthropod, especially an insect or arachnid, capable of transmitting pathogens, for example, viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:
1) Mosquitoes
   *Anopheles*: malaria, filariosis;
   *Culex*: Japanese encephalitis, filariasis, other viral diseases, transmission of worms;
   *Aedes*: yellow fever, dengue fever, filariasis, other viral diseases;
   Simuliidae: transmission of worms, in particular *Onchocerca volvulus*;
2) Lice: skin infections, epidemic typhus;
3) Fleas: plague, endemic typhus;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, epidemic typhus, borreliosis;
6) Ticks: borellioses such as *Borrelia* duttoni, tick-borne encephalitis, Q fever (*Coxiella burnetii*), babesioses (*Babesia canis canis*).

Examples of vectors in the context of the present invention are insects, for example aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dims* (malaria) and *Culex*, lice, fleas, flies, mites and ticks, which can transmit pathogens to animals and/or humans.

Vector control is also possible if the compounds of the formula (I) are resistance-breaking.

Compounds of the present invention are suitable for use in the prevention of diseases and/or pathogens transmitted by vectors. Thus, a further aspect of the present invention is the use of compounds according to the invention for vector control, for example in agriculture, in horticulture, in forestry, in gardens and in leisure facilities, and also in the protection of materials and stored products.

Protection of Industrial Materials

The compounds of the formula (I) according to the invention are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In one embodiment of the invention, the compositions or products according to the invention also comprise at least one further insecticide and/or at least one fungicide.

In a further embodiment, this composition according to the invention is a ready-to-use composition, meaning that it can be applied to the appropriate material without any further modifications. Useful further insecticides or fungicides include those mentioned above.

It has also been found that, surprisingly, the active compounds and compositions according to the invention can be used to protect objects which come into contact with saltwater or brackish water, especially hulls, screens, nets, buildings, moorings and signalling systems, against fouling. The active compounds and compositions according to the invention can again be used alone or in combinations with other active compounds as antifouling compositions.

Control of Animal Pests in the Hygiene Sector

The compounds of the formula (I) according to the invention are suitable for controlling animal pests in the hygiene sector. More particularly, the invention can be used in the domestic protection sector, in the hygiene protection sector and in the protection of stored products, particularly for control of insects, arachnids and mites encountered in enclosed spaces, for example dwellings, factory halls, offices, vehicle cabins. For controlling animal pests, the active compounds or compositions are used alone or in combination with other active compounds and/or auxiliaries. They are preferably used in domestic insecticide products. The active compounds according to the invention are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

The compounds according to the invention can be prepared by customary methods known to those skilled in the art.

Reaction Scheme 1 shows the general Preparation Process A for the compounds (Iap) according to the invention.

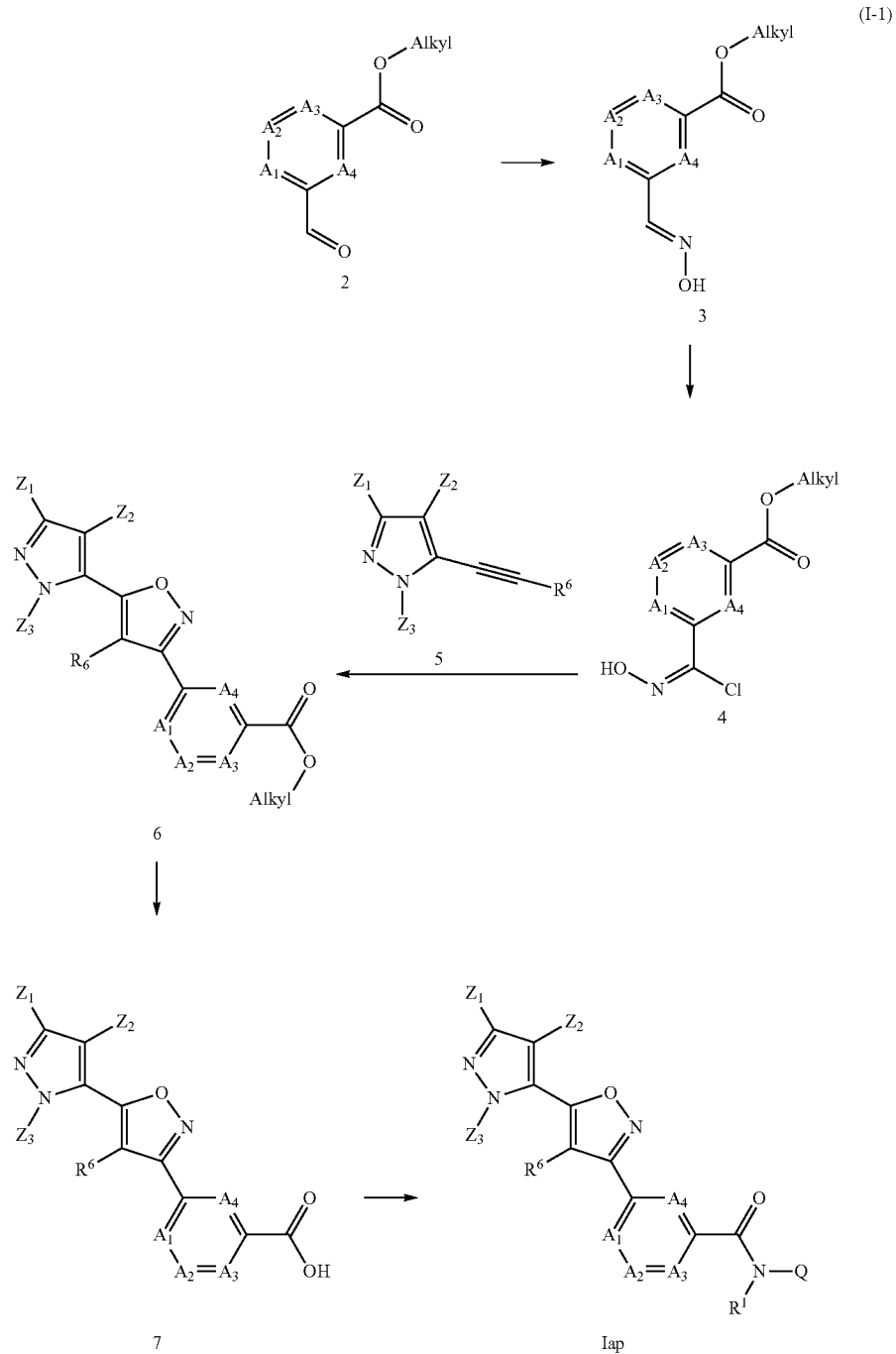

The radicals $A_1$-$A_4$, Q, $R^6$, $R^1$ and $Z^1$-$Z^3$ have the meanings described above.

Step 1 of the preparation process for the compounds (Iap) according to the invention:

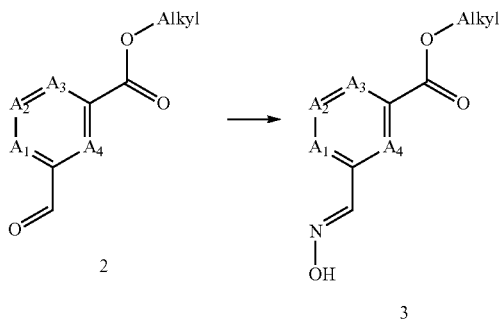

Compounds according to the invention of the general structure 3 can be prepared in analogy to methods known from the literature from the starting materials of the structure 2. The $A_1$-$A_4$ and alkyl radicals have the meanings given above. Starting materials of the structure 2 are known or can be prepared by known methods. Examples include 3-carbomethoxybenzaldehyde, 3-carbomethoxy-4-chlorobenzaldehyde, 3-carbomethoxy-4-bromobenzaldehyde, 3-carbomethoxy-4-fluorobenzaldehyde, 3-carbomethoxy-4-chloro-5-fluorobenzaldehyde and the corresponding ethyl esters. They can be prepared, for example, by the methods described in WO2010011584, pp. 19-20; Journal of Organic Chemistry, 76 (2011), pp. 1062-1071; WO2012114268, p. 137; Journal of the American Chemical Society, 108 (1986), pp. 452-461.

Some of the compounds of the structural formula 3 are known, for example 3-carbomethoxybenzaldoxime, WO2004072050, page 14; however, some have hitherto not been disclosed, for example 3-carbomethoxy-4-chlorobenzaldoxime, 3-carbomethoxy-4-fluorobenzaldoxime, 3-carbomethoxy-4-chloro-5-fluorobenzaldoxime, 3-carbomethoxy-4-bromobenzaloxime. The as yet unknown compounds 3 can be prepared in analogy to the known processes for preparing oximes from aldehydes (H. Metzger in Houben-Weyl, volume X/4, page 55 ff., Georg Thieme Verlag Stuttgart 1968). The compounds of the structural formula 3 may be present in the form of pure stereoisomers, but also in the form of mixtures of the configurational isomers.

Step 2 of the preparation process for the compounds (Iap) according to the invention:

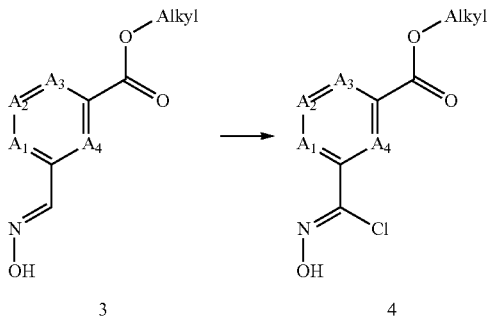

Compounds according to the invention of the general structure 4 are prepared by reacting the oximes of the structure (X2) with halogenating agents.

The A1-A4, alkyl and Z1-Z3 radicals have the meanings given above.

Typical compounds of the structure 4 are, for example, carbomethoxy-4-chloro-N-hydroxybenzimidoyl chloride, 3-carbomethoxy-4-fluoro-N-hydroxybenzimidoyl chloride, 3-carbomethoxy-4-chloro-5-fluoro-N-hydroxybenzimidoyl chloride, 3-carbomethoxy-4-bromo-N-hydroxybenzimidoyl chloride.

Suitable halogenating compounds, for example chlorine, bromine, iodine, N-chlorosuccinimide, N-bromosuccinimide, N-iodosuccinimide, 1,3-dichloro-5,5-dimethylhydantoin, 1,3-dibromo-5,5-dimethylhydantoin, benzyltrimethylammonium tetrachloroiodate and sodium hypochlorite, are known to the person skilled in the art. Preference is given to using chlorinating reagents.

The reaction can be carried out using suitable solvents.

Suitable diluents or solvents for carrying out the processes according to the invention are, in principle, all organic solvents which are inert under the specific reaction conditions. Examples include: hydrohalocarbons (e.g. hydrochlorocarbons, such as tetraethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (e.g. methanol, ethanol, isopropanol, butanol), ethers (e.g. ethyl propyl ether, methyl tert-butyl ether, n-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide), amines (e.g. trimethyl-, triethyl-, tripropyl-, tributylamine, N-methylmorpholine, pyridine and tetramethylenediamine), nitrohydrocarbons (e.g. nitromethane, nitroethane, nitropropane, nitrobenzene, chloronitrobenzene, o-nitrotoluene; nitriles such as acetonitrile, propionitrile, butyronitrile, isobutyronitrile, benzonitrile, m-chlorobenzonitrile). tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (e.g. dimethyl sulphone, diethyl sulphone, dipropyl sulphone, dibutyl sulphone, diphenyl sulphone, dihexyl sulphone, methyl ethyl sulphone, ethyl propyl sulphone, ethyl isobutyl sulphone and pentamethylene sulphone), aliphatic, cycloaliphatic or aromatic hydrocarbons (e.g. pentane, hexane, heptane, octane, nonane and industrial hydrocarbons), furthermore white spirits with components having boiling points in the range of, for example, from 40° C. to 250° C., cymene, petroleum fractions having a boiling point range from 70° C. to 190° C., cyclohexane, methylcyclohexane, petroleum ether, ligroine, octane, benzene, toluene, chlorobenzene, bromobenzene, nitrobenzene, xylene, esters (e.g. methyl acetate, ethyl acetate, butyl acetate, isobutyl acetate, dimethyl carbonate dibutyl carbonate, ethylene carbonate); amides (e.g. hexamethylenephosphoric triamide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2 (1H)-pyrimidine, octylpyrrolidone, octylcaprolactam, 1,3-dimethyl-2-imidazolinedione, N-formylpiperidine, N,N'-1,4-diformylpiperazine) and ketones (e.g. acetone, acetophenone, methyl ethyl ketone, methyl butyl ketone).

Preferred diluents used may be any solvent that does not interfere with the reaction, for example water. Useful examples are aromatic hydrocarbons such as benzene, toluene, xylene or chlorobenzene; halogenated hydrocarbons such as dichloromethane, chloroform, 1,2-dichloroethane or carbon tetrachloride, open-chain or cyclic ethers such as diethyl ether, dioxane, tetrahydrofuran or 1,2-dimethoxyethane; esters such as ethyl acetate and butyl acetate; ketones, for example acetone, methyl isobutyl ketone and cyclohexanone; amides such as dimethylformamide and dimethylacetamide, N-methylpyrrolidinone; nitriles such as acetonitrile or propionitrile; and other inert solvents such as 1,3-dimethyl-2-imidazolidinone; the solvents may be used alone or in a combination of 2 or more.

The reaction can be carried out within a wide temperature range. Usually, it is conducted within a temperature range from −78° C. to 200° C., preferably at temperatures between −10 to 150° C. The reaction can be executed under elevated or else reduced pressure. But it is preferably conducted under standard pressure. The reaction times are between 0.1 to 72 hours, preferably 1 to 24 hours.

To carry out the reaction, 1 to 3 mol, preferably 1 to 1.5 mol, of halogenating agent are reacted per mole of the compound of the structure 3 in a solvent, for example dimethylformamide (DMF).

Step 3 of the preparation process for the compounds (Iap) according to the invention:

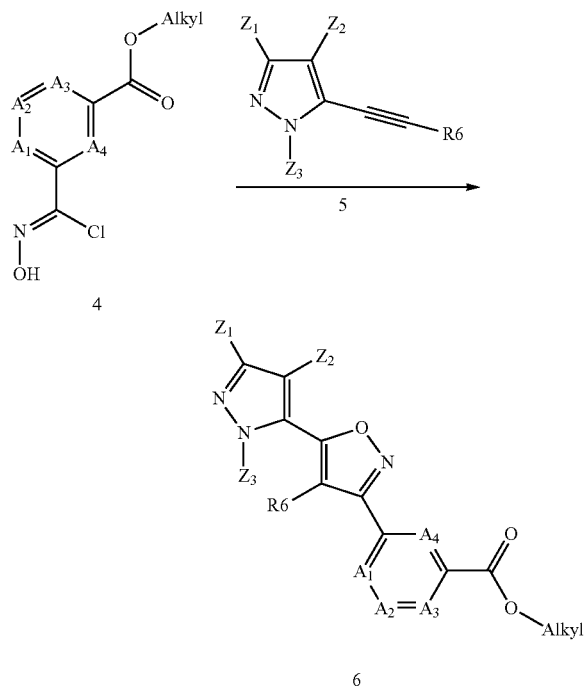

Compounds according to the invention of the general structure 6 are prepared by reacting the hydroxamoyl chlorides of the structure 4 with acetylenes of the structure 5.

The A1-A4, R6, alkyl and Z1-Z3 radicals have the meanings given above.

Typical compounds of the structure 4 are, for example, carbomethoxy-4-chloro-N-hydroxybenzimidoyl chloride, 3-carbomethoxy-4-fluoro-N-hydroxybenzimidoyl chloride, 3-carbomethoxy-4-chloro-5-fluoro-N-hydroxybenzimidoyl chloride, 3-carbomethoxy-4-bromo-N-hydroxybenzimidoyl chloride.

The reaction can be carried out using suitable solvents.

Suitable diluents or solvents for carrying out the processes according to the invention are, in principle, all organic solvents which are inert under the specific reaction conditions. Examples include: hydrohalocarbons (e.g. hydrochlorocarbons, such as tetraethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (e.g. methanol, ethanol, isopropanol, butanol), ethers (e.g. ethyl propyl ether, methyl tert-butyl ether, n-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide), amines (e.g. trimethyl-, triethyl-, tripropyl-, tributylamine, N-methylmorpholine, pyridine and tetramethylenediamine), nitrohydrocarbons (e.g. nitromethane, nitroethane, nitropropane, nitrobenzene, chloronitrobenzene, o-nitrotoluene; nitriles such as acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (e.g. dimethyl sulphone, diethyl sulphone, dipropyl sulphone, dibutyl sulphone, diphenyl sulphone, dihexyl sulphone, methyl ethyl sulphone, ethyl propyl sulphone, ethyl isobutyl sulphone and pentamethylene sulphone), aliphatic, cycloaliphatic or aromatic hydrocarbons (e.g. pentane, hexane, heptane, octane, nonane and industrial hydrocarbons), furthermore white spirits with components having boiling points in the range of, for example, from 400 C to 25O0 C, cymene, petroleum fractions having a boiling point range from 700 C to 1900 C, cyclohexane, methylcyclohexane, petroleum ether, ligroine, octane, benzene, toluene, chlorobenzene, bromobenzene, nitrobenzene, xylene, esters (e.g. methyl acetate, ethyl acetate, butyl acetate, isobutyl acetate, dimethyl carbonate dibutyl carbonate, ethylene carbonate); amides (e.g. hexamethylenephosphoric triamide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine) and ketones (e.g. acetone, acetophenone, methyl ethyl ketone, methyl butyl ketone).

Preferred Solvents

Preferred diluents used may be any solvent that does not interfere with the reaction, for example water. Useful examples are aromatic hydrocarbons such as benzene, toluene, xylene or chlorobenzene; halogenated hydrocarbons such as dichloromethane, chloroform, 1,2-dichloroethane or carbon tetrachloride, open-chain or cyclic ethers such as diethyl ether, dioxane, tetrahydrofuran or 1,2-dimethoxyethane; esters such as ethyl acetate and butyl acetate; ketones, for example acetone, methyl isobutyl ketone and cyclohexanone; amides such as dimethylformamide and dimethylacetamide, N-methylpyrrolidinone; nitriles such as acetonitrile or propionitrile; and other inert solvents such as 1,3-dimethyl-2-imidazolidinone; the solvents may be used alone or in a combination of 2 or more.

In the reactions of the compounds of the structure 4 with the acetylenes of the structure 5, it is possible to add bases.

Examples which may be mentioned are alkaline earth metal or alkali metal compounds (e.g. hydroxides, hydrides, oxides and carbonates of lithium, sodium, potassium, magnesium, calcium and barium), amidine bases or guanidine bases (e.g. 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, especially tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, β-picoline, isoquinoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethyldiamine). Furthermore, it is also possible to use silver(I) cyanide as base and activator [Journal of Organic Chemistry. 1992, 57, 4394-4400; Journal of Medicinal Chemistry 1992, 35, 3905-3918; Journal of Organic Chemistry 2003, 68, 1843-1851].

Preferred Bases

The preferred basic reaction auxiliary used can be an organic base such as triethylamine, ethyldiisopropylamine, tri-n-butylamine, pyridine and 4-dimethylaminopyridine; furthermore, it is possible to use, for example, the following bases: alkali metal hydroxides such as, for example, sodium hydroxide and potassium hydroxide; carbonates such as sodium bicarbonate and potassium carbonate; phosphates such as dipotassium hydrogenphosphate and trisodium phosphate.

The reaction can be carried out within a wide temperature range. Usually, it is conducted within a temperature range from −78° C. to 200° C., preferably at temperatures between −10 to 150° C. The reaction can be executed under elevated or else reduced pressure. But it is preferably conducted under standard pressure. The reaction times are between 0.1 to 72 hours, preferably 1 to 24 hours.

To carry out the reaction, for example, 1-2 molar equivalents of the compounds of the structure 5 and 1 molar equivalent up to a slight excess of base per mole of the compound of the structure 4 are reacted in a solvent, for example dimethylformamide (DMF).

Steps 2 and 3 for preparation of the compounds of the structure 6 can be conducted in individual steps or else as a one-pot reaction.

The last steps for the preparation of the compounds (Iap) according to the invention are the hydrolysis of the carboxylic ester 6 and amidation of the carboxylic acid 7 [WO2010-051926; WO2010-133312].

Reaction Scheme 2 shows the general Preparation Process B for the compounds (Ibg-Ibi) according to the invention.

Reaction Scheme 2

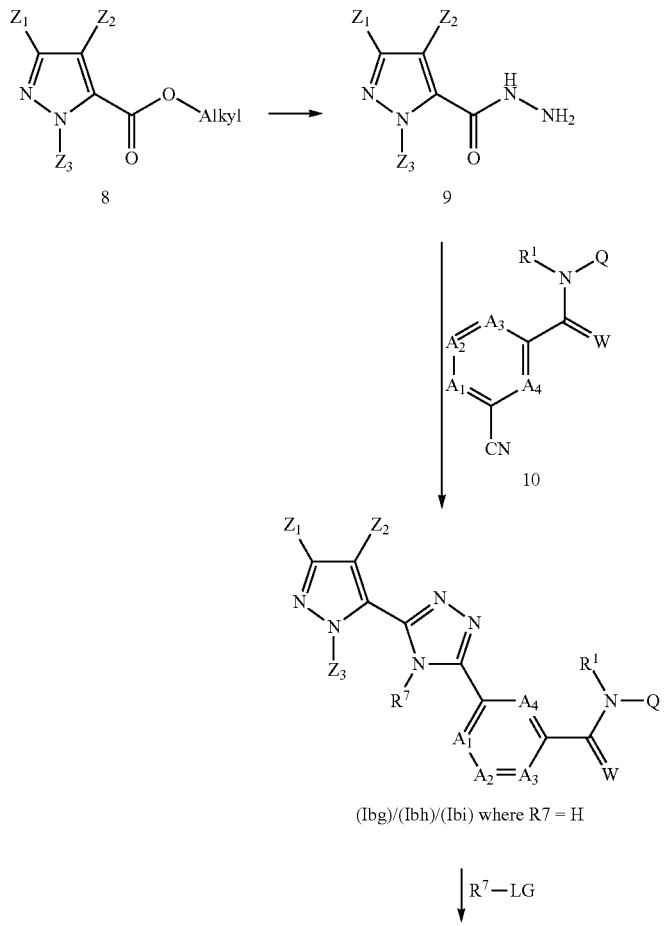

(Ibg)/(Ibh)/(Ibi) where R7 = H

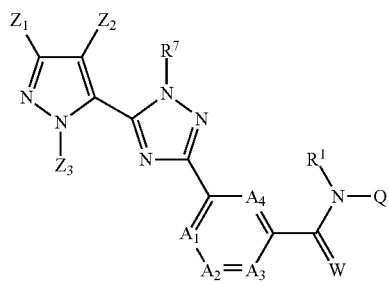

Ibg where R⁷ ≠ H

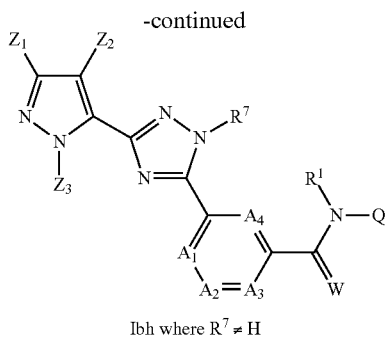

Ibh where R⁷ ≠ H

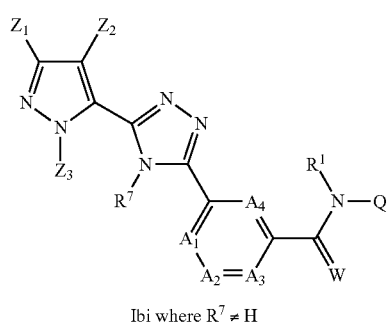

Ibi where R⁷ ≠ H

The radicals $A_1$-$A_4$, Q, W, $R^7$, $R^6$, $R^1$ and $Z^1$-$Z^3$ have the meanings described above. "Alkyl" represents an alkyl radical such as methyl or ethyl. "LG" represents a leaving group, for example, chlorine, bromine or iodine.

Step 1 of the preparation process for the compounds (Ibg)/(Ibh)/(Ibi) according to the invention:

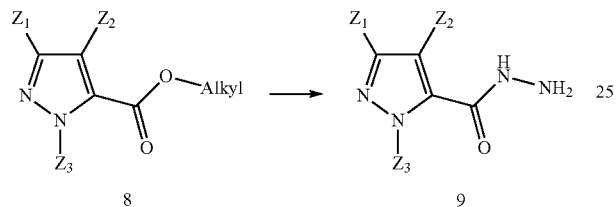

The $Z^1$-$Z^3$ radicals are as defined above. "Alkyl" represents an alkyl radical such as methyl or ethyl.

Compounds of the general structure 9 can be prepared in analogy to preparation processes known from the literature [WO2011-121137; WO2010-0071196] from the starting materials of the general structure 8.

Step 2 of the preparation process for the compounds (Ibg)/(Ibh)/(Ibi) according to the invention:

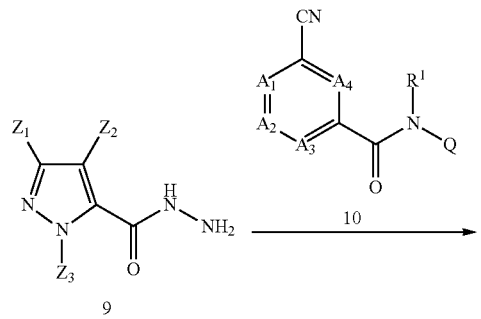

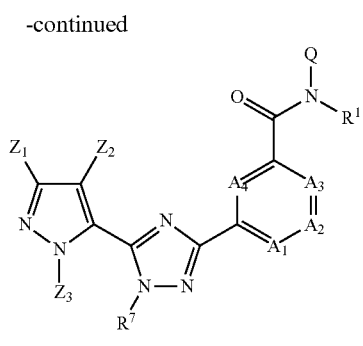

(Ibg)/(Ibh)/(Ibi) where R7 = H

The $A_1$-$A_4$, Q, W, $R^1$ and $Z^1$-$Z^3$ radicals have the meanings described above. $R^7$ represents hydrogen.

Compounds of the general structure (Ibg)/(Ibh)/(Ibi) where $R^7$=H can be prepared in analogy to preparation processes known from the literature [WO2010-025558; WO2004-052280; Tetrahedron Letters 2005, 46, 3429-3432] from the compounds of the general structures 9 and 10.

Step 3 of the preparation process for the compounds (Ibg)/(Ibh)/(Ibi) according to the invention:

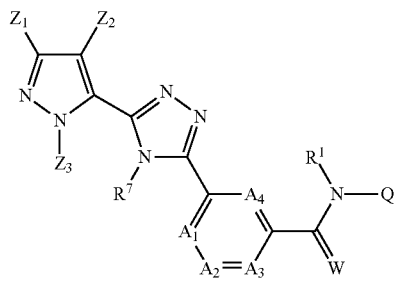

(Ibg)/(Ibh)/(Ibi) where R7 = H

↓ R⁷—LG

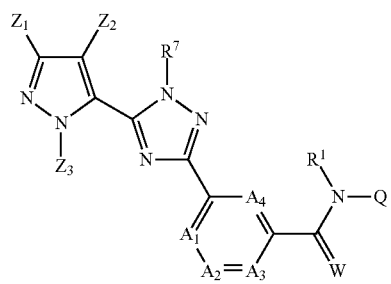
(Ibg) where $R^7 \neq H$

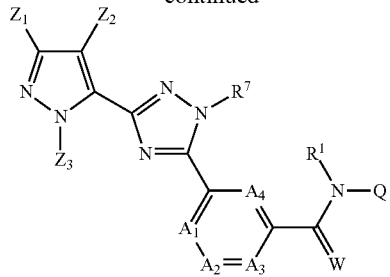
(Ibh) where $R^7 \neq H$

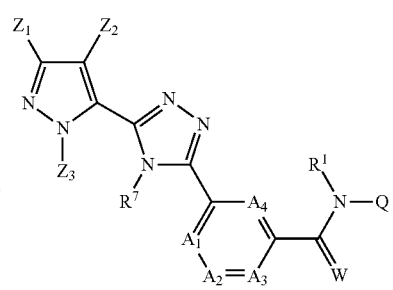
(Ibi) where $R^7 \neq H$

Compounds of the general structure (Ibg/Ibh/Ibi) where $R^7 \neq H$ can be prepared in analogy to preparation processes known from the literature [WO2007-071900; WO21012137089] from the compounds of the general structures (Ibg/Ibh/Ibi) where $R^7 = H$.

Reaction Scheme 3 shows the general Preparation Process C for the compounds (Iaa, Iac and Iaf) according to the invention.

Reaction Scheme 3

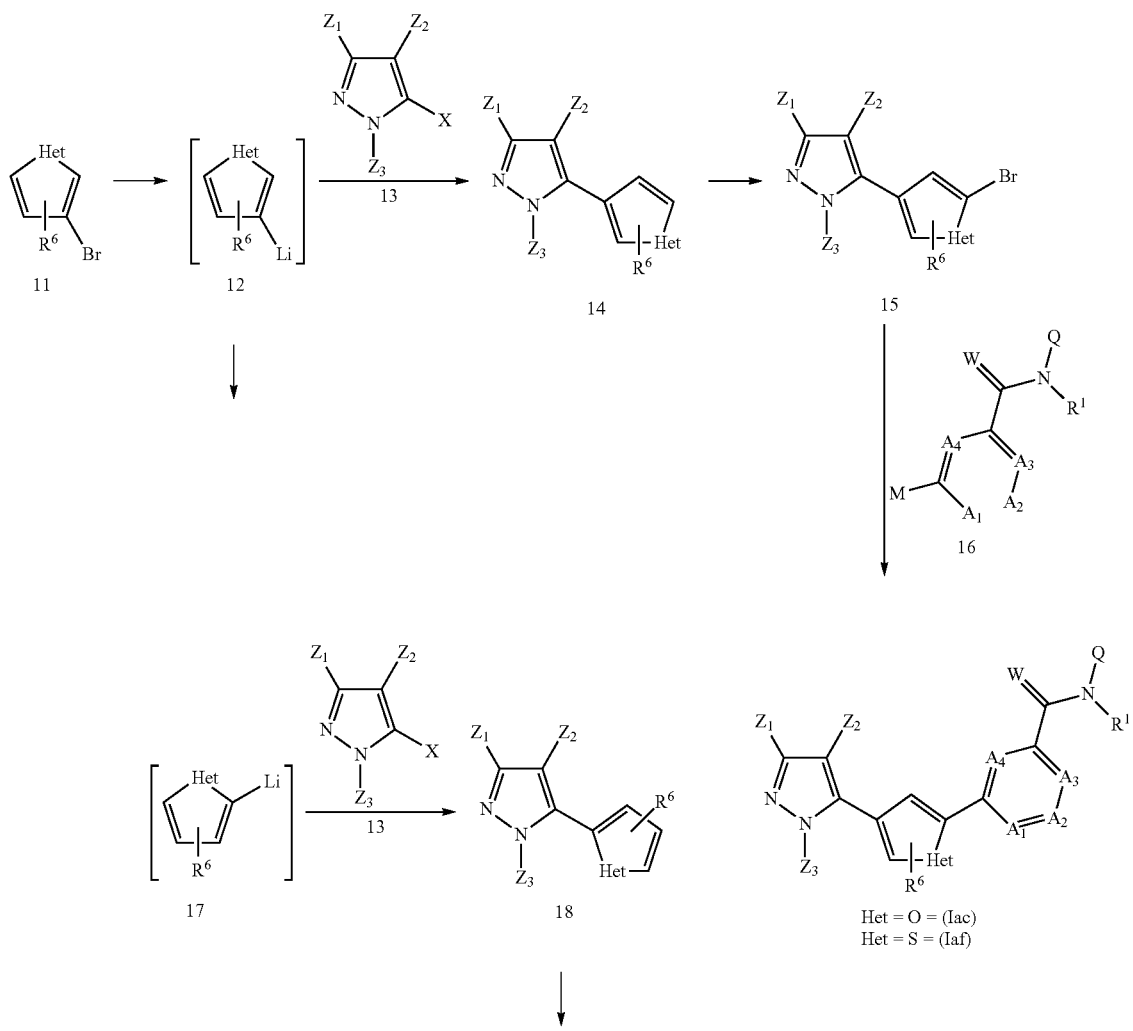

Het = O = (Iac)
Het = S = (Iaf)

-continued

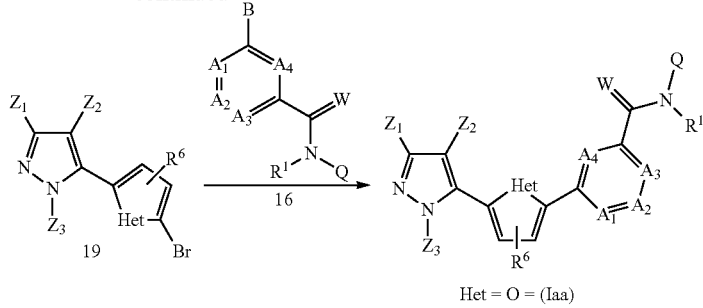

Het = O = (Iaa)

The radicals $A_1$-$A_4$, Q, W, $R^6$, $R^1$ and $Z^1$-$Z^3$ have the meanings described above. "Het" represents an oxygen or sulphur atom. "X" represents a leaving group, for example chlorine or fluorine. "M" represents a boronic acid, a boronic ester or a trifluoroboronate.

1. Step of the Preparation Process of (Iac) & (Iaf)

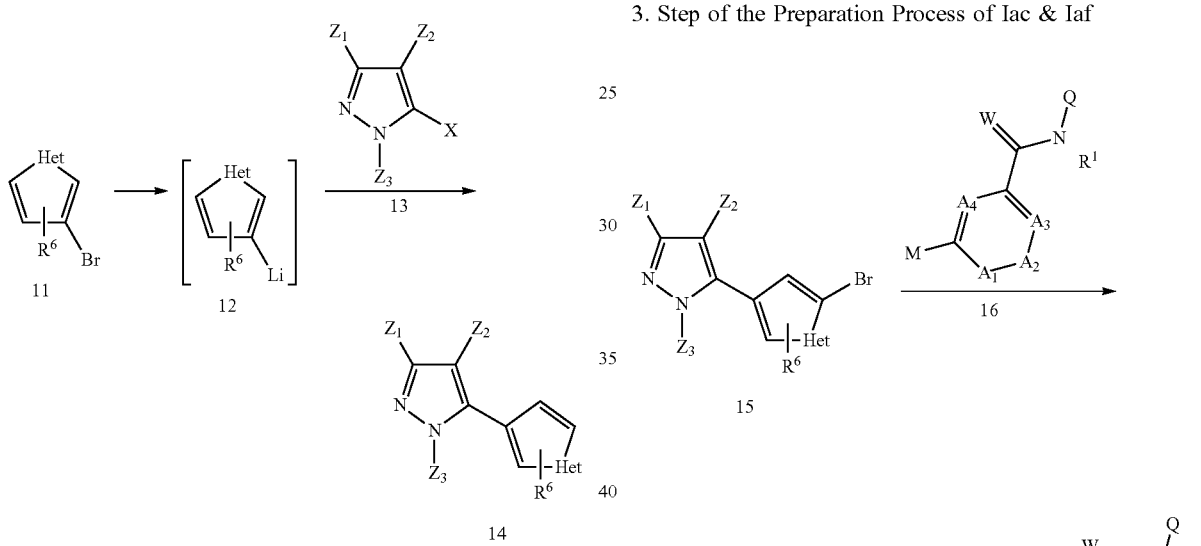

The $R^6$ and $Z^1$-$Z^3$ radicals have the meanings described above. "Het" represents an oxygen or sulphur atom. "X" represents a leaving group, for example chlorine or fluorine.

Compounds of the general structure 14 can be prepared by reacting compounds of the general structure 13 and organolithium compounds of the general structure 12, which are prepared in situ. The preparation of organolithium compounds of the general structure 12 from the corresponding bromine compounds and their reaction in nucleophilic substitution reactions is known from the literature [Tetrahedron 1988, 44 (1), 81-90].

2. Step of the Preparation Process of Iac & Iaf

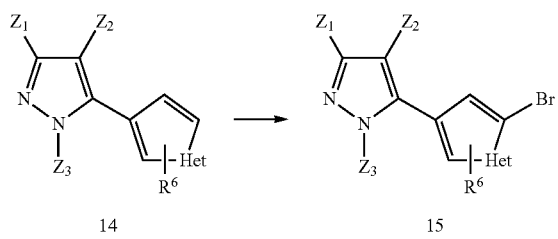

The $R^6$ and $Z^1$-$Z^3$ radicals have the meanings described above. "Het" represents an oxygen or sulphur atom.

Compounds of the general structure 15 can be prepared analogously to processes known from the literature by brominating compounds of the general structure 14 [e.g. Organic Letters 2001, 13, 2129-2131].

3. Step of the Preparation Process of Iac & Iaf

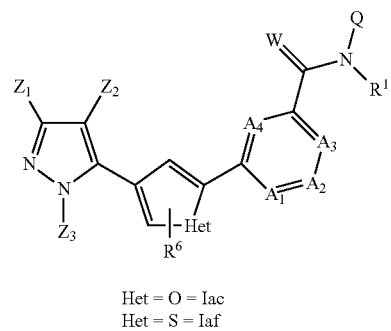

Het = O = Iac
Het = S = Iaf

The radicals $A_1$-$A_4$, Q, W, $R^6$, $R^1$ and $Z^1$-$Z^3$ have the meanings described above. "Het" represents an oxygen or sulphur atom. "M" represents a boronic acid, a boronic ester or a trifluoroboronate.

Compounds according to the invention of the general structures Iac and Iaf can be prepared in a palladium-catalysed Suzuki reaction analogously to processes known from the literature from the compounds of the general structures 15 and 16 [WO2005-040110; WO2009-089508].

1. Step of the Preparation Process of Compounds According to the Invention of the General Structure Iaa

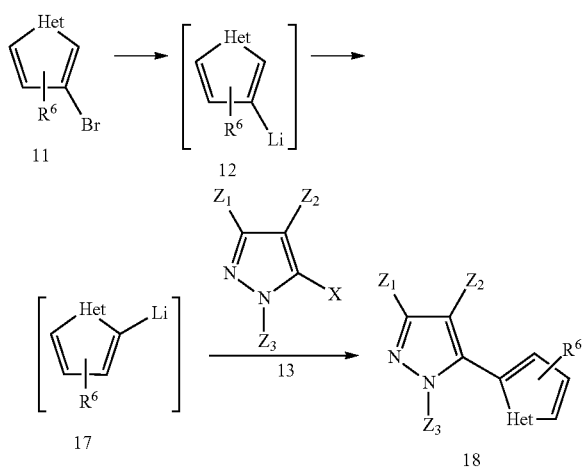

The $R^6$ and $Z^1$-$Z^3$ radicals have the meanings described above. "Het" represents an oxygen or sulphur atom. "X" represents a leaving group, for example chlorine or fluorine.

Compounds of the general structure 18 can be prepared by reacting compounds of the general structure 13 and organolithium compounds of the general structure 17, which are prepared in situ. The organolithium compounds of the general structure 17 are formed by isomerization from the organolithium compounds of the general structure 12. The organolithium compounds of the general structure 12 can be prepared from the corresponding bromine compounds. The preparation of such organolithium compounds and their conversion in nucleophilic substitution reactions is known from the literature [e.g. Tetrahedron 1988, 44 (1), 81-90].

All further reactions for preparing the compounds according to the invention of the general structure (Iaa) are carried out analogously to the processes described above for preparing (Iac) and (Iaf).

Reaction Scheme 4 shows the general Preparation Process D for the compounds (Iaj) according to the invention.

Reaction Scheme 4

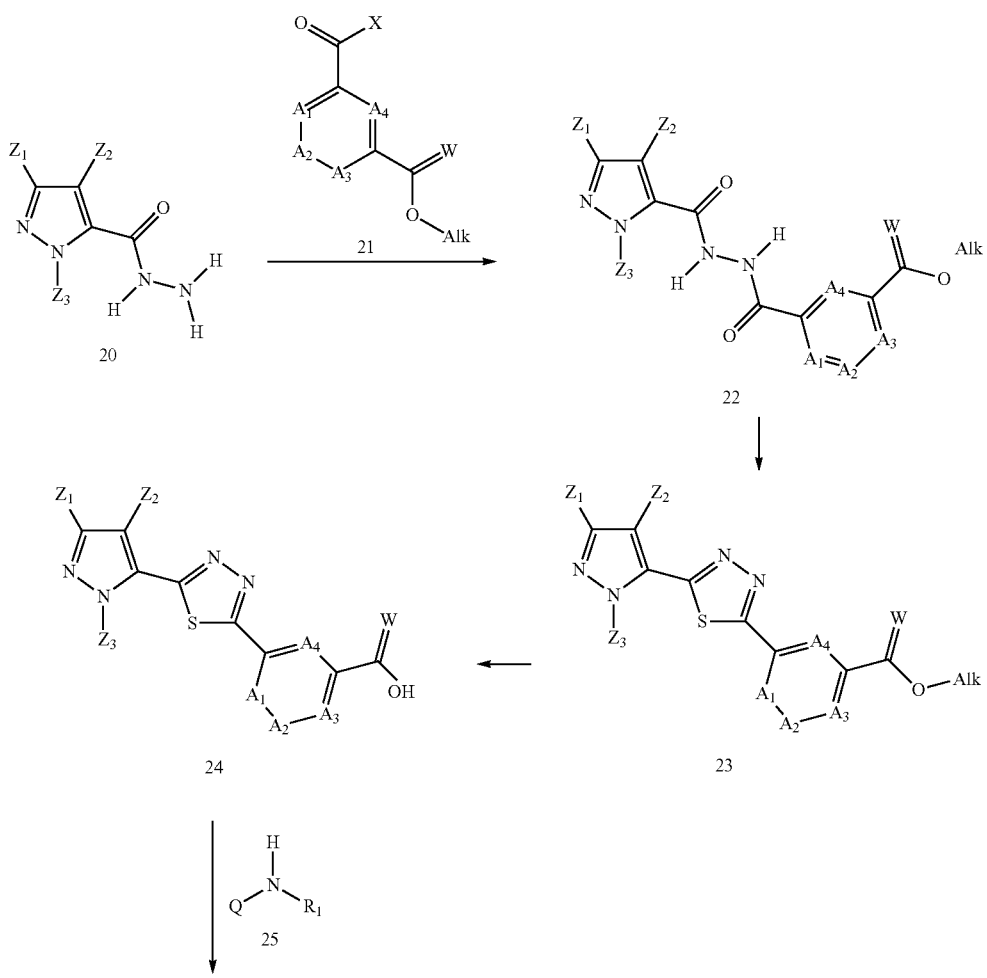

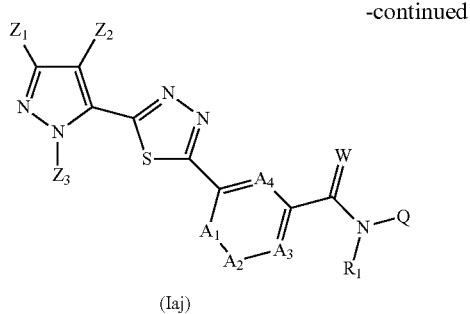

(Iaj)

The $A_1$-$A_4$, Q, W, $R^1$ and $Z^1$-$Z^3$ radicals have the meanings described above. "X" represents a leaving group, for example chlorine. "Alk" represents an alkyl group, for example methyl or ethyl.

1. Step of the Preparation Process D for Preparing the Compounds According to the Invention of the General Structure (Iaj)

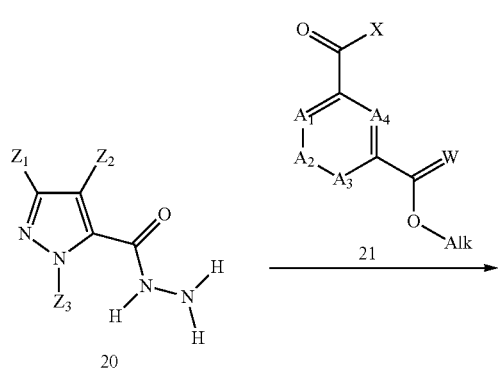

The $A_1$-$A_4$, W and $Z^1$-$Z^3$ radicals have the meanings described above. "X" represents a leaving group, for example chlorine. "Alk" represents an alkyl group, for example methyl or ethyl.

Compounds of the general structure 22 can be prepared analogously to processes known from the literature by reacting compounds of the general structure 20 with compounds of the general structure 21 [US2013-13953965].

2. Step of the Preparation Process D for Preparing the Compounds According to the Invention of the General Structure (Iaj)

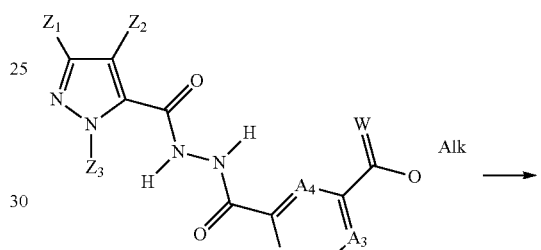

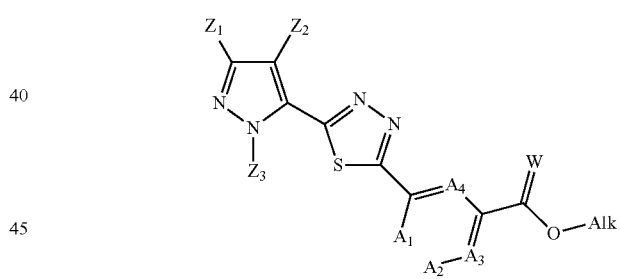

The $A_1$-$A_4$, W and $Z^1$-$Z^3$ radicals have the meanings described above. "Alk" represents an alkyl group, for example methyl or ethyl.

Compounds of the general structure 22 can be prepared analogously to processes known from the literature by reacting the compound of the general structure 23 with sulphurizing agents such as, for example, Lawesson's reagent [WO2013-149121].

The last steps for the preparation of the compounds (Iaj) according to the invention, hydrolysis of the carboxylic ester 23 and amidation of the carboxylic acid 24 with amines of the general structure 25, can be carried out analogously to processes known from the literature [WO2010-051926; WO2010-133312]Reaction Scheme 5 shows the general Preparation Process E for the compounds (Iaq) according to the invention.

Reaction Scheme 5
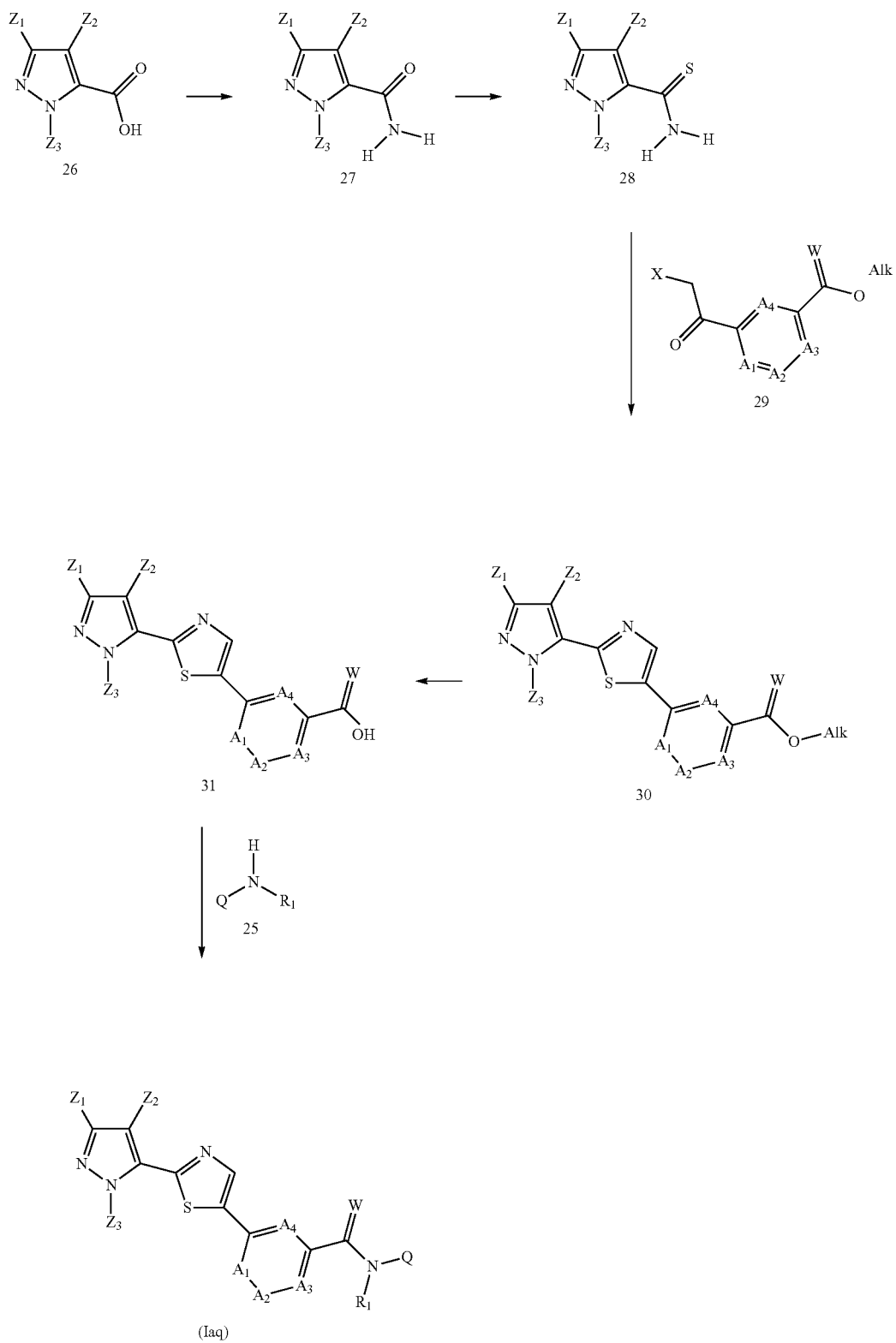
(Iaq)
The $A_1$-$A_4$, Q, W, $R^1$ and $Z^1$-$Z^3$ radicals have the meanings described above. "X" represents a leaving group, for example chlorine or bromine. "Alk" represents an alkyl group, for example methyl or ethyl.

The 1st and the 2nd Step of the Preparation Process E for preparing the compounds according to the invention of the general structure (Iaq) are carried out by processes known from the literature [amidation; WO2009-071706, thiation of the carbonyl function WO2013-018695]

3. Step of the Preparation Process E for Preparing the Compounds According to the Invention of the General Structure (Iaq)

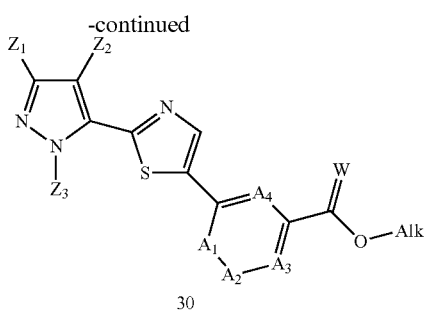

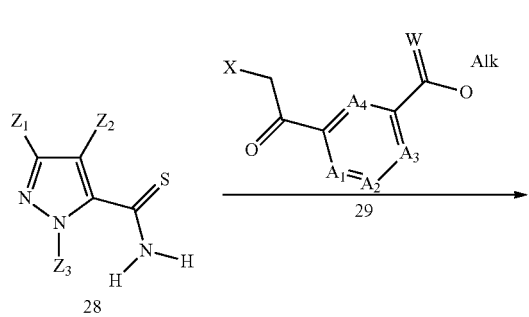

The $A_1$-$A_4$, W and $Z^1$-$Z^3$ radicals have the meanings described above. "X" represents a leaving group, for example chlorine or bromine. "Alk" represents an alkyl group, for example methyl or ethyl.

Compounds of the general structure 30 can be prepared analogously to processes known from the literature by reacting the compound of the general structure 28 with alpha-haloketones of the general structure 29 [WO2013-062027].

The last steps for the preparation of the compounds (Iaq) according to the invention, hydrolysis of the carboxylic ester 30 and amidation of the carboxylic acid 31 with amines of the general structure 25, can be carried out analogously to processes known from the literature [WO2010-051926; WO2010-133312]

Reaction Scheme 6 shows the general Preparation Process C for the compounds (Iaw) and (Iax) according to the invention.

Reaction Scheme 6

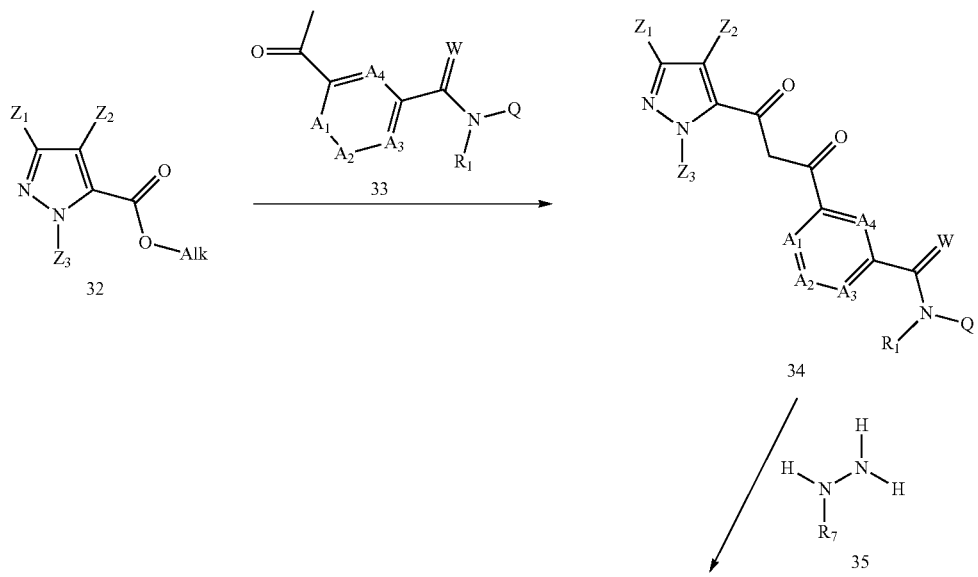

-continued

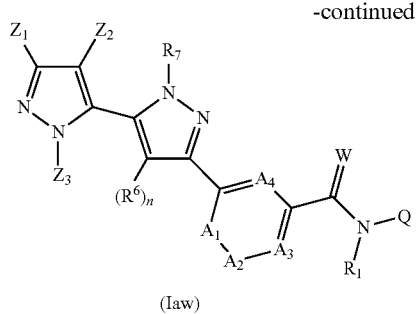

(Iaw)

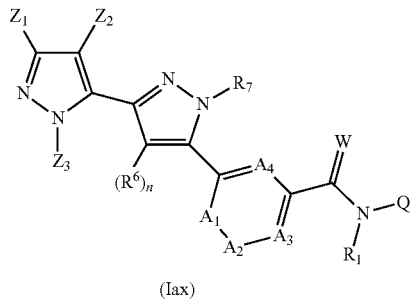

(Iax)

The radicals $A_1$-$A_4$, Q, W, $R^6$, $R^7$ and $Z^1$-$Z^3$ have the meanings described above, where n=0. $R^1$ represents the radicals described above except for hydrogen. "Alk" represents an alkyl group, for example methyl or ethyl.

1. Step of the Preparation Process E for Preparing the Compounds According to the Invention of the General Structures (Iaw) and (Iax).

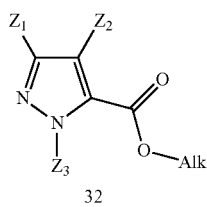

32

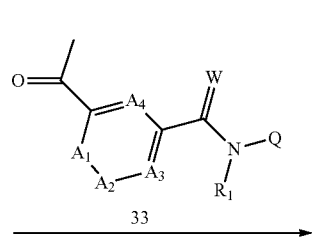

33

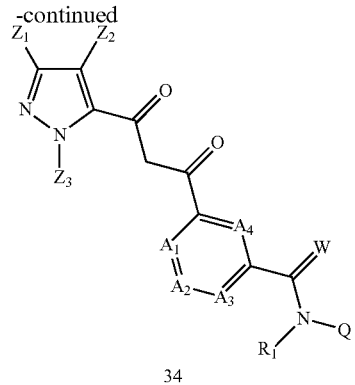

34

The $A_1$-$A_4$, W and $Z^1$-$Z^3$ radicals have the meanings described above. $R^1$ represents the radicals described above except for hydrogen. "Alk" represents an alkyl group, for example methyl or ethyl.

Compounds of the general structure 34 can be prepared analogously to processes known from the literature by reacting compounds of the general structure 32 with compounds of the general structure 33 [US2012-13684606].

2. Step of the Preparation Process F for Preparing the Compounds According to the Invention of the General Structures (Iaw) and (Iax).

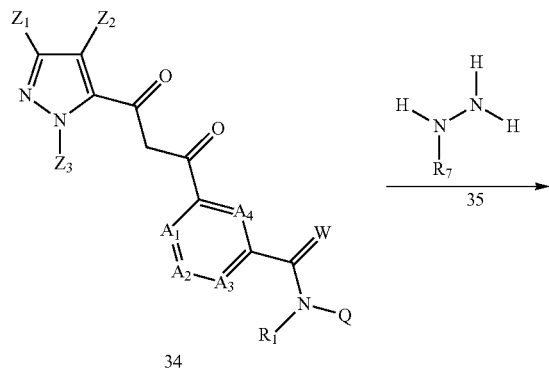

34

35

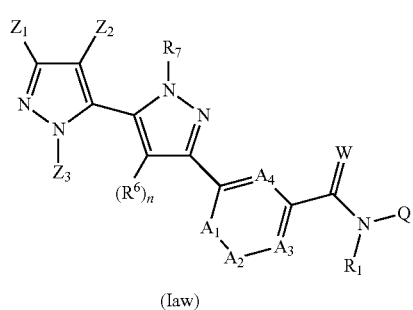
(Iaw)

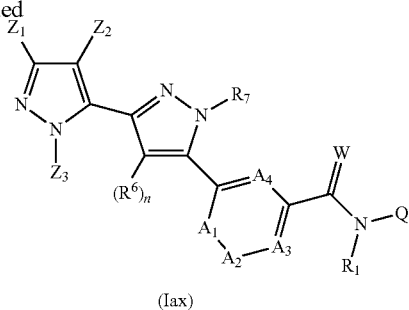
(Iax)

The radicals $A_1$-$A_4$, W, $R^6$, $R^7$ and $Z^1$-$Z^3$ have the meanings described above, where n=0. $R^1$ represents the radicals described above except for hydrogen.

Compounds of the general structure (Iaw) and (Iax) can be prepared analogously to processes known from the literature by reacting compounds of the general structure 34 with hydrazines of the general structure 35 [WO 2012052412].

Reaction Scheme 7 shows the general Preparation Process G for the compounds (Ibd) according to the invention.

Reaction Scheme 7

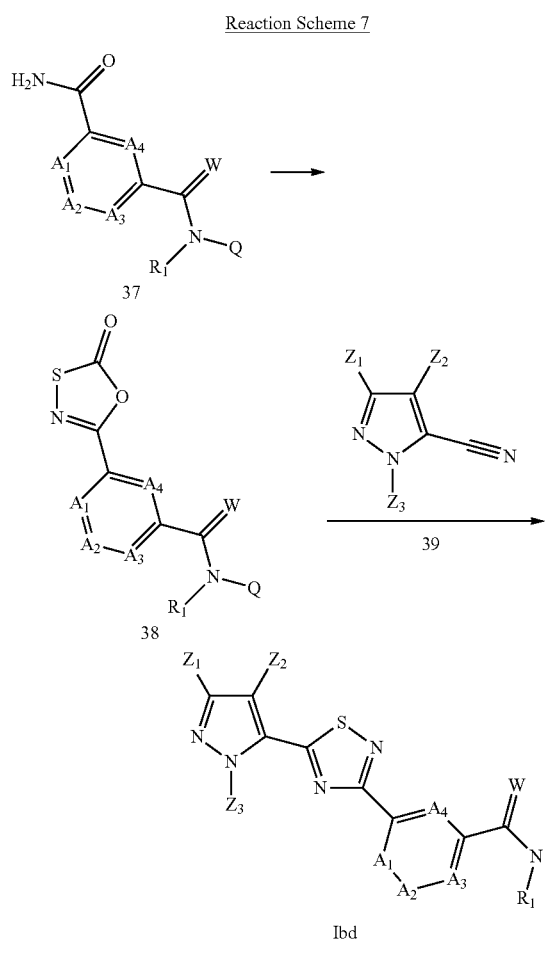

The $A_1$-$A_4$, Q, W, $R^1$ and $Z^1$-$Z^3$ radicals have the meanings described above.

1. Step of the Preparation Process G for Preparing the Compounds According to the Invention of the General Structure (Ibd).

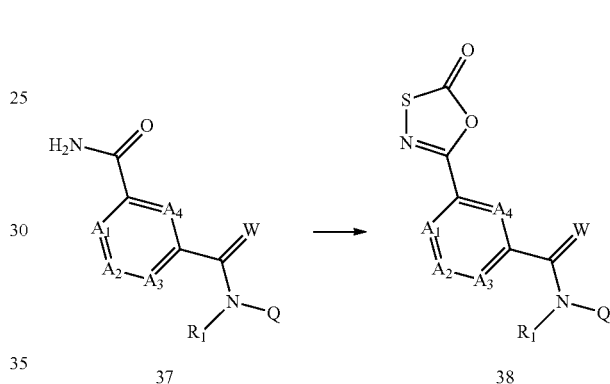

The radicals $A_1$-$A_4$, Q and W have the meanings described above.

Compounds of the general structure 38 can be prepared analogously to processes known from the literature by reacting compounds of the general structure 37 with chlorocarbonylsulphenyl chloride [WO2009-023721].

2. Step of the Preparation Process G for Preparing the Compounds According to the Invention of the General Structure (Ibd).

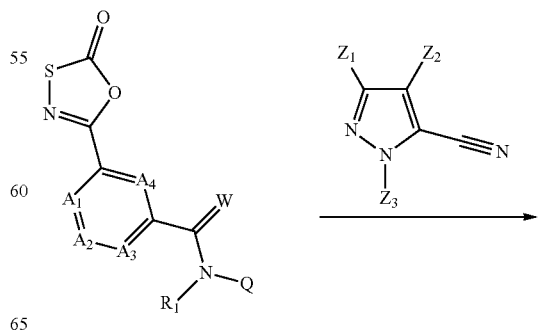

-continued

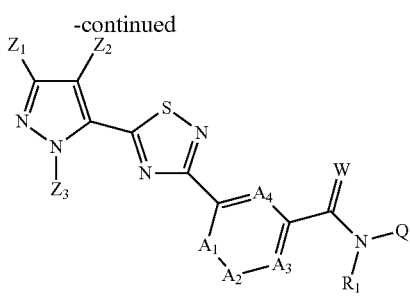

The $A_1$-$A_4$, Q, W, $R^1$ and $Z^1$-$Z^3$ radicals have the meanings described above.

Compounds of the general structure (Ibd) can be prepared analogously to processes known from the literature by reacting compounds of the general structure 38 with cyano compounds of the general structure 39 [WO2009-023721].

Reaction Scheme 8 shows the general Preparation Process H for the compounds (Ibe) according to the invention.

The $A_1$-$A_4$, Q, W, $R^1$ and $Z^1$-$Z^3$ radicals are as defined above. "X" represents a leaving group, for example chlorine or bromine. "Alk" represents an alkyl group, for example methyl or ethyl.

1. Step of the Preparation Process H for Preparing the Compounds According to the Invention of the General Structure (Ibe).

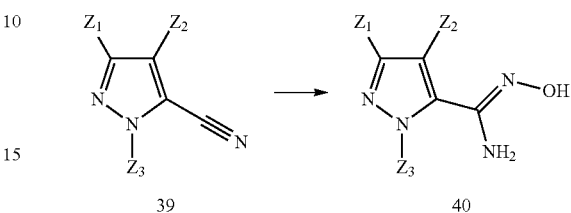

The $Z^1$-$Z^3$ radicals have the meanings described above.

Compounds of the general structure 40 can be prepared analogously to processes known from the literature by reacting compounds of the general structure 39 with N-hydroxylamine or salts thereof [WO2014-008257].

[Reaction Scheme 8]

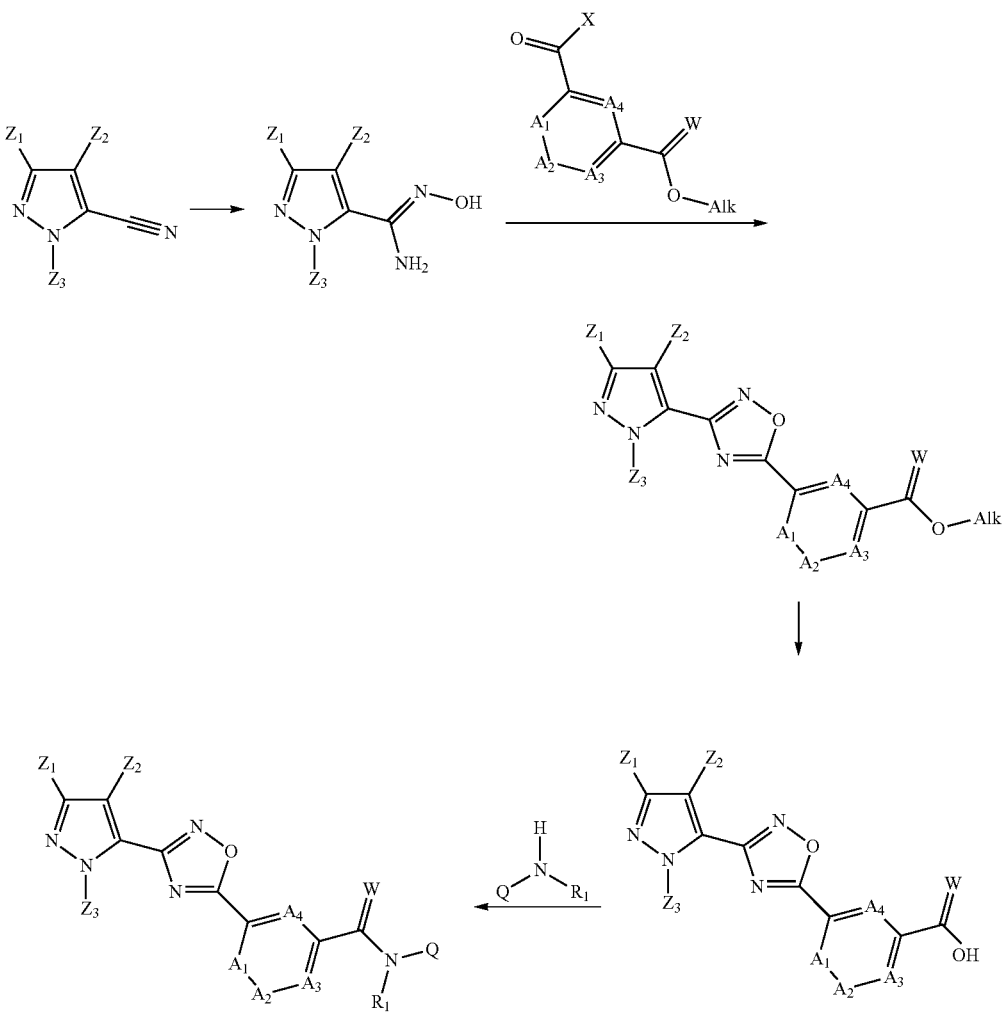

2. Step of the Preparation Process H for Preparing the Compounds According to the Invention of the General Structure (Ibe).

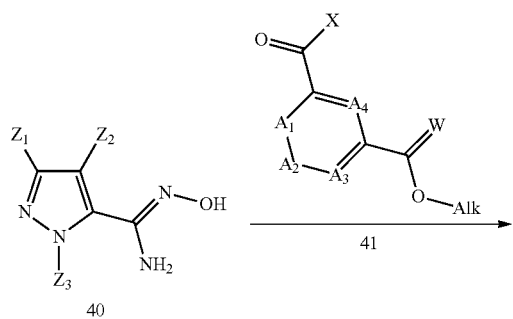

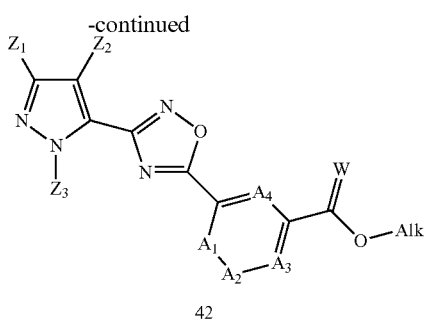

The $A_1$-$A_4$, Q, W, $R^1$ and $Z^1$-$Z^3$ radicals have the meanings described above. "X" represents a leaving group, for example chlorine or bromine. "Alk" represents an alkyl group, for example methyl or ethyl.

Compounds of the general structure 42 can be prepared analogously to processes known from the literature by reacting compounds of the general structure 40 with compounds of the general structure 41 [WO2012-035023].

The last steps for the preparation of the compounds (Ibe) according to the invention, hydrolysis of the carboxylic ester 42 and amidation of the carboxylic acid 43 with amines of the general structure 25, can be carried out analogously to processes known from the literature [WO2010-051926; WO2010-133312].

Reaction Scheme 9 shows the general Preparation Process I for the compounds (Ibf) according to the invention.

Reaction Scheme 9

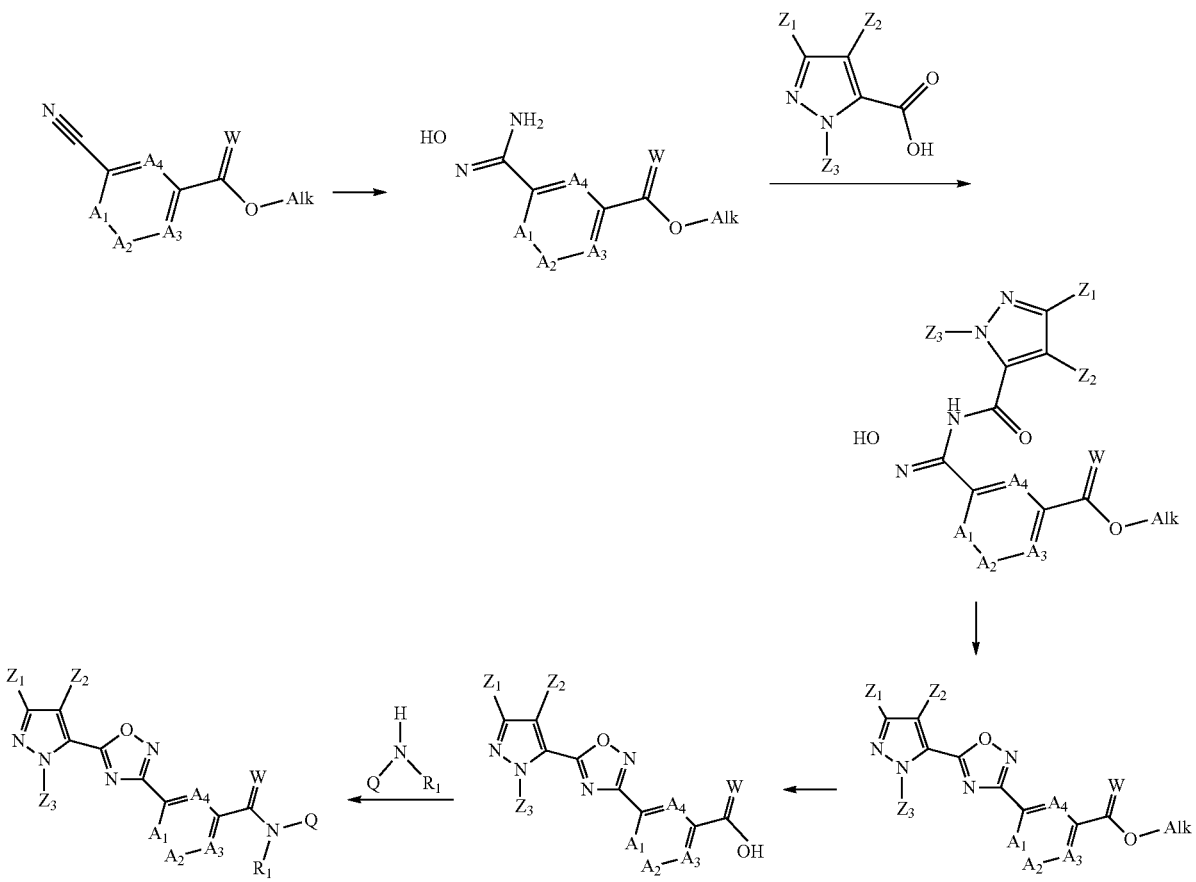

The $A_1$-$A_4$, Q, W, $R^1$ and $Z^1$-$Z^3$ radicals are as defined above. "Alk" represents an alkyl group, for example methyl or ethyl.

The 1st Step of the Preparation Process I for preparing compounds of the general structure (45) from compounds of the general structure 44 is carried out analogously to procedures known from the literature [WO2014-008257].

2. Step of the Preparation Process I for Preparing the Compounds According to the Invention of the General Structure (Ibf).

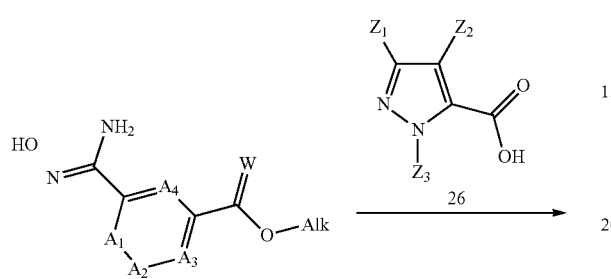

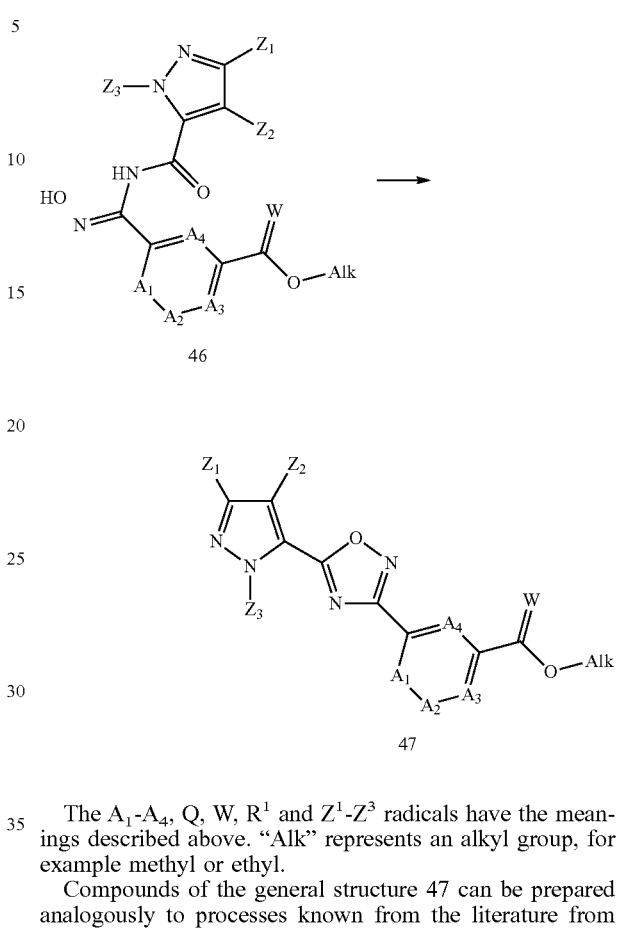

The $A_1$-$A_4$, Q, W, $R^1$ and $Z^1$-$Z^3$ radicals have the meanings described above. "Alk" represents an alkyl group, for example methyl or ethyl.

Compounds of the general structure 46 can be prepared analogously to processes known from the literature by reacting compounds of the general structure 45 with compounds of the general structure 26 [WO2008-137816].

3. Step of the Preparation Process I for Preparing the Compounds According to the Invention of the General Structure (Ibf).

The $A_1$-$A_4$, Q, W, $R^1$ and $Z^1$-$Z^3$ radicals have the meanings described above. "Alk" represents an alkyl group, for example methyl or ethyl.

Compounds of the general structure 47 can be prepared analogously to processes known from the literature from compounds of the general structure 46 [WO2008-137816].

The last steps for the preparation of the compounds (Ibf) according to the invention, hydrolysis of the carboxylic ester 47 and amidation of the carboxylic acid 48 with amines of the general structure 25, can be carried out analogously to processes known from the literature [WO2010-051926; WO2010-133312]

Reaction Scheme 10 shows the general Preparation Process J for the compounds (Iat) according to the invention.

Reaction Scheme 10

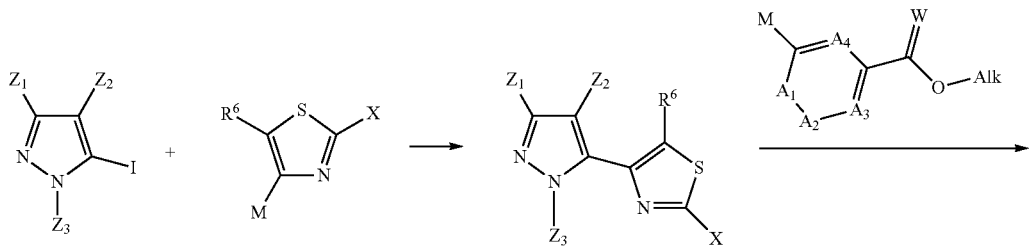

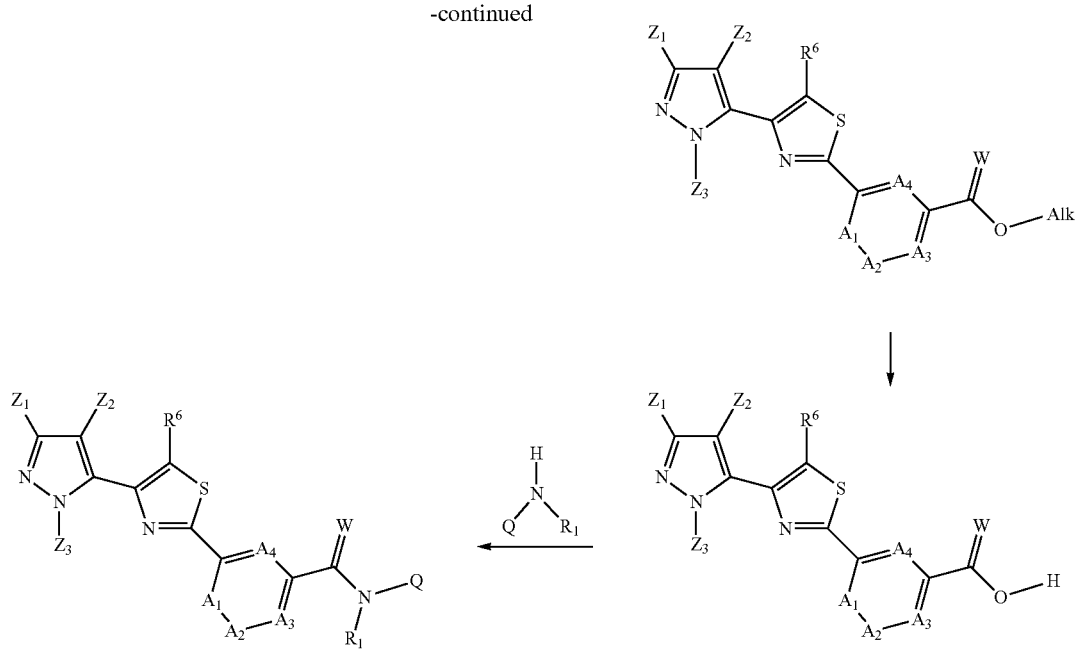

The $A_1$-$A_4$, Q, W, $R^1$ and $Z^1$-$Z^3$ radicals are as defined above. $R^6$ has the meanings described above, but preferably represents hydrogen. "X" represents chlorine or bromine, preferably chlorine. "M" represents a boronic acid, a boronic ester or a trifluoroboronate.

"Alk" represents an alkyl group, for example methyl or ethyl.

1st Step of the Preparation Process J for Preparing the Compounds According to the Invention of the General Structure (Iat).

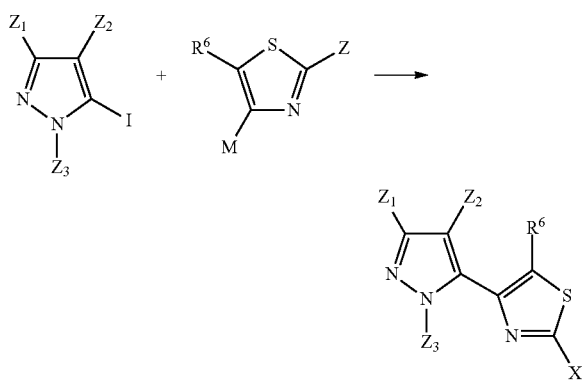

The $Z^1$-$Z^3$ radicals are as defined above. $R^6$ has the meanings described above, but preferably represents hydrogen. "X" represents chlorine or bromine, preferably chlorine. "M" represents a boronic acid, a boronic ester or a trifluoroboronate.

Compounds of the general structure 51 can be prepared analogously to processes known from the literature from compounds of the general structure 49 and 50 by transition metal-catalysed crosscoupling [WO2012142504].

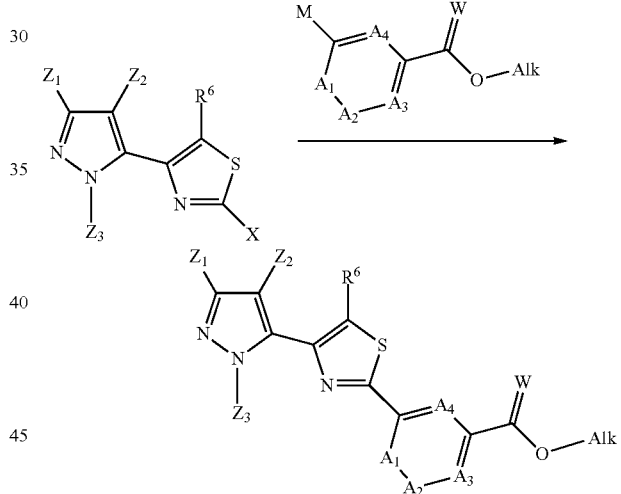

The $A_1$-$A_4$, W and $Z^1$-$Z^3$ radicals have the meanings described above. $R^6$ has the meanings described above, but preferably represents hydrogen. "X" represents chlorine or bromine, preferably chlorine. "M" represents a boronic acid, a boronic ester or a trifluoroboronate.

"Alk" represents an alkyl group, for example methyl or ethyl.

Compounds of the general structure 53 can be prepared analogously to processes known from the literature from compounds of the general structure 51 and 52 by transition metal-catalysed crosscoupling [European Journal of Organic Chemistry 2012, 31, 6248-6259].

The last steps for the preparation of the compounds (Iat) according to the invention, hydrolysis of the carboxylic ester 53 and amidation of the carboxylic acid 54 with amines of the general structure 25, can be carried out analogously to processes known from the literature [WO2010-051926; WO2010-133312].

Oxidizing agents for the oxidation of alcoholic groups are known (cf., for example, oxidation reagents in Organic Synthesis by Oxidation with Metal Compounds, Mijs, de Jonge, Plenum Verlag, New York, 1986; Manganese Compounds as Oxidizing Agents in Organic Chemistry, Arndt, Open Court Publishing Company, La Salle, Ill., 1981; The Oxidation of Organic Compounds by Permanganate Ion and Hexavalent Chromium, Lee, Open Court Publishing Company, La Salle, Ill., 1980). An oxidation can be carried out, for example, in the presence of permanganates (for example potassium permanganate), metal oxides (for example manganese dioxide, chromium oxides which are used, for example, in dipyridinechromium(VI) oxide as Collins reagent (cf. J. C. Collins et al., Tetrahedron Lett. 30, 3363-3366, 1968)). Likewise in the presence of pyridinium chlorochromate (for example Corey's reagent) (cf. also R. O. Hutchins et al., Tetrahedron Lett. 48, 4167-4170, 1977; D. Landini et al. Synthesis 134-136, 1979) or ruthenium tetroxide (cf. S.-I. Murahashi, N. Komiya Ruthenium-catalyzed Oxidation of Alkenes, Alcohols, Amines, Amides, β-Lactams, Phenols and Hydrocarbons, in: Modern Oxidation Methods, Baeckvall, Jan-Erling (Eds.), Wiley-VCH-Verlag GmbH & Co. KGaA, 2004). Likewise suitable are ultrasound-induced oxidation reactions and the use of potassium permanganate (cf. J. Yamawaki et al., Chem. Lett. 3, 379-380, 1983).

All known suitable acidic or basic reaction auxiliaries can be used according to the procedures described in the literature to deblock/remove the protecting group SG. When protecting groups of the carbamate type are used for amino groups, preference is given to using acidic reaction auxiliaries. When the t-butylcarbamate protecting group (BOC group) is used, for example, mixtures of mineral acids such as hydrochloric acid, hydrobromic acid, nitric acid, sulphuric acid, phosphoric acid, or organic acids such as benzoic acid, formic acid, acetic acid, trifluoroacetic acid, methanesulphonic acid, benzenesulphonic acid or toluenesulphonic acid, and a suitable diluent such as water and/or an organic solvent such as tetrahydrofuran, dioxane, dichloromethane, chloroform, ethyl acetate, ethanol or methanol are used. Preference is given to mixtures of hydrochloric acid or acetic acid with water and/or an organic solvent such as ethyl acetate.

It is known that some reactions and preparation processes are performable particularly efficiently in the presence of diluents or solvents and basic or acidic reaction auxiliaries. It is likewise possible to use mixtures of the diluents or solvents. The diluents or solvents are advantageously used in such an amount that the reaction mixture has good stirrability over the entire process.

Useful diluents or solvents for conducting the processes according to the invention in principle include all organic solvents which are inert under the specific reaction conditions. Examples include: hydrohalocarbons (e.g. hydrochlorocarbons, such as tetraethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (e.g. methanol, ethanol, isopropanol, butanol), ethers (e.g. ethyl propyl ether, methyl tert-butyl ether, n-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide), amines (e.g. trimethyl-, triethyl-, tripropyl-, tributylamine, N-methylmorpholine, pyridine and tetramethylenediamine), nitrohydrocarbons (e.g. nitromethane, nitroethane, nitropropane, nitrobenzene, chloronitrobenzene, o-nitrotoluene; nitriles such as acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (e.g. dimethyl, diethyl, dipropyl, dibutyl, diphenyl, dihexyl, methyl ethyl, ethyl propyl, ethyl isobutyl and pentamethylene sulphone), aliphatic, cycloaliphatic or aromatic hydrocarbons (e.g. pentane, hexane, heptane, octane, nonane and technical hydrocarbons), and also what are called "white spirits" with components having boiling points in the range from, for example, 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, nitrobenzene, xylene, esters (e.g. methyl, ethyl, butyl and isobutyl acetate, dimethyl, dibutyl and ethylene carbonate); amides (e.g. hexamethylphosphoramide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine) and ketones (e.g. acetone, acetophenone, methyl ethyl ketone, methyl butyl ketone).

The basic reaction auxiliaries used to perform the processes according to the invention may be all suitable acid binders. Examples include, alkaline earth metal or alkali metal compounds (e.g. hydroxides, hydrides, oxides and carbonates of lithium, sodium, potassium, magnesium, calcium and barium), amidine bases or guanidine bases (e.g. 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, especially tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, α-picoline, isoquinoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethyldiamine).

Acidic reaction auxiliaries used for performance of the processes according to the invention may be all mineral acids (e.g. hydrohalic acids such as hydrofluoric acid, hydrochloric acid, hydrobromic acid or hydriodic acid, and also sulphuric acid, phosphoric acid, phosphorous acid, nitric acid), Lewis acids (e.g. aluminium(III) chloride, boron trifluoride or its etherate, titanium(V) chloride, tin(V) chloride, and organic acids (e.g. formic acid, acetic acid, propionic acid, malonic acid, lactic acid, oxalic acid, fumaric acid, adipic acid, stearic acid, tartaric acid, oleic acid, methanesulphonic acid, benzoic acid, benzenesulphonic acid or para-toluenesulphonic acid).

If protecting groups are envisaged in the reaction schemes, it is possible to use any commonly known protecting groups. Especially those which are described by Greene T. W., Wuts P. G. W. in Protective Groups in Organic Synthesis; John Wiley & Sons, Inc. 1999, "Protection for the hydroxyl group including 1,2- and 1,3-diols".

Further suitable protecting groups are also
of the substituted methyl ether type (e.g. methoxymethyl ether (MOM), methylthiomethyl ether (MTM), (phenyldimethylsilyl)methoxymethyl ether (SNOM-OR), benzyloxymethyl ether (BOM-OR), para-methoxybenzyloxymethyl ether (PMBM-OR), para-nitrobenzyloxymethyl-ether, ortho-nitrobenzyloxymethyl ether (NBOM-OR), (4-methoxyphenoxy)methyl ether (p-AOM-OR), guaiacolmethyl ether (GUM-OR), t-butoxymethyl ether, 4-pentyloxymethyl ether (POM-OR), silyloxymethyl ether, 2-methoxyethoxymethyl ether (MEM-OR), 2,2,2-trichloroethoxymethyl ether, bis(2-chloroethoxy)methyl ether, 2-(trimethylsilyl)ethoxymethyl ether (SEM-OR), methoxymethyl ether (MM-OR));
of the substituted ethyl ether type (e.g. 1-ethoxyethyl ether (EE-OR), 1-(2-chloroethoxy)ethyl ether (CEE-OR), 1-[2-(trimethylsilyl)ethoxy]ethyl ether (SEE-OR), 1-methyl-1-methoxyethyl ether (MIP-OR), 1-methyl-1-benzyloxyethyl ether (MBE-OR), 1-methyl-1-benzyloxy-2-fluoroethyl ether (MIP-OR), 1-methyl-1-phenoxyethyl ether, 2,2-trichloroethyl ether, 1,1-dianisyl-2,2,2-trichloroethyl ether (DATE-OR), 1,1,1,3,3,3-hexafluoro-2-phenylisopropyl ether (HIP-OR), 2-trimethylsilylethyl ether, 2-(benzylthio)ethyl ether, 2-(phenylselenyl)ethyl ether), of an ether (e.g. tetrahydropyranyl ether (THP-OR), 3-bromotetrahydropyranyl ether (3-BrTHP-OR), tetrahydrothiopyranyl ether, 1-methoxycyclohexyl ether, 2- and 4-picolyl ether, 3-methyl-2-picolyl-N-oxido ether, 2-quinolinylmethyl ether (Qm-OR), 1-pyrenylmethyl ether, diphenylmethyl ether (DPM-OR), para, para'-dinitrobenzhydryl ether (DNB-OR), 5-dibenzosuberyl ether, triphenylmethyl ether (Tr-OR), alpha-naphthyldiphenylmethyl ether, para-methoxyphenyldiphenylmethyl ether (MMTrOR), di(para-methoxyphenyl)phenylmethyl ether (DMTr-OR), tri(para-methoxyphenyl)phenylmethyl ether (TMTr-OR), 4-(4'-bromophenacyloxy) phenyldiphenylmethyl ether, 4,4',4"-tris(4,5-dichlorophthalimidophenyl) methyl ether (CPTr-OR), 4,4',4"-tris(benzoyloxyphenyl) methyl ether (TBTr-OR), 4,4'-dimethoxy-3"-[N-(imidazolylmethyl)]trityl ether (IDTr-OR), 4,4'-dimethoxy-3"-[N-(imidazolylethyl)carbamoyl]trityl ether (IETr-OR), 1,1-bis(4-methoxyphenyl)-1'-pyrenylmethyl ether (Bmpm-OR), 9-anthryl ether, 9-(9-phenyl)xanthenyl ether (pixyl-OR), 9-(9-phenyl-10-oxo)anthryl ether (tritylone ether), 4-methoxytetrahydropyranyl ether (MTHP-OR), 4-methoxytetrahydrothiopyranyl ether, 4-methoxytetrahydrothiopyranyl S,S-dioxide, 1-[(2-chloro-4-methyl)phenyl]-4-methoxypiperidin-4-yl ether (CTMP-OR), 1-(2-fluorophenyl)-4-methoxypiperidin-4-yl ether (Fpmp-OR), 1,4-dioxan-2-yl ether, tetrahydrofuranyl ether, tetrahydrothiofuranyl ether, 2,3,3a,4,5,6,7,7a-octahydro-7,8,8-trimethyl-4,7-methanebenzofuran-2-yl ether (MBF-OR), t-butyl ether, allyl ether, propargyl ether, para-chlorophenyl ether, para-methoxyphenyl ether, para-nitrophenyl ether, para-2,4-dinitrophenyl ether (DNP-OR), 2,3,5,6-tetrafluoro-4-(trifluoromethyl)phenyl ether, benzyl ether (Bn-OR));
of the substituted benzyl ether type (for example para-methoxybenzyl ether (MPM-OR), 3,4-dimethoxybenzyl ether (DMPM-OR), ortho-nitrobenzyl ether, para-nitrobenzyl ether, para-halobenzyl ether, 2,6-dichlorobenzyl ether, para-aminoacylbenzyl ether (PAB-OR), para-azidobenzyl ether (Azb-OR), 4-azido-3-chlorobenzyl ether, 2-trifluoromethylbenzyl ether, para-(methylsulphinyl)benzyl ether (Msib-OR));
of the silyl ether type (e.g. trimethylsilyl ether (TMS-OR), triethylsilyl ether (TES-OR), triisopropylsilyl ether (TIPS-OR), dimethylisopropylsilyl ether (IPDMS-OR), diethylisopropylsilyl ether (DEIPS-OR), dimethylhexylsilyl ether (TDS-OR), t-butyldimethylsilyl ether (TBDMS-OR), t-butyldiphenylsilyl ether (TBDPS-OR), tribenzylsilyl ether, tri-para-xylylsilyl ether, triphenylsilyl ether (TPS-OR), diphenylmethylsilyl ether (DPMS-OR), di-t-butylmethylsilyl ether (DTBMS-OR), tris(trimethylsilyl)silyl ether (sisyl ether), di-t-butylmethylsilyl ether (DTBMS-OR), tris(trimethylsilyl)silyl ether (sisyl ether), (2-hydroxystyryl)dimethylsilyl ether (HSDMS-OR), (2-hydroxystyryl)diisopropylsilyl ether (HSDIS-OR), t-butylmethoxyphenylsilyl ether (TBMPS-OR), t-butoxydiphenylsilyl ether (DPTBOS-OR));
of the ester type (e.g. formate ester, benzoylformate ester, acetate ester (Ac-OR), chloroacetate ester, dichloroacetate ester, trichloroacetate ester, trifluoroacetate ester, (TFA-OR), methoxyacetate ester, triphenylmethoxyacetate ester, phenoxyacetate ester, para-chlorophenoxyacetate ester, phenylacetate ester, diphenylacetate ester (DPA-OR), nicotinate ester, 3-phenylpropionate ester, 4-pentoate ester, 4-oxopentoate ester (levulinate) (Lev-OR) 4,4-(ethylenedithio)pentanoate ester (LevS-OR), 5-[3-bis(4-methoxyphenyl)hydroxymethoxyphenyl]evulinate ester, pivaloate ester (Pv-OR), 1-adamantanoate ester, crotonate ester, 4-methoxycrotonate ester, benzoate ester (Bz-OR), para-phenylbenzoate ester, 2,4,6-trimethylbenzoate ester (mesitoate), 4-(methylthiomethoxy)butyrate ester (MTMB-OR), 2-(methylthiomethoxymethyl)benzoate ester (MTMT-OR), of the ester type (e.g. methyl carbonate, methoxymethyl carbonate, 9-fluorenylmethyl carbonate (Fmoc-OR), ethyl carbonate, 2,2,2-trichloroethyl carbonate (Troc-OR), 1,1-dimethyl-2,2,2-trichloroethyl carbonate (TCBOC-OR), 2-(trimethylsilyl)ethyl carbonate (TMS-OR), 2-(phenylsulphonyl)ethyl carbonate (Ps-OR), 2-(triphenylphosphonio) ethyl carbonate (Peoc-OR), t-butyl carbonate (Boc-OR), isobutyl carbonate, vinyl carbonate, allyl carbonate (Alloc-OR), para-nitrophenyl carbonate, benzyl carbonate (Z-OR), para-methoxybenzyl carbonate, 3,4-dimethoxybenzyl carbonate, ortho-nitrobenzyl carbonate, para-nitrobenzyl carbonate, 2-dansylethyl carbonate (Dnseoc-OR), 2-(4-nitrophenyl)ethyl carbonate (Npeoc-OR), 2-(2,4-dinitrophenyl) ethyl carbonate (Dnpeoc)), and of the sulphate type (e.g. allylsulphonate (Als-OR), methanesulphonate (Ms-OR), benzylsulphonate, tosylate (Ts-OR), 2-[(4-nitrophenyl) ethyl]sulphonate (Npes-OR)).

Catalysts suitable for performance of a catalytic hydrogenation in the process according to the invention are all the customary hydrogenation catalysts, for example platinum catalysts (e.g. platinum sheet, platinum sponge, platinum black, colloidal platinum, platinum oxide, platinum wire), palladium catalysts (e.g. palladium sponge, palladium black, palladium oxide, palladium-charcoal, colloidal palladium, palladium barium sulphate, palladium barium carbonate, palladium hydroxide), nickel catalysts (e.g. reduced nickel, nickel oxide, Raney nickel), ruthenium catalysts, cobalt catalysts (e.g. reduced cobalt, Raney cobalt), copper catalysts (e.g. reduced copper, Raney copper, Ullmann copper). Preference is given to using noble metal catalysts (e.g. platinum and palladium or ruthenium catalysts) which have optionally been applied to a suitable support (e.g. carbon or silicon), rhodium catalysts (e.g. tris(triphenylphosphine)rhodium(I) chloride in the presence of triphenylphosphine). In addition, it is possible to use "chiral hydrogenation catalysts" (for example those which contain chiral diphosphine ligands such as (2S,3S)-(−)-2,3-bis(diphenylphosphino)butane [(S,S)-Chiraphos] or (R)-(+)-2,2'- or (S)-(−)-2,2'-bis(diphenylphosphino)-1,1'-binaphthalene [R(+)-BINAP or S(−)-BINAP]), which increases the proportion of one isomer in the isomer mixture or virtually completely prevents the formation of another isomer.

Salts of the compounds according to the invention are prepared by standard methods. Representative acid addition salts are, for example, those which are formed by reaction with inorganic acids, for example sulphuric acid, hydrochloric acid, hydrobromic acid, phosphoric acid, or organic carboxylic acids such as acetic acid, trifluoroacetic acid, citric acid, succinic acid, butyric acid, lactic acid, formic acid, fumaric acid, maleic acid, malonic acid, camphoric acid, oxalic acid, phthalic acid, propionic acid, glycolic acid, glutaric acid, stearic acid, salicylic acid, sorbic acid, tartaric acid, cinnamic acid, valeric acid, picric acid, benzoic acid, or organic sulphonic acids such as methanesulphonic acid and 4-toluenesulphonic acid.

Also representative are salts of compounds according to the invention which are formed from organic bases, for example pyridine or triethylamines, or those which are formed from inorganic bases, for example hydrides, hydroxides or carbonates of sodium, lithium, calcium, magnesium or barium, when the compounds of the general formula (I) have a structural element suitable for formation of this salt.

Synthesis methods for preparation of heterocyclic N-oxides and t-amines are known. They can be obtained with peroxy acids (e.g. peracetic acid and meta-chloroperbenzoic acid (MCPBA), hydrogen peroxide), alkyl hydroperoxides (e.g. t-butyl hydroperoxide), sodium perborate and dioxiranes (e.g. dimethyldioxirane). These methods are described, for example, by T. L. Gilchrist, in Comprehensive Organic Synthesis, vol. 7, p. 748-750, 1992, S. V. Ley, (Ed.), Pergamon Press; M. Tisler, B. Stanovnik, in Comprehensive Heterocyclic Chemistry, vol. 3, p. 18-20, 1984, A. J. Boulton, A. McKillop, (Eds.), Pergamon Press; M. R. Grimmett, B. R. T. Keene in Advances in Heterocyclic Chemistry, vol. 43, p. 149-163, 1988, A. R. Katritzky, (Ed.), Academic Press; M. Tisler, B. Stanovnik, in Advances in Heterocyclic Chemistry, vol. 9, p. 285-291, 1968, A. R. Katritzky, A. J. Boulton (Eds.), Academic Press; G. W. H. Cheeseman, E. S. G. Werstiuk in Advances in Heterocyclic Chemistry, vol. 22, p. 390-392, 1978, A. R. Katritzky, A. J. Boulton, (Eds.), Academic Press.

EXPERIMENTAL PART

Preparation Process A

Descriptions of the Experiments

Example Iap-1

The preparation of 4-chloro-3-carbomethoxybenzaldehyde has already been described in the literature (WO2010011584, pages 19-20; Molinaro, Carmela; Roy, Amelie; Lau, Stephen; Trinh, Thao; Angelaud, Remy; O'Shea, Paul D.; Shultz, Scott; Cameron, Mark; Corley, Ed; Steinhuebel, Dietrich; Weisel, Mark; Krska, Shane; Abele, Stefan; Funel, Jacques-Alexis Journal of Organic Chemistry, 76 (2011) 1062-1071; WO2012114268, page 137).

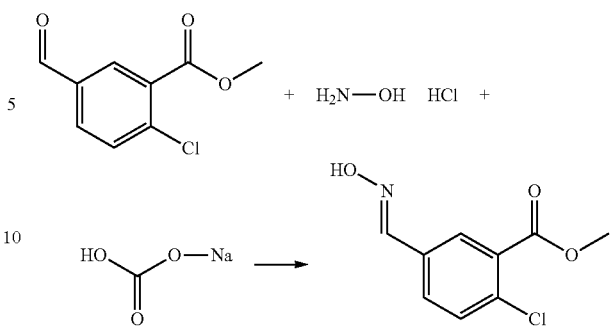

4.1 g (20.6 mmol) of 4-chloro-3-carbomethoxybenzaldehyde were dissolved in 82 ml of methanol, 1.734 g (20.6 mmol) of sodium hydrogencarbonate were added and the mixture was cooled to 0° C. 5.738 g (82.5 mmol) of hydroxylamine hydrochloride were then added and the mixture was stirred at room temperature for 2.5 hours. For workup, the mixture was then concentrated on a rotary evaporator under reduced pressure, and the residue was taken up in 100 ml of ethyl acetate. The solids were filtered off and the filtrate was concentrated on a rotary evaporator under reduced pressure. For purification, the residue was then chromatographed on a cartridge containing 120 g of silica gel using a gradient of cyclohexane/ethyl acetate 9:1 to 7:3 (v/v), giving 2.68 g of methyl 2-chloro-5-[(hydroxyimino)methyl]benzoate.

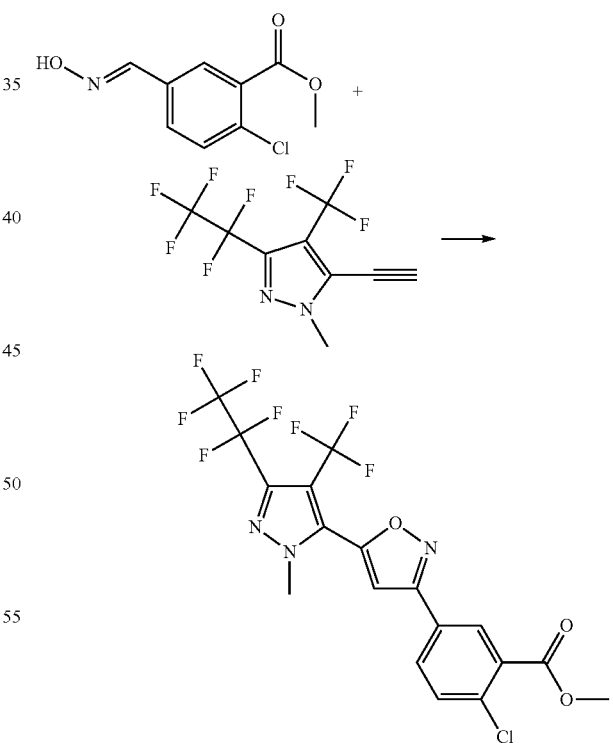

1.1 g (5.14 mmol) of methyl 2-chloro-5-[(hydroxyimino)methyl]benzoate were initially charged in 15 ml of dimethylformamide, and 756 mg (5.66 mmol) of N-chlorosuccinimide were added. The mixture was stirred at room temperature for 3.5 hours, a further 190 mg (1.42 mmol) of N-chlorosuccinimide were then added and the mixture was stirred at room temperature for a further 2 hours. The mixture was then cooled to 0° C., and a solution of 1.5 g (5.14 mmol) of 5-ethynyl-1-methyl-3-(pentafluoroethyl)-4-(trifluoromethyl)-1H-pyrazole in 5 ml of dimethylformamide was added dropwise, followed by 1.15 g (11.39 mmol) of triethylamine. The mixture was stirred at room temperature overnight. For workup, water was added and the mixture was extracted twice with dichloromethane. The combined extracts were washed four times with water, dried with sodium sulphate and concentrated on a rotary evaporator under reduced pressure. The residue was purified on a cartridge containing 40 g of silica gel using a gradient from pure cyclohexane to cyclohexane/ethyl acetate of 8:2 (v/v). This gave 0.57 g of methyl 2-chloro-5-{5-[1-methyl-3-(pentafluoroethyl)-4-(trifluoromethyl)-1H-pyrazol-5-yl]-1,2-oxazol-3-yl}benzoate.

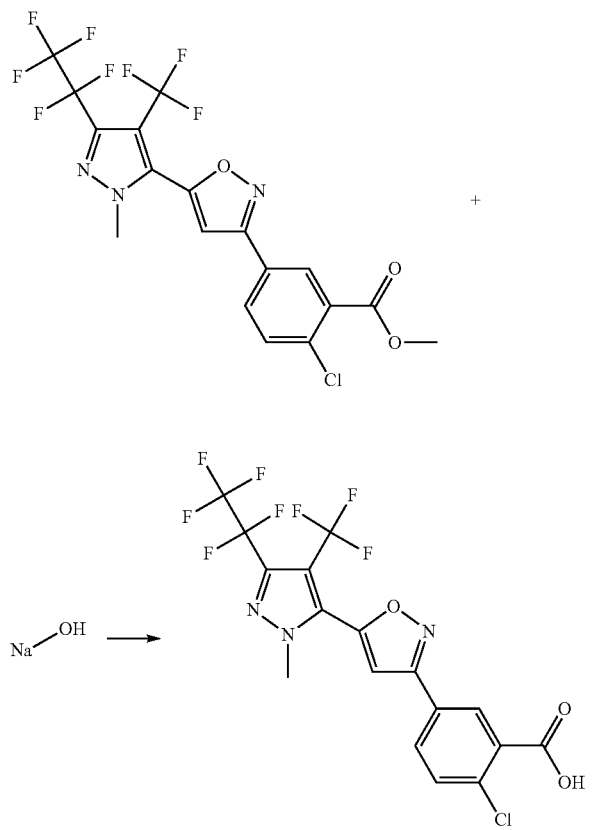

0.5 g (1.11 mmol) of methyl 2-chloro-5-{5-[1-methyl-3-(pentafluoroethyl)-4-(trifluoromethyl)-1H-pyrazol-5-yl]-1,2-oxazol-3-yl}benzoate was initially charged in 28 ml of methanol, and 1.11 ml (1.11 mmol) of 1 M aqueous sodium hydroxide solution were added. The mixture was then heated under reflux for 6 hours. The mixture was then concentrated on a rotary evaporator under reduced pressure. The residue was acidified with dilute aqueous hydrochloric acid and extracted three times with ethyl acetate, and the combined extracts were then washed once with saturated sodium chloride solution, dried with sodium sulphate and concentrated on a rotary evaporator under reduced pressure. This gave 0.54 g of 2-chloro-5-{5-[1-methyl-3-(pentafluoroethyl)-4-(trifluoromethyl)-1H-pyrazol-5-yl]-1,2-oxazol-3-yl}benzoic acid as residue.

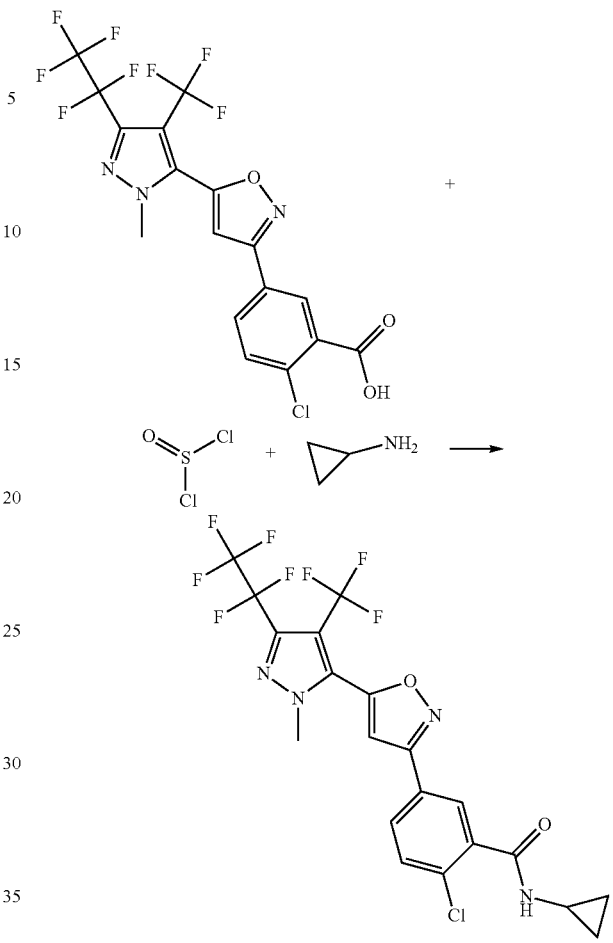

0.1 g (0.2 mmol) of 2-chloro-5-{5-[1-methyl-3-(pentafluoroethyl)-4-(trifluoromethyl)-1H-pyrazol-5-yl]-1,2-oxazol-3-yl}benzoic acid was dissolved in 1 ml of toluene, and 122 mg (1.02 mmol) of thionyl chloride were added. The mixture was heated at 80° C. for 2 hours and then concentrated on a rotary evaporator under reduced pressure. To remove residual thionyl chloride, 1 ml of dry toluene was then added and the mixture was concentrated again. The residue was then dissolved in 0.5 ml of dichloromethane, and the solution was added dropwise to a solution of 29 mg (51 mmol) of cyclopropylamine in 0.5 ml of dichloromethane at 0° C. The mixture was then stirred without cooling for one hour. For workup, the mixture was washed with 5% aqueous NaH$_2$PO$_4$ solution, dried with sodium sulphate and concentrated on a rotary evaporator under reduced pressure. The residue was purified on a 40 g cartridge containing silica gel using a gradient from cyclohexane/ethyl acetate 9:1 to cyclohexane/ethyl acetate 7:3 (v/v). This gave 63 mg of 2-chloro-N-cyclopropyl-5-{5-[1-methyl-3-(pentafluoroethyl)-4-(trifluoromethyl)-1H-pyrazol-5-yl]-1,2-oxazol-3-yl}benzamide.

HPLC-MS$^{a)}$: log P=4.06, mass (m/z)=529 [M+H]+.

$^1$H-NMR (400 MHz, d$_3$-acetonitrile): δ=7.97 (s, 1H), 7.95-7.96 (dd, J1=7.4 Hz, J2=1.5 Hz, 1H), 7.6-7.62 (dd, J1=7.4 Hz, J2=1.5 Hz, 1H), 7.31 (s, 1H), 7.02 (s (broad), 1H (N—H)), 3.97 (s, 3H), 2.83-2.88 (m, 1H), 0.76-0.8 (m, 2H), 0.586-0.625 (m, 2H).

Preparation Process B

Synthesis of N-benzyl-3-{5-[1-methyl-3-(pentafluoroethyl)-4-(trifluoromethyl)-1H-pyrazol-5-yl]-1H-1,2,4-triazol-3-yl}benzamide (Ibg-1), N-benzyl-3-{1-methyl-5-[1-methyl-3-(pentafluoroethyl)-4-(trifluoromethyl)-1H-pyrazol-5-yl]-1H-1,2,4-triazol-3-yl}benzamide (Ibg-15) and N-benzyl-3-{1-methyl-3-[1-methyl-3-(pentafluoroethyl)-4-(trifluoromethyl)-1H-pyrazol-5-yl]-1H-1,2,4-triazol-5-yl}benzamide (Ibh-2)

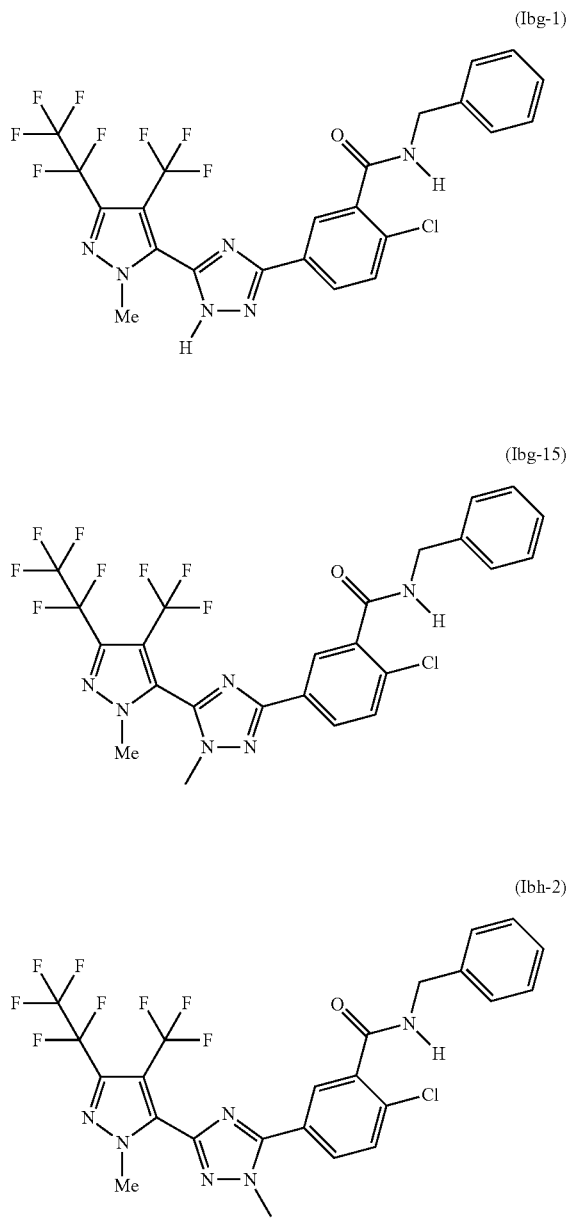

Step 1

8.4 g of methyl 1-methyl-3-(pentafluoroethyl)-4-(trifluoromethyl)-1H-pyrazole-5-carboxylate (25.7 mmol) were dissolved in 50.0 ml of ethanol p.a., and 12.5 ml of hydrazine hydrate (257 mmol) were then added dropwise. The reaction mixture was heated under reflux for 16 h. The cooled reaction mixture was diluted with 50.0 ml of water. The ethanol was removed on a rotary evaporator under reduced pressure. The aqueous phase was then extracted three times with in each case 50.0 ml of ethyl acetate. The combined organic phases were dried over anhydrous magnesium sulphate, filtered and then concentrated to dryness on a rotary evaporator.

This gave 7.80 g of 1-methyl-3-(pentafluoroethyl)-4-(trifluoromethyl)-1H-pyrazole-5-carbohydrazide as a colourless solid. The crude product was reacted further without purification.

HPLC-MS$^{a)}$: log P=2.12, mass (m/z)=327 [M+H]+.

$^1$H-NMR (400 MHz, d3-acetonitrile): δ=10.15 (s, 1H), 4.81 (s, 2H), 3.92 (s, 3H).

Step 2

200 mg of 1-methyl-3-(pentafluoroethyl)-4-(trifluoromethyl)-1H-pyrazole-5-carbohydrazide (0.61 mmol), 290 mg of N-benzyl-3-cyanobenzamide (1.22 mmol) and 42 mg of potassium carbonate (0.3 mmol) were suspended in 4.00 ml of n-butan-1-ol, and the mixture was then heated in a microwave at 150° C. for 2 h. The reaction solution was concentrated to dryness on a rotary evaporator. Twice, toluene was added to the residue and each time the mixture was concentrated again to dryness. The crude product was purified by MPLC on silica.

This gave 130 mg of N-benzyl-3-{5-[1-methyl-3-(pentafluoroethyl)-4-(trifluoromethyl)-1H-pyrazol-5-yl]-1H-1,2,4-triazol-3-yl}benzamide (Ibg-1) as a colourless solid.

HPLC-MS$^{a)}$: log P=3.80, mass (m/z)=545 [M+H]+.

$^1$H-NMR (400 MHz, d6-DMSO): δ=15.37 (s, 1H), 9.24 (t, 1H), 8.58 (s, 1H), 8.20 (d, 1H), 8.07 (d, 1H), 7.71 (t, 1H), 7.22-7.36 (m, 5H), 4.52 (d, 2H), 4.08 (s, 3H).

Step 3

102 mg (0.18 mmol) of N-benzyl-3-{4-[1-methyl-3-(pentafluoroethyl)-4-(trifluoromethyl)-1H-pyrazol-5-yl]-1H-1,2,4-triazol-3-yl}benzamide (Ibg-1) were dissolved in 4 ml of THF p.a., and 52 mg (0.36 mmol) of potassium carbonate and 26.6 mg (0.18 mmol) of methyl iodide were then added in succession with ice bath cooling. The reaction mixture was stirred at room temperature for 14 h and then diluted with water. The aqueous phase was extracted repeatedly with ethyl acetate. The combined organic phases were dried over sodium sulphate, filtered and concentrated on a rotary evaporator under reduced pressure. The crude product was purified by MPLC on silica gel.

This gave 35 mg of N-benzyl-3-{1-methyl-5-[1-methyl-3-(pentafluoroethyl)-4-(trifluoromethyl)-1H-pyrazol-5-yl]-1H-1,2,4-triazol-3-yl}benzamide (Ibg-15).

HPLC-MS$^{a)}$: log P=4.24, mass (m/z)=559 [M+H]+.

$^1$H-NMR (400 MHz, d3-acetonitrile): δ=8.53 (d, 1H), 8.23 (d, 1H), 7.80 (d, 1H), 7.67 (s, 1H), 7.59 (t, 1H), 7.39-7.32 (m, 3H) 7.29-7.24 (m, 1H), 4.57 (d, 2H), 3.87 (s, 3H), 3.85 (s, 3H).

This gave 11 mg of N-benzyl-3-{1-methyl-3-[1-methyl-3-(pentafluoroethyl)-4-(trifluoromethyl)-1H-pyrazol-5-yl]-1H-1,2,4-triazol-5-yl}benzamide (Ibh-2).

HPLC-MS$^{a)}$: log P=4.16, mass (m/z)=559 [M+H]+.

$^1$H-NMR (400 MHz, d3-acetonitrile): δ=8.23-8.22 (m, 1H), 8.02-8.00 (m, 1H), 7.96-7.93 (m, 1H), 7.70-7.66 (m, 2H), 7.40-7.34 (m, 3H), 7.29-7.25 (m, 1H), 4.58 (d, 2H), 4.06 (s, 3H), 4.03 (s, 3H).

Preparation Process C

Synthesis of 2-chloro-N-(1-cyanocyclopropyl)-5-{4-[1-methyl-3-(pentafluoroethyl)-4-(trifluoromethyl)-1H-pyrazol-5-yl]-2-furyl}benzamide (Iac-1)

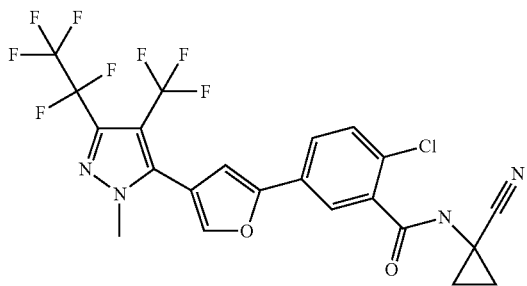 [SMILES: Cn1nc(C(F)(F)C(F)(F)F)c(C(F)(F)F)c1-c1coc(-c2ccc(Cl)c(C(=O)NC3(C#N)CC3)c2)c1]

Step 1

At −78° C., 6.50 g (44.2 mmol) of 3-bromofuran were initially charged in 65.0 ml of abs. tetrahydrofuran, and 27.6 ml of 1.6 M (44.2 mmol) n-butyllithium solution were then added. The reaction mixture was stirred at −65° C. for 15 minutes, and a solution of 12.7 g (44.2 mmol) of 5-fluoro-1-methyl-3-(pentafluoroethyl)-4-(trifluoromethyl)-1H-pyrazole in 20.0 ml of abs. tetrahydrofuran was then added at −65° C. The reaction mixture was warmed to room temperature. After 2 h at room temperature, the reaction mixture was quenched carefully with water. The tetrahydrofuran was removed under reduced pressure on a rotary evaporator. The aqueous phase was then extracted repeatedly with chloroform. The combined org. phases were dried over sodium sulphate, filtered and concentrated on a rotary evaporator under reduced pressure. The crude product was purified by MPLC on silica.

This gave 4.00 g of 5-(3-furyl)-1-methyl-3-(pentafluoroethyl)-4-(trifluoromethyl)-1H-pyrazole.

GC-MS: index=1276, mass (m/z)=334 [M]+.

$^1$H-NMR (400 MHz, d6-DMSO): δ=8.15 (s, 1H), 7.93-7.95 (m, 1H), 6.81 (s, 1H), 3.85 (s, 3H).

Step 2

1.28 g (7.19 mmol) of N-bromosuccinimide were added to 2.00 g (5.99 mmol) of 5-(3-furyl)-1-methyl-3-(pentafluoroethyl)-4-(trifluoromethyl)-1H-pyrazole dissolved in 20.0 ml THF pa. The reaction mixture was heated at 50° C. for 2 h. After cooling to room temperature, an aqueous sodium bisulphite solution was added to the reaction mixture. The mixture was extracted repeatedly with chloroform. The combined organic phases were concentrated on a rotary evaporator and the crude product obtained was purified by MPLC on silica.

This gave 1.00 g of 5-(5-bromo-3-furyl)-1-methyl-3-(pentafluoroethyl)-4-(trifluoromethyl)-1H-pyrazole of a purity of 55% according to LCMS.

HPLC-MS$^{a)}$: log P=4.49, mass (m/z)=415 [M+H]+.

Step 3

Under an atmosphere of protective gas, 31.2 ml of 2-propanol and 7.68 ml of 1M aqueous sodium bicarbonate were added to 1.04 g (2.52 mmol) of 5-(5-bromo-3-furyl)-1-methyl-3-(pentafluoroethyl)-4-(trifluoromethyl)-1H-pyrazole, 747 mg (2.52 mmol) of methyl 2-chloro-5-(4,4,5,5-tetramethyl-1,3,2-dioxaborolan-2-yl)benzoate and 145 mg (0.13 mmol) of tetrakis(triphenylphosphine)palladium(0). Prior to use, both solvents were saturated with argon by passing argon through the solvents for at least 15 minutes. The reaction mixture was stirred at 90° C. for 7 h and then at room temperature for 14 h. The reaction mixture was concentrated to dryness on a rotary evaporator under reduced pressure. The residue was taken up in a mixture of chloroform and water. The aqueous phase was extracted three times with chloroform. The combined organic phases were dried over sodium sulphate, filtered and concentrated on a rotary evaporator under reduced pressure. The crude product was purified by MPLC on silica.

This gave 350 mg of methyl 2-chloro-5-{4-[1-methyl-3-(pentafluoroethyl)-4-(trifluoromethyl)-1H-pyrazol-5-yl]-2-furyl}benzoate.

HPLC-MS$^{a)}$: log P=5.20, mass (m/z)=503 [M+H]+.

Step 4

200 mg (0.40 mmol) of methyl 2-chloro-5-{4-[1-methyl-3-(pentafluoroethyl)-4-(trifluoromethyl)-1H-pyrazol-5-yl]-2-furyl}benzoate were dissolved in a mixture of 1.43 ml of water and 11.4 ml of methanol. 19 mg (0.79 mmol) of lithium hydroxide were added to the solution, and the mixture was heated at 50° C. for 30 minutes. The reaction mixture was then stirred at room temperature for 14 h. The methanol was removed on a rotary evaporator under reduced pressure. The pH of the reaction mixture was then adjusted to 1-2 using 10% strength hydrochloric acid. The resulting precipitate was allowed to age at room temperature for 1 h and then filtered off. The solid was washed with water three times and then dried.

This gave 170 mg of 2-chloro-5-{4-[1-methyl-3-(pentafluoroethyl)-4-(trifluoromethyl)-1H-pyrazol-5-yl]-2-furyl}benzoic acid as a colourless solid.

HPLC-MS$^{a)}$: log P=4.13, mass (m/z)=489 [M+H]+.

$^1$H-NMR (400 MHz, d6-DMSO): δ=8.29 (s, 1H), 8.15 (d, 1H), 7.91 (dd, 1H), 7.66 (d, 1H), 7.46 (s, 1H), 3.92 (s, 3H).

Step 5

85 mg (0.17 mmol) of 2-chloro-5-{4-[1-methyl-3-(pentafluoroethyl)-4-(trifluoromethyl)-1H-pyrazol-5-yl]-2-furyl}benzoic acid were dissolved in 2 ml of N,N-dimethylformamide pa, and 61.4 mg (0.19 mmol) of TBTU were added. After five minutes, 91 µl (0.52 mmol) of N,N-diisopropylethylamine and 22.7 mg (0.19 mmol) of 1-aminocyclopropanecarbonitrile hydrochloride (1:1) were added. The reaction mixture was stirred at room temperature for 1 h and at 50° C. for five minutes. Without further work-up, the reaction mixture was purified by MPLC on RP18 silica gel.

This gave 40 mg of 2-chloro-N-(1-cyanocyclopropyl)-5-{4-[1-methyl-3-(pentafluoroethyl)-4-(trifluoromethyl)-1H-pyrazol-5-yl]-2-furyl}benzamide (Iac-1).

HPLC-MS$^{a)}$: log P=4.02, mass (m/z)=553 [M+H]+.

$^1$H-NMR (600 MHz, d3-acetonitrile): δ=7.86 (s, 1H), 7.83 (d, 1H), 7.80 (dd, 1H), 7.58 (s, 1H), 7.55 (d, 1H), 7.05 (s, 1H), 3.83 (s, 3H), 1.56-1.59 (m, 2H), 1.34-1.36 (m, 2H).

Preparation Process D

Synthesis of N-cyclopropyl-3-{4-[1-methyl-3-(pentafluoroethyl)-4-(trifluoromethyl)-1H-pyrazol-5-yl]-1,3,4-thiadiazol-2-yl}benzamide (Iaj-1)

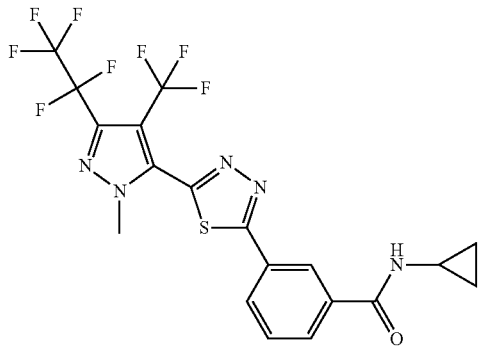 [SMILES: Cn1nc(C(F)(F)C(F)(F)F)c(C(F)(F)F)c1-c1nnc(-c2cccc(C(=O)NC3CC3)c2)s1]

Step 1

300 mg (0.92 mmol) of 1-methyl-3-(pentafluoroethyl)-4-(trifluoromethyl)-1H-pyrazole-5-carbohydrazide and 166 mg (0.92 mmol) of 3-(methoxycarbonyl)benzoic acid were dissolved in 10.5 ml of dichloromethane, and the solution was cooled to 0° C. 135 mg (1.10 mmol) of DMAP and 194 mg (1.01 mmol) of EDCl were added, and the mixture was then stirred with ice cooling for 2 h and at room temperature for 14 h. The reaction mixture was diluted with dichloromethane and washed successively with aqueous sodium bicarbonate solution and 10% strength aqueous citric acid solution. The precipitated product was filtered off and dried.

This gave 230 mg of methyl 3-[(2-{[1-methyl-3-(pentafluoroethyl)-4-(trifluoromethyl)-1H-pyrazol-5-yl]carbonyl}hydrazino)carbonyl]benzoate as a colourless solid.

HPLC-MS$^{f)}$: log P=2.06, mass (m/z)=489 [M+H]+.

$^1$H-NMR (400 MHz, d6-DMSO): δ=8.55 (s, 1H), 8.19-8.21 (m, 2H), 7.72 (t, 1H), 4.17 (s, 3H), 3.92 (s, 3H).

Step 2

In a microwave vessel, 200 mg (0.41 mmol) of methyl 3-[(2-{[1-methyl-3-(pentafluoroethyl)-4-(trifluoromethyl)-1H-pyrazol-5-yl]carbonyl}hydrazino)carbonyl]benzoate and 190 mg (0.47 mmol) of 2,4-bis(4-methoxyphenyl)-1,3,2,4-dithiadiphosphetane 2,4-disulphide (Lawesson's reagent) were dissolved in 2.6 ml of toluene, and the solution was heated at an oil bath temperature of 120° C. for 12 h. The reaction mixture was filtered and the filtrate was diluted with 5 ml of dichloromethane. The organic phase was washed once with saturated aqueous sodium bicarbonate solution. The reaction mixture was concentrated to dryness on a rotary evaporator. The crude product was purified by MPLC on silica gel.

This gave 140 mg of methyl 3-{5-[1-methyl-3-(pentafluoroethyl)-4-(trifluoromethyl)-1H-pyrazol-5-yl]-1,3,4-thiadiazol-2-yl}benzoate as a virtually colourless solid.

HPLC-MS$^{a)}$: log P=3.93, mass (m/z)=487 [M+H]+.

$^1$H-NMR (400 MHz, d6-DMSO): δ=8.61 (s, 1H), 8.38 (d, 1H), 8.21 (d, 1H), 7.80 (t, 1H), 3.98 (s, 3H), 3.94 (s, 3H).

Step 3

120 mg (0.25 mmol) of methyl 3-{5-[1-methyl-3-(pentafluoroethyl)-4-(trifluoromethyl)-1H-pyrazol-5-yl]-1,3,4-thiadiazol-2-yl}benzoate were dissolved in a 1:1 mixture of THF and water, and a solution of 21 mg (0.49 mmol) of lithium hydroxide monohydrate in 1 ml of water was added. The reaction mixture was stirred at room temperature for 14 h and then concentrated on a rotary evaporator. The residue was repeatedly extracted with tert-butyl methyl ether. The combined organic phases were concentrated to dryness on a rotary evaporator.

This gave 114 mg of 3-{5-[1-methyl-3-(pentafluoroethyl)-4-(trifluoromethyl)-1H-pyrazol-5-yl]-1,3,4-thiadiazol-2-yl}benzoic acid.

HPLC-MS$^{a)}$: log P=3.58, mass (m/z)=473 [M+H]+.

$^1$H-NMR (400 MHz, d6-DMSO): δ=8.49 (s, 1H), 8.10 (d, 1H), 8.06 (d, 1H), 7.53 (t, 1H), 3.98 (s, 3H).

Step 4

90 mg (0.19 mmol) of 3-{5-[1-methyl-3-(pentafluoroethyl)-4-(trifluoromethyl)-1H-pyrazol-5-yl]-1,3,4-thiadiazol-2-yl}benzoic acid and 11 mg (0.19 mmol) of cyclopropylamine were dissolved in 1.5 ml of dichloromethane, and the solution was cooled to 0° C. 28 mg (0.23 mmol) of DMAP and 40 mg (0.21 mmol) of EDCl were added, and the mixture was then stirred with ice cooling for 2 h and at room temperature for 14 h. The reaction mixture was diluted with dichloromethane and washed successively with aqueous sodium bicarbonate solution and 10% strength aqueous citric acid solution. The crude product was purified by MPLC on silica gel.

This gave 42 mg of N-cyclopropyl-3-{5-[1-methyl-3-(pentafluoroethyl)-4-(trifluoromethyl)-1H-pyrazol-5-yl]-1,3,4-thiadiazol-2-yl}benzamide (Iaj-1). HPLC-MS$^{a)}$: log P=3.72, mass (m/z)=512 [M+H]+.

$^1$H-NMR (400 MHz, d6-DMSO): δ=8.74 (d, 1H), 8.49 (s, 1H), 8.25 (d, 1H), 8.08 (d, 1H), 7.71 (t, 1H), 3.97 (s, 3H), 2.87-2.92 (m, 1H), 0.71-0.76 (m, 2H), 0.58-0.63 (m, 2H).

Preparation Process E

Synthesis of N-(1-cyanocyclopropyl)-3-{2-[1-methyl-3-(pentafluoroethyl)-4-(trifluoromethyl)-1H-pyrazol-5-yl]-1,3-thiazol-5-yl}benzamide (Iaq-1)

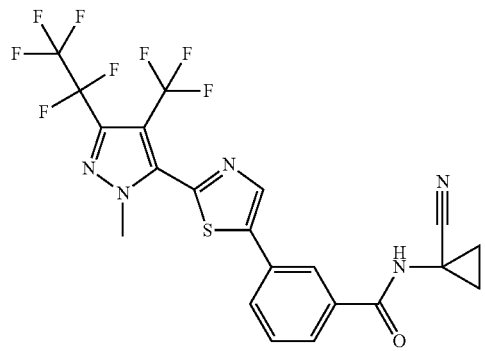 [SMILES: Cn1nc(C(F)(F)C(F)(F)F)c(C(F)(F)F)c1-c1ncc(-c2cccc(C(=O)NC3(C#N)CC3)c2)s1]

Step 1

5.00 g (16.0 mmol) of 1-methyl-3-(pentafluoroethyl)-4-(trifluoromethyl)-1H-pyrazole-5-carboxylic acid were suspended in 50 ml of dichloromethane, and 2 drops of dimethylformamide were added. A solution of 2.10 ml (24.0 mmol) of oxalyl chloride and 10 ml of dichloromethane were added dropwise to the reaction mixture. The reaction mixture was initially warmed at room temperature for 3 h and then to 40° C. for another 5 minutes. The solvents were removed using a rotary evaporator. The residue was dissolved in 5 ml of dichloromethane and added dropwise to a 33% strength ice bath-cooled solution of ammonia in water. The reaction mixture was stirred at room temperature for one hour and then concentrated to half of its volume on a rotary evaporator. The solid formed was filtered off and dried.

This gave 3.80 g of 1-methyl-3-(pentafluoroethyl)-4-(trifluoromethyl)-1H-pyrazole-5-carboxamide as a colourless solid.

HPLC-MS[a)]: log P=2.33, mass (m/z)=312 [M+H]+.

$^1$H-NMR (400 MHz, d6-DMSO): δ=8.55 (s, 1H), 8.43 (s, 1H), 3.95 (s, 3H).

Step 2

500 mg (1.61 mmol) of 1-methyl-3-(pentafluoroethyl)-4-(trifluoromethyl)-1H-pyrazole-5-carboxamide were initially charged in 12 ml of toluene, and the mixture was heated to 80° C. 390 mg (0.96 mmol) of 2,4-bis(4-methoxyphenyl)-1,3,2,4-dithiadiphosphetane 2,4-disulphide (Lawesson's reagent) were added to the reaction mixture. After 3 h, the temperature of the reaction mixture was increased from 80° C. to 95° C., and the mixture was stirred at this temperature for 14 h. After cooling, the reaction mixture was diluted with ethyl acetate and washed once with saturated aqueous sodium bicarbonate solution. The organic phase was concentrated to dryness on a rotary evaporator. The crude product was purified by MPLC on silica gel.

This gave 300 g of 1-methyl-3-(pentafluoroethyl)-4-(trifluoromethyl)-1H-pyrazole-5-carbothioamide. HPLC-MS[a)]: log P=2.92, mass (m/z)=328 [M+H]+.

$^1$H-NMR (400 MHz, d1-chloroform): δ=7.97 (s, 1H), 7.34 (s, 1H), 4.03 (s, 3H).

Step 3

Under an atmosphere of protective gas, 100 mg (0.30 mmol) of 1-methyl-3-(pentafluoroethyl)-4-(trifluoromethyl)-1H-pyrazole-5-carbothioamide, 119 mg (0.30 mmol) of methyl 3-(bromoacetyl)benzoate and 24 mg (0.30 μmol) of pyridine p.a. in ethanol p.a. were heated under reflux for 6 h. The reaction mixture was concentrated to dryness on a rotary evaporator and the resulting crude product was purified by MPLC on silica gel.

This gave 95 mg of methyl 3-{2-[1-methyl-3-(pentafluoroethyl)-4-(trifluoromethyl)-1H-pyrazol-5-yl]-1,3-thiazol-5-yl}benzoate.

HPLC-MS[a)]: log P=4.96, mass (m/z)=486 [M+H]+.

$^1$H-NMR (400 MHz, d1-chloroform): δ=8.59 (s, 1H), 8.17 (d, 1H), 8.08 (d, 1H), 7.93 (s, 1H), 7.56 (t, 1H), 4.04 (s, 3H), 3.97 (s, 3H).

Step 4

85 mg (0.18 mmol) of methyl 3-{2-[1-methyl-3-(pentafluoroethyl)-4-(trifluoromethyl)-1H-pyrazol-5-yl]-1,3-thiazol-5-yl}benzoate were dissolved in a mixture of 4 ml of THF p.a. and 2 ml of dist. water, and a solution of 15 mg (0.35 mmol) of lithium hydroxide monohydrate in 1.0 ml of dist. water was added. The reaction mixture was stirred at room temperature for 14 h. The THF was removed on a rotary evaporator under reduced pressure. With ice cooling, the aqueous reaction mixture was acidified with 1N hydrochloric acid. The resulting precipitate was filtered off and then dried.

This gave 60 mg of 3-{2-[1-methyl-3-(pentafluoroethyl)-4-(trifluoromethyl)-1H-pyrazol-5-yl]-1,3-thiazol-5-yl}benzoic acid.

HPLC-MS[a)]: log P=4.04, mass (m/z)=472 [M+H]+.

$^1$H-NMR (400 MHz, d6-DMSO): δ=8.76 (s, 1H), 8.58 (s, 1H), 8.27 (d, 1H), 7.98 (d, 1H), 7.64 (t, 1H), 3.99 (s, 3H).

Step 5

40 mg (0.09 mmol) of 3-{2-[1-methyl-3-(pentafluoroethyl)-4-(trifluoromethyl)-1H-pyrazol-5-yl]-1,3-thiazol-5-yl}benzoic acid and 12 mg (0.10 mmol) of 1-aminocyclopropanecarbonitrile hydrochloride (1:1) were suspended/dissolved in 10.0 ml of dichloromethane, and the mixture was cooled to 0° C. 25 mg (0.20 mmol) of DMAP and 18 mg (0.09 mmol) of EDCl were added, and the mixture was then stirred with ice cooling for 2 h and at room temperature for 14 h. The reaction mixture was washed successively with 1N hydrochloric acid and 1N aqueous sodium hydroxide solution. The organic phase was dried over sodium sulphate, filtered and concentrated to dryness on a rotary evaporator under reduced pressure. The crude product was purified by MPLC on silica gel.

This gave 23 mg of N-(1-cyanocyclopropyl)-3-{2-[1-methyl-3-(pentafluoroethyl)-4-(trifluoromethyl)-1H-pyrazol-5-yl]-1,3-thiazol-5-yl}benzamide (Iaq-1).

HPLC-MS[a)]: log P=3.93, mass (m/z)=536 [M+H]+.

$^1$H-NMR (400 MHz, d6-DMSO): δ=9.46 (s, 1H), 8.69 (s, 1H), 8.47 (s, 1H), 8.22 (d, 1H), 7.87 (d, 1H), 7.62 (t, 1H), 3.99 (s, 3H), 1.56-1.61 (m, 2H), 1.29-1.33 (m, 2H).

Preparation Process F

Synthesis of N-cyclopropyl-3-[2,2'-dimethyl-5'-(pentafluoroethyl)-4'-(trifluoromethyl)-2H,2'H-3,3'-bipyrazol-5-yl]-N-methylbenzamide (Iaw-1) and N-cyclopropyl-3-[1,2'-dimethyl-5'-(pentafluoroethyl)-4'-(trifluoromethyl)-1H,2'H-3,3'-bipyrazol-5-yl]-N-methylbenzamide (Iax-1)

(Iaw-1)

(Iax-1)

Step 1

Under an atmosphere of protective gas, 250 mg (1.15 mmol) of 3-acetyl-N-cyclopropyl-N-methylbenzamide were dissolved in 5 ml of THF p.a., and the solution was cooled to −78° C. Over a period of 20 minutes, 1.44 ml of a 2 M solution of lithium diisopropylamide in THF/heptane/ethylbenzene were added to the reaction solution. The reaction mixture was stirred at −78° C. for 30 minutes, and a solution of 418 mg of 1-methyl-3-(pentafluoroethyl)-4-(trifluoromethyl)-1H-pyrazole-5-carbonyl chloride, which had been freshly prepared and co-distilled repeatedly with toluene, in THF p.a., was then added. The reaction mixture was stirred at −78° C. for 1 h and then warmed to room temperature. After 30 minutes at room temperature, the reaction was quenched by addition of saturated ammonium chloride solution. The reaction mixture was extracted repeatedly with dichloromethane. The combined org. phases were washed with saturated sodium chloride solution, dried over sodium sulphate and filtered. The solvent was concentrated on a rotary evaporator. The crude product was purified by MPLC on silica gel.

This gave 160 mg of N-cyclopropyl-N-methyl-3-{3-[1-methyl-3-(pentafluoroethyl)-4-(trifluoromethyl)-1H-pyrazol-5-yl]-3-oxopropanoyl}benzamide in a purity of 86% (according to LCMS).

HPLC-MS$^{a)}$: log P=4.39, mass (m/z)=512 [M+H]+.

Step 2

100 mg (0.20 mmol) of N-cyclopropyl-N-methyl-3-{3-[1-methyl-3-(pentafluoroethyl)-4-(trifluoromethyl)-1H-pyrazol-5-yl]-3-oxopropanoyl}benzamide and 9.01 mg (0.20 mmol) of N-methylhydrazine in 10 ml of ethanol were heated under reflux. The solvent was removed on a rotary evaporator under reduced pressure. The crude product was purified by MPLC on silica gel.

This gave 16.0 mg of N-cyclopropyl-3-[2,2'-dimethyl-5'-(pentafluoroethyl)-4'-(trifluoromethyl)-2H,2'H-3,3'-bipyrazol-5-yl]-N-methylbenzamide (Iaw-1).

HPLC-MS$^{a)}$: log P=3.94, mass (m/z)=522 [M+H]+.

$^1$H-NMR (400 MHz, d6-DMSO): δ=7.85-7.92 (m, 2H), 7.47-7.51 (m, 2H), 7.27 (s, 1H), 3.86 (s, 3H), 3.76 (s, 3H), 2.99 (s, 3H), 0.33-0.63 (m, 4H).

Also isolated were 11.0 mg of N-cyclopropyl-3-[1,2'-dimethyl-5'-(pentafluoroethyl)-4'-(trifluoromethyl)-1H,2'H-3,3'-bipyrazol-5-yl]-N-methylbenzamide (tax-1).

HPLC-MS$^{a)}$: log P=4.13, mass (m/z)=522 [M+H]+.

$^1$H-NMR (400 MHz, d6-DMSO): δ=7.65-7.74 (m, 2H), 7.55-7.60 (m, 2H), 6.89 (s, 1H), 4.00 (s, 3H), 3.97 (s, 3H), 3.04 (s, 3H), 0.33-0.63 (m, 4H).

Preparation Process G

Synthesis of 2-chloro-N-cyclopropyl-5-{5-[1-methyl-3-(pentafluoroethyl)-4-(trifluoromethyl)-1H-pyrazol-5-yl]-1,2,4-thiadiazol-3-yl}benzamide (Ibd-3)

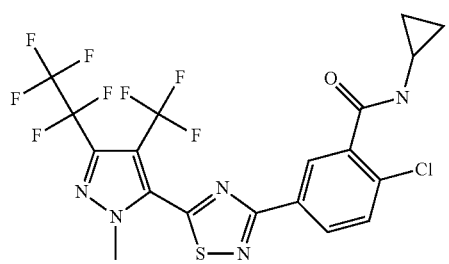 [SMILES: Cn1nc(C(F)(F)C(F)(F)F)c(C(F)(F)F)c1-c1nc(-c2ccc(Cl)c(C(=O)NC3CC3)c2)ns1]

Step 1

5.00 g (21.0 mmol) of 4-chloro-N-cyclopropylisophthalamide, 120 ml of a 3:1 toluene/1,4-dioxane mixture, 2.50 g (18.09 mmol) of potassium carbonate and 5.50 g (42.0 mmol) of chloro(chlorosulphanyl)oxomethane were initially charged successively in a 250 ml three-necked flask. The reaction mixture was stirred at 100° C. for 2 h. After cooling to room temperature, the reaction was quenched by addition of 200 ml of water, and the resulting precipitate was filtered off and dried.

This gave 2.99 g of 2-chloro-N-cyclopropyl-5-(2-oxo-1,3,4-oxathiazol-5-yl)benzamide.

$^1$H-NMR (300 MHz, d6-DMSO): δ=8.67-8.68 (m, 1H), 7.92-7.96 (m, 1H), 7.84-7.85 (m, 1H), 7.69-7.72 (m, 1H), 2.79-2.86 (m, 1H), 0.68-0.75 (m, 2H), 0.53-0.57 (m, 2H).

Step 2

593 mg (2 mmol) of 2-chloro-N-cyclopropyl-5-(2-oxo-1,3,4-oxathiazol-5-yl)benzamide were initially charged in 20 ml of decane, and 2.93 g (10 mmol) of 1-methyl-3-(pentafluoroethyl)-4-(trifluoromethyl)-1H-pyrazole-5-carbonitrile were added. In a microwave, the reaction mixture was heated at 200° C. for 1 h. The reaction mixture was poured into ice-water and the aqueous phase was extracted three times with in each case 20 ml of ethyl acetate. The combined organic phases were washed three times with in each case 10 ml of saturated sodium chloride solution, dried over sodium sulphate, filtered and concentrated on a rotary evaporator under reduced pressure. The crude product was purified by preparative HPLC (C18).

This gave 35 mg of 2-chloro-N-cyclopropyl-5-{4-[1-methyl-3-(pentafluoroethyl)-4-(trifluoromethyl)-1H-pyrazol-5-yl]-1,2,4-thiadiazol-3-yl}benzamide (Ibd-3) as a colourless solid.

HPLC-MS$^{b)}$: retention time=2.31 min; mass (m/z)=546 [M+H]+.

$^1$H-NMR (300 MHz, d6-DMSO): δ=8.64-8.66 (m, 1H), 8.26-8.29 (m, 1H), 8.18-8.19 (m, 1H), 7.71-7.73 (m, 1H), 3.97 (s, 3H), 2.80-2.87 (m, 1H), 0.70-0.73 (m, 2H), 0.54-0.56 (m, 2H).

Preparation Process H

Synthesis of 2-chloro-N-cyclopropyl-5-{3-[1-methyl-3-(pentafluoroethyl)-4-(trifluoromethyl)-1H-pyrazol-5-yl]-1,2,4-oxadiazol-5-yl}benzamide (Ibe-1)

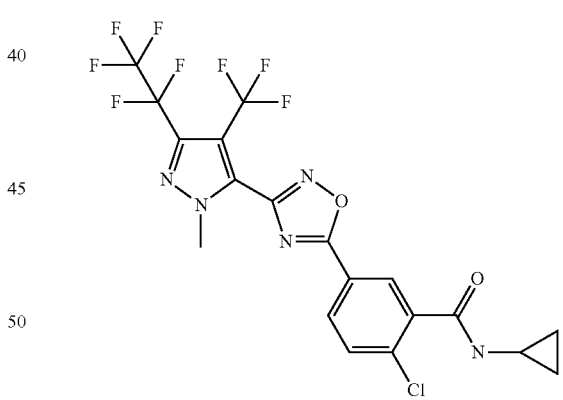

Step 1

6.0 g (20.5 mmol) of 1-methyl-3-(pentafluoroethyl)-4-(trifluoromethyl)-1H-pyrazole-5-carbonitrile were dissolved in 150 ml of ethanol, and a 50% strength solution of N-hydroxylamine in water was added. The reaction solution was stirred at room temperature for 3 h and then concentrated to dryness on a rotary evaporator under reduced pressure.

This gave 2.8 g of N'-hydroxy-1-methyl-3-(pentafluoroethyl)-4-(trifluoromethyl)-1H-pyrazole-5-carboximidamide as a yellow solid.

HPLC-MS$^{d)}$: retention time=0.93 min; mass (m/z)=237 [M+H]+.

Step 2

Successively, 2.8 g (8.59 mmol) of N'-hydroxy-1-methyl-3-(pentafluoroethyl)-4-(trifluoromethyl)-1H-pyrazole-5-carboximidamide, 100 ml of dichloromethane, 2.6 g (25.7 mmol) of triethylamine and finally 4.7 g (17.1 mmol) of tert-butyl 2-chloro-5-(chlorocarbonyl)benzoate were initially charged in a round-bottom flask. After 1 h at room temperature, the solvent was removed on a rotary evaporator. The residue was dissolved in 20 ml of DMSO, and 2.6 g (25.7 mmol) of triethylamine were added. The reaction mixture was heated in the microwave at 140° C. for 1 h. The reaction mixture was cooled to room temperature and diluted with 50 ml of water. The resulting solution was extracted three times with in each case 50 ml of ethyl acetate. The combined organic phases were washed with saturated sodium chloride solution, dried over sodium sulphate and filtered. The crude product was purified by column chromatography on silica gel.

This gave 960 mg of tert-butyl 2-chloro-5-{3-[1-methyl-3-(pentafluoroethyl)-4-(trifluoromethyl)-1H-pyrazol-5-yl]-1,2,4-oxadiazol-5-yl}benzoate as a yellow solid.

HPLC-MS[d]: retention time=1.77 min; mass (m/z)=547 [M+H]+.

Step 3

960 mg (1.76 mmol) of tert-butyl 2-chloro-5-{3-[1-methyl-3-(pentafluoroethyl)-4-(trifluoromethyl)-1H-pyrazol-5-yl]-1,2,4-oxadiazol-5-yl}benzoate were dissolved in 30 ml of trifluoroacetic acid, and the mixture was stirred at room temperature for 12 h. The reaction mixture was concentrated on a rotary evaporator under reduced pressure. The precipitated solid was filtered off and dried.

This gave 800 mg of 2-chloro-5-{3-[1-methyl-3-(pentafluoroethyl)-4-(trifluoromethyl)-1H-pyrazol-5-yl]-1,2,4-oxadiazol-5-yl}benzoic acid as a yellow solid.

HPLC-MS[e]: retention time=1.88 min; mass (m/z)=489 [M−H]−.

Step 4

Successively, 200 mg (0.41 mmol) of 2-chloro-5-{3-[1-methyl-3-(pentafluoroethyl)-4-(trifluoromethyl)-1H-pyrazol-5-yl]-1,2,4-oxadiazol-5-yl}benzoic acid, 20 ml of dimethylformamide, 158 mg (1.23 mmol) of N,N-diisopropylethylamine, 188 mg (0.5 mmol) of HATU and 46 mg (0.82 mmol) of cyclopropylamine were initially charged in a round-bottom flask. The reaction mixture was stirred at 50° C. for 2 h. The reaction mixture was diluted with 5 ml of water and the resulting solution was extracted three times with in each case 5 ml of ethyl acetate. The combined organic phases were washed with 10 ml of saturated sodium chloride solution, dried over sodium sulphate, filtered and concentrated on a rotary evaporator under reduced pressure. The crude product was purified by preparative HPLC.

This gave 26 mg of 2-chloro-N-cyclopropyl-5-{3-[1-methyl-3-(pentafluoroethyl)-4-(trifluoromethyl)-1H-pyrazol-5-yl]-1,2,4-oxadiazol-5-yl}benzamide (Ibe-1) as a colourless solid.

HPLC-MS[a]: log P=4.16, mass (m/z)=530 [M+H]+.

1H-NMR (300 MHz, d6-DMSO): δ=8.71-8.73 (m, 1H), 8.22-8.26 (m, 1H), 8.16-8.17 (m, 1H), 7.83-7.86 (m, 1H), 4.15 (s, 3H), 2.83-2.89 (m, 1H), 0.73-0.74 (m, 2H), 0.56-0.59 (m, 2H).

Preparation Process I

Synthesis of 2-chloro-N-cyclopropyl-5-{5-[1-methyl-3-(pentafluoroethyl)-4-(trifluoromethyl)-1H-pyrazol-5-yl]-1,2,4-oxadiazol-3-yl}benzamide (Ibf-1)

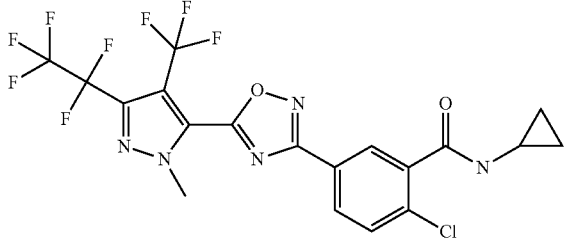 [SMILES: Cn1nc(C(F)(F)C(F)(F)F)c(C(F)(F)F)c1-c1nc(-c2ccc(Cl)c(C(=O)NC3CC3)c2)no1]

Step 1

10.0 g (51.1 mmol) of methyl 2-chloro-5-cyanobenzoate were dissolved in 150 ml of ethanol, and 2.6 g (255 mmol) of a 50% strength solution of N-hydroxylamine in water were added. The reaction mixture was stirred at room temperature overnight. The reaction mixture was concentrated on a rotary evaporator under reduced pressure. The residue was taken up in 100 ml of water and the aqueous phase was then extracted three times with in each case 100 ml of ethyl acetate. The combined organic phases were dried over sodium sulphate and then filtered. The filtrate was concentrated to dryness on a rotary evaporator under reduced pressure.

This gave 6.0 g of methyl 2-chloro-5-(N'-hydroxycarbamimidoyl)benzoate as a colourless solid.

1H-NMR (300 MHz, d6-DMSO): δ 9.86 (s, 1H), 8.1 (d, 1H), 7.85, (dd, 1H), 7.60 (d, 3H), 5.98 (brs, 2H), 3.90 (s, 3H).

Step 2

3.12 g (10.0 mmol) of 1-methyl-3-(pentafluoroethyl)-4-(trifluoromethyl)-1H-pyrazole-5-carboxylic acid, 4.41 g (15.0 mmol) of EDCI, 2.03 g (10.0 mmol) of HOBt and 2.97 g (15.0 mmol) of N,N-diisopropylethylamine were taken up in 80 ml of THF, and the mixture was stirred at room temperature for 1 h. 3.43 g (15.0 mmol) of methyl 2-chloro-5-(N'-hydroxycarbamimidoyl)benzoate were added to the reaction solution and the mixture was stirred at room temperature for 14 h. The reaction mixture was concentrated to dryness on a rotary evaporator. The residue was extracted three times with in each case 50 ml of ethyl acetate, and the combined organic phases were washed three times with in each case 50 ml of water and once with 50 ml of saturated sodium chloride solution. The organic phase was dried over sodium sulphate, filtered and concentrated to dryness on a rotary evaporator. The crude product was purified by column chromatography on silica gel.

This gave 5.26 g of methyl 2-chloro-5-(N'-hydroxy-N-{[1-methyl-3-(pentafluoroethyl)-4-(trifluoromethyl)-1H-pyrazol-5-yl]carbonyl}carbamimidoyl)benzoate.

HPLC-MS[d]: retention time=1.64 min; mass (m/z)=523 [M+H]+.

Step 3

5.23 g (10.0 mmol) of methyl 2-chloro-5-(N'-hydroxy-N-{[1-methyl-3-(pentafluoroethyl)-4-(trifluoromethyl)-1H-pyrazol-5-yl]carbonyl}carbamimidoyl)benzoate in 60 ml of toluene were heated under reflux for 14 h. The reaction mixture was concentrated on a rotary evaporator under reduced pressure. The crude product was purified by column chromatography on silica gel.

This gave 2.02 g of methyl 2-chloro-5-{5-[1-methyl-3-(pentafluoroethyl)-4-(trifluoromethyl)-1H-pyrazol-5-yl]-1,2,4-oxadiazol-3-yl}benzoate.

HPLC-MS[d]: retention time=1.80 min; mass (m/z)=not detectable

Step 4

228 mg (0.45 mmol) of methyl 2-chloro-5-{4-[1-methyl-3-(pentafluoroethyl)-4-(trifluoromethyl)-1H-pyrazol-5-yl]-1,2,4-oxadiazol-3-yl}benzoate were dissolved in 70 ml of methanol, and 15 ml (15 mmol) of 1 M aqueous sodium hydroxide solution were then added. The reaction mixture was stirred at room temperature for 14 h. The pH of the solution was adjusted to pH 3 using 1 N hydrochloric acid. The reaction solution was concentrated on a rotary evaporator under reduced pressure. The residue was extracted three times with in each case 25 ml of ethyl acetate. The combined organic phases were washed with saturated sodium chloride solution, dried over sodium sulphate and filtered. The solvent was removed on a rotary evaporator under reduced pressure.

This gave 198 g of 2-chloro-5-{5-[1-methyl-3-(pentafluoroethyl)-4-(trifluoromethyl)-1H-pyrazol-5-yl]-1,2,4-oxadiazol-3-yl}benzoic acid.

HPLC-MS[e]: retention time=1.70 min; mass (m/z)=489 [M+H]+.

Step 5

Successively, 196 mg (0.4 mmol) of 2-chloro-5-{4-[1-methyl-3-(pentafluoroethyl)-4-(trifluoromethyl)-1H-pyrazol-5-yl]-1,2,4-oxadiazol-3-yl}benzoic acid, 10 ml of dichloromethane, 10 ml of THF, 115 mg (0.6 mmol) of EDCI, 54 mg (0.4 mmol) of HOBt, 77 mg (0.6 mmol) of N,N-diisopropylethylamine were initially charged in a round-bottom flask and stirred at room temperature for 1 h. The reaction mixture was cooled using an ice/water bath, and 48 mg (0.48 mmol) of cyclopropylamine were then added. The reaction solution was stirred at room temperature for 14 h and then concentrated on a rotary evaporator under reduced pressure. The residue was extracted three times with in each case 25 ml of ethyl acetate. The combined organic phases were washed three times with saturated sodium chloride solution, dried over sodium sulphate and filtered. The solvent was removed on a rotary evaporator under reduced pressure and the crude product was then purified by column chromatography on silica gel.

This gave 62.9 mg of 2-chloro-N-cyclopropyl-5-{4-[1-methyl-3-(pentafluoroethyl)-4-(trifluoromethyl)-1H-pyrazol-5-yl]-1,2,4-oxadiazol-3-yl}benzamide (Ibf-2) as a colourless solid.

HPLC-MS[b]: retention time=5.04 min; mass (m/z)=530 [M+H]+.

1H-NMR (300 MHz, d6-DMSO): δ 8.69 (s, 1H), 8.15 (dd, 1H), 8.06 (d, 1H), 7.78 (d, 1H), 4.33 (s, 3H), 2.90-2.81 (m, 1H), 0.76-0.50 (m, 4H).

Preparation Process J

Synthesis of N-cyclopropyl-2-fluoro-5-{4-[1-methyl-3-(pentafluoroethyl)-4-(trifluoromethyl)-1H-pyrazol-5-yl]-1,3-thiazol-2-yl}benzamide (Iat-1)

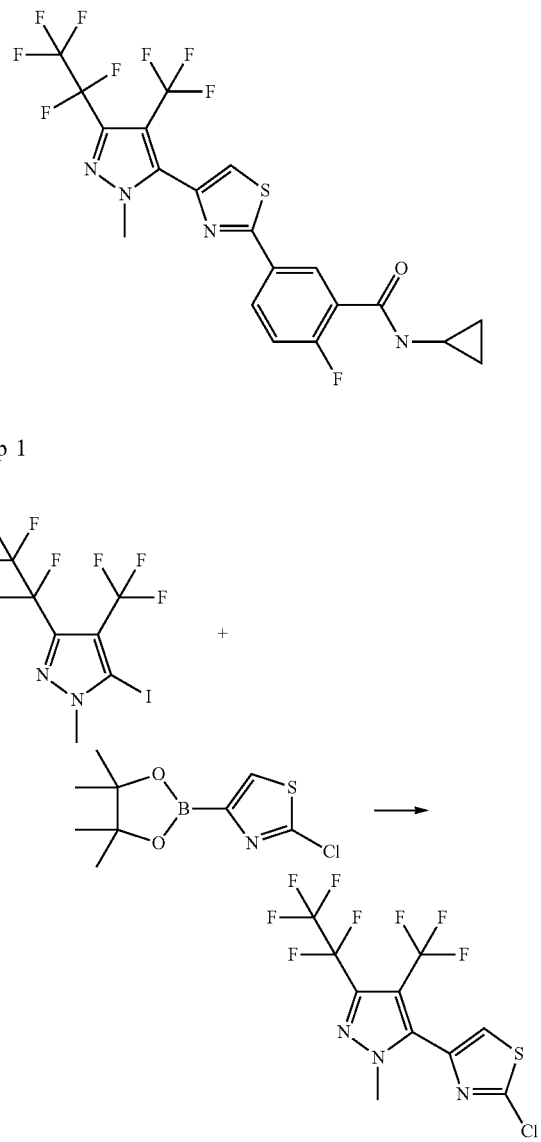

Step 1

0.5 g (1.27 mmol) of 5-iodo-1-methyl-3-(pentafluoroethyl)-4-(trifluoromethyl)-1H-pyrazole, 0.375 g (1.53 mmol) of 2-chloro-4-(4,4,5,5-tetramethyl-1,3,2-dioxaborolan-2-yl)-1,3-thiazole, 0.31 g (2.04 mmol) of caesium fluoride and 0.071 g (0.061 mmol) of tetrakis(triphenylphosphine)palladium(0) in 10 ml of dimethoxyethane were dissolved in a microwave vial. Using a canula, Ar was passed through the solution for 3 min. The reaction vessel was then closed with a crimp lid and reacted in the microwave at 100° C. for 4 h. The reaction mixture was filtered through Celite and concentrated. The crude product was dissolved in acetonitrile and purified by preparative HPLC using an RP18 column and a water/acetonitrile gradient from 9/1 to 1/9.

The target product fractions were identified by LC-MS, combined and concentrated. This gave 0.031 g of 2-chloro-4-[1-methyl-3-(pentafluoroethyl)-4-(trifluoromethyl)-1H-pyrazol-5-yl]-1,3-thiazole.

Step 2

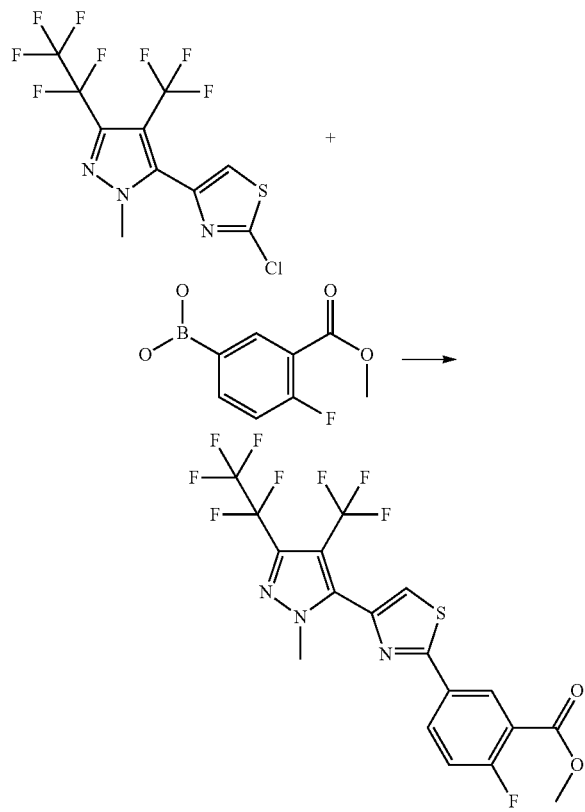

35.0 mg (0.087 mmol) of 2-chloro-4-[1-methyl-3-(pentafluoroethyl)-4-(trifluoromethyl)-1H-pyrazol-5-yl]-1,3-thiazole, 17.2 mg (0.087 mmol) of 4-fluoro-3-(methoxycarbonyl)phenylboronic acid, 8.1 mg (0.017 mmol) of 2-dicyclohexylphosphino-2',6'-diisopropoxybiphenyl and 14.22 mg (0.017 mmol) of chloro(2-dicyclohexylphosphino-2',6'-diisopropyl-1,1'-biphenyl)(2-(2-aminoethyl)phenyl) palladium (II) and 27.7 mg (0.13 mmol) of potassium phosphate were dissolved in 2 ml of dioxane in a microwave vial. Using a canula, Ar was passed through the solution for 3 min. The reaction vessel was then closed with a crimp lid and reacted in the microwave at 120° C. for 3 h. The reaction mixture was filtered through Celite and concentrated, and 2 ml of water were added. The reaction mixture was extracted 3 times with 5 ml of ethyl acetate. The org. phase was extracted with saturated NaCl solution and dried over $Na_2SO_4$. The org. phase was concentrated to dryness. The crude product was dissolved in acetonitrile and purified by preparative HPLC using an RP18 column nd a water/acetonitrile gradient from 9/1 to 1/9.

The target product fractions were identified by LC-MS, combined and concentrated. This gave 10.4 mg of methyl 2-fluoro-5-{4-[1-methyl-3-(pentafluoroethyl)-4-(trifluoromethyl)-1H-pyrazol-5-yl]-1,3-thiazol-2-yl}benzoate.

Step 3

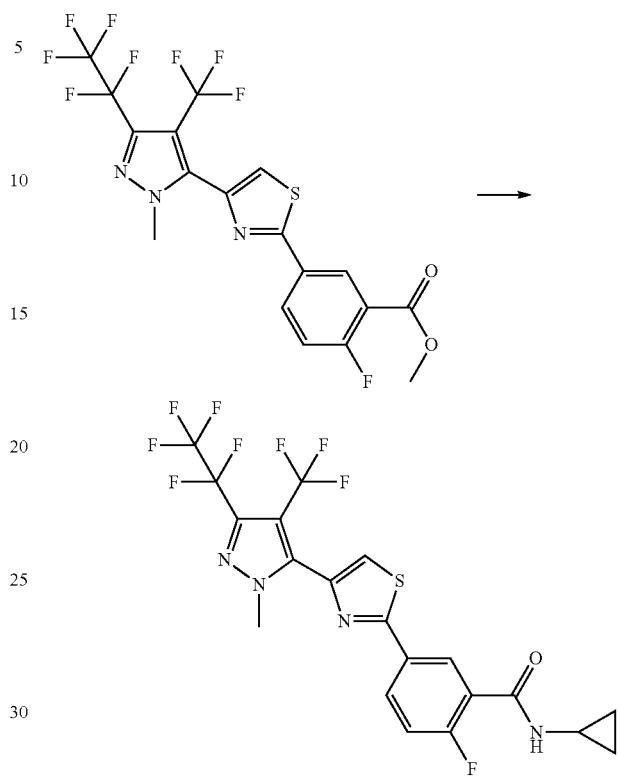

10.4 mg (0.13 mmol) of methyl 2-fluoro-5-{4-[1-methyl-3-(pentafluoroethyl)-4-(trifluoromethyl)-1H-pyrazol-5-yl]-1,3-thiazol-2-yl}benzoate were dissolved in 3 ml of dioxane, 5 mg of LiOH, dissolved in about 0.2 ml of water were added, and the reaction mixture was stirred for 12 h. This solution was neutralized with 1N HCl solution. The reaction mixture was extracted 3 times with 5 ml of ethyl acetate. The org. phase was extracted with saturated NaCl solution and dried over $Na_2SO_4$. The org. phase was concentrated to dryness. The residue was taken up in 1 ml of dichloromethane, and 1 μl of cyclopropylamine, 6 mg of HATU and 3 μl of DIEPA were added. Following reaction at 60° C. in the microwave for 30 min, the reaction mixture was concentrated and dissolved in 7 ml of acetonitrile and purified by preparative HPLC on an RP18 column using a water/acetonitrile gradient from 9/1 to 1/9.

The target product fractions were identified by LC-MS, combined and concentrated. This gave 2.5 mg of 2-chloro-4-[1-methyl-3-(pentafluoroethyl)-4-(trifluoromethyl)-1H-pyrazol-5-yl]-1,3-thiazole.

N-Cyclopropyl-2-fluoro-5-{4-[1-methyl-3-(pentafluoroethyl)-4-(trifluoromethyl)-1H-pyrazol-5-yl]-1,3-thiazol-2-yl}benzamide (Iat-1)

HPLC-MS[c]: rt=1.24 min, mass (m/z)=529 [M+H]+.

$^1$H-NMR see below Peak list

In addition to the compounds already described, the compounds listed in Tables 1-11 were prepared using the Preparation Processes A to I described above.

TABLE 1

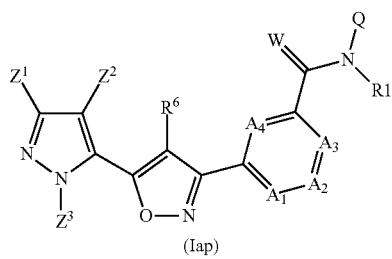

(Iap)

| Ex. No. | $Z^1$ | $Z^2$ | $Z^3$ | $R^1$ | $R^6$ | $A_4$ | $A_3$ | $A_2$ | $A_1$ | W | Q | logP[a] | Mass [m/z][a)1)] | Preparation process |
|---|---|---|---|---|---|---|---|---|---|---|---|---|---|---|
| Iap-2 | $C_2F_5$ | $CF_3$ | $CH_3$ | H | H | CH | CCl | CH | CH | O | $CH_2CF_3$ | 4.42 | 571 | A |
| Iap-3 | $C_2F_5$ | $CF_3$ | $CH_3$ | H | H | CH | CCl | CH | CH | O | 1-(cyano)cyclopropyl | 3.96 | 554 | A |
| Iap-4 | $C_2F_5$ | $CF_3$ | $CH_3$ | H | H | CH | CCl | CH | CH | O | thiethan-3-yl | 4.37 | 561 | A |
| Iap-5 | $C_2F_5$ | $CF_3$ | $CH_3$ | H | H | CH | CCl | CH | CH | O | 1-(tri-fluoromethyl)cyclopropyl | 4.55 | 597 | A |
| Iap-6 | $C_2F_5$ | $CF_3$ | $CH_3$ | H | H | CH | CCl | CH | CH | O | 2-oxo-2-(2,2,2-trifluoroethylamino)ethyl | 3.87 | 628 | A |

TABLE 2

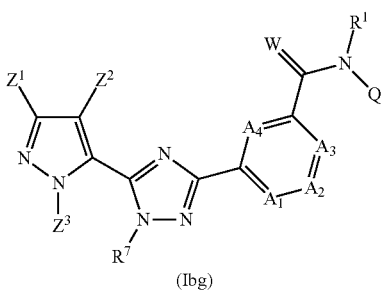

(Ibg)

| Ex. No. | $Z^1$ | $Z^2$ | $Z^3$ | $R^1$ | R7 | $A_4$ | $A_3$ | $A_2$ | $A_1$ | W | Q | logP[a] | Mass [m/z][a)1)] | Preparation process |
|---|---|---|---|---|---|---|---|---|---|---|---|---|---|---|
| Ibg-2 | $C_2F_5$ | $CF_3$ | $CH_3$ | H | H | CH | CH | CH | CH | O | cyclopropyl | 3.24 | 495 | B |
| Ibg-3 | $C_2F_5$ | $CF_3$ | $CH_3$ | H | H | CH | CH | CH | CH | O | 2,2,2-trifluoroethyl | 3.54 | 537 | B |
| Ibg-4 | $C_2F_5$ | $CF_3$ | $CH_3$ | H | $CH_3$ | CH | CCl | CH | CH | O | 2,2,2-trifluoroethyl | 4.14 | 585 | B |
| Ibg-5 | $C_2F_5$ | $CF_3$ | $CH_3$ | H | Et | CH | CCl | CH | CH | O | cyclopropyl | 4.09 | 557 | B |
| Ibg-6 | $C_2F_5$ | $CF_3$ | $CH_3$ | H | Et | CH | CCl | CH | CH | O | 2,2,2-trifluoroethyl | 4.41 | 599 | B |
| Ibg-7 | $C_2F_5$ | $CF_3$ | $CH_3$ | H | $CH_3$ | CH | CCl | CH | CH | O | cyclopropyl | 3.80 | 543 | B |
| Ibg-8 | $C_2F_5$ | $CF_3$ | $CH_3$ | H | iPr | CH | CCl | CH | CH | O | benzyl | 4.93 | 621 | B |
| Ibg-9 | $C_2F_5$ | $CF_3$ | $CH_3$ | H | Et | CH | CCl | CH | CH | O | benzyl | 4.71 | 607 | B |
| Ibg-10 | $C_2F_5$ | $CF_3$ | $CH_3$ | H | Me | CH | CCl | CH | CH | O | benzyl | 4.43 | 593 | B |
| Ibg-11 | $C_2F_5$ | $CF_3$ | $CH_3$ | H | iPr | CH | CCl | CH | CH | O | phenyl | 5.13 | 607 | B |
| Ibg-12 | $C_2F_5$ | $CF_3$ | $CH_3$ | H | Et | CH | CCl | CH | CH | O | phenyl | 4.85 | 593 | B |
| Ibg-13 | $C_2F_5$ | $CF_3$ | $CH_3$ | H | iPr | CH | CCl | CH | CH | O | cyclopropyl | 4.35 | 571 | B |
| Ibg-14 | $C_2F_5$ | $CF_3$ | $CH_3$ | H | Me | CH | CCl | CH | CH | O | phenyl | 4.56 | 579 | B |

TABLE 3

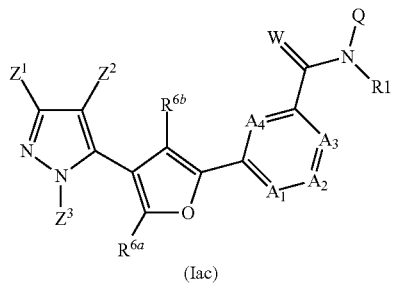

(Iac)

| Ex. No. | $Z^1$ | $Z^2$ | $Z^3$ | $R^1$ | $R^{6a}$ | $R^{6b}$ | $A_4$ | $A_3$ | $A_2$ | $A_1$ | W | Q | logP[a] | Mass [m/z][a)1)] | Preparation process |
|---|---|---|---|---|---|---|---|---|---|---|---|---|---|---|---|
| Iac-3 | $C_2F_5$ | $CF_3$ | $CH_3$ | H | H | H | CH | CCl | CH | CH | O | cyclopropyl | 4.08 | 528 | C |

TABLE 4

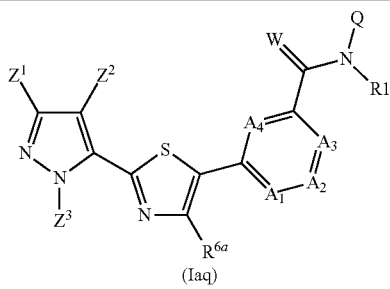

(Iaq)

| Ex. No. | $Z^1$ | $Z^2$ | $Z^3$ | $R^1$ | $R^{6a}$ | $A_4$ | $A_3$ | $A_2$ | $A_1$ | W | Q | logP[a] | Mass [m/z][a)1)] | Preparation process |
|---|---|---|---|---|---|---|---|---|---|---|---|---|---|---|
| Iaq-2 | $C_2F_5$ | $CF_3$ | $CH_3$ | H | H | CH | CH | CH | CH | O | H | 3.38 | 471 | E |

TABLE 5

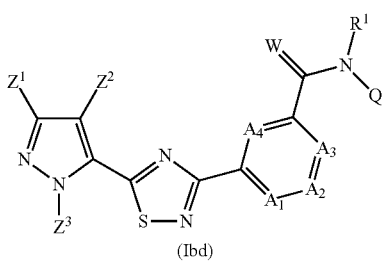

(Ibd)

| Ex. No. | $Z^1$ | $Z^2$ | $Z^3$ | $R^1$ | $A_4$ | $A_3$ | $A_2$ | $A_1$ | W | Q | logP[a] | Mass [m/z][a)1)] | Preparation process |
|---|---|---|---|---|---|---|---|---|---|---|---|---|---|
| Ibd-1 | $C_2F_5$ | $CF_3$ | $CH_3$ | H | CH | CCl | CH | CH | O | benzyl | 5.00 | 596 | G |
| Ibd-2 | $C_2F_5$ | $CF_3$ | $CH_3$ | H | CH | CCl | CH | CH | O | 4-fluorophenyl | 5.17 | 600 | G |

TABLE 6

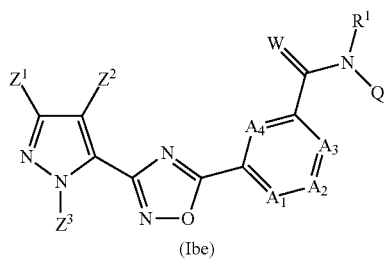

(Ibe)

| Ex. No. | $Z^1$ | $Z^2$ | $Z^3$ | $R^1$ | $A_4$ | $A_3$ | $A_2$ | $A_1$ | W | Q | logP$^{a)}$ | Mass [m/z]$^{a)1)}$ | Preparation process |
|---|---|---|---|---|---|---|---|---|---|---|---|---|---|
| Ibe-2 | $C_2F_5$ | $CF_3$ | $CH_3$ | H | CH | CCl | CH | CH | O | benzyl | 4.76 | 580 | H |
| Ibe-3 | $C_2F_5$ | $CF_3$ | $CH_3$ | H | CH | CCl | CH | CH | O | 4-fluorophenyl | 4.91 | 584 | H |
| Ibe-4 | $C_2F_5$ | $CF_3$ | $CH_3$ | H | CH | CCl | CH | CH | O | 1-(cyano)cyclopropyl | 4.01 | 555 | H |

TABLE 7

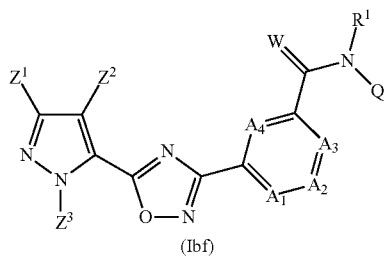

(Ibf)

| Ex. No. | $Z^1$ | $Z^2$ | $Z^3$ | $R^1$ | $A_4$ | $A_3$ | $A_2$ | $A_1$ | W | Q | logP$^{a)}$ | Mass [m/z]$^{a)1)}$ | Preparation process |
|---|---|---|---|---|---|---|---|---|---|---|---|---|---|
| Ibf-2 | $C_2F_5$ | $CF_3$ | $CH_3$ | H | CH | CCl | CH | CH | O | 1-(cyano)cyclopropyl | 4.14 | 555 | I |
| Ibf-3 | $C_2F_5$ | $CF_3$ | $CH_3$ | H | CH | CCl | CH | CH | O | cyclopropyl | 4.26 | 530 | I |

TABLE 8

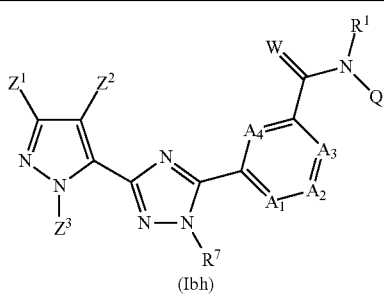

(Ibh)

| Ex. No. | $Z^1$ | $Z^2$ | $Z^3$ | $R^1$ | $R^7$ | $A_4$ | $A_3$ | $A_2$ | $A_1$ | W | Q | logP$^{a)}$ | Mass [m/z]$^{a)1)}$ | Preparation process |
|---|---|---|---|---|---|---|---|---|---|---|---|---|---|---|
| Ibh-3 | $C_2F_5$ | $CF_3$ | $CH_3$ | H | Me | CH | CCl | CH | CH | O | 2,2,2-trifluoroethyl | 3.99 | 585 | B |
| Ibh-4 | $C_2F_5$ | $CF_3$ | $CH_3$ | H | Et | CH | CCl | CH | CH | O | cyclopropyl | 3.99 | 557 | B |
| Ibh-5 | $C_2F_5$ | $CF_3$ | $CH_3$ | H | Et | CH | CCl | CH | CH | O | 2,2,2-trifluoroethyl | 4.32 | 599 | B |
| Ibh-6 | $C_2F_5$ | $CF_3$ | $CH_3$ | H | iPr | CH | CCl | CH | CH | O | cyclopropyl | 4.39 | 571 | B |
| Ibh-7 | $C_2F_5$ | $CF_3$ | $CH_3$ | H | iPr | CH | CCl | CH | CH | O | 2,2,2-trifluoroethyl | 4.68 | 613 | B |
| Ibh-8 | $C_2F_5$ | $CF_3$ | $CH_3$ | H | Me | CH | CCl | CH | CH | O | cyclopropyl | 3.67 | 543 | B |
| Ibh-9 | $C_2F_5$ | $CF_3$ | $CH_3$ | H | iPr | CH | CCl | CH | CH | O | benzyl | 4.98 | 621 | B |
| Ibh-10 | $C_2F_5$ | $CF_3$ | $CH_3$ | H | Et | CH | CCl | CH | CH | O | benzyl | 4.59 | 607 | B |
| Ibh-11 | $C_2F_5$ | $CF_3$ | $CH_3$ | H | Me | CH | CCl | CH | CH | O | benzyl | 4.29 | 593 | B |
| Ibh-12 | $C_2F_5$ | $CF_3$ | $CH_3$ | H | iPr | CH | CCl | CH | CH | O | phenyl | 5.23 | 607 | B |

TABLE 8-continued

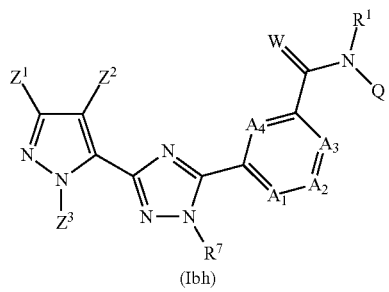

(Ibh)

| Ex. No. | $Z^1$ | $Z^2$ | $Z^3$ | $R^1$ | $R^7$ | $A_4$ | $A_3$ | $A_2$ | $A_1$ | W | Q | logP$^{a)}$ | Mass [m/z]$^{a)1)}$ | Preparation process |
|---|---|---|---|---|---|---|---|---|---|---|---|---|---|---|
| Ibh-13 | $C_2F_5$ | $CF_3$ | $CH_3$ | H | Et | CH | CCl | CH | CH | O | phenyl | 4.73 | 593 | B |
| Ibh-14 | $C_2F_5$ | $CF_3$ | $CH_3$ | H | Me | CH | CCl | CH | CH | O | phenyl | 4.42 | 579 | B |

TABLE 9

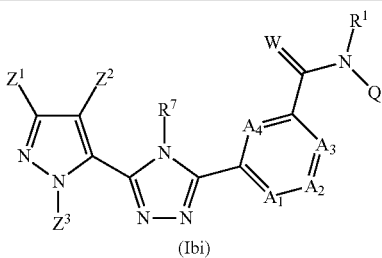

(Ibi)

| Ex. No. | $Z^1$ | $Z^2$ | $Z^3$ | $R^1$ | $R^7$ | $A_4$ | $A_3$ | $A_2$ | $A_1$ | W | Q | logP$^{a)}$ | Mass [m/z]$^{a)1)}$ | Preparation process |
|---|---|---|---|---|---|---|---|---|---|---|---|---|---|---|
| Ibi-1 | $C_2F_5$ | $CF_3$ | $CH_3$ | H | H | CH | CCl | CH | CH | O | benzyl | 4.00 | 579 | B |
| Ibi-2 | $C_2F_5$ | $CF_3$ | $CH_3$ | H | H | CH | CCl | CH | CH | O | 2,2,2-trifluoroethyl | 3.73 | 571 | B |
| Ibi-3 | $C_2F_5$ | $CF_3$ | $CH_3$ | H | H | CH | CCl | CH | CH | O | cyclopropyl | 3.40 | 529 | B |
| Ibi-4 | $C_2F_5$ | $CF_3$ | $CH_3$ | H | H | CH | CCl | CH | CH | O | phenyl | 4.13 | 565 | B |

TABLE 10

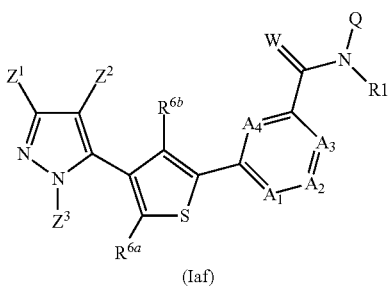

(Iaf)

| Ex. No. | $Z^1$ | $Z^2$ | $Z^3$ | $R^1$ | $R^{6a}$ | $R^{6b}$ | $A_4$ | $A_3$ | $A_2$ | $A_1$ | W | Q | logP$^{a)}$ | Mass [m/z]$^{a)1)}$ | Preparation process |
|---|---|---|---|---|---|---|---|---|---|---|---|---|---|---|---|
| Iaf-1 | $C_2F_5$ | $CF_3$ | $CH_3$ | H | H | H | CH | CCl | CH | CH | O | cyclopropyl | 4.31 | 544 | C |

TABLE 11

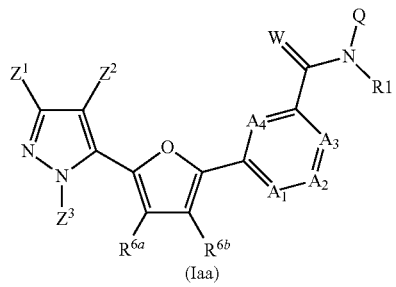

(Iaa)

| Ex. No. | $Z^1$ | $Z^2$ | $Z^3$ | $R^1$ | $R^{6a}$ | $R^{6b}$ | $A_4$ | $A_3$ | $A_2$ | $A_1$ | W | Q | logP[a] | Mass [m/z][a)1)] | Preparation process |
|---|---|---|---|---|---|---|---|---|---|---|---|---|---|---|---|
| Iaa-1 | $C_2F_5$ | $CF_3$ | $CH_3$ | H | H | H | CH | CCl | CH | CH | O | 1-(cyano)cyclopropyl | 4.08 | 553 | C |

[1] The stated mass is the peak of the isotope pattern of the [M+H]+ ion of the highest intensity; if the [M−H]− ion was detected, the stated mass is identified with [2].

[2] The stated mass is the peak of the isotope pattern of the [M−H]− ion of the highest intensity.

[a)] Note regarding the determination of the log P values and mass detection: The determination of the given log P values was carried out in accordance with EEC Directive 79/831 Annex V.A8 by HPLC (High Performance Liquid Chromatography) on a reversed-phase column (C18). Agilent 1100 LC system; 50*4.6 Zorbax Eclipse Plus C18 1.8 micron; mobile phase A: acetonitrile (0.1% formic acid); mobile phase B: water (0.09% formic acid); linear gradient from 10% acetonitrile to 95% acetonitrile in 4.25 min, then 95% acetonitrile for a further 1.25 min; oven temperature 55° C.; flow rate: 2.0 ml/min. Mass detection is effected by means of an Agilend MSD system.

[b)] Note regarding the determination of the retention time and mass detection: The stated retention times were determined on a reversed-phase column (C18) Shimadzu LCMS 2020; 50*3.0 Shimadzu shim-pack XR-ODS 2.2 micron; mobile phase A: water (0.05% TFA); mobile phase B: acetonitrile; linear gradient from 5% acetonitrile to 95% acetonitrile in 6.00 min, then 95% acetonitrile for a further 1.1 min; oven temperature 40° C.; flow rate: 1.0 ml/min.

[c)] Note regarding the determination of the retention time and mass detection: Instrument: Waters ACQUITY SQD UPLC system; column. Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A oven: 50° C.; flow rate: 0.40 ml/min; UV detection: 208-400 nm.

[d)] Note regarding the determination of the retention time and mass detection: The stated retention times were determined on a reversed-phase column (C18) Shimadzu LCMS 2020; 50*3.0 Shimadzu shim-pack XR-ODS 2.2 micron; mobile phase A: water (0.05% TFA); mobile phase B: acetonitrile; linear gradient from 5% acetonitrile to 100% acetonitrile in 1.2 min, then 100% acetonitrile for a further 1.1 min; oven temperature 40° C.; flow rate: 1.0 ml/min.

[e)] Note regarding the determination of the retention time and mass detection: The stated retention times were determined on a reversed-phase column (C18) Shimadzu LCMS 2020; 50*3.0 Shimadzu shim-pack XR-ODS 2.2 micron; mobile phase A: water (0.1% formic acid); mobile phase B: acetonitrile (0.1% formic acid); linear gradient from 5% acetonitrile to 100% acetonitrile in 1.2 min, then 100% acetonitrile for a further 1.1 min; oven temperature 40° C.; flow rate: 1.0 ml/min.

[f)] Note regarding the determination of the log P values and mass detection: The determination of the given log P values was carried out in accordance with EEC Directive 79/831 Annex V.A8 by HPLC (High Performance Liquid Chromatography) on a reversed-phase column (C18). Agilent 1100 LC system; 50*4.6 Zorbax Eclipse Plus C18 1.8 micron; mobile phase A: acetonitrile; mobile phase B: water (+79 mg of ammonium bicarbonate/l); linear gradient from 10% acetonitrile to 95% acetonitrile in 4.25 min, then 95% acetonitrile for a further 1.55 min; oven temperature 55° C.; flow rate: 2.0 ml/min. Mass detection is effected by means of an Agilend MSD system.

NMR Data of Selected Examples
NMR Peak List Method

The 1H NMR data of selected examples are stated in the form of 1H NMR peak lists. For each signal peak, first the δ value in ppm and then the signal intensity in round brackets are listed. The δ value—signal intensity number pairs for different signal peaks are listed with separation from one another by semicolons.

The peak list for one example therefore takes the form of: $\delta_1$ (intensity$_1$); $\delta_2$ (intensity$_2$); . . . ; $\delta_i$ (intensity$_i$); . . . ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of 1H NMR spectra we use tetramethylsilane and/or the chemical shift of the solvent, particularly in the case of spectra measured in DMSO. Therefore, the tetramethylsilane peak may, but need not, occur in NMR peak lists.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds, which likewise form the subject-matter of the invention, and/or peaks of impurities.

In the reporting of compound signals in the delta range of solvents and/or water, our lists of 1H NMR peaks show the usual solvent peaks, for example peaks of DMSO in DMSO-$D_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in this case to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in Research Disclosure Database Number 564025.

Example Iaa-1: $^1$H-NMR (600.1 MHz, CD3CN): δ =
7.832(3.2); 7.828(4.1); 7.811(2.4); 7.807(1.7); 7.797(2.5); 7.793(2.1); 7.603(1.5); 7.545(3.8); 7.531(3.4); 7.089(4.0); 7.083(4.6); 7.011(3.7); 7.005(3.2); 5.447(1.2); 3.995(16.0); 2.142(7.2); 1.957(0.6); 1.953(0.7); 1.949(3.8); 1.945(6.7); 1.941(9.8); 1.937(6.6); 1.933(3.3); 1.594(1.7); 1.585(4.1); 1.580 (4.1); 1.571(2.0); 1.360(2.1); 1.350(4.1); 1.346(4.3); 1.336(1.7); 0.000(1.3)

Example Iac-1: $^1$H-NMR (600.1 MHz, CD3CN): δ =
7.863(5.5); 7.827(3.2); 7.823(4.0); 7.805(2.1); 7.801(1.6); 7.790(2.2); 7.787(1.9); 7.782(0.3); 7.582(1.6); 7.552(3.7); 7.538(3.3); 7.424(0.4); 7.048(5.0); 3.835(16.0); 3.810(4.4); 3.638(0.9); 3.412(0.3); 3.282(1.7); 3.273(1.7); 2.142(1.6); 1.964(0.8); 1.956(2.3); 1.952(2.8); 1.948(15.4); 1.944(26.8); 1.939(39.4); 1.935(26.8); 1.931(13.6); 1.591(1.6); 1.581(4.2); 1.577(4.2); 1.568(2.0); 1.364(2.0); 1.354(4.1); 1.350(4.3); 1.340(1.7); 1.272(0.3); 0.000 (5.2)

Example Iac-3: $^1$H-NMR (400.0 MHz, $d_6$-DMSO): δ =
8.582(2.5); 8.571(2.4); 8.315(1.2); 8.270(6.0); 8.078(0.4); 8.074(0.4); 7.813(1.8); 7.807(2.4); 7.792(2.1); 7.784(6.0); 7.602(3.8); 7.592(0.5); 7.582(3.1); 7.551(0.4); 7.529(0.4); 7.421(5.8); 7.178(0.4); 6.924(0.4); 6.919(0.4); 5.755(2.7); 3.907(16.0); 3.710(1.4); 3.324(129.5); 3.301(1.6); 2.861(0.8); 2.852(1.1); 2.843(1.6); 2.833(1.5); 2.824(1.1); 2.815(0.7); 2.676(0.6); 2.671(0.7); 2.667(0.5); 2.506(84.3); 2.502(105.1); 2.498(79.3); 2.333(0.6); 2.329 (0.7); 0.735(1.0); 0.723(2.9); 0.718(3.7); 0.705(3.6); 0.700(3.0); 0.688(1.4); 0.672(0.4); 0.667(0.4); 0.565(1.4); 0.555(3.8); 0.548(3.7); 0.539(3.1); 0.527(0.9); 0.464(0.5); 0.457(0.4); 0.146(0.5); 0.009(10.9); 0.000(109.4); −0.149(0.6)

Example Iaf-1: $^1$H-NMR (400.0 MHz, $d_6$-DMSO): δ =
8.578(2.3); 8.567(2.4); 8.051(4.9); 7.842(4.8); 7.752(1.5); 7.746(2.1); 7.725(7.0); 7.572(3.6); 7.552(2.9); 3.862(0.7); 3.846(16.0); 3.565(0.5); 3.327 (38.2); 2.854(0.6); 2.844(1.0); 2.836(1.4); 2.826(1.4); 2.817(1.0); 2.808(0.7); 2.671(0.5); 2.502(71.9); 2.329(0.5); 2.086(0.4); 1.398(4.4); 0.731(0.8); 0.713(3.6); 0.701(3.4); 0.695(3.0); 0.684(1.2); 0.563(1.1); 0.552(3.6); 0.545(3.7); 0.537(3.2); 0.524(0.9); 0.000(41.8)

Example Iaj-1: $^1$H-NMR (400.0 MHz, $d_6$-DMSO): δ =
8.749(1.8); 8.739(1.8); 8.486(3.8); 8.316(0.4); 8.263(1.8); 8.243(1.9); 8.086(1.9); 8.066(2.1); 7.727(1.9); 7.708(3.5); 7.688(1.6); 5.756(0.8); 4.288(1.0); 3.973(16.0); 3.324(145.3); 2.917(0.6); 2.908(0.9); 2.899(1.4); 2.889(1.4); 2.881(0.9); 2.871(0.7); 2.675(0.6); 2.671(0.9); 2.667(0.6); 2.524(1.9); 2.506(96.8); 2.502(127.5); 2.498(94.2); 2.333(0.6); 2.329(0.9); 2.324(0.6); 0.760(0.8); 0.746(2.3); 0.742(3.4); 0.730(3.0); 0.723(2.7); 0.713(1.2); 0.674 (0.4); 0.634(1.2); 0.623(3.7); 0.616(3.3); 0.608(2.6); 0.595(0.8); 0.008(1.8); 0.000(56.9); −0.008(2.4)

Example Iap-1: $^1$H-NMR (400.0 MHz, CD3CN): δ =
7.969(8.9); 7.965(3.7); 7.950(2.8); 7.945(1.6); 7.621(2.7); 7.617(1.5); 7.602(1.6); 7.598(2.4); 7.312(7.0); 7.019(1.0); 5.448(0.9); 3.967(16.0); 2.879 (0.7); 2.870(1.0); 2.861(1.6); 2.851(1.6); 2.843(1.1); 2.833(0.8); 2.473(0.4); 2.468(0.8); 2.464(1.0); 2.459(0.7); 2.454(0.4); 2.167(275.2); 2.120(0.7); 2.114(1.0); 2.108(1.2); 2.101(0.9); 2.095(0.5); 1.964(7.0); 1.958(20.9); 1.952(84.6); 1.946(148.5); 1.940(190.5); 1.934(131.6); 1.928(67.1); 1.781(0.5); 1.775(0.9); 1.769(1.1); 1.763(0.8); 1.756(0.4); 1.270(1.2); 0.804(0.8); 0.791(2.8); 0.786(3.4); 0.773(3.7); 0.768(2.6); 0.756(1.1); 0.625(1.1); 0.615 (3.0); 0.613(3.1); 0.608(3.3); 0.604(3.0); 0.599(2.7); 0.586(0.8); 0.146(2.4); 0.027(0.3); 0.000(539.7); −0.009(31.0); −0.037(0.4); −0.039(0.4); −0.041(0.4); −0.042(0.4); −0.045(0.4); −0.150(2.4)

Example Iap-2: $^1$H-NMR (400.0 MHz, CD3CN): δ =
8.020(7.6); 8.001(2.4); 7.996(1.5); 7.671(2.3); 7.649(2.1); 7.485(0.8); 7.328(7.0); 4.153(0.8); 4.137(0.9); 4.130(2.4); 4.113(2.4); 4.106(2.5); 4.090(2.4); 4.083(1.0); 4.066(0.9); 3.969(16.0); 2.467(0.3); 2.463(0.4); 2.458(0.3); 2.165(115.1); 2.113(0.4); 2.107(0.4); 1.971(1.0); 1.964(2.6); 1.958(6.5); 1.952(29.7); 1.946(52.8); 1.940(69.5); 1.934(47.9); 1.928(24.4); 1.768(0.4); 1.437(0.9); 1.270(0.8); 1.203(0.3); 0.146(1.5); 0.007(17.8); −0.001(270.7); −0.150(1.5)

Example Iap-3: $^1$H-NMR (601.6 MHz, CD3CN): δ =
8.020(9.9); 8.018(3.7); 8.008(3.1); 8.004(1.9); 7.654(2.7); 7.652(1.8); 7.641(1.9); 7.639(3.0); 7.634(1.5); 7.324(8.4); 3.970(16.0); 2.146(107.9); 2.060 (0.3); 2.056(0.6); 2.052(0.9); 2.048(0.6); 1.973(1.5); 1.966(3.5); 1.958(9.3); 1.954(11.2); 1.950(58.9); 1.946(104.1); 1.942(152.2); 1.937(102.4); 1.933 (51.4); 1.917(0.4); 1.831(0.6); 1.827(0.9); 1.823(0.6); 1.601(1.8); 1.591(4.2); 1.587(4.3); 1.578(2.1); 1.437(0.4); 1.375(2.2); 1.366(4.1); 1.362(4.4); 1.352(1.8); 1.216(0.4); 1.204(0.7); 1.192(0.4); 0.005(2.1); 0.000(64.8); −0.006(2.3)

Example Iap-4: $^1$H-NMR (601.6 MHz, CD3CN): δ =
8.008(3.1); 8.005(4.1); 7.991(2.6); 7.987(1.7); 7.977(2.6); 7.973(2.1); 7.640(3.7); 7.626(3.4); 7.489(0.6); 7.477(0.6); 7.321(8.1); 5.330(0.8); 5.316(1.6); 5.303(1.6); 5.288(0.9); 3.970(16.0); 3.542(2.3); 3.540(1.3); 3.526(3.8); 3.514(1.5); 3.512(2.8); 3.374(2.8); 3.371(1.6); 3.360(4.0); 3.357(3.8); 3.346 (1.3); 3.344(2.3); 3.279(0.8); 3.270(0.8); 2.141(321.1); 2.110(0.3); 2.059(0.9); 2.055(1.5); 2.051(2.2); 2.047(1.5); 2.043(0.8); 1.965(9.0); 1.957(23.2); 1.952(26.0); 1.949(154.0); 1.945(264.8); 1.940(384.0); 1.936(266.4); 1.932(137.2); 1.924(2.4); 1.834(0.8); 1.830(1.5); 1.826(2.2); 1.822(1.4); 1.817(0.7); 1.270(0.4); 0.005(1.6); 0.000(57.9); −0.006(1.9)

Example Iap-5: $^1$H-NMR (601.6 MHz, CD3CN): δ =
7.999(2.0); 7.996(2.6); 7.985(1.9); 7.982(3.1); 7.971(4.2); 7.968(3.0); 7.643(3.7); 7.629(3.4); 7.535(1.3); 7.317(8.5); 3.968(16.0); 2.141(240.0); 2.059 (0.8); 2.055(1.3); 2.051(1.9); 2.047(1.2); 2.043(0.6); 1.965(7.2); 1.957(19.0); 1.953(21.7); 1.949(124.7); 1.945(218.2); 1.940(315.9); 1.936(211.0); 1.932(109.2); 1.924(1.6); 1.834(0.6); 1.830(1.2); 1.826(1.8); 1.822(1.2); 1.818(0.6); 1.399(1.5); 1.389(3.5); 1.386(3.8); 1.376(2.1); 1.269(1.6); 1.259 (2.9); 1.248(0.7); 1.217(0.5); 0.005(1.4); 0.000(48.0); −0.006(1.4)

Example Iap-6: $^1$H-NMR (601.6 MHz, CD3CN): δ =
8.111(3.3); 8.108(3.3); 8.002(2.1); 7.999(2.0); 7.988(2.4); 7.985(2.2); 7.663(3.7); 7.650(3.5); 7.362(0.7); 7.324(6.5); 7.095(0.5); 5.448(0.3); 4.058(6.7); 4.048(6.7); 3.977(0.8); 3.969(16.0); 3.961(2.3); 3.950(2.3); 3.946(2.4); 3.935(2.3); 3.930(0.9); 3.919(0.8); 3.891(0.9); 3.270(0.3); 2.141(353.9); 2.108(0.3); 2.059(0.9); 2.055(1.5); 2.051(2.2); 2.047(1.5); 2.043(0.7); 1.972(1.1); 1.965(9.1); 1.957(23.6); 1.953(27.2); 1.949(155.9); 1.945(269.4); 1.940(394.3); 1.936(268.2); 1.932(136.9); 1.834(0.9); 1.830(1.5); 1.826(2.2); 1.822(1.5); 1.817(0.8); 1.285(0.6); 1.271(1.2); 1.204(0.5); 0.005(1.7); 0.000(57.4); −0.006(1.8)

Example Iaq-1: $^1$H-NMR (400.0 MHz, $d_6$-DMSO): δ =
9.455(4.1); 8.692(7.3); 8.466(4.0); 8.316(0.4); 8.231(2.1); 8.211(2.2); 7.876(2.0); 7.856(2.3); 7.642(1.8); 7.622(3.1); 7.603(1.5); 7.250(0.8); 7.232(0.7); 7.182(0.9); 7.164(0.8); 7.144(0.4); 3.989(16.0); 3.323(50.6); 2.671(0.8); 2.502(114.6); 2.329(0.7); 2.300(3.4); 1.605(1.5); 1.591(4.2); 1.584(4.7); 1.571(2.0); 1.329(1.9); 1.316(4.3); 1.309(4.6); 1.295(1.6); 1.234(0.8); 1.056(0.5); 0.146(0.4); 0.000(78.0); −0.150(0.4)

Example Iaq-2: $^1$H-NMR (400.0 MHz, $d_6$-DMSO): δ =
8.670(8.8); 8.509(3.7); 8.316(0.8); 8.181(1.9); 8.162(2.0); 8.094(1.6); 7.910(1.8); 7.890(2.0); 7.599(1.9); 7.579(3.4); 7.560(1.6); 7.479(1.6); 5.756(0.6); 3.995(16.0); 3.322(87.9); 2.676(0.9); 2.671(1.2); 2.667(0.9); 2.564(0.3); 2.524(3.4); 2.511(65.5); 2.506(132.2); 2.502(176.6); 2.498(132.7); 2.333(0.7); 2.329(1.1); 2.324(0.8); 1.235(0.9); 0.146(0.8); 0.008(6.3); 0.000(164.7); −0.008(8.4); −0.150(0.8)

Example Iat-1: ¹H-NMR (400 MHz, CHLOROFORM-d) δ [ppm]: 0.000(1.72); 0.645(0.48); 0.658(1.74); 0.662(1.89); 0.668(1.94); 0.672(1.77); 0.675(1.43); 0.685(0.59); 0.897(0.61); 0.910(1.68); 0.915(1.96); 0.929(2.03); 0.933(1.46); 0.946(0.46); 1.255(0.42); 1.570(16.00); 2.968(0.54); 2.977(0.69); 2.979(0.64); 2.986(0.68); 2.995(0.50); 3.998(9.61); 6.808(0.46); 6.840(0.46); 7.216(0.90); 7.237(1.12); 7.244(1.18); 7.639(2.98); 8.138(0.57); 8.144(0.65); 8.150(0.66); 8.156(0.74); 8.159(0.72); 8.165(0.64); 8.171(0.61); 8.177(0.51); 8.641(1.00); 8.647(0.96); 8.658(1.02); 8.665(0.90).

Example Iaw-1: ¹H-NMR (601.6 MHz, CDCl₃): δ = 7.946(0.7); 7.886(1.0); 7.884(1.3); 7.872(1.4); 7.869(1.0); 7.476(0.6); 7.464(1.5); 7.452(1.9); 7.439(0.7); 7.265(6.2); 6.770(6.3); 5.671(1.1); 5.300(2.4); 4.266(1.3); 4.005(0.7); 3.979(1.2); 3.846(0.7); 3.821(11.9); 3.780(0.9); 3.767(16.0); 3.123(1.2); 3.114(1.3); 2.890(0.6); 2.875(0.6); 2.869(0.8); 2.863 (1.2); 2.857(0.9); 2.851(0.7); 2.845(0.4); 2.371(0.4); 1.966(0.5); 1.644(1.1); 1.428(0.4); 1.334(0.4); 1.318(0.4); 1.285(0.6); 1.255(1.5); 0.621(0.4); 0.505(0.5); 0.000(2.6)

Example Iax-1: ¹H-NMR (400.0 MHz, d₆-DMSO): δ = 8.318(0.3); 7.733(1.4); 7.703(0.8); 7.698(0.9); 7.688(1.2); 7.681(1.4); 7.676(1.3); 7.599(3.3); 7.586(2.2); 7.567(0.4); 7.472(0.3); 7.461(0.4); 7.267(0.5); 6.891(4.9); 5.757(0.4); 4.038(0.6); 4.020(0.5); 3.995(16.0); 3.974(12.2); 3.934(0.6); 3.887(0.3); 3.879(0.8); 3.858(1.1); 3.754(1.3); 3.330(99.3); 3.036(0.4); 2.996(2.4); 2.931(0.6); 2.919(0.5); 2.811(1.2); 2.676(0.6); 2.672(0.5); 2.667(0.7); 2.507(96.6); 2.503(128.0); 2.498(97.5); 2.333(0.6); 2.329 (0.8); 2.325(0.6); 1.989(1.6); 1.706(0.6); 1.398(5.4); 1.351(0.4); 1.336(0.4); 1.287(0.5); 1.271(0.6); 1.259(0.5); 1.249(0.7); 1.233(1.8); 1.216(0.5); 1.193(0.5); 1.175(0.9); 1.157(0.5); 0.539(1.1); 0.451(1.0); 0.000(1.3)

Example Ibd-1: ¹H-NMR (400.0 MHz, d₆-DMSO): δ = 9.171(1.0); 9.156(2.1); 9.141(1.0); 8.315(2.0); 8.310(2.3); 8.294(1.9); 8.289(2.7); 8.266(4.6); 8.261(3.6); 7.757(3.9); 7.736(3.7); 7.392(1.3); 7.376(11.0); 7.359(5.0); 7.339(1.4); 7.291(0.8); 7.286(1.3); 7.270(1.5); 7.254(0.7); 4.501(4.7); 4.486(4.7); 3.977(16.0); 3.901(0.6); 3.368(0.3); 3.323(127.1); 2.671(0.7); 2.667(0.5); 2.506(86.7); 2.502(110.7); 2.498(83.2); 2.333(0.5); 2.329(0.7); 2.324(0.5); 1.236(0.4); 0.000(3.3)

Example Ibd-2: ¹H-NMR (400.0 MHz, d₆-DMSO): δ = 10.716(4.1); 8.391(3.3); 8.386(3.8); 8.373(2.4); 8.368(1.5); 8.352(2.3); 8.347(1.9); 7.825(3.4); 7.804(3.2); 7.764(2.4); 7.752(2.8); 7.742(2.9); 7.729 (2.6); 7.238(2.6); 7.216(4.8); 7.194(2.4); 3.975(16.0); 3.902(0.5); 3.366(0.4); 3.325(92.4); 2.672(0.6); 2.503(91.0); 2.329(0.5); 1.235(0.4); 0.000(2.2)

Example Ibd-3: ¹H-NMR (400.0 MHz, d₆-DMSO): δ = 8.656(2.1); 8.646(2.1); 8.314(0.3); 8.291(2.0); 8.286(2.3); 8.270(2.1); 8.265(2.5); 8.197(4.3); 8.191(3.9); 7.728(4.0); 7.707(3.7); 4.000(0.5); 3.967(16.0); 3.902(1.4); 3.323(130.7); 2.868(0.6); 2.858(0.9); 2.849(1.4); 2.839(1.4); 2.831(0.9); 2.821(0.7); 2.676(0.5); 2.671(0.7); 2.667(0.5); 2.541(0.5); 2.507(88.6); 2.502(115.2); 2.498(86.8); 2.333(0.5); 2.329(0.7); 2.325(0.5); 1.260(0.4); 1.235(1.1); 0.740(0.8); 0.727(2.4); 0.722(3.4); 0.710(3.2); 0.704 (2.7); 0.693(1.1); 0.567(1.1); 0.557(3.3); 0.550(3.1); 0.547(3.0); 0.541(2.8); 0.529(0.8); 0.000(3.6)

Example Ibe-1: ¹H-NMR (601.6 MHz, d₆-DMSO): δ = 8.741(2.0); 8.734(2.0); 8.243(2.1); 8.240(2.3); 8.229(2.2); 8.226(2.5); 8.166(4.1); 8.162(3.7); 7.887(0.5); 7.883(0.4); 7.845(3.9); 7.831(3.6); 7.665(0.4); 7.651(0.4); 4.163(0.6); 4.150(16.0); 3.872(2.3); 3.330(624.0); 3.051(0.5); 2.869(0.6); 2.862(0.9); 2.857(1.3); 2.850(1.3); 2.844(0.9); 2.838(0.7); 2.831(0.4); 2.828(0.7); 2.617(1.7); 2.614(2.3); 2.611(1.7); 2.523(4.2); 2.520(5.4); 2.517(5.6); 2.508(133.3); 2.505(273.9); 2.502(372.9); 2.499(282.1); 2.474(1.3); 2.390(1.7); 2.387(2.3); 2.384(1.7); 1.639(0.8); 1.235(1.6); 0.854(0.4); 0.744(0.8); 0.735(2.4); 0.732(3.3); 0.724(3.1); 0.720(2.7); 0.712 (1.4); 0.699(0.6); 0.582(1.0); 0.574(2.9); 0.570(2.9); 0.567(2.7); 0.564(2.8); 0.556(0.8); 0.544(0.5); 0.540(0.5); 0.537(0.5); 0.534(0.4); 0.000(4.9)

Example Ibe-2: ¹H-NMR (400.0 MHz, d₆-DMSO): δ = 9.232(0.9); 9.217(1.9); 9.202(1.0); 8.313(0.5); 8.272(1.7); 8.266(2.2); 8.251(1.8); 8.245(2.6); 8.216(4.2); 8.211(3.6); 7.875(3.7); 7.854(3.4); 7.403(1.3); 7.383(9.7); 7.367(4.6); 7.355(0.6); 7.347(1.6); 7.298(0.8); 7.293(1.2); 7.288(0.7); 7.277(1.5); 7.265(0.5); 7.260(0.7); 7.255(0.4); 4.516(4.5); 4.501 (4.5); 4.151(16.0); 4.134(0.4); 3.901(1.7); 3.390(0.3); 3.325(329.8); 3.279(0.6); 2.675(0.8); 2.671(1.1); 2.667(0.9); 2.506(139.0); 2.502(186.0); 2.498 (145.3); 2.333(0.8); 2.329(1.1); 2.324(0.9); 1.258(0.4); 1.235(1.3); 0.913(0.3); 0.000(4.9)

Example Ibe-3: ¹H-NMR (400.0 MHz, d₆-DMSO): δ = 10.764(3.7); 8.396(3.4); 8.390(3.9); 8.328(1.9); 8.323(1.7); 8.314(0.6); 8.307(2.1); 8.301(1.9); 7.938(3.5); 7.917(3.2); 7.765(2.4); 7.752(2.6); 7.747 (1.9); 7.742(2.8); 7.730(2.6); 7.251(2.5); 7.229(4.7); 7.207(2.4); 4.162(16.0); 3.902(1.0); 3.325(256.2); 2.671(1.0); 2.668(0.8); 2.507(135.0); 2.503 (174.0); 2.498(133.6); 2.329(1.1); 2.325(0.9); 1.336(0.3); 1.277(0.5); 1.261(1.0); 1.245(0.9); 1.235(0.9); 0.000(4.3)

Example Ibe-4: ¹H-NMR (400.0 MHz, d₆-DMSO): δ = 9.628(4.2); 8.297(1.6); 8.292(2.4); 8.273(9.0); 7.892(2.6); 7.870(2.4); 4.143(16.0); 3.377(0.4); 3.325(314.7); 3.280(0.5); 2.671(1.2); 2.666(1.0); 2.541 (23.4); 2.506(148.1); 2.502(190.5); 2.498(147.5); 2.328(1.2); 2.324(0.9); 1.618(1.4); 1.604(3.9); 1.597(4.2); 1.584(1.8); 1.357(1.8); 1.344(4.0); 1.337 (4.2); 1.323(1.5); 1.297(0.3); 1.286(0.3); 1.258(2.0); 1.235(2.2); 0.854(0.4); 0.000(1.5)

Example Ibf-1: ¹H-NMR (400.0 MHz, d₆-DMSO): δ = 10.753(3.7); 8.314(0.4); 8.275(3.5); 8.270(4.5); 8.246(2.5); 8.240(1.8); 8.225(2.6); 8.219(2.2); 7.883(4.0); 7.862(3.6); 7.771(2.5); 7.758(2.8); 7.753 (1.7); 7.748(2.9); 7.735(2.7); 7.248(2.7); 7.242(1.0); 7.226(4.9); 7.209(0.9); 7.203(2.5); 4.340(16.0); 3.902(1.7); 3.323(249.1); 3.286(0.4); 2.675(0.9); 2.671(1.2); 2.666(0.9); 2.524(4.4); 2.511(79.5); 2.506(155.9); 2.502(201.8); 2.497(147.7); 2.493(72.7); 2.333(0.9); 2.329(1.2); 2.324(0.9); 1.234(1.2); 0.000(6.4)

Example Ibf-2: ¹H-NMR (400.0 MHz, d₆-DMSO): δ = 9.595(4.1); 8.313(0.4); 8.215(1.8); 8.211(1.9); 8.195(1.9); 8.190(2.2); 8.146(4.0); 8.141(3.4); 7.838(3.4); 7.817(3.1); 4.329(16.0); 3.901(1.5); 3.382 (0.4); 3.322(189.7); 2.671(1.2); 2.502(195.8); 2.328(1.2); 1.619(1.4); 1.605(3.9); 1.598(4.1); 1.585(1.7); 1.344(1.7); 1.330(4.0); 1.324(4.1); 1.309(1.4); 1.235(0.5); 0.000(4.5)

Example Ibf-3: ¹H-NMR (400.0 MHz, d₆-DMSO): δ = 8.694(2.3); 8.684(2.2); 8.164(2.0); 8.159(2.1); 8.143(2.3); 8.138(2.3); 8.063(4.3); 8.058(3.7); 7.790(3.5); 7.769(3.2); 4.332(16.0); 3.901(0.4); 3.327 (145.2); 2.882(0.8); 2.872(1.1); 2.864(1.5); 2.854(1.5); 2.846(1.1); 2.836(0.7); 2.826(0.3); 2.672(0.8); 2.506(103.4); 2.502(120.8); 2.329(0.7); 0.751 (1.0); 0.734(3.6); 0.721(3.6); 0.716(3.0); 0.704(1.2); 0.577(1.4); 0.566(3.9); 0.560(3.9); 0.551(3.2); 0.539(0.9); 0.000(2.6)

Example Ibg-1: ¹H-NMR (400.0 MHz, d₆-DMSO): δ = 15.366(3.2); 9.256(1.1); 9.241(2.2); 9.226(1.0); 8.584(3.7); 8.316(0.7); 8.209(1.9); 8.189(1.9); 8.078(1.8); 8.059(1.9); 7.734(1.7); 7.714(3.1); 7.695 (1.5); 7.352(16.0); 7.344(8.1); 7.339(9.2); 7.327(1.4); 7.318(0.9); 7.275(1.0); 7.267(1.3); 7.262(1.3); 7.260(1.3); 7.253(1.6); 7.247(1.1); 7.241(0.8); 7.232(0.4); 4.530(4.3); 4.515(5.0); 4.494(0.3); 4.076(15.4); 3.996(0.3); 3.903(3.9); 3.892(0.3); 3.331(332.8); 2.681(0.4); 2.676(0.9); 2.672(1.3); 2.667 (0.9); 2.663(0.4); 2.542(0.7); 2.525(3.9); 2.512(78.5); 2.507(156.8); 2.503(204.8); 2.498(146.8); 2.494(70.0); 2.339(0.4); 2.334(0.9); 2.329(1.2); 2.325 (0.9); 1.259(0.3); 1.245(0.3); 1.234(0.6); 0.941(0.5); 0.876(0.4); 0.000(0.8)

Example Ibg-2: ¹H-NMR (400.0 MHz, CD3CN): δ = 13.369(0.4); 8.515(5.2); 8.172(1.6); 8.153(1.7); 7.910(2.1); 7.890(2.4); 7.655(1.6); 7.636(2.8); 7.617(1.4); 7.588(0.4); 7.288(1.2); 4.031(16.0); 2.919 (0.3); 2.910(1.0); 2.900(1.5); 2.892(2.1); 2.882(2.1); 2.873(1.5); 2.864(1.0); 2.855(0.4); 2.473(0.5); 2.469(0.7); 2.464(0.6); 2.460(0.3); 2.159(219.6); 2.126(1.7); 2.120(1.5); 2.114(1.7); 2.108(2.2); 2.102(1.5); 2.095(0.9); 2.087(0.6); 2.024(0.4); 2.010(0.4); 1.996(0.4); 1.965(7.4); 1.959(18.5); 1.953 (96.5); 1.947(173.4); 1.940(233.2); 1.934(161.4); 1.928(83.8); 1.884(0.3); 1.781(0.7); 1.775(1.1); 1.769(1.5); 1.763(1.1); 1.756(0.6); 1.546(0.4); 1.527 (0.4); 1.508(0.4); 1.487(0.4); 1.429(0.4); 1.419(0.4); 1.410(0.3); 1.400(0.4); 1.380(0.4); 1.340(0.8); 1.270(13.3); 1.217(1.0); 1.177(0.5); 1.161(0.4); 1.151(0.4); 1.126(0.4); 1.116(0.4); 1.104(0.4); 0.974(0.4); 0.932(0.4); 0.913(0.5); 0.881(2.6); 0.864(1.7); 0.857(1.6); 0.836(1.2); 0.817(0.6); 0.798(1.4); 0.786(3.7); 0.781(5.1); 0.768(4.9); 0.763(4.0); 0.751(1.9); 0.730(0.5); 0.712(0.4); 0.696(0.4); 0.686(0.4); 0.657(1.8); 0.646(4.8); 0.639(4.8); 0.636 (4.4); 0.630(3.9); 0.617(1.3); 0.146(1.9); 0.079(3.5); 0.008(15.8); 0.000(413.3); −0.009(19.0); −0.150(2.0)

Example Ibg-3: ¹H-NMR (400.0 MHz, d₆-DMSO): δ = 15.396(3.1); 9.328(1.6); 9.313(3.1); 9.297(1.5); 8.582(5.4); 8.316(0.7); 8.249(2.5); 8.230(2.6); 8.070(2.1); 8.051(2.4); 7.763(1.7); 7.744(2.9); 7.724 (1.4); 4.184(0.8); 4.160(2.6); 4.144(2.8); 4.136(2.9); 4.120(2.7); 4.095(1.4); 4.077(16.0); 3.903(2.5); 3.332(329.6); 2.677(1.0); 2.672(1.3); 2.668(1.0); 2.542(0.8); 2.525(4.1); 2.512(84.7); 2.508(167.9); 2.503(218.4); 2.499(158.5); 2.494(77.6); 2.335(1.0); 2.330(1.3); 2.325(1.0); 1.235(0.4); 0.000(0.8)

-continued

Example Ibg-4: $^1$H-NMR (400.0 MHz, d$_6$-DMSO): δ =
9.321(1.0); 9.305(1.9); 9.289(0.9); 8.122(1.7); 8.117(1.8); 8.101(1.8); 8.096(2.0); 8.051(0.4); 8.046(0.4); 8.027(3.8); 8.022(3.4); 7.703(3.2); 7.682(2.9); 4.286(1.4); 4.153(0.6); 4.130(1.7); 4.114(1.8); 4.106(1.9); 4.089(1.7); 4.066(0.6); 3.930(14.7); 3.911(16.0); 3.323(100.6); 2.672(0.6); 2.506(82.4); 2.502(100.9); 2.329(0.6); 0.000(2.4)

Example Ibg-5: $^1$H-NMR (400.0 MHz, d$_6$-DMSO): δ =
8.617(2.4); 8.606(2.3); 8.074(1.9); 8.070(2.0); 8.053(2.1); 8.049(2.2); 7.982(4.1); 7.977(3.7); 7.646(3.5); 7.625(3.2); 4.212(0.7); 4.194(1.4); 4.176(1.6); 4.167(1.6); 4.149(1.4); 4.132(0.7); 3.899(16.0); 3.323(124.1); 2.857(0.7); 2.847(1.0); 2.838(1.4); 2.829(1.4); 2.820(1.0); 2.811(0.6); 2.671(0.7); 2.502(125.5); 2.329(0.7); 1.429(4.5); 1.411(9.2); 1.393(4.4); 0.732(0.8); 0.714(3.5); 0.701(3.4); 0.697(3.0); 0.685(1.1); 0.562(1.2); 0.551(3.7); 0.545 (3.8); 0.537(3.2); 0.524(0.9); 0.000(2.5)

Example Ibg-6: $^1$H-NMR (400.0 MHz, d$_6$-DMSO): δ =
9.319(1.0); 9.303(2.1); 9.287(1.0); 8.313(0.4); 8.132(2.0); 8.127(2.1); 8.111(2.2); 8.106(2.4); 8.034(4.2); 8.029(3.8); 7.701(3.9); 7.680(3.6); 4.219(0.5); 4.201(1.2); 4.183(1.3); 4.175(1.3); 4.156(1.5); 4.138(1.2); 4.130(1.9); 4.114(1.8); 4.106(1.9); 4.090(1.8); 4.065(0.6); 3.902(16.0); 3.365(0.4); 3.322 (232.0); 3.282(0.4); 2.675(0.8); 2.671(1.0); 2.667(0.8); 2.506(135.5); 2.502(173.4); 2.497(129.5); 2.333(0.8); 2.329(1.1); 2.324(0.8); 1.429(4.6); 1.411 (9.7); 1.393(4.5); 0.000(5.1)

Example Ibg-7: $^1$H-NMR (400.0 MHz, d$_6$-DMSO): δ =
8.615(1.9); 8.604(1.9); 8.065(1.7); 8.059(1.9); 8.044(1.8); 8.038(2.1); 7.974(3.7); 7.969(3.3); 7.648(3.4); 7.627(3.1); 4.282(0.6); 3.942(0.6); 3.928(13.6); 3.904(16.0); 3.324(76.1); 2.856(0.6); 2.846(0.8); 2.838(1.2); 2.828(1.2); 2.819(0.8); 2.810(0.6); 2.676(0.3); 2.672(0.4); 2.667(0.4); 2.507(57.9); 2.502(73.9); 2.498(55.8); 2.329(0.5); 0.731(0.7); 0.718(2.2); 0.713(2.9); 0.701(2.8); 0.696(2.3); 0.684(0.9); 0.560(1.0); 0.549(3.0); 0.543(2.8); 0.534 (2.5); 0.521(0.7); 0.000(2.1)

Example Ibg-8: $^1$H-NMR (400.0 MHz, d$_6$-DMSO): δ =
9.181(0.9); 9.166(1.9); 9.151(0.9); 7.836(1.2); 7.830(1.4); 7.815(2.2); 7.810(3.3); 7.791(4.5); 7.787(3.5); 7.780(4.9); 7.760(2.2); 7.398(1.1); 7.393(1.6); 7.377(5.9); 7.370(6.4); 7.352(4.7); 7.332(1.7); 7.286(0.9); 7.282(0.8); 7.278(0.8); 7.271(0.8); 7.265(1.7); 7.252(0.5); 7.248(0.7); 4.875(0.4); 4.858 (1.1); 4.842(1.6); 4.826(1.1); 4.810(0.4); 4.501(4.3); 4.487(4.4); 4.096(15.6); 3.902(3.1); 3.365(0.3); 3.325(137.0); 2.676(0.5); 2.671(0.6); 2.667(0.5); 2.542(0.6); 2.525(1.8); 2.511(40.8); 2.507(79.3); 2.502(102.4); 2.498(75.9); 2.494(38.4); 2.334(0.4); 2.329(0.6); 2.325(0.4); 1.501(16.0); 1.485(15.9); 1.236(0.6); 0.000(3.5)

Example Ibg-9: $^1$H-NMR (400.0 MHz, d$_6$-DMSO): δ =
9.128(0.9); 9.114(2.0); 9.099(1.0); 8.100(1.9); 8.095(2.3); 8.079(2.0); 8.074(2.7); 8.047(4.6); 8.042(3.7); 7.676(3.9); 7.655(3.6); 7.388(0.9); 7.374(13.6); 7.368(6.0); 7.358(5.3); 7.338(1.1); 7.287(0.8); 7.282(1.2); 7.273(1.1); 7.266(1.4); 7.251(0.7); 7.245(0.4); 4.487(4.6); 4.472(4.6); 4.213(0.5); 4.196 (1.1); 4.177(1.3); 4.169(1.3); 4.151(1.2); 4.133(0.5); 3.900(16.0); 3.324(140.1); 3.290(0.4); 2.675(0.4); 2.671(0.6); 2.667(0.4); 2.524(1.9); 2.506 (79.5); 2.502(102.9); 2.497(77.7); 2.333(0.5); 2.329(0.6); 2.324(0.5); 1.427(4.7); 1.409(9.9); 1.391(4.6); 0.000(2.9)

Example Ibg-10: $^1$H-NMR (400.0 MHz, d$_6$-DMSO): δ =
9.130(0.8); 9.115(1.7); 9.100(0.8); 8.090(1.7); 8.084(2.0); 8.069(1.8); 8.064(2.5); 8.039(4.1); 8.034(3.3); 7.677(3.4); 7.656(3.1); 7.373(12.2); 7.366 (5.4); 7.358(5.0); 7.343(0.5); 7.337(0.9); 7.288(0.7); 7.281(1.0); 7.274(1.0); 7.266(1.2); 7.258(0.8); 7.252(0.6); 4.486(4.0); 4.471(4.0); 3.928(13.2); 3.904(16.0); 3.397(0.6); 3.390(0.4); 3.384(0.6); 3.323(87.8); 2.690(0.4); 2.675(0.3); 2.671(0.5); 2.667(0.4); 2.511(30.1); 2.506(59.5); 2.502(77.9); 2.497(59.2); 2.333(0.3); 2.329(0.5); 2.324(0.4); 0.000(2.5)

Example Ibg-11: $^1$H-NMR (400.0 MHz, d$_6$-DMSO): δ =
10.684(0.9); 10.628(3.9); 8.325(0.4); 8.169(3.3); 8.164(4.8); 8.153(2.7); 8.148(1.7); 8.133(2.5); 8.127(2.1); 7.947(1.0); 7.942(1.1); 7.886(0.3); 7.865 (0.8); 7.860(0.8); 7.838(1.3); 7.817(0.5); 7.736(7.8); 7.716(7.6); 7.388(3.1); 7.369(5.5); 7.349(3.5); 7.148(1.8); 7.130(3.0); 7.111(1.3); 4.868(0.4); 4.554 (0.4); 4.538(1.2); 4.521(1.7); 4.505(1.3); 4.489(0.5); 4.100(4.3); 3.902(6.6); 3.883(16.0); 3.330(291.3); 3.174(0.3); 2.677(0.8); 2.672(1.2); 2.668 (0.9); 2.542(0.6); 2.508(153.1); 2.503(199.2); 2.499(155.8); 2.334(0.9); 2.330(1.2); 2.325(1.0); 1.512(4.2); 1.496(4.4); 1.480(6.4); 1.464(6.5); 1.443 (6.5); 1.427(6.2); 1.258(0.4); 1.235(0.7); 0.000(5.4)

Example Ibg-12: $^1$H-NMR (400.0 MHz, d$_6$-DMSO): δ =
10.615(4.0); 8.169(3.3); 8.164(4.9); 8.154(2.8); 8.149(1.7); 8.134(2.5); 8.128(2.1); 7.740(4.6); 7.733(4.5); 7.719(5.0); 7.714(5.1); 7.387(2.5); 7.368 (4.4); 7.348(2.7); 7.147(1.4); 7.129(2.4); 7.110(1.1); 4.223(0.6); 4.207(1.3); 4.189(1.5); 4.178(1.5); 4.160(1.3); 4.143(0.6); 3.908(16.0); 3.326(121.7); 3.282(0.4); 2.676(0.5); 2.672(0.6); 2.668(0.5); 2.507(78.8); 2.503(102.2); 2.498(80.4); 2.334(0.5); 2.330(0.6); 2.325(0.5); 1.439(4.8); 1.421(10.0); 1.403 (4.7); 1.245(0.3); 1.235(0.4); 0.000(2.6)

Example Ibg-13: $^1$H-NMR (400.0 MHz, d$_6$-DMSO): δ =
8.657(2.0); 8.646(2.0); 7.805(1.2); 7.800(1.4); 7.784(2.6); 7.779(3.1); 7.750(4.7); 7.728(5.4); 7.722(3.8); 4.834(0.4); 4.818(1.1); 4.802(1.6); 4.786(1.2); 4.770(0.4); 4.111(0.5); 4.090(15.3); 3.902(0.4); 3.325(105.2); 2.862(0.6); 2.852(0.9); 2.844(1.3); 2.834(1.3); 2.825(0.9); 2.816(0.6); 2.676(0.4); 2.672(0.5); 2.667(0.4); 2.507(62.6); 2.503(82.0); 2.498(62.5); 2.334(0.4); 2.330(0.5); 2.325(0.4); 1.495(16.0); 1.479(16.0); 1.235(0.7); 0.738(0.8); 0.725 (2.4); 0.720(3.3); 0.708(3.0); 0.702(2.7); 0.691(1.0); 0.560(1.1); 0.550(3.1); 0.544(3.1); 0.540(3.0); 0.534(2.8); 0.522(0.8); 0.000(2.4)

Example Ibg-14: $^1$H-NMR (400.0 MHz, d$_6$-DMSO): δ =
10.614(3.2); 8.161(2.7); 8.156(4.0); 8.145(2.2); 8.140(1.3); 8.125(2.1); 8.119(1.7); 7.742(3.3); 7.731(3.5); 7.721(3.5); 7.712(3.8); 7.386(2.1); 7.367 (3.6); 7.346(2.3); 7.146(1.2); 7.128(2.0); 7.109(0.9); 4.146(0.9); 4.085(0.8); 4.067(0.3); 3.937(13.7); 3.917(16.0); 3.902(2.0); 3.872(0.4); 3.427(0.4); 3.410(0.4); 3.324(62.1); 2.676(0.4); 2.672(0.5); 2.667(0.4); 2.542(0.5); 2.538(0.5); 2.507(59.0); 2.503(75.2); 2.498(56.3); 2.329(0.4); 2.325(0.3); 1.236 (0.7); 1.161(0.5); 0.000(2.5)

Example Ibg-15: $^1$H-NMR (600.1 MHz, CD3CN): δ =
8.532(1.4); 8.530(2.5); 8.527(1.4); 8.240(1.0); 8.238(1.3); 8.235(0.9); 8.227(1.0); 8.225(1.4); 8.222(0.9); 7.909(0.9); 7.907(1.2); 7.906(1.1); 7.904(0.9); 7.896(1.0); 7.894(1.3); 7.893(1.3); 7.891(0.9); 7.659(0.5); 7.601(1.3); 7.588(2.4); 7.576(1.2); 7.384(1.0); 7.382(1.4); 7.370(3.1); 7.359(2.6); 7.355 (0.6); 7.346(3.0); 7.336(0.7); 7.333(1.3); 7.281(0.5); 7.278(0.8); 7.276(0.5); 7.266(1.2); 7.254(0.5); 4.579(3.6); 4.569(3.6); 3.873(11.8); 3.853(16.0); 2.139(4.6); 1.971(1.2); 1.964(0.6); 1.955(1.6); 1.951(2.0); 1.947(10.6); 1.943(18.4); 1.939(26.8); 1.935(18.3); 1.931(9.1); 1.216(0.3); 1.204(0.7); 1.192 (0.3); 0.000(7.4)

Example Ibh-2: $^1$H-NMR (600.1 MHz, CD3CN): δ =
8.225(1.3); 8.223(2.2); 8.220(1.3); 8.020(0.8); 8.018(1.1); 8.016(0.8); 8.007(0.9); 8.0054(1.1); 8.0045(1.1); 8.003(0.8); 7.953(0.9); 7.951(1.1); 7.950 (1.0); 7.948(0.8); 7.940(1.0); 7.938(1.1); 7.937(1.1); 7.935(0.8); 7.693(1.2); 7.680(2.3); 7.667(1.3); 7.388(1.3); 7.376(2.7); 7.375(2.6); 7.360(2.0); 7.356 (0.5); 7.348(2.6); 7.335(1.1); 7.280(0.7); 7.268(1.1); 7.256(0.4); 4.588(3.1); 4.578(3.1); 4.062(16.0); 4.033(10.1); 3.935(0.6); 2.137(45.4); 1.971 (0.6); 1.963(0.6); 1.955(1.6); 1.951(2.0); 1.947(10.6); 1.943(18.5); 1.939(26.9); 1.935(18.2); 1.931(9.2); 1.285(0.4); 1.277(0.3); 1.272(0.4); 0.000(6.0)

Example Ibh-3: $^1$H-NMR (400.0 MHz, d$_6$-DMSO): δ =
9.355(0.7); 9.339(1.5); 9.324(0.7); 7.990(1.3); 7.984(1.5); 7.969(1.6); 7.963(1.9); 7.902(3.1); 7.896(2.7); 7.802(3.0); 7.782(2.5); 4.164(0.4); 4.140(1.4); 4.121(16.0); 4.100(1.4); 4.091(0.8); 4.076(12.0); 3.902(0.5); 3.323(102.8); 2.676(0.4); 2.671(0.6); 2.667(0.4); 2.511(36.8); 2.507(70.9); 2.502(91.4); 2.498(68.1); 2.494(34.9); 2.333(0.4); 2.329(0.5); 2.324(0.4); 0.000(2.8)

Example Ibh-4: $^1$H-NMR (400.0 MHz, d$_6$-DMSO): δ =
8.646(2.0); 8.635(2.0); 8.313(0.6); 7.859(1.8); 7.853(2.0); 7.838(2.4); 7.833(2.9); 7.784(4.4); 7.779(3.8); 7.747(4.5); 7.726(3.2); 4.421(1.4); 4.403(4.4); 4.384(4.4); 4.366(1.4); 4.104(0.6); 4.084(16.0); 3.901(1.9); 3.322(227.3); 2.862(0.6); 2.852(0.9); 2.844(1.3); 2.834(1.3); 2.825(0.9); 2.816(0.6); 2.680(0.5); 2.676(0.9); 2.671(1.2); 2.667(0.9); 2.524(3.8); 2.511(76.7); 2.507(151.3); 2.502(197.3); 2.498(147.9); 2.493(75.9); 2.333(0.9); 2.329(1.2); 2.324(0.9); 1.461(5.0); 1.443(11.1); 1.425(5.0); 1.411(0.4); 1.236(0.4); 0.738(0.8); 0.725(2.4); 0.720(3.4); 0.708(3.2); 0.702(2.8); 0.691(1.1); 0.559 (1.1); 0.549(3.2); 0.542(3.2); 0.539(3.0); 0.533(2.8); 0.521(0.9); 0.000(6.0)

Example Ibh-5: $^1$H-NMR (400.0 MHz, d$_6$-DMSO): δ =
9.359(0.9); 9.344(2.0); 9.328(1.0); 8.035(0.4); 8.030(0.4); 7.923(1.6); 7.918(1.8); 7.902(2.2); 7.897(2.6); 7.823(4.1); 7.818(3.8); 7.802(4.3); 7.781(3.2); 7.701(0.4); 7.680(0.4); 4.437(1.3); 4.419(4.1); 4.401(4.2); 4.383(1.3); 4.165(0.6); 4.141(1.8); 4.125(1.8); 4.116(2.1); 4.100(2.0); 4.088(16.0); 3.902 (2.1); 3.350(0.6); 3.323(88.4); 2.676(0.4); 2.672(0.5); 2.667(0.4); 2.542(0.4); 2.511(33.9); 2.507(66.6); 2.503(87.4); 2.498(66.3); 2.494(34.9); 2.333 (0.4); 2.329(0.5); 2.325(0.4); 1.472(4.7); 1.454(10.3); 1.436(4.7); 1.412(1.1); 1.394(0.5); 0.000(2.5)

Example Ibh-6: $^1$H-NMR (400.0 MHz, d$_6$-DMSO): δ =
8.643(0.3); 8.618(2.4); 8.608(2.4); 8.076(1.9); 8.071(2.1); 8.055(2.1); 8.050(2.3); 7.984(4.2); 7.979(3.9); 7.779(0.4); 7.749(0.5); 7.728(0.7); 7.642(3.7); 7.621(3.4); 4.542(0.5); 4.526(1.3); 4.510(1.7); 4.493(1.3); 4.478(0.5); 4.090(1.9); 3.902(3.2); 3.874(16.0); 3.323(125.9); 3.268(0.3); 3.170(0.5); 2.859(0.7); 2.850(1.1); 2.841(1.6); 2.831(1.6); 2.823(1.1); 2.813(0.8); 2.671(0.8); 2.502(130.6); 2.445(0.4); 2.329(0.8); 1.495(2.2); 1.475(7.5); 1.459 (7.0); 1.436(6.9); 1.420(6.6); 1.265(0.4); 1.259(0.5); 1.247(0.5); 1.236(0.7); 0.734(0.9); 0.716(3.7); 0.703(3.6); 0.699(3.1); 0.687(1.1); 0.565(1.2); 0.554 (3.7); 0.548(4.1); 0.540(3.5); 0.527(1.0); 0.000(2.9)

Example Ibh-7: $^1$H-NMR (400.0 MHz, d$_6$-DMSO): δ =
9.316(1.0); 9.301(2.1); 9.285(1.0); 8.135(2.3); 8.130(2.5); 8.114(2.5); 8.109(2.9); 8.035(4.8); 8.030(4.3); 7.843(0.3); 7.804(0.5); 7.765(0.4); 7.760(0.4); 7.697(4.4); 7.676(4.1); 4.548(0.5); 4.531(1.3); 4.515(1.8); 4.499(1.3); 4.483(0.5); 4.156(0.6); 4.140(0.8); 4.132(1.8); 4.116(1.9); 4.107(1.9); 4.092 (3.3); 4.067(0.6); 3.902(2.1); 3.878(16.0); 3.323(129.0); 3.294(0.4); 2.676(0.5); 2.671(0.7); 2.667(0.5); 2.542(0.4); 2.525(2.2); 2.511(45.3); 2.507 (90.1); 2.502(117.6); 2.498(87.5); 2.493(44.1); 2.334(0.5); 2.329(0.7); 2.324(0.5); 1.503(1.9); 1.487(2.4); 1.478(6.3); 1.462(6.4); 1.437(6.3); 1.421(6.1); 0.000(4.2)

Example Ibh-8: $^1$H-NMR (400.0 MHz, d$_6$-DMSO): δ =
8.643(1.5); 8.632(1.5); 7.926(1.4); 7.920(1.6); 7.905(1.7); 7.899(2.1); 7.859(3.4); 7.854(2.8); 7.748(3.2); 7.727(2.6); 4.128(0.6); 4.109(16.0); 4.092 (0.6); 4.074(12.1); 3.902(0.5); 3.349(0.6); 3.323(77.8); 2.866(0.5); 2.857(0.7); 2.848(1.0); 2.838(1.0); 2.829(0.6); 2.820(0.5); 2.676(0.4); 2.671(0.5); 2.667(0.4); 2.511(31.8); 2.507(60.0); 2.502(76.6); 2.498(56.9); 2.494(29.1); 2.333(0.3); 2.329(0.5); 2.325(0.3); 0.739(0.6); 0.727(1.9); 0.722(2.5); 0.709 (2.4); 0.704(2.0); 0.692(0.8); 0.562(0.8); 0.552(2.4); 0.546(2.4); 0.542(2.2); 0.536(2.1); 0.524(0.6); 0.000(2.5)

Example Ibh-10: $^1$H-NMR (400.0 MHz, d$_6$-DMSO): δ =
9.172(0.9); 9.157(1.9); 9.142(0.9); 8.312(0.5); 7.887(1.5); 7.882(2.0); 7.867(1.9); 7.861(3.4); 7.851(4.7); 7.846(3.1); 7.791(0.7); 7.777(4.3); 7.756(2.9); 7.397(1.0); 7.393(1.6); 7.376(6.1); 7.371(8.3); 7.353(4.7); 7.333(1.7); 7.287(0.9); 7.283(1.4); 7.278(0.8); 7.266(1.6); 7.253(0.5); 7.249(0.7); 7.245 (0.4); 7.197(0.6); 7.168(0.5); 6.793(0.3); 6.765(0.4); 6.749(0.4); 6.721(0.4); 5.979(0.5); 5.935(0.5); 5.441(0.6); 5.411(0.5); 4.500(4.5); 4.485(4.5); 4.440 (1.3); 4.422(4.3); 4.403(4.3); 4.385(1.4); 4.090(16.0); 3.985(0.4); 3.959(1.1); 3.933(1.1); 3.907(0.5); 3.901(1.2); 3.373(0.9); 3.329(435.0); 3.280 (0.6); 3.270(0.5); 3.254(0.3); 2.676(0.9); 2.671(1.2); 2.667(0.9); 2.541(0.7); 2.525(3.6); 2.511(77.3); 2.507(153.6); 2.502(200.6); 2.498(149.2); 2.493 (75.5); 2.457(0.5); 2.383(4.1); 2.334(1.0); 2.329(1.3); 2.325(1.0); 1.470(5.0); 1.452(11.0); 1.434(4.9); 0.000(8.9); −0.008(0.3)

Example Ibh-11: $^1$H-NMR (400.0 MHz, d$_6$-DMSO): δ =
9.165(0.8); 9.150(1.6); 9.135(0.8); 7.953(1.1); 7.948(1.9); 7.936(2.8); 7.931(7.1); 7.778(2.7); 7.772(0.9); 7.761(0.7); 7.755(2.2); 7.395(1.3); 7.378(4.7); 7.373(6.1); 7.354(3.7); 7.335(1.4); 7.283(1.1); 7.266(1.3); 7.249(0.5); 4.502(3.6); 4.487(3.6); 4.125(16.0); 4.080(12.7); 3.901(0.8); 3.365(0.4); 3.325(252.8); 3.295(0.8); 2.675(0.6); 2.671(0.8); 2.667(0.6); 2.524(2.6); 2.506(110.0); 2.502(141.9); 2.498(106.6); 2.333(0.6); 2.329(0.9); 2.324(0.6); 0.000(3.9)

Example Ibh-12: $^1$H-NMR (400.0 MHz, d$_6$-DMSO): δ =
10.618(4.0); 8.168(3.2); 8.163(4.7); 8.154(2.8); 8.149(1.6); 8.133(2.5); 8.128(2.1); 7.737(6.0); 7.734(4.8); 7.717(6.4); 7.391(2.6); 7.371(4.4); 7.351 (2.7); 7.151(1.4); 7.132(2.4); 7.114(1.1); 4.554(0.5); 4.538(1.2); 4.522(1.7); 4.505(1.3); 4.489(0.5); 3.882(16.0); 3.440(0.7); 3.427(0.6); 3.420(0.5); 3.398(1.5); 3.343(1284.7); 3.292(1.6); 3.282(1.1); 3.269(1.2); 3.252(0.6); 3.237(0.4); 3.225(0.4); 3.192(0.4); 3.184(0.3); 2.676(1.1); 2.672(1.5); 2.667 (1.2); 2.542(50.5); 2.525(3.9); 2.507(188.0); 2.503(247.6); 2.498(187.6); 2.433(0.4); 2.368(0.3); 2.334(1.2); 2.329(1.6); 2.325(1.2); 1.650(0.3); 1.479 (6.3); 1.463(6.5); 1.441(6.5); 1.425(6.2); 1.298(0.6); 1.279(0.6); 1.261(1.2); 1.259(1.1); 1.236(1.8); 0.853(0.4); 0.000(1.9)

Example Ibh-13: $^1$H-NMR (400.0 MHz, d$_6$-DMSO): δ =
10.652(3.7); 8.313(0.4); 8.005(3.7); 8.000(4.1); 7.941(1.9); 7.935(1.6); 7.920(2.6); 7.914(2.4); 7.838(4.3); 7.817(3.0); 7.732(4.0); 7.713(4.2); 7.389 (2.6); 7.370(4.3); 7.350(2.7); 7.149(1.5); 7.131(2.4); 7.112(1.1); 4.461(1.4); 4.443(4.2); 4.425(4.2); 4.407(1.4); 4.094(16.0); 3.921(0.5); 3.901(1.0); 3.323(218.2); 2.676(0.8); 2.671(1.1); 2.667(0.8); 2.511(73.2); 2.507(138.4); 2.502(179.0); 2.497(133.8); 2.493(69.0); 2.333(0.8); 2.329(1.1); 2.324(0.8); 1.483(4.9); 1.465(10.4); 1.447(4.7); 1.437(0.5); 1.234(0.3); 0.000(5.9)

Example Ibh-14: $^1$H-NMR (400.0 MHz, d$_6$-DMSO): δ =
10.656(3.1); 8.314(0.4); 8.075(3.0); 8.070(3.4); 8.006(1.6); 8.001(1.4); 7.985(1.9); 7.980(1.8); 7.839(3.3); 7.818(2.6); 7.736(3.3); 7.717(3.6); 7.390 (2.1); 7.371(3.6); 7.351(2.2); 7.150(1.2); 7.131(2.0); 7.113(0.9); 4.145(16.0); 4.084(13.5); 3.901(0.9); 3.323(240.5); 2.676(0.8); 2.671(1.0); 2.667(0.8); 2.506(126.1); 2.502(164.7); 2.498(125.8); 2.333(0.7); 2.329(1.0); 2.324(0.7); 0.000(4.5)

Example Ibh-9: $^1$H-NMR (400.0 MHz, d$_6$-DMSO): δ =
9.127(1.1); 9.112(2.3); 9.097(1.1); 8.102(1.8); 8.097(2.2); 8.081(2.0); 8.076(2.6); 8.049(4.5); 8.044(3.7); 7.672(4.0); 7.651(3.7); 7.391(1.2); 7.375(12.0); 7.358(5.3); 7.338(1.4); 7.287(0.8); 7.282(1.3); 7.272(1.0); 7.266(1.6); 7.250(0.8); 4.541(0.5); 4.525(1.3); 4.509(1.8); 4.490(5.6); 4.475(5.2); 4.095 (0.6); 3.901(1.5); 3.876(16.0); 3.389(0.4); 3.359(0.4); 3.322(132.8); 2.671(0.7); 2.666(0.5); 2.540(0.5); 2.506(86.3); 2.502(112.9); 2.498(87.2); 2.333 (0.5); 2.329(0.7); 2.325(0.5); 1.501(0.7); 1.475(6.2); 1.459(6.3); 1.435(6.3); 1.419(6.1); 1.235(0.7); 0.000(3.1)

Example Ibi-1: $^1$H-NMR (400.0 MHz, d$_6$-DMSO): δ =
15.389(2.6); 9.171(1.2); 9.157(2.4); 9.142(1.3); 8.313(0.6); 8.118(7.0); 8.097(3.8); 8.092(2.9); 7.783(2.5); 7.763(2.3); 7.403(2.1); 7.384(16.0); 7.367 (7.9); 7.347(2.5); 7.298(1.3); 7.293(2.0); 7.287(1.2); 7.276(2.5); 7.265(0.9); 7.260(1.1); 4.506(6.9); 4.491(6.9); 4.107(1.0); 4.075(13.0); 3.901(1.1); 3.325(266.4); 3.262(0.4); 3.169(0.4); 2.676(1.1); 2.671(1.4); 2.667(1.1); 2.542(1.0); 2.511(97.3); 2.507(184.9); 2.502(236.9); 2.498(176.5); 2.494(90.6); 2.435(0.4); 2.334(1.1); 2.329(1.4); 2.325(1.1); 0.008(7.8); 0.000(7.8)

Example Ibi-2: $^1$H-NMR (400.0 MHz, d$_6$-DMSO): δ =
15.412(3.0); 9.356(1.9); 9.341(3.5); 9.326(1.8); 8.313(1.1); 8.148(3.9); 8.143(4.5); 8.127(4.1); 8.122(5.5); 8.099(6.3); 7.809(3.0); 7.788(2.7); 4.176 (1.2); 4.152(3.8); 4.136(4.0); 4.128(4.2); 4.112(4.1); 4.070(16.0); 3.902(2.8); 3.509(0.4); 3.406(0.5); 3.323(628.3); 3.260(0.3); 3.175(0.6); 3.164(0.6); 2.676(2.3); 2.671(3.1); 2.667(2.3); 2.541(3.4); 2.511(208.3); 2.507(394.7); 2.502(503.7); 2.498(374.4); 2.493(190.0); 2.333(2.2); 2.329(2.9); 2.324 (2.2); 1.235(0.5); 0.008(0.7); 0.000(15.5); −0.008(0.6)

Example Ibi-3: $^1$H-NMR (400.0 MHz, d$_6$-DMSO): δ =
15.339(0.8); 8.654(3.1); 8.644(3.0); 8.314(0.3); 8.094(2.6); 8.089(3.5); 8.073(2.6); 8.068(4.4); 8.056(5.9); 8.051(4.2); 7.747(2.8); 7.726(2.5); 4.281 (0.6); 4.085(0.9); 4.063(16.0); 3.902(1.1); 3.391(0.4); 3.328(198.2); 3.278(0.4); 3.176(0.4); 3.163(0.4); 2.891(0.3); 2.881(0.9); 2.872(1.4); 2.863(2.0); 2.853(2.0); 2.844(1.3); 2.835(1.0); 2.825(0.4); 2.676(0.7); 2.672(0.9); 2.668(0.7); 2.542(0.7); 2.511(61.3); 2.507(117.2); 2.503(151.2); 2.498(113.6); 2.334(0.7); 2.330(0.9); 2.325(0.7); 0.753(1.2); 0.740(3.8); 0.736(5.1); 0.723(4.8); 0.718(4.1); 0.706(1.6); 0.565(1.7); 0.554(5.0); 0.548(4.8); 0.544 (4.6); 0.539(4.3); 0.526(1.3); 0.000(4.5)

Example Ibi-4: $^1$H-NMR (400.0 MHz, d$_6$-DMSO): δ =
15.391(3.5); 10.670(4.2); 8.247(4.2); 8.242(4.0); 8.225(0.4); 8.177(3.0); 8.171(2.4); 8.156(3.1); 8.150(2.5); 7.852(3.4); 7.831(3.0); 7.744(5.7); 7.741 (6.4); 7.722(6.8); 7.402(3.7); 7.383(6.0); 7.362(3.4); 7.161(2.0); 7.143(3.1); 7.125(1.4); 4.291(0.6); 4.084(16.0); 4.000(0.5); 3.902(2.3); 3.330(89.2); 3.171(1.0); 2.677(0.6); 2.673(0.7); 2.668(0.5); 2.512(68.5); 2.508(104.9); 2.503(119.4); 2.499(82.4); 2.495(38.3); 2.335(0.6); 2.330(0.7); 2.326(0.5); 1.259(0.4); 1.235(0.7); 0.000(4.1)

Preparation of the Starting Materials:

All starting materials employed can either be prepared by or analogously to processes known from the literature or are commercially available.

Synthesis of methyl 1-methyl-3-(pentafluoroethyl)-4-(trifluoromethyl)-1H-pyrazole-5-carboxylate

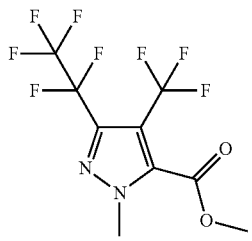 [SMILES: COC(=O)c1c(C(F)(F)F)c(C(F)(F)C(F)(F)F)nn1C]

10.0 g of 1-methyl-3-(pentafluoroethyl)-4-(trifluoromethyl)-1H-pyrazole-5-carboxylic acid (32 mmol) were initially charged in 250 ml of dichloromethane p.a., and 8.39 ml of oxalyl chloride (96.1 mmol) were then added with stirring. The reaction mixture was stirred at room temperature for 30 minutes and then under reflux for 30 minutes. The reaction mixture was concentrated to dryness on a rotary evaporator and taken up in 100 ml of chloroform. The resulting solution was then added dropwise to a suspension of 6.43 g of silver(I) cyanide, 65 ml of methanol p.a. and 150 ml of chloroform. The reaction mixture was then heated under reflux for 16 h and cooled to room temperature. The suspension was then filtered through silica and the filter cake was rinsed with dichloromethane. The solvent was evaporated to dryness on a rotary evaporator.

This gave 8.40 g of methyl 1-methyl-3-(pentafluoroethyl)-4-(trifluoromethyl)-1H-pyrazole-5-carboxylate as a colourless liquid.

HPLC-MS[a)]: log P=3.42, mass (m/z)=327 [M+H]+.

$^1$H-NMR (400 MHz, d3-acetonitrile): δ=4.08 (s, 3H), 3.97 (s, 3H).

Biological Working Examples for Applications in Crop Protection and in the Animal Health Sector

*Ctenocephalides felis*—In Vitro Contact Tests with Adult Cat Fleas

For the coating of the test tubes, 9 mg of active compound are first dissolved in 1 ml of acetone p.a. and then diluted to the desired concentration with acetone p.a. 250 μl of the solution are distributed homogeneously on the inner walls and the base of a 25 ml test tube by turning and rocking on an orbital shaker (rocking rotation at 30 rpm for 2 h). With 900 ppm active compound solution and internal surface 44.7 cm$^2$, given homogeneous distribution, an area-based dose of 5 μg/cm$^2$ is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the test tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 μg/cm$^2$. 100% efficacy means that all the fleas were dead or moribund. 0% efficacy means that no fleas were harmed.

In this test, for example, the following compounds from the preparation examples show an efficacy of 100% at an application rate of 5 μg/cm$^2$ (500 g/ha): Iac-1, Iaf-1, Iap-1, Iap-3

*Rhipicephalus sanguineus*—In Vitro Contact Tests with Adult Brown Dog Ticks

For the coating of the test tubes, 9 mg of active compound are first dissolved in 1 ml of acetone p.a. and then diluted to the desired concentration with acetone p.a. 250 μl of the solution are distributed homogeneously on the inner walls and the base of a 25 ml test tube by turning and rocking on an orbital shaker (rocking rotation at 30 rpm for 2 h). With 900 ppm active compound solution and internal surface 44.7 cm$^2$, given homogeneous distribution, an area-based dose of 5 μg/cm$^2$ is achieved.

After the solvent has evaporated off, the tubes are populated with 5-10 adult dog ticks (*Rhipicephalus sanguineus*), sealed with a perforated plastic lid and incubated in a horizontal position in the dark at room temperature and ambient humidity. After 48 h, efficacy is determined. To this end, the ticks are knocked to the floor of the tube and incubated on a hotplate at 45-50° C. for not more than 5 min. Ticks which remain motionless on the floor or move in such an uncoordinated manner that they are unable to deliberately avoid the heat by climbing upwards are considered to be dead or moribund.

A substance shows good activity against *Rhipicephalus sanguineus* if, in this test, an efficacy of at least 80% was achieved at an application rate of 5 μg/cm$^2$. An efficacy of 100% means that all the ticks were dead or moribund. 0% efficacy means that none of the ticks had been harmed.

In this test, for example, the following compounds from the preparation examples show an efficacy of 100% at an application rate of 5 μg/cm$^2$ (500 g/ha): Iaf-1, Iap-1, Iap-3, Iap-4

In this test, for example, the following compounds from the preparation examples show an efficacy of 80% at an application rate of 5 μg/cm$^2$ (500 g/ha): Ibf-2

In this test, for example, the following compounds from the preparation examples show an efficacy of 80% at an application rate of 1 μg/cm$^2$ (100 g/ha): Iap-2

*Amblyomma hebaraeum* test (AMBYHE)

Solvent: dimethyl sulphoxide

To produce a suitable active compound formulation, 10 mg of active compound are mixed with 0.5 ml of dimethyl sulphoxide, and the concentrate is diluted with water to the desired concentration.

Tick nymphs (*Amblyomma hebraeum*) are placed into perforated plastic beakers and immersed in the desired concentration for one minute. The ticks are transferred on filter paper into a Petri dish and stored in a climate-controlled cabinet.

After 42 days, the kill in % is determined. 100% means that all of the ticks have been killed; 0% means that none of the ticks have been killed.

In this test, for example, the following compounds of the preparation examples show an efficacy of 100% at an application rate of 100 ppm: Iac-1, Iac-3, Iaf-1, Iap-1

*Boophilus microplus*—Dip Test

Test animals: cattle ticks (*Boophilus microplus*) Parkhurst strain, SP-resistant Solvent: dimethyl sulphoxide 10 mg of active compound are dissolved in 0.5 ml of dimethyl sulphoxide. For the purpose of producing a suitable formulation, the active compound solution is diluted with water to the concentration desired in each case.

This active compound preparation is pipetted into tubes. 8-10 engorged adult female cattle ticks (*Boophilus microplus*) are transferred into a further tube with holes. The tube is immersed into the active compound preparation, and all the ticks are completely wetted. After the liquid has run out, the ticks are transferred on filter discs into plastic dishes and stored in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 100% at an application rate of 100 ppm: Iac-1, Iac-3, Iaf-1, Iap-1

*Boophilus microplus*—Injection Test
Solvent: dimethyl sulphoxide

To produce a suitable preparation of active compound, 10 mg of active compound are mixed with 0.5 ml of solvent and the concentrate is diluted with solvent to the desired concentration.

1 μl of the active compound solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 100% at an application rate of 20 μg/animal: Iaa-1, Iac-1, Iac-3, Iaf-1, Iap-1, Iap-2, Iap-3, Iap-4, Iap-5, Ibe-4, Ibf-2, Ibf-3, Ibh-4

*Ctenocephalides felis*—Oral Test
Solvent: dimethyl sulphoxide

To produce a suitable preparation of active compound, 10 mg of active compound are mixed with 0.5 ml of dimethyl sulphoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active compound preparation, which can be imbibed by the fleas through the parafilm membrane.

After 2 days, the kill in % is determined. 100% means that all of the fleas have been killed; 0% means that none of the fleas have been killed.

In this test, for example, the following compounds from the preparation examples show an efficacy of 100% at an application rate of 100 ppm: Iaa-1, Iac-1, Iac-3, Iaf-1, Iap-1, Iap-2, Iap-3, Iap-4, Iap-5, Ibe-4, Ibf-2, Ibf-3

In this test, for example, the following compounds from the preparation examples show an efficacy of 90% at an application rate of 100 ppm: Ibh-4

*Lucilia cuprina* Test
Solvent: dimethyl sulphoxide

To produce a suitable preparation of active compound, 10 mg of active compound are mixed with 0.5 ml of dimethyl sulphoxide, and the concentrate is diluted with water to the desired concentration.

About 20 L1 larvae of the Australian sheep blowfly (*Lucilia cuprina*) are transferred into a test vessel containing minced horsemeat and the active compound preparation of the desired concentration.

After 2 days, the kill in % is determined. 100% means that all the larvae have been killed; 0% means that no larvae have been killed.

In this test, for example, the following compounds from the preparation examples show an efficacy of 100% at an application rate of 100 ppm: Iaa-1, Iac-1, Iac-3, Iaf-1, Iap-1, Iap-2, Iap-3, Iap-4, Iap-5, Ibe-4, Ibf-2, Ibf-3, Ibh-4

*Musca domestica* Test
Solvent: dimethyl sulphoxide

To produce a suitable preparation of active compound, 10 mg of active compound are mixed with 0.5 ml of dimethyl sulphoxide, and the concentrate is diluted with water to the desired concentration.

Vessels containing a sponge treated with sugar solution and the active compound preparation of the desired concentration are populated with 10 adult houseflies (*Musca domestica*).

After 2 days, the kill in % is determined. 100% means that all of the flies have been killed; 0% means that none of the flies have been killed.

In this test, for example, the following compounds from the preparation examples show an efficacy of 100% at an application rate of 100 ppm: Iaa-1, Iac-1, Iac-3, Iap-1, Iap-2, Iap-3, Iap-5, Ibe-4, Ibf-2

In this test, for example, the following compounds from the preparation examples show an efficacy of 90% at an application rate of 100 ppm: Ibh-4

In this test, for example, the following compounds from the preparation examples show an efficacy of 80% at an application rate of 100 ppm: Ibf-3

*Myzus persicae*—Spray Test
Solvent: 78 parts by weight of acetone
1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) infested by all stages of the green peach aphid (*Myzus persicae*) are sprayed with an active compound preparation of the desired concentration.

After 6 days, the efficacy in % is determined. 100% means that all the aphids have been killed; 0% means that no aphids have been killed.

In this test, for example, the following compounds from the preparation examples show an efficacy of 90% at an application rate of 100 g/ha: Iaf-1

*Phaedon cochleariae*—Spray Test
Solvent: 78.0 parts by weight of acetone
1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 100% at an application rate of 500 g/ha: Iaj-1, Iap-4, Ibd-3, Ibe-1, Ibe-3, Ibe-4, Ibf-2, Ibf-3, Ibg-13, Ibg-5, Ibg-7, Ibg-8, Ibg-9, Ibh-3, Ibh-4, Ibh-5, Ibh-6, Ibh-8

In this test, for example, the following compounds from the preparation examples show an efficacy of 100% at an application rate of 100 g/ha: Iaa-1, Iac-1, Iac-3, Iaf-1, Iap-1, Iap-2, Iap-3, Iap-5, Iap-6, Iaq-1, Iax-1

*Spodoptera frugiperda*—Spray Test
Solvent: 78.0 parts by weight of acetone
  1.5 parts by weight of dimethylformamide
Emulsifier: alkylaryl poly glycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Leaf discs of maize (*Zea mays*) are sprayed with an active compound preparation of the desired concentration and, after drying, populated with caterpillars of the armyworm (*Spodoptera frugiperda*).

After 7 days, the efficacy in % is determined. 100% means that all the caterpillars have been killed; 0% means that no caterpillars have been killed.

In this test, for example, the following compounds from the preparation examples show an efficacy of 100% at an application rate of 500 g/ha: Ibe-1, Ibe-4, Ibf-2, Ibf-3, Ibh-3

In this test, for example, the following compounds from the preparation examples show an efficacy of 83% at an application rate of 500 g/ha: Ibh-8

In this test, for example, the following compounds from the preparation examples show an efficacy of 80% at an application rate of 500 g/ha: Iap-4

In this test, for example, the following compounds from the preparation examples show an efficacy of 100% at an application rate of 100 g/ha: Iaa-1, Iac-1, Iac-3, Iaf-1, Iap-1, Iap-2, Iap-3

*Tetranychus urticae*—Spray Test, OP-Resistant
Solvent: 78.0 parts by weight of acetone
  1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of bean leaves (*Phaseolus vulgaris*) infested by all stages of the greenhouse red spider mite (*Tetranychus urticae*) are sprayed with an active compound preparation of the desired concentration.

After 6 days, the efficacy in % is determined. 100% means that all the spider mites have been killed; 0% means that no spider mites have been killed.

In this test, for example, the following compounds from the preparation examples show an efficacy of 100% at an application rate of 500 g/ha: Ibh-4

In this test, for example, the following compounds from the preparation examples show an efficacy of 90% at an application rate of 500 g/ha: Iap-4, Ibe-4, Ibg-5, Ibh-3

In this test, for example, the following compounds from the preparation examples shows an efficacy of 100% at an application rate of 100 g/ha: Iac-1, Iac-3, Iaf-1, Iap-3

*Tetranychus urticae*—Spray Test, OP-Resistant
Solvent: 7 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water. If the addition of ammonium salts or/and penetrants is required, these are each added in a concentration of 1000 ppm to the formulation solution.

Bean plants (*Phaseolus vulgaris*) heavily infested by all stages of the greenhouse red spider mite (*Tetranychus urticae*) are treated by spraying with the active compound preparation of the desired concentration.

After 7 days, the efficacy in % is determined. 100% means that all the spider mites have been killed; 0% means that no spider mites have been killed.

In this test, for example, the following compounds of the preparation examples show an efficacy of 100% at an application rate of 20 ppm: Iap-1

The invention claimed is:
1. A compound of formula (I)

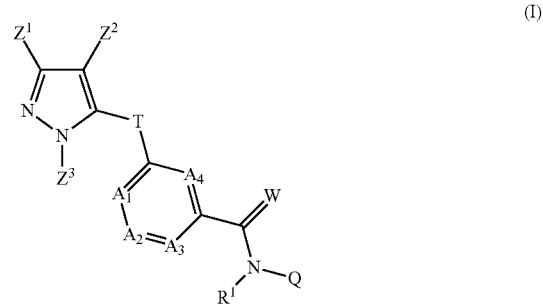

in which
  $R^1$ represents hydrogen, optionally substituted alkyl, alkenyl, alkynyl, cycloalkyl, cycloalkylalkyl, alkylcarbonyl, alkoxycarbonyl, arylalkyl, heteroarylalkyl,
the chemical moieties
  $A_1$ represents $CR^2$ or nitrogen,
  $A_2$ represents $CR^3$ or nitrogen,
  $A_3$ represents $CR^4$ or nitrogen, and
  $A_4$ represents $CR^5$ or nitrogen,
  but where not more than three of the chemical moieties $A_1$ to $A_4$ simultaneously represent nitrogen;
  $R^2$, $R^3$, $R^4$ and $R^5$ independently of one another represent hydrogen, halogen, cyano, nitro, optionally substituted alkyl, cycloalkyl, alkoxy, N-alkoxyiminoalkyl, alkylsulphanyl, alkylsulphinyl, alkylsulphonyl, N-alkylamino or N,N-dialkylamino;
  if neither of the $A_2$ and $A_3$ moieties is nitrogen, $R^3$ and $R^4$ together with the carbon atom to which they are bonded may form a 5- or 6-membered ring containing 0, 1 or 2 nitrogen atoms and/or 0 or 1 oxygen atom and/or 0 or 1 sulphur atom, or if neither of the A₁ and A₂ moieties is nitrogen, R² and R³ together with the carbon atom to which they are bonded may form a 6-membered ring containing 0, 1 or 2 nitrogen atoms;

W represents oxygen or sulphur;

Q represents hydrogen, formyl, hydroxy, amino or one of the optionally substituted moieties alkyl, alkyloxy, alkenyl, alkynyl, cycloalkyl, heterocycloalkyl, cycloalkylalkyl, heterocycloalkylalkyl, arylalkyl, heteroarylalkyl or represents a moiety N-alkylamino, N-alkylcarbonylamino, N,N-dialkylamino; or Q represents a mono- to polyunsaturated 5- to 6-membered carbocycle which may optionally be interrupted by heteroatoms and is optionally mono- to polysubstituted by V, where V represents halogen, cyano, nitro, optionally substituted alkyl, alkenyl, alkynyl, cycloalkyl, alkoxy, N-alkoxyiminoalkyl, alkylsulphanyl, alkylsulphinyl, alkylsulphonyl, N,N-dialkylamino;

T represents one of the 5-membered heteroaromatic systems T1-T35 shown below, where the bond to the pyrazolyl head group is indicated by an asterisk,

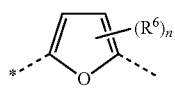 T1

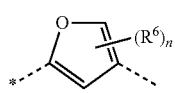 T2

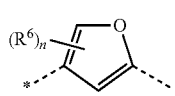 T3

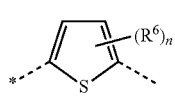 T4

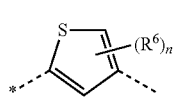 T5

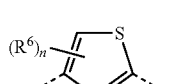 T6

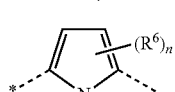 T7

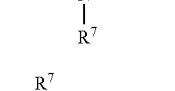 T8

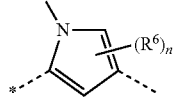 T9

-continued

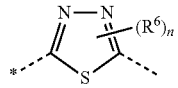 T10

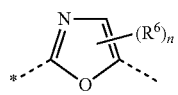 T11

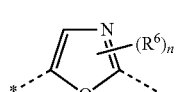 T12

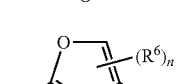 T13

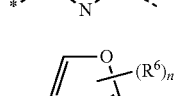 T14

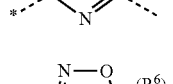 T15

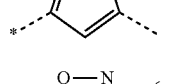 T16

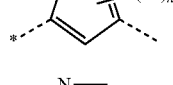 T17

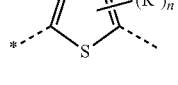 T18

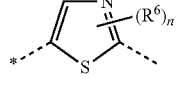 T19

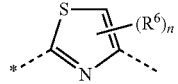 T20

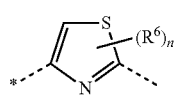 T21

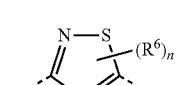 T22

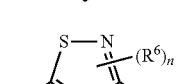 T23

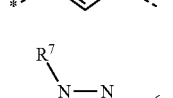 T24

-continued

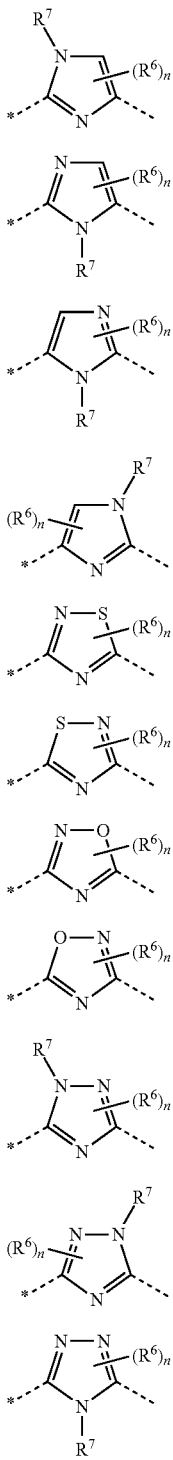

where
R⁶ independently of one another represent halogen, cyano, nitro, amino or optionally substituted alkyl, alkyloxy, alkylcarbonyl, alkylsulphanyl, alkylsulphinyl, alkylsulphonyl, and
n represents the values 0-2;
R⁷ represents hydrogen, optionally substituted alkyl or cycloalkyl in which optionally one methylene group is substituted by a heteroatom;

$Z^1$ represents optionally substituted haloalkyl or halocycloalkyl, and
$Z^2$ represents hydrogen, halogen, cyano, nitro, amino or optionally substituted alkyl, alkylcarbonyl, alkylsulphanyl, alkylsulphinyl, alkylsulphonyl, and
$Z^3$ represents hydrogen or optionally substituted alkyl, cycloalkyl, heterocycloalkyl, alkenyl, alkynyl, where
if T is T23 or T24, one of the radicals $Z^1$, $Z^2$ or $Z^3$ is substituted by at least 3 halogen atoms.

2. A compound according to claim 1 in which
$R^1$ represents hydrogen, optionally substituted $C_1$-$C_6$-alkyl, $C_3$-$C_6$-alkenyl, $C_3$-$C_6$-alkynyl, $C_3$-$C_7$-cycloalkyl, $C_3$-$C_7$-cycloalkyl-$C_1$-$C_3$-alkyl, $C_1$-$C_6$-alkylcarbonyl, $C_1$-$C_6$-alkoxycarbonyl, aryl-($C_1$-$C_3$)-alkyl, heteroaryl-($C_1$-$C_3$)-alkyl,
the chemical moieties
$A_1$ represents $CR^2$ or nitrogen,
$A_2$ represents $CR^3$ or nitrogen,
$A_3$ represents $CR^4$ or nitrogen, and
$A_4$ represents $CR^5$ or nitrogen,
but where not more than three of the chemical moieties $A_1$ to $A_4$ simultaneously represent nitrogen;
$R^2$, $R^3$, $R^4$ and $R^5$ independently of one another represent hydrogen, halogen, cyano, nitro, optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino, N,N-di-$C_1$-$C_6$-alkylamino, or
if neither of the $A_2$ and $A_3$ moieties is nitrogen, $R^3$ and $R^4$ together with the carbon atom to which they are bonded may form a 5- or 6-membered ring containing 0, 1 or 2 nitrogen atoms and/or 0 or 1 oxygen atom and/or 0 or 1 sulphur atom, or
if neither of the $A_1$ and $A_2$ moieties is nitrogen, $R^2$ and $R^3$ together with the carbon atom to which they are bonded may form a 6-membered ring containing 0, 1 or 2 nitrogen atoms;
W represents oxygen or sulphur;
Q represents hydrogen, formyl, hydroxy, amino or one of the optionally substituted moieties $C_1$-$C_6$-alkyl, $C_3$-$C_6$-alkenyl, $C_3$-$C_6$-alkynyl, $C_3$-$C_6$-cycloalkyl, $C_1$-$C_5$-heterocycloalkyl, $C_1$-$C_4$-alkoxy, $C_3$-$C_6$-cycloalkyl-$C_1$-$C_6$-alkyl, aryl-($C_1$-$C_3$)-alkyl, heteroaryl-($C_1$-$C_3$)-alkyl or represents a moiety N—$C_1$-$C_4$-alkylamino, N—$C_1$-$C_4$-alkylcarbonylamino, N,N-di-$C_1$-$C_4$-alkylamino; or
Q represents a mono- to triunsaturated 5- to 6-membered carbocycle which is optionally mono- or polysubstituted by V or a mono- to triunsaturated 5- or 6-membered heterocyclic ring which is optionally polysubstituted by V, where
V independently of one another represent halogen, cyano, nitro, optionally substituted $C_1$-$C_6$-alkyl, $C_1$-$C_4$-alkenyl, $C_1$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N,N-di-($C_1$-$C_6$-alkyl)amino;
T represents one of the 5-membered heteroaromatic systems T1-T35 shown below, where the bond to the pyrazolyl head group is indicated by an asterisk,

T1

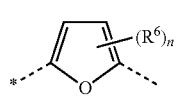

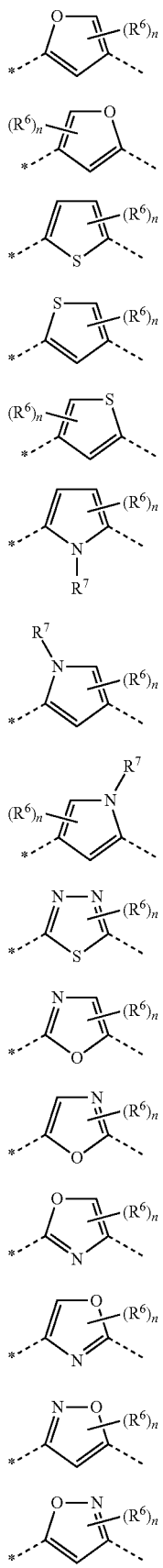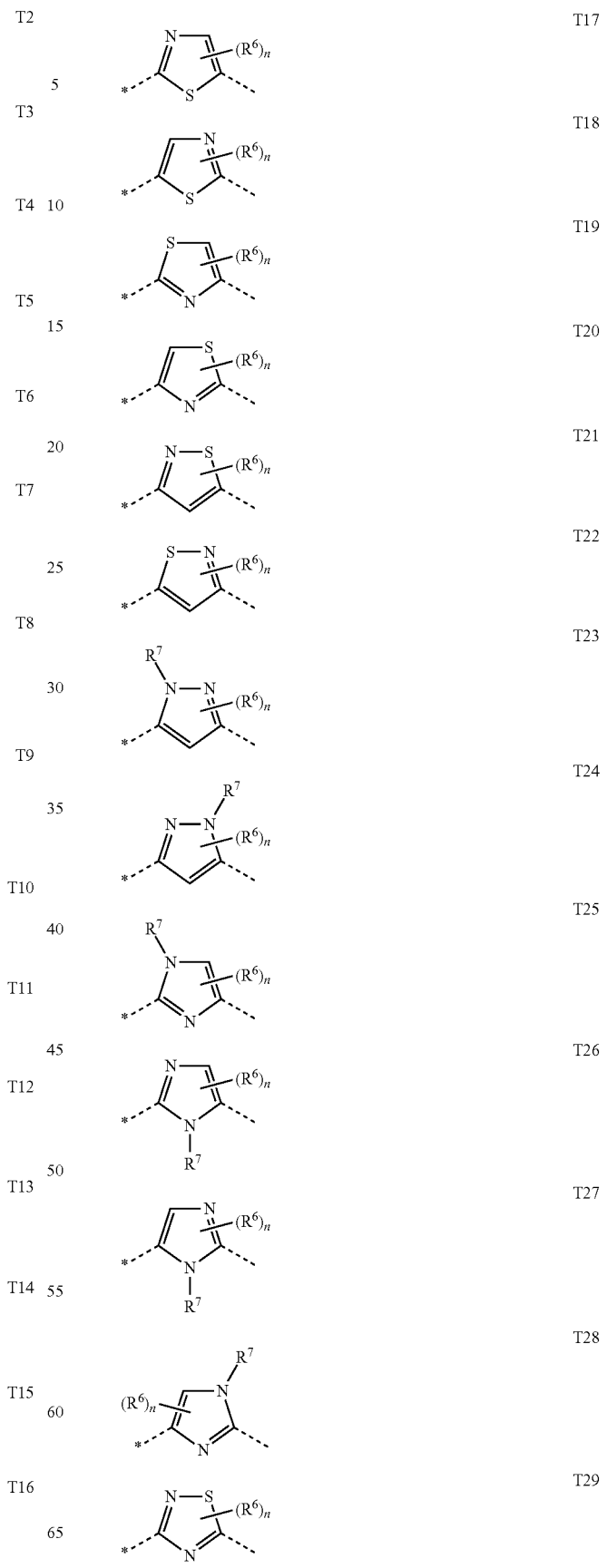

-continued

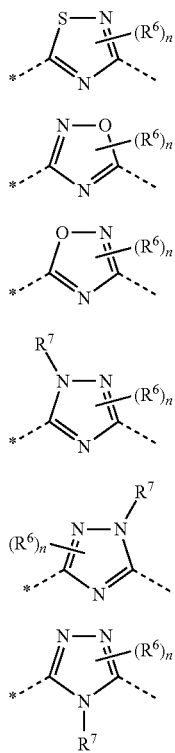

where
R⁶ independently of one another represent halogen, cyano, nitro, amino or optionally halogen-substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and n represents the values 0-1;

R⁷ represents hydrogen, or optionally substituted $C_1$-$C_6$-alkyl or $C_3$-$C_6$-cycloalkyl in which optionally one methylene group may be substituted by heteroatoms;

Z¹ represents optionally substituted $C_1$-$C_6$-haloalkyl, $C_3$-$C_6$-halocycloalkyl, and Z² represents hydrogen, halogen, cyano, nitro, amino or optionally substituted $C_1$-$C_6$-alkyl, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and Z³ represents hydrogen or optionally substituted $C_1$-$C_6$-alkyl, $C_3$-$C_6$-cycloalkyl, $C_3$-$C_5$-heterocycloalkyl, $C_3$-$C_6$-alkenyl, $C_3$-$C_6$-alkynyl, where if T is T23 or T24, one of the radicals Z¹, Z² or Z³ is substituted by at least 3 halogen atoms.

3. A compound according to claim 1 in which
R¹ represents hydrogen or represents $C_1$-$C_6$-alkyl, $C_3$-$C_6$-alkenyl, $C_3$-$C_6$-alkynyl, $C_3$-$C_7$-cycloalkyl, $C_3$-$C_7$-cycloalkyl-$C_1$-$C_3$-alkyl, $C_1$-$C_6$-alkylcarbonyl, $C_1$-$C_6$-alkoxycarbonyl, aryl-($C_1$-$C_3$)-alkyl, heteroaryl-($C_1$-$C_3$)-alkyl which are optionally mono- to pentasubstituted independently of one another by fluorine, chlorine, cyano, alkoxy and alkoxycarbonyl, the chemical moieties
A₁ represents CR² or nitrogen,
A₂ represents CR³ or nitrogen,
A₃ represents CR⁴ or nitrogen, and
A₄ represents CR⁵ or nitrogen, but where not more than three of the chemical moieties A₁ to A₄ simultaneously represent nitrogen;

R², R³, R⁴ and R⁵ independently of one another represent hydrogen, fluorine, chlorine, bromine, iodine, cyano, nitro or represent $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino or N,N-di-$C_1$-$C_6$-alkylamino which are optionally mono- to pentasubstituted by fluorine, chlorine, cyano or $C_1$-$C_4$-alkoxy;

W represents oxygen or sulphur;

Q represents hydrogen, hydroxy, formyl, amino or one of the moieties $C_1$-$C_6$-alkyl, $C_3$-$C_6$-alkenyl, $C_3$-$C_6$-alkynyl, $C_3$-$C_6$-cycloalkyl, $C_2$-$C_6$-heterocycloalkyl, $C_1$-$C_4$-alkoxy, $C_1$-$C_6$-alkyl-$C_3$-$C_6$-cycloalkyl, $C_3$-$C_6$-cycloalkyl-$C_1$-$C_6$-alkyl, $C_1$-$C_6$-hydroxyalkyl, aryl-($C_1$-$C_3$)-alkyl, heteroaryl-($C_1$-$C_3$)-alkyl, N—$C_1$-$C_4$-alkylamino, N—$C_1$-$C_4$-alkylcarbonylamino or N,N-di-$C_1$-$C_4$-alkylamino which are optionally mono- or polysubstituted independently of one another by hydroxy, nitro, amino, fluorine, chlorine, bromine, iodine, $C_1$-$C_4$-alkoxy, cyano, hydroxycarbonyl, $C_1$-$C_4$-alkoxycarbonyl, carbamoyl, thiocarbamoyl, $C_1$-$C_4$-alkylcarbamoyl, $C_3$-$C_6$-cycloalkylcarbamoyl, phenyl; or Q represents aryl substituted by 0, 1, 2 or 3 substituents V or a 5- or 6-membered heteroaromatic system substituted by 0, 1, 2 or 3 substituents V, where V independently of one another represent fluorine, chlorine, bromine, iodine, cyano, nitro, optionally substituted $C_1$-$C_6$-alkyl, $C_2$-$C_4$-alkenyl, $C_2$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N,N-di-($C_1$-$C_6$-alkyl)amino;

T represents one of the 5-membered heteroaromatic systems T1-T35 shown below, where the bond to the pyrazolyl head group is indicated by an asterisk,

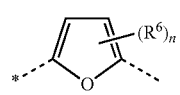
T1

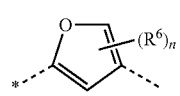
T2

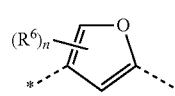
T3

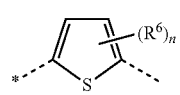
T4

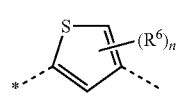
T5

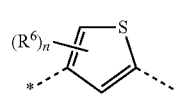
T6

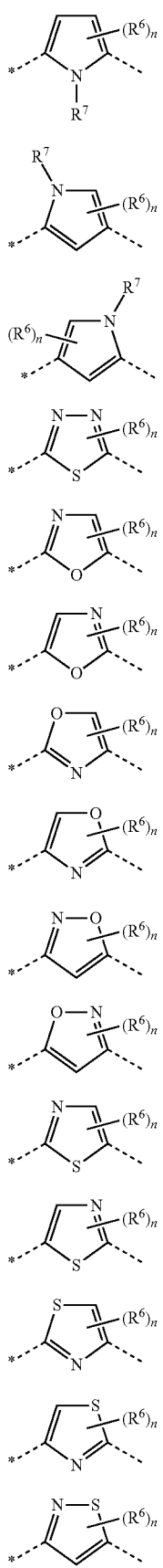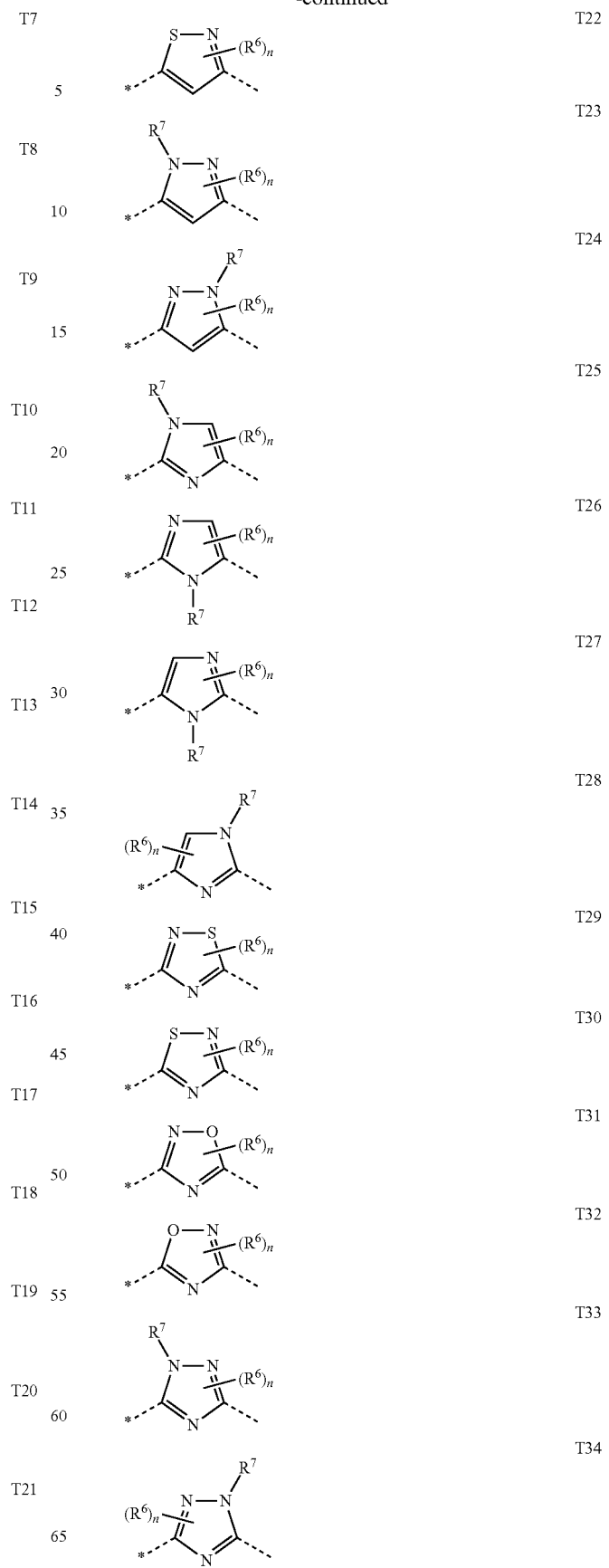

-continued

T35

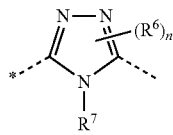

where
- $R^6$ independently of one another represent fluorine, chlorine, bromine, iodine, cyano, nitro, amino or represent $C_1$-$C_6$-alkyl, $C_1$-$C_6$-alkoxy, $C_1$-$C_6$-alkylcarbonyl, $C_1$-$C_6$-alkylsulphanyl, $C_1$-$C_6$-alkyl sulphinyl, $C_1$-$C_6$-alkyl sulphonyl which are optionally mono- to pentasubstituted by fluorine or chlorine, and
- n represents the values 0-1;
- $R^7$ represents hydrogen, or $C_1$-$C_6$-alkyl or $C_3$-$C_6$-cycloalkyl in which optionally one methylene group may be substituted by heteroatoms and which are optionally mono- to pentasubstituted by fluorine, chlorine, cyano or $C_1$-$C_4$-alkoxy; $Z^1$ represents optionally substituted $C_1$-$C_6$-haloalkyl, $C_3$-$C_6$-halocycloalkyl, and
- $Z^2$ represents hydrogen, halogen, cyano, nitro, amino or optionally mono- to pentasubstituted $C_1$-$C_6$-alkyl, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and
- $Z^3$ represents hydrogen or represents $C_1$-$C_6$-alkyl, $C_3$-$C_6$-cycloalkyl, $C_1$-$C_4$-alkenyl, $C_1$-$C_4$-alkynyl which are optionally mono- to pentasubstituted by fluorine, chlorine, cyano or $C_1$-$C_4$-alkoxy;
- where if T is T23 or T24, one of the radicals $Z^1$, $Z^2$ or $Z^3$ is substituted by at least 3 halogen atoms.

4. A compound according to claim 1, in which
- $R^1$ represents hydrogen, methyl, ethyl, n-propyl, isopropyl, n-butyl, isobutyl, s-butyl, t-butyl, 2,2-difluoroethyl, 2,2,2-trifluoroethyl, methoxymethyl, ethoxymethyl, propoxymethyl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 6-chloropyrid-3-ylmethyl;
- the chemical moieties
  - $A_1$ represents $CR^2$ or nitrogen,
  - $A_2$ represents $CR^3$ or nitrogen,
  - $A_3$ represents $CR^4$ or nitrogen, and
  - $A_4$ represents $CR^5$ or nitrogen,
  - but where not more than three of the chemical moieties $A_1$ to $A_4$ simultaneously represent nitrogen;
- $R^2$ and $R^5$ independently of one another represent hydrogen, methyl, fluorine or chlorine and
- $R^3$ and $R^4$ independently of one another represent hydrogen, fluorine, chlorine, bromine, iodine, cyano, nitro, methyl, ethyl, cyclopropyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, trifluoromethylsulphinyl;
- W represents oxygen or sulphur;
- Q represents hydrogen, methyl, ethyl, n-propyl, 1-methylethyl, 1,1-dimethylethyl, 1-methylpropyl, n-butyl, 2-methylpropyl, 2-methylbutyl, hydroxyethyl, 2-hydroxypropyl, cyanomethyl, 2-cyanoethyl, 2-fluoroethyl, 2,2-difluoroethyl, 2,2,2-trifluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-methylcyclopropyl, 1-trifluoromethylcyclopropyl, 1-carbamoylcyclopropyl, 1-thiocarbamoylcyclopropyl, 1-methoxycarbonylcyclopropyl, 1-(N-methylcarbamoyl)cyclopropyl, 1-(N-cyclopropylcarbamoyl)cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, oxetan-3-yl, thietan-3-yl, 1-oxidothietan-3-yl, 1,1-dioxidothietan-3-yl, isoxazol-3-ylmethyl, 1,2,4-triazol-3-ylmethyl, 3-methyloxetan-3-ylmethyl, benzyl, 2,6-difluorophenylmethyl, 3-fluorophenylmethyl, 2-fluorophenylmethyl, 4-fluorophenylmethyl, 2,5-difluorophenylmethyl, 1-phenylethyl, 4-chlorophenylethyl, 2-trifluoromethylphenylethyl, 1-pyridin-2-ylethyl, pyridin-2-ylmethyl, 5-fluoropyridin-2-ylmethyl, (6-chloropyridin-3-yl)methyl, pyrimidin-2-ylmethyl, methoxy, 2-ethoxyethyl, 2-(methyl sulphanyl)ethyl, 1-methyl-2-(ethylsulphanyl)ethyl, 2-methyl-1-(methyl sulphanyl)propan-2-yl, methoxycarbonyl, methoxycarbonylmethyl, $NH_2$, N-ethylamino, N-allylamino, N,N-dimethylamino, N,N-diethylamino; or
- Q represents phenyl, naphthyl, pyridazine, pyrazine, pyrimidine, triazine, pyridine, pyrazole, thiazole, isothiazole, oxazole, isoxazole, triazole, imidazole, furan, thiophene, pyrrole, oxadiazole, thiadiazole each substituted by 0, 1, 2 or 3 substituents V, where
- V independently of one another represent fluorine, chlorine, bromine, iodine, cyano, nitro, methyl, ethyl, difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino;
- T represents one of the 5-membered heteroaromatic systems T1-T35 shown below, where the bond to the pyrazolyl head group is indicated by an asterisk,

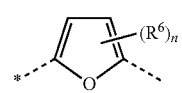

T1

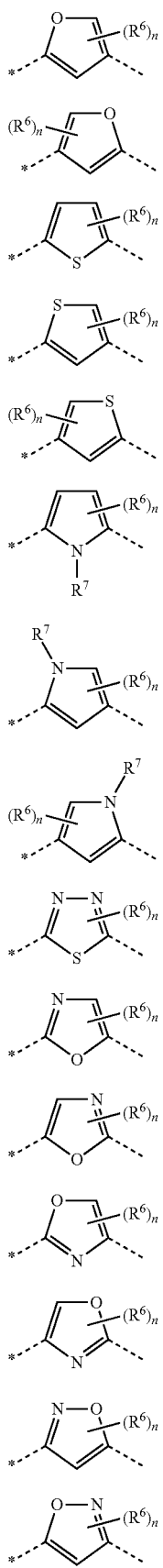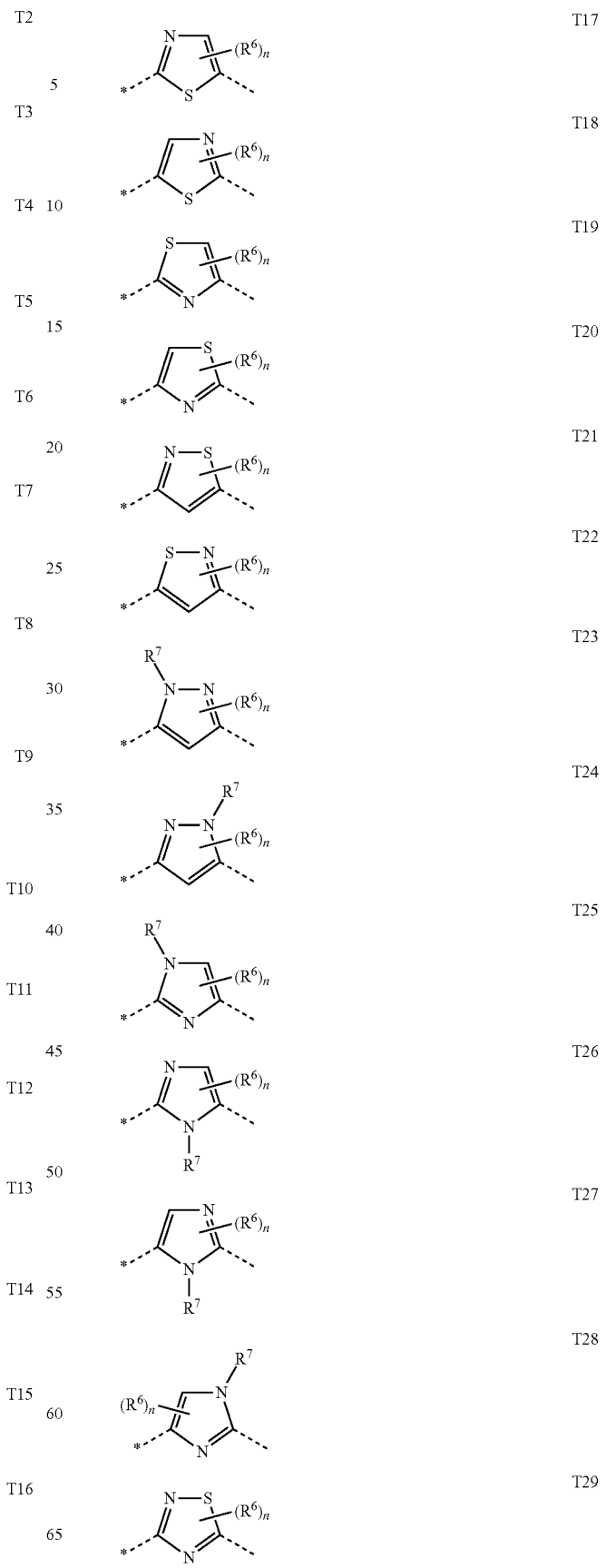

-continued

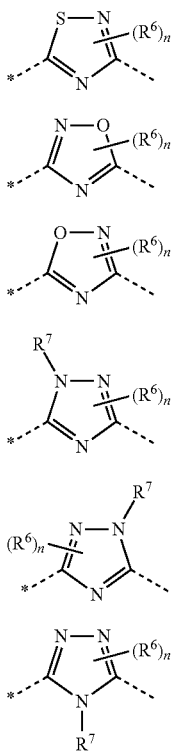

where
- R⁶ independently of one another represent fluorine, chlorine, bromine, iodine, cyano, nitro, amino, methyl, ethyl, n-propyl, 1-methylethyl, tert-butyl, trifluoromethyl, difluoromethyl, methoxy, ethoxy, trifluoromethoxy, 2,2-difluoroethoxy, 2,2,2-trifluoroethoxy, methylcarbonyl, ethylcarbonyl, trifluoromethylcarbonyl, methylsulphanyl, methylsulphinyl, methylsulphonyl, trifluoromethylsulphonyl, trifluoromethylsulphanyl, trifluoromethylsulphinyl, and
- n represents the values 0-1;
- R⁷ represents hydrogen, methyl, ethyl, n-propyl, isopropyl, n-butyl, isobutyl, s-butyl, t-butyl, ethenyl, 1-propenyl, 2-propenyl, 1-propynyl, 1-butynyl, difluoromethyl, trifluoromethyl, 1-fluoroethyl, 1-fluoro-1-methylethyl, 2-fluoroethyl, 2,2-difluoroethyl, 2,2,2-trifluoroethyl, cyclopropyl, cyclobutyl, cyclopentyl, cyclohexyl;
- Z¹ represents difluoromethyl, trichloromethyl, chlorodifluoromethyl, dichlorofluoromethyl, trifluoromethyl, bromodichloromethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, heptafluoro-n-propyl, heptafluoroisopropyl, nonafluoro-n-butyl, 1-chlorocyclopropyl, 1-fluorocyclopropyl, 1-bromocyclopropyl, 1-trifluoromethylcyclopropyl or 2,2-difluoro-1-methylcyclopropyl, and
- Z² represents hydrogen, fluorine, chlorine, bromine, iodine, cyano, nitro, amino, methyl, ethyl, n-propyl, 1-methylethyl, 1,1-dimethylethyl, difluoromethyl, trichloromethyl, chlorodifluoromethyl, dichlorofluoromethyl, trifluoromethyl, bromodichloromethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-t-butyl, heptafluoro-n-propyl, heptafluoroisopropyl, nonafluoro-n-butyl, methylsulphanyl, methylsulphinyl, methylsulphonyl, ethylsulphanyl, ethylsulphinyl, ethylsulphonyl, trifluoromethylsulphanyl, trifluoromethylsulphinyl, trifluoromethylsulphonyl, chlorodifluoromethylsulphanyl, chlorodifluoromethylsulphinyl, chlorodifluoromethylsulphonyl, dichlorofluoromethylsulphanyl, dichlorofluoromethylsulphinyl, dichlorofluoromethylsulphonyl and
- Z³ represents hydrogen, methyl, ethyl, n-propyl, isopropyl, n-butyl, isobutyl, s-butyl, t-butyl, prop-2-enyl, prop-2-ynyl, but-3-ynyl, difluoromethyl, trifluoromethyl, 1-fluoroethyl, 1-fluoro-1-methylethyl, 2-fluoroethyl, 2,2-difluoroethyl, 2,2,2-trifluoroethyl;
- where if T is T23 or T24, one of the radicals Z¹, Z² or Z³ is substituted by at least 3 halogen atoms.

5. A compound according to claim 1, in which
- Z¹ represents trifluoromethyl, 1-chlorocyclopropyl, 1-fluorocyclopropyl or pentafluoroethyl,
- Z² represents trifluoromethyl, nitro, methylsulphanyl, methylsulphinyl, methylsulphonyl, fluorine, chlorine, bromine, cyano or iodine;
- Z³ represents methyl, ethyl, n-propyl or hydrogen,
- R¹ represents hydrogen, methyl, ethyl, n-propyl, isopropyl, n-butyl, isobutyl, s-butyl, t-butyl, methoxymethyl, ethoxymethyl, propoxymethyl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 6-chloropyrid-3-ylmethyl,
- A¹ and A⁴ represent CH and A² represents CH or N,
- A₃ represents CR⁴ and
- R⁴ represents fluorine, chlorine, bromine, iodine or methyl,
- T represents one of the 5-membered heteroaromatic systems T1-T35 shown below, where the bond to the pyrazolyl head group is indicated by an asterisk,

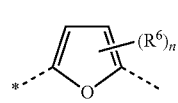

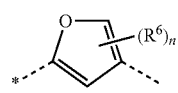

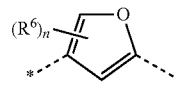

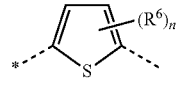

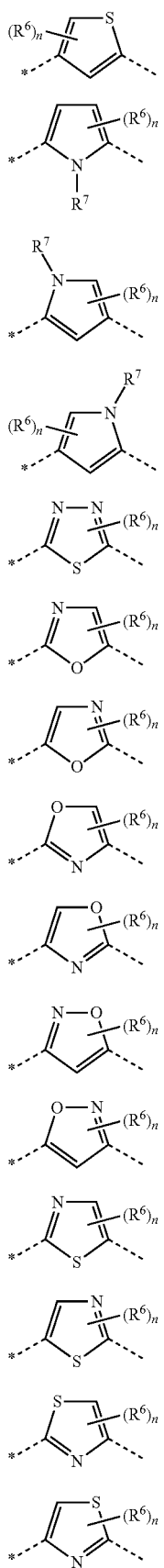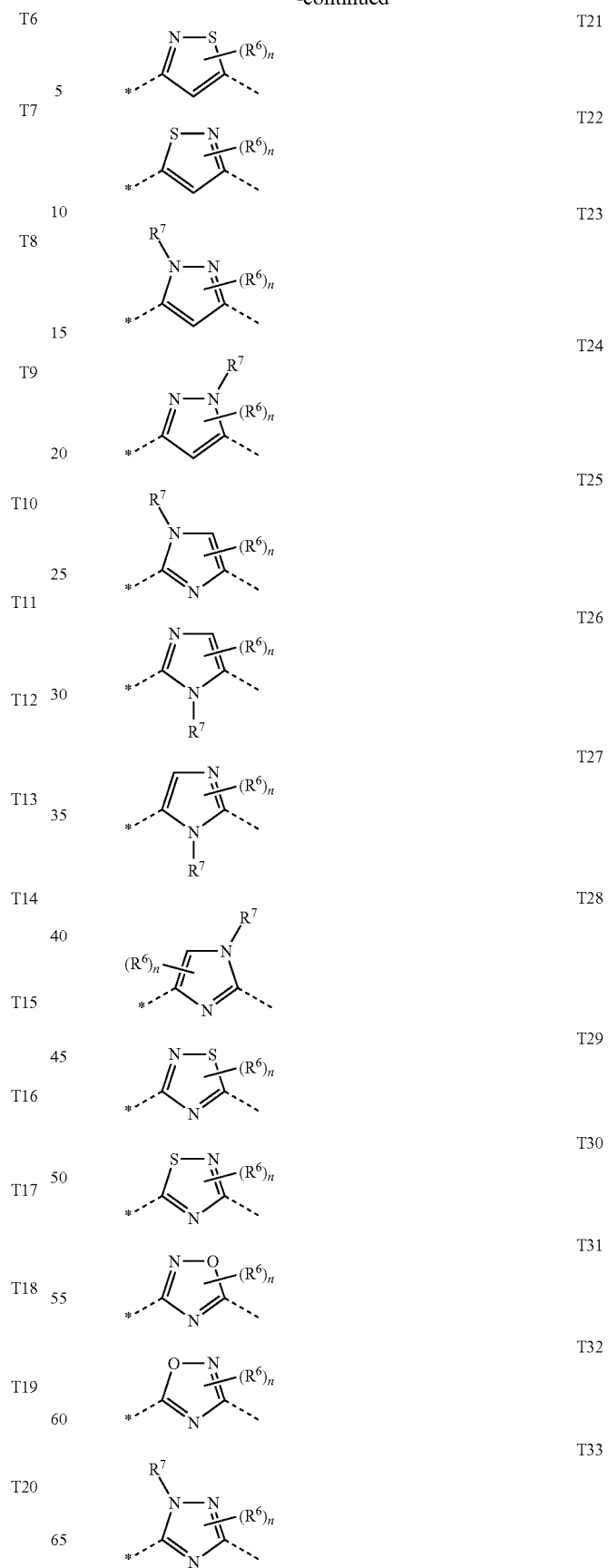

-continued

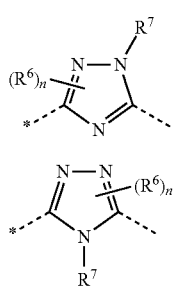

T34

T35 where
R⁶ represents hydrogen, methyl, ethyl, 2-methylethyl, 2,2-dimethylethyl, fluorine, chlorine, bromine, iodine, nitro, trifluoromethyl, amino, and
n represents the values 0-1;
W represents oxygen and
Q represents hydrogen, methyl, ethyl, n-propyl, 1-methylethyl, 1,1-dimethylethyl, n-butyl, 1-methylpropyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-methylcyclopropyl, 1-trifluoromethylcyclopropyl, 1-carbamoylcyclopropyl, 1-thiocarbamoylcyclopropyl, 1-methoxycarbonylcyclopropyl, 1-(N-methylcarbamoyl)cyclopropyl, 1-(N-cyclopropylcarbamoyl)cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, oxetan-3-yl, thietan-3-yl, 1-oxidothietan-3-yl, 1,1-dioxidothietan-3-yl, isoxazol-3-ylmethyl, 1,2,4-triazol-3-ylmethyl, 3-methyloxetan-3-ylmethyl, benzyl, 2,6-difluorophenylmethyl, 3-fluorophenylmethyl, 2-fluorophenylmethyl, 4-fluorophenylmethyl, 2,5-difluorophenylmethyl, 1-phenylethyl, 4-chlorophenylethyl, 2-trifluoromethylphenylethyl, 1-pyridin-2-ylethyl, pyridin-2-ylmethyl, (6-chloropyridin-3-yl) methyl, 5-fluoropyridin-2-ylmethyl, pyrimidin-2-ylmethyl, methoxy, 2-ethoxyethyl, 2-(methyl sulphanyl)ethyl, 1-methyl-2-(ethylsulphanyl)ethyl, 2-methyl-1-(methyl sulphanyl)propan-2-yl, methoxycarbonyl, methoxycarbonylmethyl, $NH_2$, N-ethylamino, N-allylamino, N,N-dimethylamino, N,N-diethylamino; or
Q represents phenyl, naphthyl, pyridazine, pyrazine, pyrimidine, triazine, pyridine, pyrazole, thiazole, isothiazole, oxazole, isoxazole, triazole, imidazole, furan, thiophene, pyrrole, oxadiazole, thiadiazole substituted by 0, 1, 2 or 3 substituents V, where
V independently of one another represent fluorine, chlorine, bromine, iodine, cyano, nitro, methyl, ethyl, difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino;
where if T is T23 or T24, one of the radicals $Z^1$, $Z^2$ or $Z^3$ is substituted by at least 3 halogen atoms.

6. A compound according to claim 1 and according to one of formulae (Iaa)-(Ibi) below (Iaa)

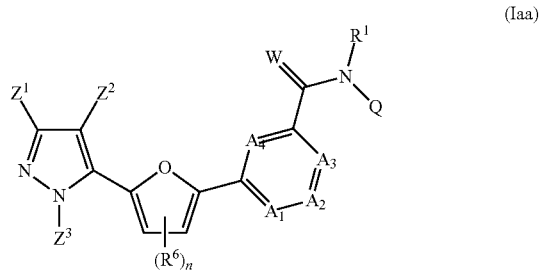

(Iab)

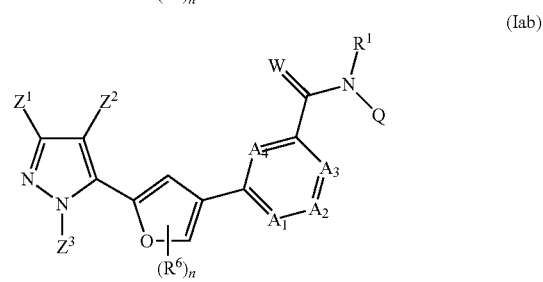

(Iac)

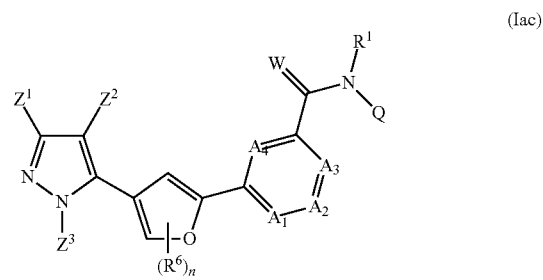

(Iad)

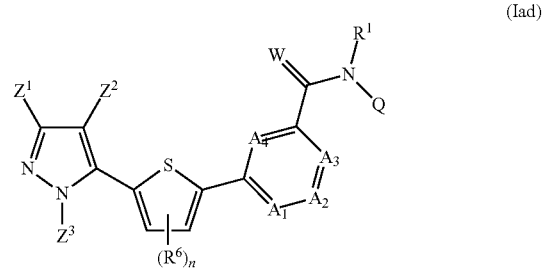

(Iae)
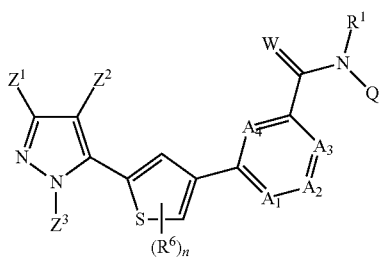
(Iaf)
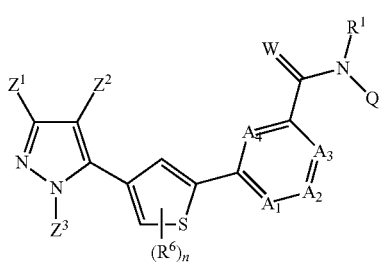
(Iag)
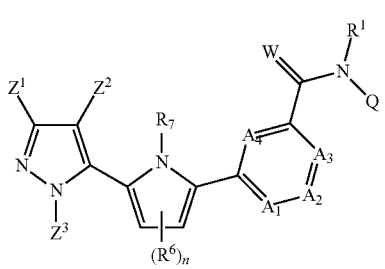
(Iah)
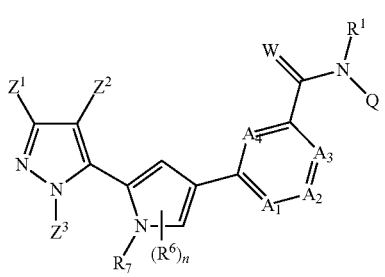
(Iai)
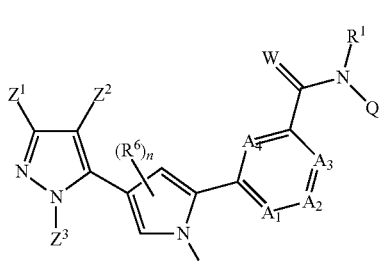
(Iaj)
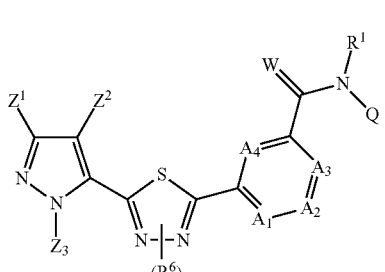
(Iak)
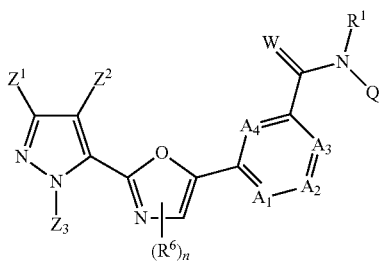
(Ial)
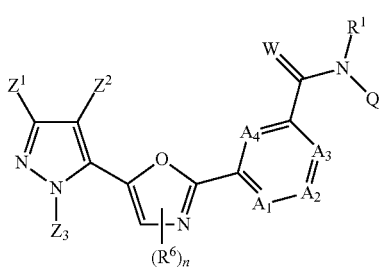
(Iam)
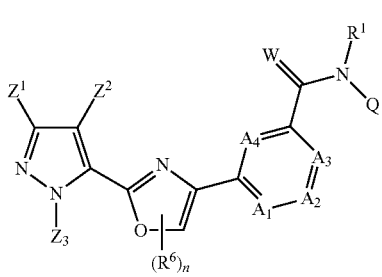
(Ian)
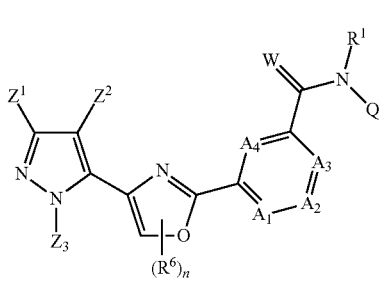
(Iao)
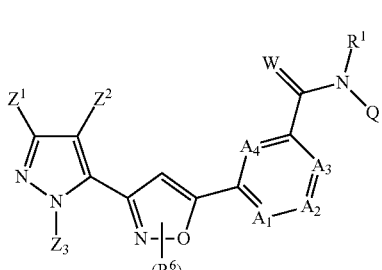
(Iap)
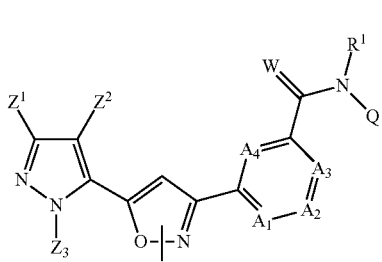

-continued
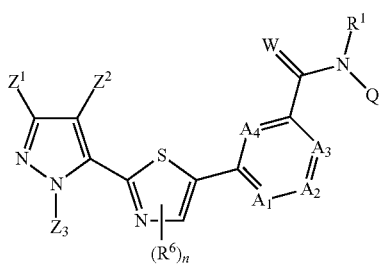
(Iaq)
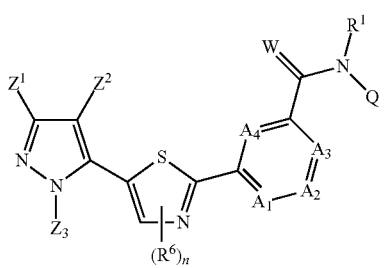
(Iar)
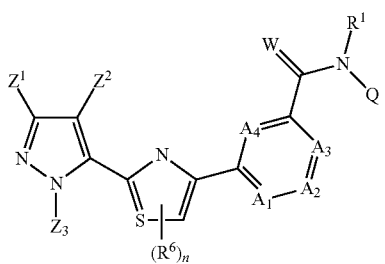
(Ias)
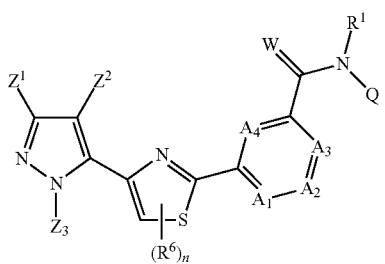
(Iat)
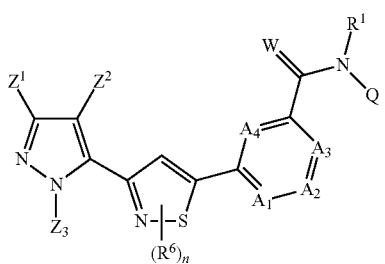
(Iau)
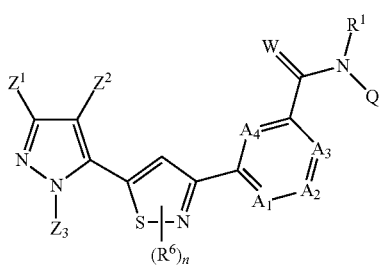
(Iav)
-continued
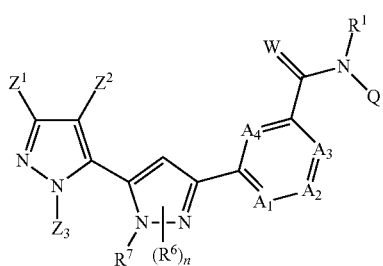
(Iaw)
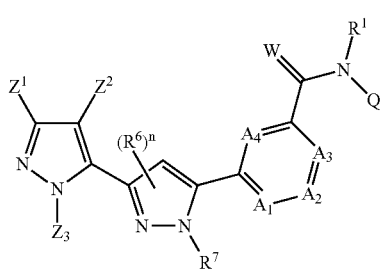
(Iax)
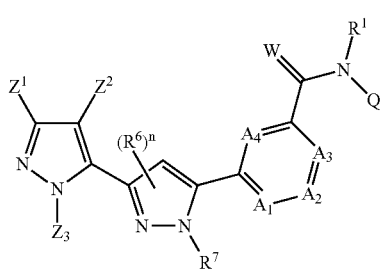
(Iay)
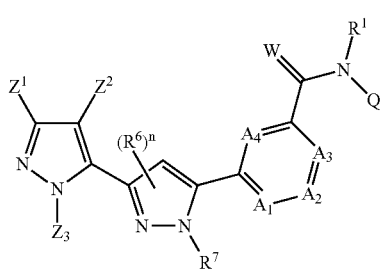
(Iaz)
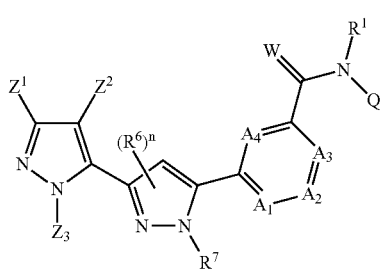
(Iba)
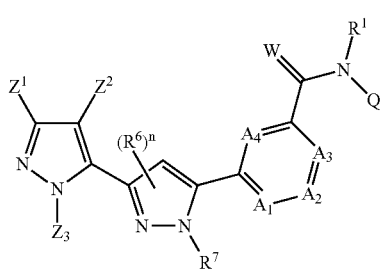
(Ibb)

-continued

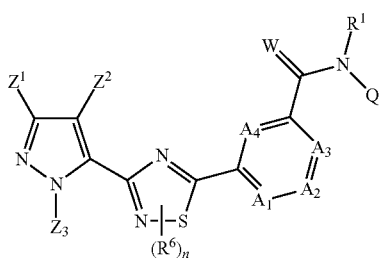
(Ibc)

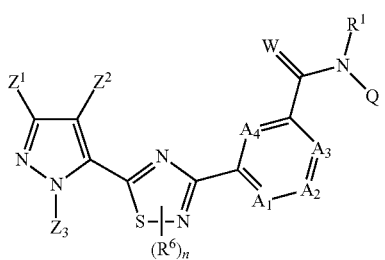
(Ibd)

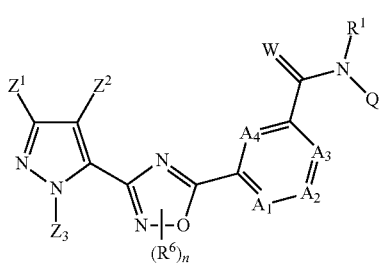
(Ibe)

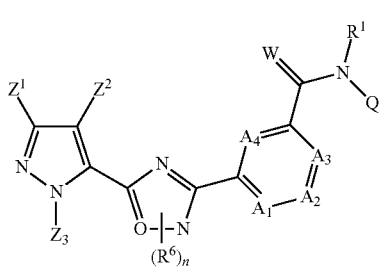
(Ibf)

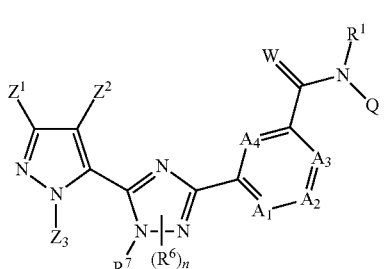
(Ibg)

-continued

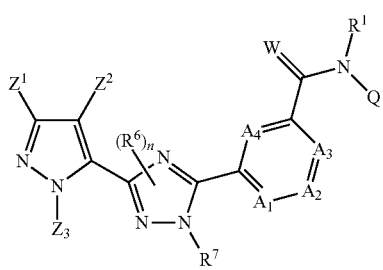
(Ibh)

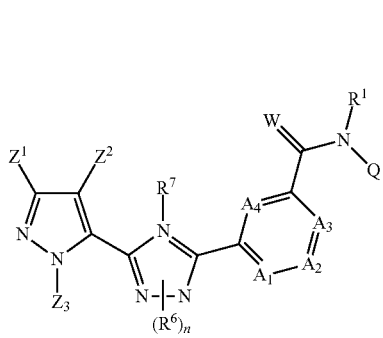
(Ibi)

7. A compound according to claim 6 in which $Z^1$ represents $CF_2CF_3$, $Z^2$ represents $CF_3$, $Z^3$ represents $CH_3$, the radicals $R^1$ and $R^6$ represent hydrogen, $A^1$ and $A^4$ represent CH, $A^2$ represents CH or N, $A^3$ represents C—Cl, W represents oxygen and Q represents 1-cyanocyclopropyl or cyclopropyl.

8. A compound formula (I) according to claim 1 for controlling one or more insects, arachnids and/or nematodes.

9. A pharmaceutical composition comprising at least one compound according to claim 1.

10. A compound according to claim 1 for use as a medicament.

11. A compound according to claim 1 for producing a pharmaceutical composition for controlling one or more parasites on animals.

12. A process for producing a crop protection composition comprising mixing a compound according to claim 1 and one or more customary extenders and/or surfactants.

13. A method for controlling one or more pests, comprising allowing a compound according to claim 1 to act on the pests and/or a habitat thereof.

14. A compound according to claim 1 for protecting the propagation material of one or more plants.

* * * * *